(12) United States Patent
Yano et al.

(10) Patent No.: US 7,527,809 B2
(45) Date of Patent: May 5, 2009

(54) POLYHYDROXYALKANOATE-CONTAINING MAGNETIC STRUCTURE, AND MANUFACTURING METHOD AND USE THEREOF

(75) Inventors: Tetsuya Yano, Atsugi (JP); Tsuyoshi Nomoto, Tokyo (JP); Shinya Kozaki, Tokyo (JP); Takeshi Imamura, Chigasaki (JP); Tsutomu Honma, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 381 days.

(21) Appl. No.: 10/553,221

(22) PCT Filed: Apr. 30, 2004

(86) PCT No.: PCT/JP2004/006296

§ 371 (c)(1),
(2), (4) Date: Oct. 17, 2005

(87) PCT Pub. No.: WO2004/096188

PCT Pub. Date: Nov. 11, 2004

(65) Prior Publication Data

US 2006/0263432 A1    Nov. 23, 2006

(30) Foreign Application Priority Data

May 2, 2003 (JP) ............................. 2003-127503

(51) Int. Cl.
*A61K 9/14* (2006.01)
*A61K 9/50* (2006.01)

(52) U.S. Cl. .................. 424/489; 424/94.1; 424/848.2; 427/213.3; 427/213.34; 428/408.24; 428/800; 528/275; 528/276; 528/277; 528/278; 528/279; 528/280

(58) Field of Classification Search ............ 428/402.24, 428/928, 800, 848.2; 427/127–130
See application file for complete search history.

(56) References Cited

U.S. PATENT DOCUMENTS

| | | | |
|---|---|---|---|
| 4,358,388 A | 11/1982 | Daniel et al. ............. 252/62.54 |
| 4,393,167 A | 7/1983 | Holmes et al. ................ 525/64 |
| 4,477,654 A | 10/1984 | Holmes et al. ............. 528/361 |
| 4,652,441 A | 3/1987 | Okada et al. .................. 424/19 |
| 4,654,267 A | 3/1987 | Ugelstad ..................... 428/407 |
| 4,675,189 A | 6/1987 | Kent et al. .................. 424/490 |
| 4,711,782 A | 12/1987 | Okada et al. ................ 424/455 |
| 4,774,265 A | 9/1988 | Ugelstad ..................... 521/55 |
| 4,876,331 A | 10/1989 | Doi ........................... 528/361 |
| 4,917,893 A | 4/1990 | Okada et al. ................ 424/423 |
| 4,954,298 A | 9/1990 | Yamamoto et al. ........... 464/4.6 |
| 5,004,664 A | 4/1991 | Fuller et al. |
| 5,051,261 A | 9/1991 | McGinity et al. ........... 424/464 |
| 5,061,492 A | 10/1991 | Okada et al. ................ 424/423 |
| 5,135,859 A | 8/1992 | Witholt et al. ............... 435/135 |
| 5,200,332 A | 4/1993 | Yamane et al. .............. 435/135 |
| 5,271,945 A | 12/1993 | Yoshioka et al. ............ 424/489 |
| 5,292,860 A | 3/1994 | Shiotani et al. ............. 528/361 |
| 5,330,767 A | 7/1994 | Yamamoto et al. .......... 424/497 |
| 5,334,698 A | 8/1994 | Witholt et al. ............... 528/354 |
| 5,476,663 A | 12/1995 | Okada et al. ................ 424/423 |
| 5,480,656 A | 1/1996 | Okada et al. ................ 424/439 |
| 5,631,020 A | 5/1997 | Okada et al. ................ 424/451 |
| 5,631,021 A | 5/1997 | Okada et al. ................ 424/451 |
| 5,643,607 A | 7/1997 | Okada et al. ................ 424/493 |
| 5,656,299 A | 8/1997 | Kino et al. .................. 424/489 |
| 5,814,342 A | 9/1998 | Okada et al. ................ 424/493 |
| 6,113,941 A | 9/2000 | Takada et al. ............... 424/451 |
| 6,117,455 A | 9/2000 | Takada et al. ............... 424/501 |
| 6,146,665 A | 11/2000 | Marchessault et al. ...... 424/497 |
| 6,167,313 A | 12/2000 | Gray et al. .................. 607/103 |
| 6,565,887 B1 | 5/2003 | Gray et al. .................. 424/489 |
| 6,635,782 B2 | 10/2003 | Honma et al. ................. 560/53 |
| 6,645,743 B1 | 11/2003 | Honma et al. .............. 435/146 |
| 6,649,380 B1 | 11/2003 | Yano et al. .................. 435/135 |
| 6,777,153 B2 | 8/2004 | Yano et al. |
| 6,872,788 B2 | 3/2005 | Imamura et al. ............ 525/440 |
| 6,911,521 B2 | 6/2005 | Kenmoku et al. ........... 528/295 |
| 6,951,745 B2 | 10/2005 | Nomoto et al. |
| 7,056,708 B2 | 6/2006 | Kenmoku et al. ........... 435/130 |
| 7,078,200 B2 | 7/2006 | Honma et al. ............... 435/135 |

(Continued)

FOREIGN PATENT DOCUMENTS

| | | |
|---|---|---|
| EP | 0 586 238 A2 | 3/1994 |
| EP | 0 647 449 A1 | 4/1995 |
| EP | 0 765 660 A2 | 4/1997 |
| EP | 0 945 137 A1 | 9/1999 |
| EP | 1 002 529 A1 | 5/2000 |
| EP | 1 275 378 A2 | 1/2003 |
| JP | 57-118512 | 7/1982 |
| JP | 59-221302 | 12/1984 |
| JP | 60-100516 | 6/1985 |
| JP | 61-43119 | 3/1986 |

(Continued)

OTHER PUBLICATIONS

Bruce A. Ramsay et al., "Effect of Nitrogen Limitation on Long-Side-Chain Poly-β-Hydroxyalkanoate Synthesis by *Pseudomonas resinovarans*," 58(2) *Appl. Environ. Microbiol.* 744-46 (1992).

(Continued)

*Primary Examiner*—Herbert J. Lilling
(74) *Attorney, Agent, or Firm*—Fitzpatrick, Cella, Harper & Scinto

(57) ABSTRACT

A structure containing polyhydroxyalkanoate and a magnetic substance includes an external phase part containing polyhydroxyalkanoate and an internal phase part contained in the external phase part, at least one of the external phase part and the internal phase part containing a magnetic substance. Accordingly, provided is a microcapsule, which can be suitably used for formation of an active ingredient of a sustained release pharmaceutical preparation or an ultrasonic contrast agent.

21 Claims, 1 Drawing Sheet

U.S. PATENT DOCUMENTS

| | | | |
|---|---|---|---|
| 7,135,540 B2 | 11/2006 | Honma et al. | 528/272 |
| 7,153,622 B2 | 12/2006 | Honma et al. | |
| 2002/0064844 A1* | 5/2002 | Shi et al. | 435/183 |
| 2003/0113368 A1* | 6/2003 | Nomoto et al. | 424/450 |
| 2003/0194443 A1 | 10/2003 | Yano et al. | 424/497 |
| 2005/0196521 A1 | 9/2005 | Kozaki et al. | 427/2.24 |
| 2006/0040366 A1 | 2/2006 | Kenmoku et al. | 435/135 |
| 2006/0079662 A1 | 4/2006 | Fukui et al. | 528/272 |
| 2006/0211100 A1 | 9/2006 | Kenmoku et al. | 435/135 |
| 2006/0263432 A1 | 11/2006 | Yano et al. | |

FOREIGN PATENT DOCUMENTS

| | | |
|---|---|---|
| JP | 61-63613 | 4/1986 |
| JP | 8-151321 | 6/1986 |
| JP | 62-201816 | 9/1987 |
| JP | 1-57087 | 12/1989 |
| JP | 2-124814 | 5/1990 |
| JP | 2-503315 | 10/1990 |
| JP | 4-3088 | 1/1992 |
| JP | 4-208217 | 7/1992 |
| JP | 4-321622 | 11/1992 |
| JP | 5-7492 | 1/1993 |
| JP | 5-10808 | 2/1993 |
| JP | 5-93049 | 4/1993 |
| JP | 6-15604 B2 | 3/1994 |
| JP | 7-14352 B2 | 2/1995 |
| JP | 7-265065 | 10/1995 |
| JP | 8-19227 B2 | 2/1996 |
| JP | 8-151322 | 6/1996 |
| JP | 8-217691 | 8/1996 |
| JP | 2642937 | 5/1997 |
| JP | 9-191893 | 7/1997 |
| JP | 11-199514 | 7/1999 |
| JP | 2989175 | 10/1999 |
| JP | 2001-69968 | 3/2001 |
| JP | 2001-78753 | 3/2001 |
| WO | WO 94/10982 A1 | 5/1994 |
| WO | WO 96/07399 A1 | 3/1996 |
| WO | WO 97/43005 A1 | 11/1997 |
| WO | WO 2004/097417 A1 | 11/2004 |
| WO | WO 2005/121204 A2 | 12/2005 |
| WO | WO 2005/121205 A1 | 12/2005 |
| WO | WO 2005/121206 A1 | 12/2005 |
| WO | WO 2005/121207 A1 | 12/2005 |
| WO | WO 2005/121208 A1 | 12/2005 |

OTHER PUBLICATIONS

Hideki Abe et al., "Biosynthesis from Gluconate of a Random Copolyester Consisting of 3-Hydroxybutyrate and Medium-Chain-Length 3-Hydroxyalkanoates by *Pseudomonas* sp. 61-3," 16(3) *Int. J. Biol. Macromol.* 115-19 (Jun. 1994).

Y.B. Kim et al., "Preparation and Characterization of Poly (β-Hydroxyalkanoates) Obtained from *Pseudomonas oleovorans* with Mixtures of 5-Phenylvaleric Acid and n-Alkanoic Acids," 24 Macromol. 5256-60 (1991).

Katharina Fritzsche et al., "An Unusual Bacterial Polyester with a Phenyl Pendant Group," 191 *Macromol. Chem.* 1957-65 (1990).

Safwat Antoun et al., "Production of Chiral Polyester by *Pseudomonas oleovorans* Grown with 5-Phenyl-2,4-Pentadienoic Acid," 3(6) *Chirality* 492-94 (1991).

Joanne M. Curley et al., "Production of Poly(3-Hydroxyalkanoates) Containing Aromatic Substituents by *Pseudomonas oleovorans*," 29 *Macromol.* 1762-1766 (1996).

Suzette M. Aróstegui et al., "Bacterial Polyesters Produced by *Pseudomonas oleovorans* Containing Nitrophenyl Groups," 32 *Macromol.* 2889-95 (1999).

Helmut Ritter et al., "Bacterial Production of Polyesters Bearing Phenoxy Groups in the Side Chains, 1 Poly(3-Hydroxy-5-Phenoxypentanoate- co-3-Hydroxy-9-Phenoxy-Nonanoate) from *Pseudomonas oleovorans* ," 195 *Macromol. Chem. Phys.* 1665-72 (1994).

Young Baek Kim et al., "Poly-3-Hydroxyalkanoates Produced from *Pseudomonas oleovorans* Grown with ω-Polyhydroxyalkanoates," 29 *Macromol.* 3432-35 (1996).

Ohyoung Kim et al., "Bioengineering of Poly( β-hydroxyalkanoates) for Advanced Material Applications: Incorporation of Cyano and Nitrophenoxy Side Chain Substituents," 41 (Supp. 1) *Can. J. Microbiol.* 32-43 (1995).

Marianela Andújar et al., "Polyesters Produced by *Pseudomonas oleovorans* Containing Cyclohexyl Groups," 30 *Macromol.* 1611-15 (1997).

Henry J. Vogel et al., "Acetylorinithinase of *Escherichia coli* : Partial Purification and Some Properties," 218 *J. Biol. Chem.* 97-106 (1956).

Geoffrey A.R. Nobes et al., "Growth and Kinetics of *in vitro* Poly([R]0(-)-3-hydroxybutyrate) Granules Interpreted as Particulate Polymerization with Coalescence," 21 *Macromol. Rapid Commun.* 77-84 (2000).

Robert W. Lenz et al., "Extracellular Polymerization of 3-Hydroxyalkanoate Monomers with the Polymerase of *Alcaligenes eutrophus*," 25 *Intl J. Biol. Macromol.* 55-60 (1999).

T.U. Gerngross et al., "Enzyme-Catalyzed Synthesis of Poly[(R)-(-)-3-Hydroxybutyrate]: Formation of Macroscopic Granules *in vitro*," 92 *Proc. Natl. Acad. Sci.* USA 6279-83 (1995).

J. Sambrook et al., *Molecular Cloning: A Laboratory Manual*, 2nd ed., p. 5.72 (1989).

John L. Speier et al., "The Addition of Silicon Hydrides to Olefinic Double Bonds. Part I. The Use of Phenylsilane, Diphenylsilane, Phenylmethylsilane, Amylsilane and Tribromosilane," 78 *J. Amer. Chem. Soc.* 2278-81 (1956).

Marjan Nienke Kraak et al., "In vivo Activities of Granule-Bound Poly[(R)-3-Hydroxyalkanoate] Polymerase C1 of *Pseudomonas oleovorans*: Development of an Activity Test for Medium-Chain-Length-Poly(3-hydroxyalkanoate) Polymerases," 250 *Eur. J. Biochem.* 432-39 (1997).

Q. Qi et al., "In vitro Synthesis of Poly(3-Hydroxydecanoate); Purification and Enzymatic Characterization of Type II Polyhydroxyalkanoate Synthases PhaC1 and PhaC2 from *Pseudomonas aeruginosa*," 54 *Appl. Microbiol. Biotechnol.* 37-43 (Jul. 2000).

Ralf Jossek et al., "In vitro Synthesis of Poly(30Hydroxybutyric Acid) by Using an Enzymatic Coenzyme A Recycling System," 168 *FEMS Microbiol. Lett.* 319-24 (1998).

Katharina Fritzsche et al., "Production of Unsaturated Polyesters by *Pseudomonas oleovorans*," 12 *Int. J. Macromol.* 85-91 (Apr. 1990).

Won Ho Park et al., "Expoxidation of Bacterial Polyesters with Unsaturated Side Chains. I. Production and Epoxidation of Polyesters from10-Undecanoic Acid," 31 *Macromol.* 1480-86 (1998).

Yasuo Takagi et al., "Biosynthesis of Polyhydroxyalkanoate with a Thiophenoxy Side Groups Obtained from *Pseudomonas putida*," 32 *Macromol.* 8315-18 (1999).

Bernd H.A. Rehm et al., "A New Metabolic Link Between Fatty Acid de Novo Synthesis and Polyhydroxyalkanoic Acid Synthesis," 273(37) *J. Biol. Chem.* 24044-51 (1998).

Masao Yamaguchi et al., "Oxidation of ω-(Benzoyloxy)alkanols with an Oxoaminium Salt," 55 *J. Org. Chem.* 1490-92 (1990).

Hiroki Okada et al., "Biodegradable Microspheres in Drug Delivery," 12(1) *Critical Reviews in Therapeutic Drug Carrier Systems* 1-9 (1995).

G. Spehnlehauer et al., "Formation and Characterization of Cisplatin Loaded Poly(*d-I*-Lactide) Microspheres for Chemoemobilization," 75(8) *J. Pharma. Sci.* 750-55 (Aug. 1986).

Yuiji Yamamoto et al., "An Experimental Study on the Releasing Rate of Poly (3-Hydroxybutyrate) Microspheres," 7(5) *DDS* 367-71 (1992).

Yuiji Yamamoto et al., "An Experimental Study on the Releasing Rate of Poly (3-Hydroxybutyrate) Microspheres—II," 8(2) *DDS* 131-36 (1993).

Urs O. Häfeli et al., "Effective Targeting of Magnetic Radioactive $^{90}$Y-Microspheres to Tumor Cells by an Externally Applied Magnetic Field. Preliminary In Vitro and In Vivo Results," 22(2) *Nucl. Med. Biol.* 147-55 (1995).

S.A. Gómez-Lopera et al., "Synthesis and Characterization of Spherical Magnetite/Biodegradable Polymer Composite Particles," 240 *J. Colloid. Interface Sci.* 40-47 (2001).

* cited by examiner

POLYHYDROXYALKANOATE-CONTAINING MAGNETIC STRUCTURE, AND MANUFACTURING METHOD AND USE THEREOF

TECHNICAL FIELD

The present invention relates to a structure including an external phase part consisting of a solid phase that contains polyhydroxyalkanoate (hereinafter, occasionally abbreviated as PHA) including 3-hydroxyalkanoic acid as a monomer unit and an internal phase part contained in the external phase part, where at least one of these parts contains a magnetic substance, and its manufacturing method and its use.

BACKGROUND ART

Microcapsules have been studied for their applications to various kinds of uses in many fields such as pharmaceuticals, pesticides, foods, adhesives, and liquid crystals. For instance, in the field of pharmaceuticals, the microcapsules have been studied for their applications as sustained release pharmaceutical preparations by improving drugs used to be short in drug effect duration so as to exert their effects for long time. In addition to the persistence of pharmacological effects, expectations have been placed on a reduction in amount of a drug used, a reduction in side effect, an improvement in noncompliance, and so on. In recent years, furthermore, various release-controlled pharmaceutical compositions, which can release a drug at constant rates and have substantially zero-order drug-releasing rates, have been particularly proposed as sustained release pharmaceutical compositions. Those release-controlled agents, such as oral formulations, injectable formulations, and skin patch formulations, are in the process of developing.

In addition, for example, in the field of cosmetics as well as medical and pharmaceutical fields, the microcapsules have been expected to be materials that selectively transfer active ingredients having troubles in stability to the affected areas and permit their sustained release. Furthermore, for example, pesticides and fertilizers having sustained-release functions have been studied in the field of agriculture and also the application of various kinds of capsule ink has been studied in the field of recording materials.

In the field of pharmaceuticals, the specification of U.S. Pat. No. 614,665 discloses a method of manufacturing a pharmaceutical composition as a composition formed as a drug-encapsulating capsule using polyhydroxyalkanoate, in the form of fine particles in which a hydrophilic drug is entrapped in porous granules made of polyhydroxyalkanoate, or oil drops dissolving a lipophilic drug as a core material and encapsulated in a shell.

Among them, oral formulations have been extensively studied and developed and many pharmaceutical preparations have been placed on the market. On the other hand, regarding injectable formulations, insulin depot preparations have been partly used in the medical field. The reasons thereof include no development of a high molecular compound for imparting the ability of sustained release. The high molecular compounds used for oral formulations do not necessarily have to be decomposed in the living body. On the other hand, the decomposition, metabolism, and excretion of those for injectable formulations without the expression of toxicity in the living body are substantially indispensable prerequisites. Besides, there is a need of severe conditions of which, for example, no local disorder should be caused at the administration site.

Under such circumferences, many high molecular compounds have been studied in recent years. Among them, a polylactic acid, a lactate/glycolate copolymer, a hydroxybutyrate/glycolate copolymer, and so on, which are used for suture in an operation have been expected to be safe and useful high molecular compounds (JP 01-057087 B, WO94/10982, JP 08-151322 A, and JP 08-217691 A). Actually, for the purpose of preparing sustained release pharmaceutical preparations, many micro-encapsulation technologies using those high molecular compounds have been reported. In addition, with respect to poly-3-hydroxybutyrate (hereinafter, occasionally abbreviated as PHB), a microcapsule for a regulatory peptide from which the discharge of an active ingredient is controlled and a microcapsule containing Lastet have been reported (JP 61-431119 A, Drug Delivery System, 7(5), 367-371, 1992, and the same 8(2), 131-136, 1993). Furthermore, with respect to a 3-hydroxybutyrate/4-hydroxybutyrate copolymer, a sustained release pharmaceutical preparation where the rate of releasing a physiologically active substance is controlled by a monomer unit ratio has been disclosed (JP 11-199514 A).

Most of those technologies include water-soluble drugs. For instance, JP 60-100516 A and JP 62-201816 A each disclose a method of manufacturing a sustained-release microcapsule of a water-soluble drug having good dispersing qualities at a high trap rate by a underwater dry process. In addition, JP 01-158529 A and JP 02-124814 A each disclose a method of including a water-soluble drug in a polylactate/glycolate copolymer. Furthermore, a physiologically active polypeptide-containing sustained release pharmaceutical preparation is disclosed in JP 03-032302 A, an EGF-containing sustained release pharmaceutical preparation is disclosed in JP 02-330741 A, and disclosed in JP 04-321622 A is a long term sustained-release microcapsule that contains a copolymer or homopolymer of 7,000 to 30,000 in weight average molecular weight at a lactate/glycolate composition rate of 80/20 to 100/0 and performs zero-order release of a polypeptide for two or more months.

In this way, the conventional methods for manufacturing microcapsules can be grouped into three methods: a chemical method such as an interfacial polymerization method or an in-situ polymerization method; a physicochemical method such as a phase separation method (a coacervation method), an interfacial precipitation method, a submerged dry method, or an orifice method; and a mechanical method such as a spray drying method or a dry mixing method. Among them, interface polymerization method, in-situ polymerization method, submerged drying method, orifice method, phase-separation method (coacervation method), and so on have been proposed to be adopted as a method of micro-encapsulating the water-soluble drug.

There are many reports about sustained-release microcapsules of various physiologically active polypeptides and low-molecular water-soluble drugs (Critical Reviews in Therapeutic Drug Carrier Systems), vol. 12, pages 1-9, 1995; JP 02-503315 A; EPA 0586238; J. Pharm. Sci., vol. 75, pages 750-755 (1986); and JP 57-118512 A). At present, most of them cannot attain satisfactory long-term sustained release depending on their uses because: (1) a drug is encapsulated at a low rate because the drug leaks into an external water phase at a high rate in the manufacturing step; (2) the resulting capsules are generally porous and release a large quantity thereof at an initial stage; (3) a sufficient biological utilization factor cannot be obtained because a physiologically active substance is modified in the manufacturing step; and so on.

Regarding an improvement in sustained release of microcapsule, for the purpose of preventing a decrease in rate of releasing active ingredients after passing a predetermined time from the administration of a microcapsule in which polylactate is provided as a base material, JP 61-063613 A describes that fat-soluble additives (such as medium-chain fatty acid triglyceride and lower fatty acid triglyceride), which can be dissolved in a polylactate organic solvent and digested in the living body, are uniformly dissolved in the solvent solution. However, there is no suggestion about the application to other base materials and the preparation of a microcapsule using an aqueous solution of active ingredients. JP 08-151321 A discloses a microcapsule that contains an amorphous water-soluble physiologically active substance and a high molecular polymer and manufactured from an S/O/W type emulsion. However, there is no description with respect to a method of manufacturing a microcapsule using an aqueous solution of a drug as an internal water phase and a method using a metal complex of a water-soluble physiologically active peptide. Furthermore, EP 0765660 describes a microcapsule that contains an amorphous 2-pyperazinone-1-acetate derivative, and an S/O/W type emulsion is used in its manufacture. However, there is no description about a method of manufacturing a microcapsule in which an aqueous solution of a drug is used as an internal water phase and a method of using a metal complex of a water-soluble physiologically active peptide. Generally, in the manufacture of a microcapsule of a water-soluble physiologically active substance, the W/O type is superior in terms of uniformity and operability of the drug content to the S/O type in which a drug is used in a solid state. In industrial scale mass production, it is desired to use the W/O type.

In this way, a problem which is often pointed out in drug-releasing control using a sustained release pharmaceutical preparation is the presence of a phenomenon (an initial burst phenomenon) in which a large amount of the drug compound is released at once at the initial stage of releasing the drug after the administration of the sustained release pharmaceutical preparation into the body. The occurrence of the initial burst of the sustained release pharmaceutical preparation may cause the drug compound concentration in blood to exceed its acceptable level in the living body to thereby jeopardize the patient. A method of avoiding the initial burst to some extent by, for example, selecting the type of the drug compound and the structure of a biodegradable polymer has been discovered. However, any basic solution to prevent the initial burst phenomenon has not been found yet. On the other hand, furthermore, it has been desired to include a drug compound in a microcapsule in as high a concentration as possible, for releasing the drug compound for long time, or for including an expensive drug in a small amount of the pharmaceutical preparation as cost-effectively as possible.

However, in the conventional method of preparing microcapsules, the proportion (uptake rate) of a drug compound taken within a microcapsule tended to be low. In particular, when a water-soluble drug was used as the drug, there was a large problem in that the encapsulation rate of the drug was low because the drug was easy to scatter out of a membrane. In addition, a microcapsule prepared by a method that would allow an increase in uptake rate had a disadvantage in that an initial burst phenomenon tended to take place at the time of releasing the drug.

In addition, in the field of ultrasonic diagnosis or examination, it has been proposed to administer a microballoon, a miniature ball of a polymer, as an ultrasonic reflector in the body. Conventionally, it has been known that minute air bubbles dispersed in a liquid, i.e., micro-bubbles, are ultrasonic reflectors extremely effective in ultrasonic diagnosis or examination. However, the micro-bubbles disappear in the shortest possible time, or within minutes even when they are added with a stabilizer. Therefore, there is a need of administrating micro-bubbles in the body immediately after the preparation of the bubbles, so that the use thereof in the actual medical field has been difficult. In addition, after the administration in the body, for making the transmission of a bubble through a blood vessel easy, the size of the bubble must be in the range of about 1 to 10 µm. In micro-bubbles, most of bubbles formed are approximately 40 to 50 µm in size. In this respect, it has not been suitable for administering micro-bubbles in the living body to be utilized in ultrasonic diagnosis.

For solving the problems that the micro-bubbles involve, administration of a microballoon which is a miniature ball of a polymer as described above in the living body has been proposed (e.g., JP 03-503684 A). However, the microballoon obtained by the conventional method should be administered in large quantities to obtain a higher cystographic effect (contrast effect). In particular, a problem was that there was no effective contrast agent that sufficiently satisfies a high cystographic effect (a contrast effect) being desired particularly in the case of contrasting the cardiac muscle. The factors thereof include difficulty in obtaining uniform fine particles that contain many air bubbles because they do not have hollow structures in their insides. Besides, the massive administration of microballoon may place excessive burdens on the living body. Thus, a problem which should be improved has remained from the point of view of safety.

Furthermore, because a capsule structure that contains a magnetic substance can be easily collected by magnetic force, mainly in the field of biochemistry, its excellent effects have been expected as a medical diagnostic drug carrier, a bacteria- or cell-separating carrier, a carrier for separating and purifying a nucleic acid or a protein, a drug delivery carrier, an enzyme reaction carrier, a cell culture carrier, and so on. Examples of a method of synthesizing a capsule structure that contains a magnetic substance include: a method in which a magnetic substance imparted with lipophilicity is dispersed in a polymerizable monomer and the dispersion is subjected to suspension polymerization (JP 59-221302 A); a method in which a magnetic substance imparted with lipophilicity is dispersed in a polymerizable monomer in the same way and the mixture is homogenized in water with a homogenizer and polymerized to obtain magnetic particles having comparatively small particle sizes (JP 04-03088 B); and a method in which a magnetic substance is introduced into the inside of porous polymer particles having a specific functional group by oxidizing an iron compound after the precipitation of the iron compound in the presence of the porous polymer particles to obtain magnetic particles having large particle sizes and uniformity in size (JP 05-10808 B).

However, when the capsule structures containing the magnetic substances obtained by those synthetic methods are used for medical diagnostic drug carriers or the like, even in the case where many magnetic substances are located inside the capsule structure, sensitivity may fall sharply, a nonspecific reaction may be shown, or the like. Thus, sufficient performance is hardly obtained in many cases. This is probably because the magnetic substance component may be eluted to impair practical performance as the magnetic substance is partially exposed on the surface of the capsule structure containing the magnetic substance or a micropass is formed between the surface of the structure and the magnetic substance in the inside thereof. In general, the hydrophilicity of a magnetic substance is higher than that of polymer particles. In the conventional synthetic process, the localization of a magnetic substance on the surface of a capsule structure or the periphery of the surface may be one of the great causes which spoil practical performance. Thus, the conventional magnetic substance-containing capsule structure is difficult to prevent the exposure of the contained magnetic substance component on the surface of the structure and the elusion of the magnetic substance component by the formation of a micropass or the like. Therefore, the actual condition was that the conventional capsule structure was only limited to be used in the field where the elusion was insignificant.

By the way, in recent years, the production of a high molecular compound by means of biotechnology has been actively studied and partially translated in practical applications. For instance, known high molecular compounds derived from microorganisms include: PHAs such as PHB and a copolymer of 3-hydroxy-n-butyrate and 3-hydroxy-n-valerate (hereinafter, occasionally abbreviated as PHB/V); polysaccharides such as bacterial cellulose and pullulan; and polyamino acids such as poly-γ-glutamate and polylysine. In particular, like the conventional plastics, PHA can be used in various products by melt processing and so on and is excellent in biocompatibility, so that application of PHA in a medical soft material or the like has been expected.

Up to now, it has been reported that many microorganisms produce PHAs and accumulate them into the microbial cells. The production of PHB/V by microorganisms, *Alcaligenes eutrophus* Strain H16 ATCC No. 17699, *Methylobacterium* sp., *Paracoccus* sp., *Alcaligenes* sp., and *Pseudomonas* sp., have been reported (JP 05-074492 A, JP 06-015604 B, JP 07-014352 B, and JP 08-019227 B).

In addition, there is disclosed that *Comamonas acidovorans* Strain IFO 13852 produces PHA having 3-hydroxy-n-butyrate and 4-hydroxy-n-butyrate as monomer units (JP 09-191893 A). Furthermore, there is disclosed that *Aeromonas caviae* produces a copolymer of 3-hydroxy-n-butyrate and 3-hydroxyhexanoate (JP 05-093049 A and JP 07-265065 A).

The biosynthesis of those PHB and PHB/V can be carried out by an enzymatic polymerization reaction using as a substrate (R)-3-hydroxybutyryl-CoA or (R)-3-hydroxyvaleryl CoA produced from various carbon sources through various metabolic pathways in the living body.

The enzyme that catalyzes the polymerization reaction is a PHB synthetic enzyme (also referred to as a PHB polymerase or a PHB synthase). Here, "CoA" is an abbreviation for "Coenzyme A" and the chemical structure thereof is as follows.

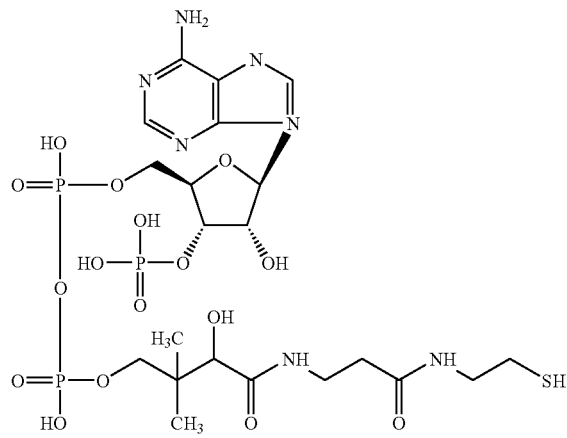

In addition, in recent years, researches have been extensively carried out with respect to polyhydroxyalkanoate composed of a 3-hydroxyalkanoate unit having a medium-chain-length of about 3 to 13 carbon atoms (occasionally abbreviated as mcl-PHA). JP 2642937 B discloses the production of PHA having a 3-hydroxyalkanoate monomer unit having 6 to 12 carbon atoms by the addition of a noncyclic aliphatic hydrocarbon to *Pseudomonas oleovorans* Strain ATCC 29347. Furthermore, Appl. Environ. Microbiol., 58, 746 (1992) reports the production of PHA by *Pseudomonas resinovorans* in which octanoic acid is used as a single carbon source and 3-hydroxy-n-butyrate, 3-hydroxyhexanoate, 3-hydroxyoctanoate, or 3-hydroxydecanoate is used as a monomer unit, and also the production of PHA by *Pseudomonas resinovorans* in which hexanoic acid is used as a single carbon source and 3-hydroxy-n-butyrate, 3-hydroxyhexanoate, 3-hydroxyoctanoate, or 3-hydroxydecanoate is used as a monomer unit. Here, a 3-hydroxyalkanoate monomer unit having a chain length longer than that of the fatty acid in a raw material may be introduced by way of a fatty acid synthesis pathway described later.

Int. J. Biol. Macromol., 16(3), 119 (1994) reports the production of PHA by *Pseudomonas* sp. strain 61-3 in which sodium gluconate is used as a single carbon source and a 3-hydroxyalkanoate such as 3-hydroxy-n-butyrate, 3-hydroxyhexanoate, 3-hydroxyoctanoate, 3-hydroxydecanoate, or 3-hydroxydodecanoate and a 3-hydroxyalkenoate such as 3-hydroxy-5-cis-decenoate or 3-hydroxy-5-cis-dodecenoate are used as units.

The above PHA is one that consists of a monomer unit having an alkyl group on its side chain (hereinafter, occasionally abbreviated as usual-PHA). However, in consideration of more wide-ranging applications, such as an application as a functional polymer, an extremely useful PHA is one in which a substituent, except an alkyl group (e.g., a phenyl group, unsaturated hydrocarbon, ester group, allyl group, cyano group, halogenated hydrocarbon, or epoxide), is introduced into the side chain (hereinafter, occasionally abbreviated as unusual-PHA).

As an example of the biosynthesis of unusual-PHA having a phenyl group, Macromolecules, 24, 5256-5260 (1991), Macromol. Chem., 191, 1957-1965 (1990), and Chirality, 3, 492-494 (1991) reports that *Pseudomonas oleovorans* produces PHA that contains a 3-hydroxy-5-phenyl valerate unit from 5-phenyl valerate. In addition, Macromolecules, 29, 1762-1766 (1996) reports that *Pseudomonas oleovorans* produces PHA that contains a 3-hydroxy-5-(4-tolyl) valerate unit from 5-(4-tolyl) valerate (5-(4-methylphenyl) valerate). Furthermore, Macromolecules, 32, 2889-2895 (1999) reports that *Pseudomonas oleovorans* produces PHA that contains a 3-hydroxy-5-(2,4-dinitrophenyl) valerate unit and a 3-hydroxy-5-(4-nitrophenyl) valerate unit from 5-(2,4-dinitrophenyl) valerate.

In addition, as an example of unusual-PHA having a phenoxy group, Macromol. Chem. Phys., 195, 1665-1672 (1994) reports that *Pseudomonas oleovorans* produces PHA that contains a 3-hydroxy-5-phenoxy valerate unit and a 3-hydroxy-9-phenoxy nonanoate unit from 11-phenoxy undecanoate. Furthermore, Macromolecules, 29, 3432-3435 (1996) reports that *Pseudomonas oleovorans* produces PHA that contains a 3-hydroxy-4-phenoxy butyrate unit and a 3-hydroxy-6-phenoxy hexanoate unit from 6-phenoxy hexanoate, PHA that contains a 3-hydroxy-4-phenoxy butyrate unit, a 3-hydroxy-6-phenoxy hexanoate unit, and a 3-hydroxy-8-phenoxy octanoate unit from 8-phenoxy octanoate, and PHA that contains a 3-hydroxy-5-phenoxy valerate unit and a 3-hydroxy-7-phenoxy heptanoate unit from 11-phenoxy undecanoate.

Furthermore, Can. J. Microbiol., 41, 32-43 (1995) reports that each of *Pseudomonas oleovorans* Strain ATCC 29347 and *Pseudomonas putida* Strain KT 2442 produces PHA that contains a 3-hydroxy-p-cyanophenoxy hexanoate unit or a 3-hydroxy-p-nitrophenoxy hexanoate unit from p-cyanophenoxy hexanoate or p-nitrophenoxy hexanoate. In addition, JP 2989175 B describes a homopolymer consisting of a 3-hydroxy-5-(monofluorophenoxy) valerate unit or of a 3-hydroxy-5-(difluorophenoxy) valerate unit, a copolymer containing at least a 3-hydroxy-5-(monofluorophenoxy) pentanoate unit or a 3-hydroxy-5-(difluorophenoxy) pentanoate unit, and their manufacturing methods.

Furthermore, as an example of unusual-PHA having a cyclohexyl group, Macromolecules, 30, 1611-1615 (1997) reports that *Pseudomonas oleovorans* produces such PHA from cyclohexyl butyrate or from cyclohexyl valerate.

Furthermore, among PHAs in which substituents are introduced into their side chains, as an example of the development of PHA having a sulfur atom in the form of sulfide (—S—) in the side chain, Macromolecules., 32, 8315-8318 (1999) reports the production of PHA that contains 3-hydroxy-5-(phenylsulfanyl) valerate and 3-hydroxy-7-(phenylsulfanyl) heptanoate as monomer units using *Pseudomonas putida* Strain 27N01 with octanoic acid and 11-(phenylsulfanyl)undecanoate as substrates. However, in that case, the method used involves: pre-incubating *Pseudomonas putida* Strain 27N01 in a culture that contains only octanoic acid as a grow substrate: and inoculating the medium of the above culture into a culture that contains only 11-(phenylsulfanyl) undecanoate as a substrate.

Furthermore, Polymer Preprints, Japan Vol. 49, No. 5, 1034 (2000) reports that the production of PHA containing 3-hydroxy-5-benzyl thiovalerate and 3-hydroxy-7-[(phenylmethyl)sulfanyl]heptanoate as monomer units using *Pseudomonas putida* Strain 27N01 with 11-[(phenylmethyl) sulfanyl]undecanoate as a substrate. However, in this case, the method used involves: pre-incubating *Pseudomonas putida* Strain 27N01 in a culture that contains only octanoic acid as a grow substrate; and inoculating the medium of the above culture into a culture that contains only 11-[(phenylmethyl)sulfanyl]undecanoate as a substrate.

The biosynthesis of those mcl-PHA and unusual-PHA is performed by enzymatic polymerization reactions, where the substrate used is (R)-3-hydroxyacyl CoA produced from various alkanoic acids used as raw materials through various metabolic pathways in the living body (e.g., a β-oxidation system and a fatty acid synthesis pathway). The enzyme that catalyzes such a polymerization reaction is a PHA-synthetic enzyme (also referred to as a PHA polymerase or PHA synthase). Here, with respect to the PHB synthetic enzyme described above, the monomer to serve as a substrate for the PHA synthetic enzyme is limited. The PHB synthetic enzyme belongs to the category of PHA synthetic enzyme.

Hereinafter, there will be described the reaction until PHA is produced from an alkanoic acid through a polymerization reaction with a β-oxidation system and a PHA synthetic enzyme.

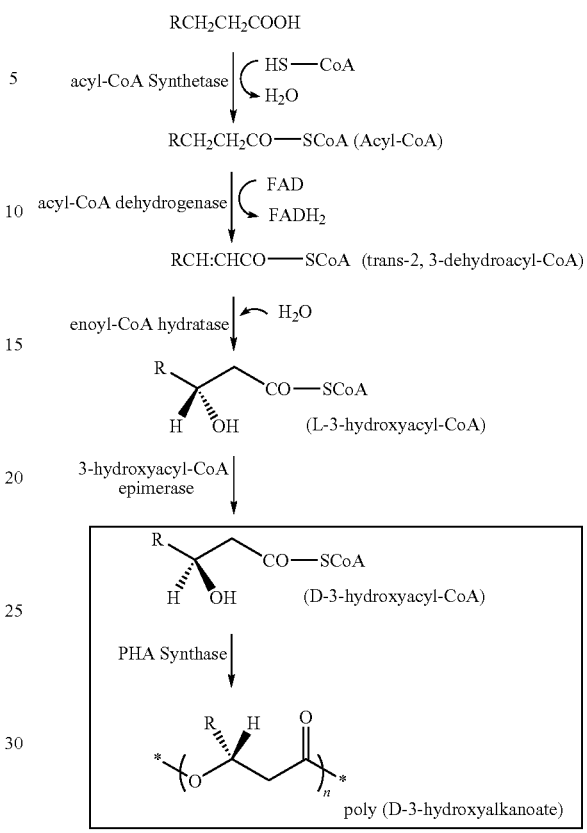

On the other hand, in the case of passing through the fatty acid synthesis pathway, PHA may be similarly synthesized using the PHA synthetic enzyme using (R)-3-hydroxyacyl-CoA as a substrate, which is converted from (R)-3-hydroxyacyl-ACP ("ACP" denotes an acyl-carrier protein) generated in the pathway.

In recent years, it has been attempted to synthesize PHA in a cell-free system (in vitro) by taking the above PHB or PHA synthetic enzyme out of microbial cells. In Proc. Natl. Acad. Sci. USA, 92, 6279-6283 (1995), the synthesis of PHB consisting of a 3-hydroxy-n-butyrate unit is achieved by acting 3-hydroxybutyryl-CoA on a PHB synthetic enzyme derived from *Alcaligenes eutrophus*. In addition, in Int. J. Biol. Macromol., 25, 55-60 (1999), the synthesis of PHA consisting of a 3-hydroxy-n-butyrate unit or a 3-hydroxy-n-valerate unit is achieved by acting 3-hydroxybutyryl-CoA or 3-hydroxyvaleryl-CoA on a PHB synthetic enzyme derived from *Alcaligenes eutrophus*. Besides, in this report, PHA consisting only of the R-isomer of 3-hydroxy-n-butyrate unit can be synthesized by acting 3-hydroxybutyryl-CoA in the form of a racemic body by virtue of the stereoselectivity of the enzyme. In addition, Macromol. Rapid Commun., 21, 77-84 (2000) reports the extracellular synthesis of PHB using a PHB synthetic enzyme derived from *Alcaligenes eutrophus*.

Furthermore, in FEMS Microbiol. Lett., 168, 319-324 (1998), the synthesis of PHB consisting of a 3-hydroxy-n-butyrate unit is achieved by acting 3-hydroxybutyryl-CoA on a PHB synthetic enzyme derived from *Chromatium vinosum*.

In Appl. Microbiol. Biotechnol., 54, 37-43 (2000), PHA consisting of a 3-hydroxydecanoate unit is synthesized by acting 3-hydroxydecanoyl-CoA on a PHA synthetic enzyme from *Pseudomonas aeruginosa*.

DISCLOSURE OF THE INVENTION

The inventors have paid their attention to a microcapsule, in which a drug is covered with a high molecular compound, as an elemental technology for providing the high molecular compound with a high additive value. Thus, a microcapsule having very useful functionality, especially the ability of sustained release, can be obtained by covering a specific drug with the high molecular compound. Many attempts to make microcapsules as described above have been conducted by means of organic synthetic approaches.

If the microcapsule can be manufactured by the biotechnological approach as described above, the use of a new high molecular compound or the addition of a new function or structure can be expected and the resources-recycling type manufacturing process with least adverse impact on the environment may be realized at low cost. For instance, very strict molecular recognition ability and stereoselectivity, which are peculiar to the catalytic action in life, are used to obtain a microcapsule covered with a new functional high molecular compound or a high molecular compound having very high chirality by a very simple process with least adverse impact on environment.

In addition, with respect to the characteristics of drug release, at present, many problems remain in inclusion of a water-soluble drug in a microcapsule of polylactate or lactate/glycolate copolymer, or the like, which is a biodegradable macromolecule. Besides, a water-soluble drug tends to scatter, and thus there is also a large problem in that the drug is not effectively retained in the structure of a microcapsule or the like and is not micro-capsulated.

Therefore, the present invention has been invented to solve the above problem and to provide a structure useful as a sustained release pharmaceutical preparation and a method of manufacturing the same. The structure does not show initial discharge which seems to be substantially brought as an obstacle, but shows zero-order release substantially allowed for a predetermined period, even if the structure is a microcapsule or the like in which a drug, especially a water-soluble drug is contained, or the structure is a microcapsule or the like in which a drug substantially insoluble in water (such drugs include those generally known as poorly water-soluble drugs) is contained. In addition, the structure has magnetic property. Thus, the present invention intends to provide a sustained release pharmaceutical preparation which has a structure such as a microcapsule stably containing a drug, especially a water-soluble drug at high content and which has magnetic property, and a method of manufacturing the same.

Furthermore, fine particles prepared by entrapping a hydrophilic drug on porous granules made of polyhydroxyalkanoate, disclosed in U.S. Pat. No. 614,665, have biodegradability without toxicity and is capable of capturing the drug in situ. However, because of its porous structure, the hydrophilic drug is quickly released by diffusion, resulting in difficulty in control of sustained release.

The present invention intends to provide magnetic drug-retaining particles excellent in retaining any of hydrophilic drugs and other water-soluble substances, or lipophilic drugs and other hydrophobic substances, by controlling the drug-retaining ability and sustained releasability of the structure of polyhydroxyalkanoate by optimizing the structure thereof.

In the microballoon obtained by the conventional method, fine particles do not have hollow structures in their insides, so that it is difficult to obtain uniform fine particles that contain many air bubbles. Therefore, the microballoon should be administered in large quantities to obtain a higher cystographic effect (a contrast effect) in ultrasonic diagnosis and examination. In particular, in the case of contrasting the cardiac muscle, a large problem was that there was no effective contrast agent that sufficiently satisfies a high cystographic effect (a contrast effect) being desired. Besides, the massive administration of microballoon may place excessive burdens on the living body. Thus, a problem which should be alleviated has also remained from the point of view of safety.

Therefore, the present invention provides a method of manufacturing a hollow magnetic structure such as a hollow microcapsule, which is capable of selectively obtaining many fine particles in the form of a hollow microcapsule having a single film of PHA for including many air bubbles in the fine particles. In addition, using such a hollow magnetic structure as a hollow microcapsule, the present invention provides an ultrasonic contrast agent that exerts a high cystographic effect and a manufacturing method thereof. More concretely, the present invention provides an ultrasonic contrast agent having a high cystographic effect, which can be used in ultrasonic diagnosis and examination of the cardiac muscle, heart chamber, or liver. In particular, the present invention provides medical diagnostic drug-retaining particle the movement of which in the living body can be controlled, contrast particles available in ultrasonic diagnosis, and drug-delivery particles that transfer a drug to an affected part of a patient.

Furthermore, the capsule structure containing a magnetic substance obtained by the conventional synthetic method has a problem in that a metal ion is eluted to the outside. At present, the structure can be only applied on the uses and applications which are not influenced by the elusion of a metal ion. Therefore, the present invention provides: a structure such as a macrocapsule that contains a magnetic substance and is excellent in dispersibility and magnetic response of the magnetic substance and is widely applicable to various uses and applications while hardly eluting a metal ion to the outside; and a manufacturing method thereof.

For solving the above problem, as a result of the intensive study conducted by the inventors of the present invention, the present invention has been completed by finding out that a magnetic structure, which may be in the form of a microcapsule or the like, can be obtained using PHA containing a 3-hydroxyalkanoate unit, such that the structure includes an external phase part consisting of a solid phase mainly made of PHA and an internal phase part included in the external phase part, and a magnetic substance is included in at least one of these parts.

According to the present invention, there is provided a structure including polyhydroxyalkanonate and a magnetic substance, including:

an external phase part containing the polyhydroxyalkanoate; and an internal phase part contained in the external phase part, at least one of the external phase part and the internal phase part containing the magnetic substance.

In this structure, the external phase part contains PHA, while the internal phase part is constructed of at least one of a solid phase, liquid phase, and gas phase. For instance, the structure may be in the form of a microcapsule in which the external phase part forms a shell part and the internal phase part forms a core part. Alternatively, the structure may be in the form of a microsphere in which a plurality of internal phase parts that contain a drug or the like are dispersed in the external phase part containing PHA. The magnetic substance may be included in at least one of the external and internal phase parts depending on the structure.

According to an aspect of the present invention, there is provided a manufacturing method for a structure having an external phase part containing polyhydroxyalkanoate and an internal phase part contained in the external phase part with at least one of the external phase part and the internal phase part containing a magnetic substance, including the steps of:

preparing a liquid raw material including an oil phase containing polyhydroxyalkanoate and an organic solvent, a water phase, and the magnetic substance; and removing the organic solvent and/or water from the liquid raw material, the inner phase part being contained in the external phase part including PHA derived from the oil phase or the water phase, and at least one of the external phase part and the internal phase part containing the magnetic substance.

According to another aspect of the present invention, there is provided a manufacturing method for a structure having an external phase part containing polyhydroxyalkanoate and an internal phase part contained in the external phase part, at least one of the external phase part and the internal phase part containing a magnetic substance, including the steps of:

preparing a water phase containing a polyhydroxyalkanoate synthetic enzyme and a 3-hydroxyacyl coenzyme A;

preparing an oil phase containing an organic solvent;

preparing an emulsion containing the water phase, the oil phase, and the magnetic substance;

synthesizing polyhydroxyalkanoate by polymerizing the 3-hydroxyacyl coenzyme A with the polyhydroxyalkanoate synthetic enzyme in the emulsion; and removing the organic solvent and/or the water from the emulsion, the inner phase part being contained in the external phase part including PHA derived from the oil phase or the water phase, and at least one of the external phase part and the internal phase part containing the magnetic substance.

Preferable concrete aspects of the manufacturing methods according to each of the above aspects include the follows.

(a) A manufacturing method for a structure constructed as described above, including the steps of: dispersing a water phase in an oil phase containing at least polyhydroxyalkanoate, an organic solvent, and a magnetic substance to prepare a W/O type emulsion; and removing the organic solvent from the W/O type emulsion to form the structure.

(b) A manufacturing method for a structure, including the steps of: dispersing the W/O type emulsion in a water phase to prepare a W/O/W type emulsion; and removing an organic solvent from the W/O/W type emulsion to form the structure.

(c) A manufacturing method for a structure, including the steps of: dispersing the oil phase into the water phase to prepare an O/W type emulsion; and removing an organic solvent and/or water from the O/W type emulsion.

(d) A manufacturing method for a structure constructed as described above, including the steps of:

(1) dispersing a water phase containing at least a polyhydroxyalkanoate synthetic enzyme and 3-hydroxyacyl coenzyme A in an oil phase containing a magnetic substance to prepare a W/o type emulsion;

(2) polymerizing the 3-hydroxyacyl coenzyme A with the polyhydroxyalkanoate synthetic enzyme to synthesize polyhydroxyalkanoate; and (3) removing an organic solvent from the W/O type emulsion to obtain the structure.

(e) A manufacturing method for a structure constructed as described above, including the steps of:

(1) dispersing a water phase in an oil phase containing a magnetic substance to prepare a W/O type emulsion;

(2) dispersing the W/O type emulsion in a water phase containing at least a polyhydroxyalkanoate synthetic enzyme and 3-hydroxyacyl coenzyme A to prepare a W/O/W type emulsion;

(3) polymerizing the 3-hydroxyacyl coenzyme A with the polyhydroxyalkanoate synthetic enzyme to synthesize polyhydroxyalkanoate; and (4) removing an organic solvent from the W/O/W type emulsion to obtain the structure.

(f) A manufacturing method for a structure constructed as described above, including the steps of:

(1) dispersing a water phase containing a polyhydroxyalkanoate synthetic enzyme and 3-hydroxyacyl coenzyme A in an oil phase containing a magnetic substance to prepare a W/O type emulsion;

(2) dispersing the W/O type emulsion in a water phase containing at least a polyhydroxyalkanoate synthetic enzyme and 3-hydroxyacyl coenzyme A to prepare a W/O/W type emulsion;

(3) polymerizing the 3-hydroxyacyl coenzyme A with the polyhydroxyalkanoate synthetic enzyme to synthesize polyhydroxyalkanoate; and (4) removing an organic solvent from the W/O/W type emulsion to obtain the structure.

(g) A manufacturing method for a structure constructed as described above, including the steps of:

(1) dispersing a water phase containing a polyhydroxyalkanoate synthetic enzyme and 3-hydroxyacyl coenzyme A in an oil phase containing a magnetic substance to: prepare a W/O type emulsion;

(2) dispersing the W/O type emulsion in a water phase to prepare a W/O/W type emulsion;

(3) polymerizing the 3-hydroxyacyl coenzyme A with the polyhydroxyalkanoate synthetic enzyme to synthesize polyhydroxyalkanoate; and (4) removing an organic solvent from the W/O/W type emulsion to obtain the structure.

(h) A manufacturing method for a structure constructed as described above, including the steps of:

(1) dispersing an oil phase containing a magnetic substance in a water phase containing at least a polyhydroxyalkanoate synthetic enzyme and 3-hydroxyacyl coenzyme A to prepare an O/W type emulsion;

(2) polymerizing the 3-hydroxyacyl coenzyme A with the polyhydroxyalkanoate synthetic enzyme to synthesize polyhydroxyalkanoate; and (3) obtaining the structure from the O/W type emulsion.

(i) A manufacturing method for a structure constructed as described above, including the steps of:

(1) dispersing an oil phase containing a magnetic substance in a water phase containing at least a polyhydroxyalkanoate synthetic enzyme and 3-hydroxyacyl coenzyme A to prepare an O/W type emulsion;

(2) dispersing the O/W type emulsion in an oil phase to prepare an O/W/O type emulsion;

(3) polymerizing the 3-hydroxyacyl coenzyme A with the polyhydroxyalkanoate synthetic enzyme to synthesize polyhydroxyalkanoate; and (4) removing an organic solvent from the O/W/O type emulsion to obtain the structure.

Depending on the surface property of the magnetic substance (whether it is hydrophilic or lipophilic), the dispersion phase of the magnetic substance in the above manufacturing method may be also suspended in a water phase but not in an oil phase containing an organic solvent.

The substance supported on the structure may be any of water- and fat-soluble substances. Those substances are, for example but not specifically limited to, drugs expected to be instable in vitro and in vivo, gradually emitted in the body, or promptly distributed over a specific organ. Thus, other substances such as bio markers, plasmids, DNA, and RNA are allowable as far as they are effective when they are administered into the living body.

The pharmaceutical preparation according to the present invention is one using the structure described above. In addition, the method of manufacturing a pharmaceutical preparation according to the present invention is a method of manufacturing a pharmaceutical preparation including the step of manufacturing the above structure. The pharmaceutical preparation is preferable as a sustained release pharmaceutical preparation having a high content of a drug, particularly a drug which is substantially insoluble in water, showing little initial discharge and a favorable long term sustained release. In addition, the pharmaceutical preparation is preferable as a sustained release pharmaceutical preparation having a high content of a drug, particularly a water-soluble drug, showing little initial discharge and a favorable long term sustained release.

Furthermore, as a result of conducting an intensive study for the purpose of developing an ultrasonic contrast agent having a high cystographic effect (a contrast effect), the inventors of the present invention have consummated an ultrasonic contrast agent of the present invention by finding out that the hollow structure of the present invention in which an inner phase has a gas phase is constructed so as to be capable of including many bubbles in an inner phase part and is a suitable hollow structure as an active ingredient of the ultrasonic contrast agent, and also finding out that a contrast agent having a higher ultrasonic cystographic effect in the living body is obtained when the hollow structure is dispersed in water and then dried under reduced pressure, and a perfulorocarbon gas is filled in a drying machine to fill the inside of the hollow structural portion of the hollow structure, i.e., the inside of air bubbles. In other words, the ultrasonic contrast agent of the present invention is an ultrasonic contrast agent having the hollow structure. In addition, the ultrasonic contrast agent of the present invention is useful for contrasting the cardiac muscle, heart chamber (spaces constructing a heart such as cardiac chambers and cardiac atriums), or liver.

BEST MODE FOR CARRYING OUT THE INVENTION

Figure 1:
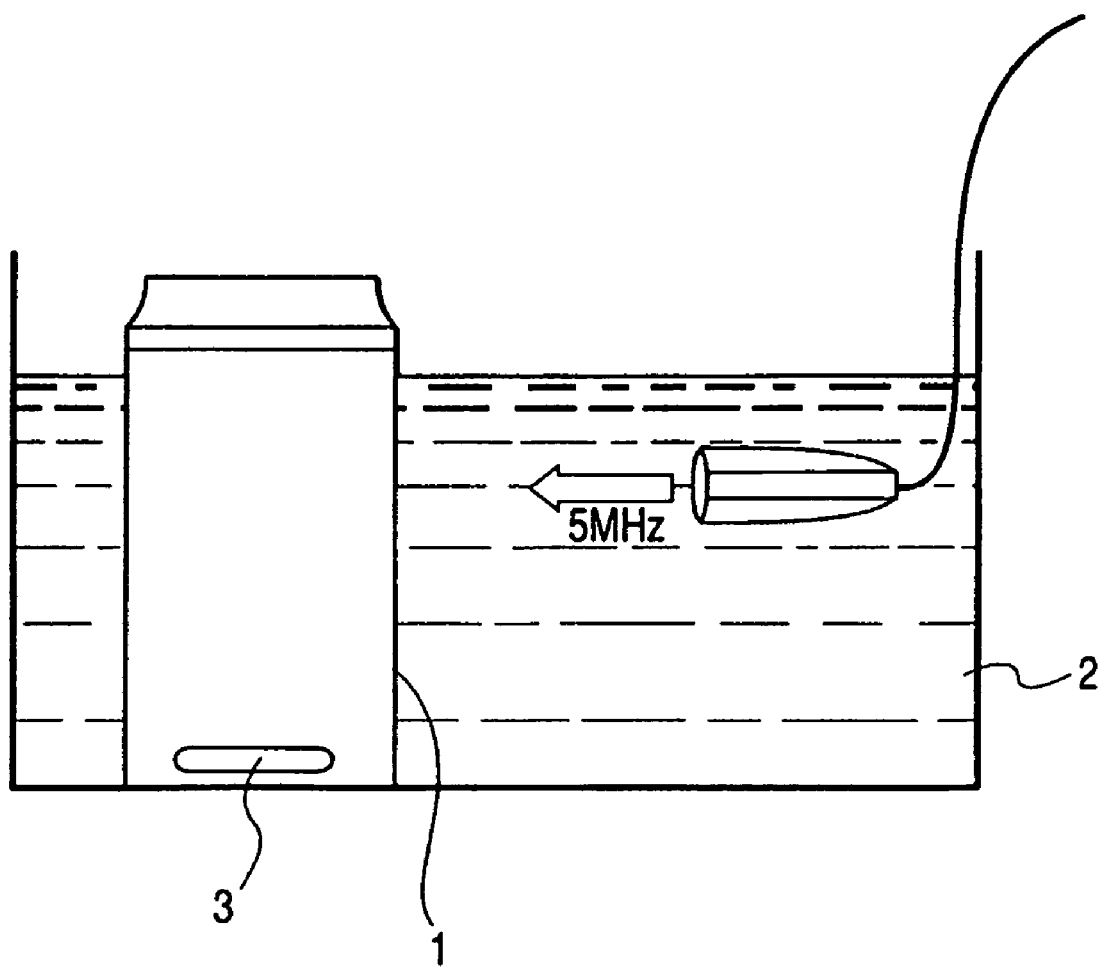
FIG. 1 is an explanation diagram that represents the principle of a test method in Example 16.

The structure of the present invention has a structure constituted by PHA including monomer units of various structures having substituents in the side chains, or a structure constituted by an external phase part made of a solid phase consisting mainly of PHA and an internal phase part included in the external phase part. The structure may be in the form of a microcapsule, but it is not limited to a double layer structure. In the final analysis, it is only needed that at least one phase out of a solid phase, a liquid phase and a gas phase be included in the solid phase. The inner phase may be constituted by at least one phase out of a solid phase, a liquid phase and a gas phase. A magnetic substance may be contained in at least one of the external phase part and internal phase part depending on the configuration of the structure. Further, PHA in the structure may also be contained in the internal phase part included in the solid phase portion. The structure of the present invention is very useful as a multifunctional microcapsule.

Hereinafter, the present invention will be described in more detail.

<Microcapsule>

The concept of the term "microcapsule" as used herein completely includes a concept, which the term generally has in a drug delivery system (DDS) and high polymer chemistry, but the concept is not always identical. The modes of scanning an electron microscopic form of a "microcapsule" used in the claims and in the specification of the present application include a mode having many protrusions like raspberry or confetti (konpeito, confeito in Portuguese), a flat mode like an erythrocyte, a spheroidal mode like a rugby ball, a spindle-shaped mode like *Escherichia coli*. The "microcapsule" referred to herein usually has characteristics of microspheres that constitute, for example, a polymer emulsion, a latex, and a polymer suspension. As described above, although the term "microcapsule" as used in the claims and the specification of the present application is not always identical to the concept that the term generally has in a drug delivery system (DDS) and high polymer chemistry, it is used for the sake of convenience when referring to the essential "mode" of a heteropolymer system according to the present invention.

For example, the modes of interrelationship between at least one phase out of a solid phase, a liquid phase and a gas phase and PHA in the microcapsule of the present invention include 1) a monolithic type consisting of a single mixed phase consisting of at least one phase out of a solid phase, a liquid phase and a gas phase dispersed/mixed in PHA that forms the solid phase in the microsphere, and 2) a reservoir type consisting of two phases, such as an outer membrane and an inside, in the form of at least one phase out of a solid phase, a liquid phase and a gas phase being contained/protected inside a thin film (cover layer) of PHA.

In the present invention, the mode 2) is more preferable from the viewpoint of incorporating at least one phase out of a solid phase, a liquid phase and a gas phase and a magnetic substance in large amounts in a microcapsule. For example, when liquid phases, which include an oil phase and a water phase, are to be included, a construction in which a water phase and an oil phase coexist in the same capsule may be adopted. Here, "oil phase" and "water phase" correspond to "a substance that has properties of an oil phase" and "a substance that has properties of a water phase", respectively. Typical but non-limiting, examples of oil phase components that can be used advantageously in the present invention, particularly in holding drugs, include oil phase components that can form an emulsion with water, such as, vegetable oils (for example, soybean oil, sesame oil, cottonseed oil, olive oil, safflower oil, corn oil, rapeseed oil, and peanut oil); medium chain fatty acid triglycerides [for example, triglycerides of fatty acids having 6 to 12 carbon atoms (for example, caprylic acid, capric acid, and lauric acid), such as PANASATE 800, 810, 1000, and 1200 manufactured by Nippon Oils And Fat Co., Ltd.]; and liquid hydrocarbons (for example, liquid paraffin, squalene, and squalane). Note that oil phases that can be used when PHA is dissolved in an oil phase to perform the microencapsulation to include the oil phase in the microcapsule include the oil phases that dissolve PHA described below. To form a water phase, aqueous solvents consisting mainly of water can be utilized. Desired substances are dissolved in these phases to make microcapsules having desired functions.

The microcapsules of the present invention include microspherical microcapsules having a diameter within the range of 1 to 10 µm.

When holding drugs or the like as solid, monolithic type fine particles (microspheres) may also be utilized advantageously. For example, examples of the mode of interrelationship between (A) a drug and (B) PHA in the structure to be contained in the sustained release pharmaceutical composition of the present invention include 1) to 4) below:

1) a mode of microcapsule having a core/shell structure in which the drug (A) is contained in a single core and the PHA (B) is contained in a shell;
2) a mode of microcapsule having a core/shell structure in which the drug (A) is contained in a plurality of cores and the PHA (B) is contained in shells;
3) a mode of microcapsule having a core/shell structure in which the drug (A) is contained in a plurality of islet portions and the PHA (B) that contains the islet portions is contained in a sea portion; and
4) a mode having a micro phase separation structure with which the drug (A) and the PHA (B) are made compatible.

The cores in those modes may be formed from the drug alone or a combination with other component or components. The shells in those modes may be formed from PHA alone or a combination with other component or components.

Modes of containing the magnetic substance may include the same modes as described above.

The structure according to the present invention includes a microspherical preparation that is constituted by a composition containing at least a drug having a medicinal effect, PHA and a magnetic substance and has a diameter within the range of 10 nm (nanometer) to 100 µm. From the viewpoint of self-emulsifiability, usually submicron sizes (average particle diameter of 1 µm or less) are preferably adopted.

Further, a hollow structure of the present invention is constituted of a portion that includes at least PHA and forms the outside shape and a portion that is at least hollow in the inside thereof. A case where a partition portion including PHA and a hollow portion, or a magnetic substance coexist in the inside is also included. In this case, the magnetic substance may be contained in at least one of the solid phase and the hollow portion.

Stating the relationship between the solid phase portion containing PHA and the gas phase portion included therein, one mode thereof includes 1) a monolithic type hollow fine particle (also called microsphere) that is a microsphere formed of PHA and is basically of a single phase having included hollow portions dispersed therein, or
2) a hollow microcapsule of reservoir type or the like that includes clear two phases, such as an outer membrane and inside in the form of a thin outer membrane containing PHA (coat or shell) having included therein a hollow portion (core) to protect it.

The mode of the "hollow structure" of the present invention includes a microspherical hollow fine particle having a diameter within the range of 1 to 10 µm including a coat that includes a composition containing at least PHA and holding a magnetic substance in the above-mentioned mode.

Further, in the hollow structure of the present invention, the form of the coat containing the hollow portion and PHA, more specifically, the modes of interrelationship between air bubble (A) and PHA (B) include 1) to 4) given below.

1) a mode of microcapsule having a core/shell structure in which the air bubble (A) is contained in a single core and the PHA (B) is contained in a shell;
2) a mode of microcapsule having a core/shell structure in which the air bubble (A) is contained in a plurality of cores and the PHA (B) is contained in shells;
3) a mode of microcapsule having a core/shell structure in which the air bubble (A) is contained in a plurality of islet portions and the PHA (B) that contains the islet portions is contained in a sea portion; and
4) a mode having a micro phase separation structure with which the air bubble (A) and the PHA (B) are made compatible.

Modes of containing the magnetic substance may include the same modes as described above.

The cores in those modes may be formed from the air bubble alone or a combination with other component or components. The shells in those modes may be formed from PHA alone or a combination with other component or components.

Further, in the structure of the present invention, the monomer unit composition of the above-mentioned polyhydroxyalkanoate may vary in the direction from the inside toward the outside of the coat of the above-mentioned structure.

In addition, a structure in which at least a portion of the above-mentioned polyhydroxyalkanoate is a chemically modified polyhydroxyalkanoate may be used. For example, the above-mentioned chemically modified polyhydroxyalkanoate may contain at least a polyhydroxyalkanoate having a graft chain as its chemical modification. In this case, the above-mentioned graft chain may be a graft chain introduced to a polyhydroxyalkanoate containing a monomer unit having at least an epoxy group as a result of chemical modification to the epoxy group. The above-mentioned graft chain may be a graft chain containing a compound having an amino group. For example, the above-mentioned compound having an amino group is preferably a terminal amino-modified compound. One example of the above-mentioned terminal amino-modified compound may be at least one polymer selected from the group consisting of polyvinylamine, polyethyleneimine, and terminal amino-modified polysiloxane.

Besides, as the above-mentioned chemically modified polyhydroxyalkanoate, at least a portion of the polyhydroxyalkanoate may be a crosslinked polyhydroxyalkanoate. For example, the above-mentioned crosslinked polyhydroxyalkanoate may be a polyhydroxyalkanoate containing a monomer unit having at least an epoxy group in which the epoxy group is crosslinked. In this case, one example of the above-mentioned crosslinked polyhydroxyalkanoate may be a polyhydroxyalkanoate that is crosslinked by any one of means selected from the group consisting of a diamine compound, succinic anhydride, 2-ethyl-4-methylimidazole, and electron beam irradiation. It is preferable that the above-mentioned diamine compound be hexaethylenediamine.

The above-mentioned microcapsule can be prepared generally by a Water in Oil in Water (W/O/W) type emulsion method, Oil in Water (O/W) type emulsion method, or the like.

More specifically, a first mode of a production method for a microcapsule containing PHA and a magnetic substance is a method including:

1) dissolving PHA and the magnetic substance in an organic solvent such as chloroform, adding an aqueous solution to the resultant, and emulsifying the mixture to obtain a W/O type emulsion;
2) adding the emulsion to a large amount of water to emulsify the mixture as necessary to obtain a W/O/W type emulsion; and 3) removing the organic solvent by evaporation under reduced pressure, or the like to produce a precipitate in the form of microsphere and recovering and drying the precipitate as necessary to prepare a microcapsule.

In addition, a second mode of a production method for a microcapsule containing PHA and a magnetic substance is a method including:
1) dissolving PHA and the magnetic substance in an organic solvent such as chloroform;
2) adding the organic phase to a large amount of water and emulsifying the mixture to obtain an O/W type emulsion; and
3) removing the organic solvent to a range above the solubility of PHA by evaporation under reduced pressure, or the like to produce a precipitate in the form of microsphere and recovering and drying the precipitate as necessary to prepare a microcapsule.

Further, a third mode of a production method for a microcapsule containing PHA and a magnetic substance includes:
1) adding an aqueous solution containing PHA synthetic enzyme and 3-hydroxyacyl CoA to an organic solvent containing the magnetic substance to emulsify the resultant to obtain a W/O type emulsion; and
2) performing a PHA synthesis reaction to produce a precipitate in the form of microsphere and recovering and drying the precipitate as necessary to prepare a microcapsule.

Further, a fourth mode of a production method for a microcapsule containing PHA and a magnetic substance includes:
1) adding an aqueous solution to an organic solvent containing the magnetic substance to emulsify the resultant to obtain a W/O type emulsion;
2) adding the emulsion to a large amount of water containing PHA synthetic enzyme and 3-hydroxyacyl CoA and emulsifying the resultant to obtain a W/O/W type emulsion; and
3) then, performing a PHA synthesis reaction to produce a precipitate in the form of microsphere and recovering and drying the precipitate as necessary to prepare a microcapsule.

Further, a fifth mode of a production method for a microcapsule containing PHA and a magnetic substance includes:
1) adding an aqueous solution containing PHA synthetic enzyme and 3-hydroxyacyl CoA to an organic solvent containing the magnetic substance to emulsify the resultant to obtain a W/O type emulsion;
2) adding the emulsion to a large amount of water containing PHA synthetic enzyme and 3-hydroxyacyl CoA and emulsifying the resultant to obtain a W/O/W type emulsion; and
3) then, performing a PHA synthesis reaction to produce a precipitate in the form of microsphere and recovering and drying the precipitate as necessary to prepare a microcapsule.

Further, a sixth mode of a production method for a microcapsule containing PHA and a magnetic substance includes:
1) adding an aqueous solution containing PHA synthetic enzyme and 3-hydroxyacyl CoA to an organic solvent containing the magnetic substance to emulsify the resultant to obtain a W/O type emulsion;
2) adding the emulsion to a large amount of water and emulsifying the resultant to obtain a W/O/W type emulsion; and
3) then, performing a PHA synthesis reaction to produce a precipitate in the form of microsphere, and recovering and drying the precipitate as necessary to prepare a microcapsule.

Further, a seventh mode of a production method for a microcapsule containing PHA and a magnetic substance includes:
1) adding an organic solvent containing the magnetic substance to a large amount of water containing PHA synthetic enzyme and 3-hydroxyacyl CoA and emulsifying the resultant to obtain an O/W type emulsion;
2) performing a PHA synthesis reaction to produce a precipitate in the form of microsphere and recovering and drying the precipitate as necessary to prepare a microcapsule.

Further, an eighth mode of a production method for a microcapsule containing PHA and a magnetic substance includes:
1) adding an organic solvent containing the magnetic substance to a large amount of water containing PHA synthetic enzyme and 3-hydroxyacyl CoA and emulsifying the resultant to obtain an O/W type emulsion;
2) adding the emulsion to a large amount of oil to obtain an O/W/O type emulsion; and
3) then, performing a PHA synthesis reaction to produce a precipitate in the form of microsphere, and recovering and drying the precipitate as necessary to prepare a microcapsule.

The dispersion phase of the magnetic substance can be suspended in a water phase but not in an oil phase containing an organic solvent depending on its surface property (whether hydrophilic or lipophilic).

<Exemplification of PHA and its Production Method>

As PHA that can be utilized in the present invention, such PHA can be exemplified that includes at least monomer units represented by the following formulae [1] to [10]:

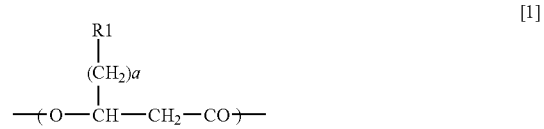

[1]

(wherein the monomer unit is at least one selected from the group consisting of monomer units having the following respective combinations of R1 and a in the formula:

a monomer unit where R1 represents a hydrogen atom (H) and a represents one of the integers from 0 to 10;

a monomer unit where R1 represents a halogen atom and a represents one of the integers from 1 to 10;

a monomer unit where R1 represents a chromophore and a represents one of the integers from 1 to 10;

a monomer unit where R1 represents a carboxyl group or a salt thereof and a represents one of the integers from 1 to 10; and a monomer unit where R1 represents

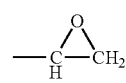

and a represents one of the integers from 1 to 7);

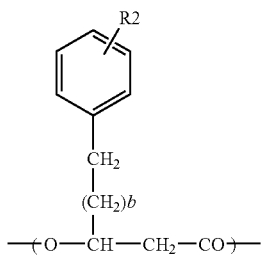
[2]

(wherein b represents one of the integers from 0 to 7, and R2 represents one selected from the group consisting of a hydrogen atom (H), a halogen atom, —CN, —NO₂, —CF₃, —C₂F₅, and —C₃F₇);

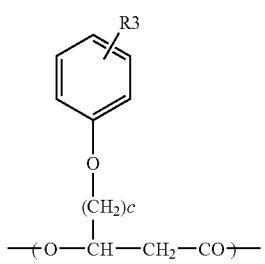
[3]

(wherein c represents one of the integers from 1 to 8, and R3 represents one selected from the group consisting of a hydrogen atom (H), a halogen atom, —CN, —NO₂, —CF₃, —C₂F₅, and —C₃F₇);

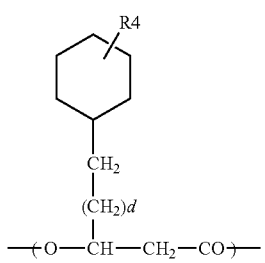
[4]

(wherein d represents one of the integers from 0 to 7, and R4 represents one selected from the group consisting of a hydrogen atom (H), a halogen atom, —CN, —NO₂, —CF₃, —C₂F₅, and —C₃F₇);

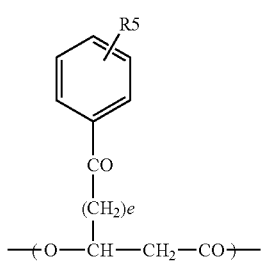
[5]

(wherein e represents one of the integers from 1 to 8, and R5 represents one selected from the group consisting of a hydrogen atom (H), a halogen atom, —CN, —NO₂, —CF₃, —C₂F₅, —C₃F₇, —CH₃, —C₂H₅, and —C₃H₇);

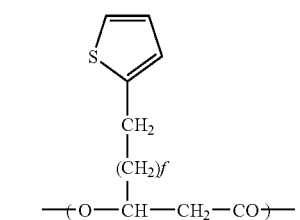
[6]

(wherein f represents one of the integers from 0 to 7);

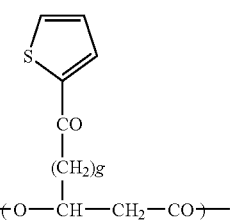
[7]

(wherein g represents one of the integers from 1 to 8);

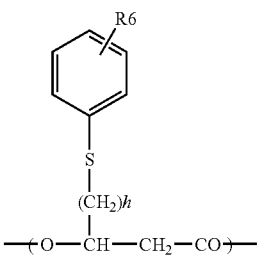
[8]

(wherein h represents one of the integers from 1 to 7, and R6 represents one selected from the group consisting of a hydrogen atom (H), a halogen atom, —CN, —NO₂, —COOR', —SO₂R", —CH₃, —C₂H₅, —C₃H₇, —CH(CH₃)₂, and —C(CH₃)₃, where R' represents one of a hydrogen atom (H), Na, K, —CH₃, and —C₂H₅ and R" represents one of —OH, —ONa, —OK, a halogen atom, —OCH₃, and —OC₂H₅);

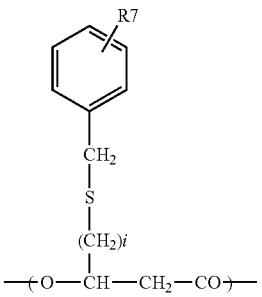
[9]

(wherein i represents one of the integers from 1 to 7, and R7 represents one selected from the group consisting of a hydrogen atom (H), a halogen atom, —CN, —NO₂, —COOR', and —SO₂R", where R' represents one of a hydrogen atom (H), Na, K, —CH₃, and —C₂H₅ and R" represents one of —OH, —ONa, —OK, a halogen atom, —OCH₃, and —OC₂H₅); and

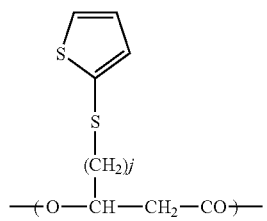

[10]

(wherein j represents one of the integers from 1 to 9).

The PHA used in the present invention is a polyester resin containing 3-hydroxyalkanoate as the monomer unit. Here, when such a compound is produced by using a microorganism, the polyester resin is an isotactic polymer consisting of an R form only. However, so far as the object of the present invention both in physical properties/function is achieved, the polyester resin is not particularly limited to an isotactic polymer, and may be an atactic polymer. PHA may also be obtained by a chemical synthesis method of performing ring opening polymerization of a lactone compound using an organometallic catalyst (for example, an organic catalyst containing aluminum, zinc, tin, or the like).

In addition, when PHA is synthesized by utilizing a polymerization reaction of 3-hydroxyacyl CoA with PHA synthetic enzyme together with preparation of a W/O type emulsion, a W/O/W type emulsion, an O/W type emulsion, or an O/W/O type emulsion, PHA is not limited particularly so far as it is PHA that can be synthesized by PHA synthetic enzyme that participates in the synthesis reaction of PHA. As described earlier, the PHA synthetic enzyme is an enzyme that catalyzes the final stage in the PHA synthesis reaction system in a living body. Therefore, any PHA that is known to be synthesized in a living body is synthesized under the catalytic action of the enzyme. Accordingly, it is possible to prepare a microcapsule containing at least one phase out of a solid phase, a liquid phase, and a gas phase and further is coated therewith by using any kind of PHA that is known to by synthesized in a living body by reacting a 3-hydroxyacyl CoA corresponding to a desired PHA on a PHA synthetic enzyme.

Further, in the present invention, side chain structures R1 to R7 can be selected from at least one atom or functional group selected from various atoms and functional groups. Although PHA containing a monomer unit corresponding to any of ortho, meta, or para-substitution position of R2 to R7 can be obtained, substitutions at meta-position and para-position can be used advantageously in terms of yield and the ease with which they are taken in a polymer when no significant difference is found in functionality and physical properties among various isomers.

Note that specific examples of the above-mentioned halogen atom include fluorine, chlorine, and bromine. Further, the above-mentioned chromophore is not particularly limited so far as PHA can be synthesized from a starting material that contains the chromophore. However, in view of steric hindrance at the time of polymer synthesis or the like, it is desirable that a methylene chain having 1 to 5 carbon atoms exist between a terminal carboxyl group of an alkanoate, which is a raw material, and the chromophore. In addition, if the chromophore has a light absorption wavelength in a visible range, a colored structure is obtained. If the chromophore has a light absorption wavelength outside the visible range, the chromophore can be used as various electronic materials. Examples of such chromophores include nitroso, nitro, azo, diarylmethanes, triarylmethanes, xanthene, acridine, quinoline, methine, thiazole, indamine, indophenol, lactone, aminoketone, hydroxyketone, stilbene, azine, oxazine, thiazine, anthraquinone, phthalocyanine, and indigoids.

PHA used in the present invention may include random-copolymers and block copolymers containing a plurality of the above-mentioned monomer units. Utilizing characteristics of each monomer unit and functional group contained allows control of the physical properties of PHA, impartation of a plurality of functions, and development of new functions by utilization of interactions of functional groups. Further, appropriate control of the addition amount and order of addition of monomer compound enables block copolymers having any desired order and compositional ratios to be synthesized. Further, after the synthesis or during the synthesis of PHA, an additional chemical modification may be performed.

For example, time-dependent change in kind, concentration or the like of 3-hydroxyacyl CoA, which is the substrate, enables the monomer unit composition of PHA to be changed in the direction from the inside toward the outside of microcapsule. Appropriate selection of a surface layer PHA and an inner layer PHA of a microcapsule allows further increase in the effects of the present invention, for example, the function of retaining a liquid phase or a gas phase, control of sustained release, and self-dispersibility in aqueous solutions. More specifically, by appropriately selecting the monomer unit of PHA and varying in the direction from the inside toward the outside of microcapsule, for example, a multilayer structure or a gradient structure can be made.

Further, introduction of a graft chain in the surface layer of PHA of the microcapsule enables functionalities, for example, the function of retaining a liquid phase or a gas phase, self-dispersibility in aqueous solutions, and control of sustained release to be developed. Further, crosslinking the surface layer of PHA of the microcapsule enables, for example, the function of retaining a liquid phase or a gas phase to increase, the mechanical strength of the microcapsule to increase, and sustained release to be controlled.

As described above, when PHA is synthesized in a microorganism (in vivo), or in a cell-free system (in vitro), PHA may contain various monomer units described above and PHA is advantageously designed so as to contain a suitable number of the monomer units in consideration of the functionality and physical properties of the polymer. Generally, the objects of the present invention can be sufficiently achieved by including up to about 6 kinds of the monomer units described above. When subtle control of functionality and physical properties is desired, PHA may be constituted by more kinds of monomer units.

Note that PHA which is synthesized by a PHA producing microorganism or by in vitro synthesis using a PHA synthetic enzyme and is used in the microcapsule of the present invention generally is an isotactic polymer consisting of an R form only.

The PHAs having desired physical properties can be obtained by selecting culture conditions and so forth of a microorganism that can synthesize PHA of the present invention. For example, control of culture time and so forth enables the number average molecular weight to be controlled. In addition, removal of low molecular weight components by using solvent extraction, reprecipitation, and the like enables the number average molecular weight to be controlled. In the in vitro synthesis, appropriate selection of the composition of the reaction mixture, reaction time, and the like enables various physical properties to be controlled.

It is desirable that the molecular weight of PHA be about 1,000 to about 10,000,000, preferably about 5,000 to about 1,000,000 in number average molecular weight. The distribution of PHA (weight average molecular weight/number average molecular weight) is preferably 1 to 10. The distribution is particularly preferably 1 to 5.

When the microcapsule of the present invention contains, for example, a liquid phase, the function of retaining and slowly releasing the liquid phase or self-dispersibility in aqueous solutions becomes important. The greatest feature of the microcapsule of the present invention is to have solved those problems. That is, the function of retaining and slowly releasing the liquid phase or self-dispersibility in aqueous solutions is controllable by controlling the kind of the monomer unit/compositional ratios/crystallinity of PHA as described above.

Further, when PHA is designed to contain a drug, particularly water-soluble drug as a sustained release pharmaceutical preparation, to control the release characteristics, it becomes necessary to control both initial release rate and subsequent release rate. The sustained release pharmaceutical preparation of the present invention has the greatest feature in having solved those problems. That is, the initial release rate of the drug can be controlled by controlling the kind of the monomer unit/compositional ratios/molecular weight/crystallinity of PHA as described above. Also, the release time of the drug can be controlled like the initial release rate by controlling the kind of the monomer unit/compositional ratios/molecular weight/crystallinity of PHA as described above. The sustained release pharmaceutical preparation of the present invention can be formulated into not only sustained release pharmaceutical preparations having a zero-order drug release characteristic, but also sustained release pharmaceutical preparations having any desired high initial release rate or having a time lag in the time of releasing the drug. They find an extremely wide range of applications.

Further, when PHA contains a drug, particularly a drug that is substantially insoluble in water, it also becomes necessary to control both initial release rate and subsequent release rate in order to control the release characteristics. The sustained release pharmaceutical preparation of the present invention has the greatest feature in having solved those problems. That is, the initial release rate of the drug can be controlled by controlling the kind of the monomer unit/compositional ratios/molecular weight/crystallinity of PHA as described above. Also, the release time of the drug can be controlled like the initial release rate by controlling the kind of the monomer unit/compositional ratios/molecular weight/crystallinity of PHA as described above. The sustained release pharmaceutical preparation of the present invention can be formulated into not only sustained release pharmaceutical preparations having a zero-order drug release characteristic, but also sustained release pharmaceutical preparations having any desired high initial release rate or having a time lag in the time of releasing the drug. They find an extremely wide range of applications.

Further, when PHA is used as an ultrasonic contrast agent, not only the amount of air bubbles contained in the hollow structure but also the function of retaining the air-bubbles become important. The ultrasonic contrast agent of the present invention has the greatest feature in having utilized the hollow structure of the present invention as an ultrasonic reflector. That is, the function of retaining the air bubbles can be controlled by controlling the kind of the monomer unit/compositional ratios/molecular weight/crystallinity of PHA as described above.

As a specific method of obtaining PHA by production by a microorganism, PHA can be produced by culturing a microorganism that can produce PHA containing at least one of the monomer units represented by formulae (1) to (10) from alkanoic acids corresponding to the monomer units represented by the formulae (1) to (10), respectively in media containing the corresponding alkanoic acids. The microorganisms that can produce PHA include microorganisms appropriately selected from microorganisms producing PHA or transformants having introduced therein a gene for a PHA synthetic enzyme of the microorganisms. The culture method will be described later on.

For example, a polyhydroxyalkanoate containing a 3-hydroxy-5-(4-fluorophenyl)valeric acid (3HFPV) monomer unit can be produced by culturing a microorganism that can produce a polyhydroxyalkanoate containing a 3HFPV monomer unit represented by the formula [21] given below from 5-(4-fluorophenyl)valeric acid (FPVA) represented by the formula [22] given below.

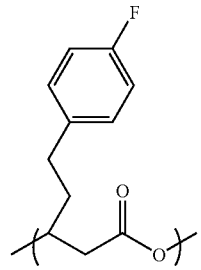

[21]

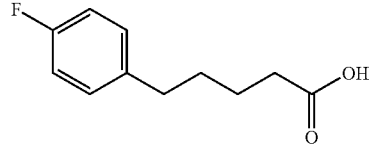

[22]

Further, a polyhydroxyalkanoate containing a 3-hydroxy-4-phenoxybutyric acid (3HPxB) monomer unit can be produced by culturing a microorganism that can produce a polyhydroxyalkanoate containing a 3HPxB monomer unit represented by the formula [23] given below from 4-phenoxybutyric acid (PxBA) represented by the formula [24] given below.

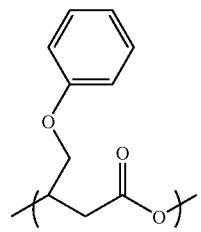

[23]

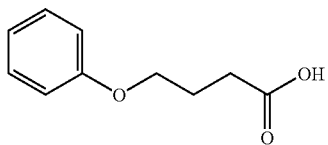
[24]

Further, a polyhydroxyalkanoate containing a 3-hydroxy-4-cyclohexylbutyric acid (3HCHB) monomer unit can be produced by culturing a microorganism that can produce a polyhydroxyalkanoate containing a 3HCHB monomer unit represented by the formula [25] given below from 4-cyclohexylbutyric acid (CHBA) represented by the formula [26] given below.

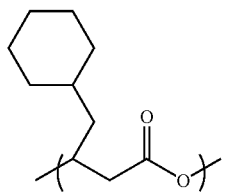
[25]

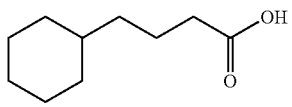
[26]

Further, a polyhydroxyalkanoate containing a 3-hydroxy-5-benzoyl valeric acid (3HBzV) monomer unit can be produced by culturing a microorganism that can produce a polyhydroxyalkanoate containing a 3HBzV monomer unit represented by the formula [27] given below from 5-benzoyl valeric acid (BzVA) represented by the formula [28] given below.

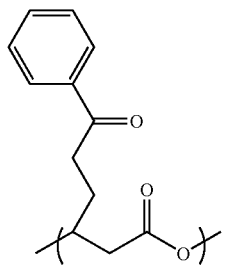
[27]

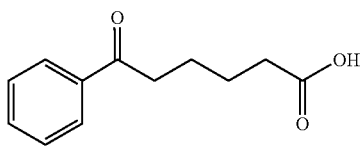
[28]

Further, a polyhydroxyalkanoate containing a 3-hydroxy-5-(4-fluorobenzoyl)valeric acid (3HFBzV) monomer unit can be produced by culturing a microorganism that can produce a polyhydroxyalkanoate containing a 3HFBzV monomer unit represented by the formula [29] given below from 5-(4-fluorobenzoyl)valeric acid (FBzVA) represented by the formula [30] given below.

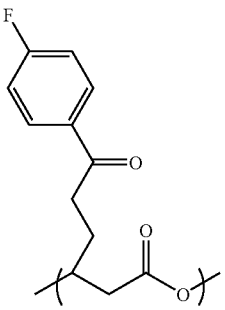
[29]

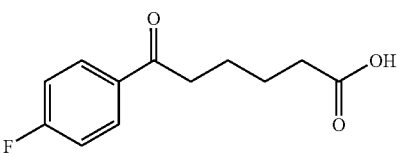
[30]

Further, a polyhydroxyalkanoate containing a 3-hydroxy-5-thienylvaleric acid (3HTV) monomer unit can be produced by culturing a microorganism that can produce a polyhydroxyalkanoate containing a 3HTV monomer unit represented by the formula [31] given below from 5-thienylvaleric acid represented by the formula [32] given below.

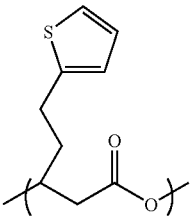
[31]

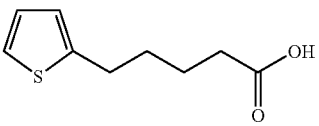
[32]

Further, a polyhydroxyalkanoate containing a 3-hydroxy-5-thienoylvaleric acid (3HtoV) monomer unit can be produced by culturing a microorganism that can produce a polyhydroxyalkanoate containing a 3HToV monomer unit represented by the formula [33] given below from 5-thienoylvaleric acid (ToVA) represented by the formula [34] given below.

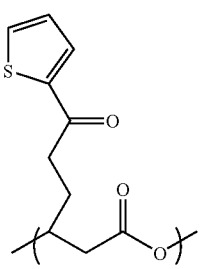
[33]

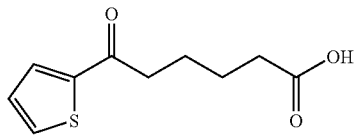

[34]

Further, a polyhydroxyalkanoate containing a 3-hydroxy-5-(4-fluorothiophenoxy)valeric acid (3HFTPxV) monomer unit can be produced by culturing a microorganism that can produce a polyhydroxyalkanoate containing a 3HFTPxV monomer unit represented by the formula [35] given below from 5-(4-fluorothiophenoxy)valeric acid (FTPxVA) represented by the formula [36] given below.

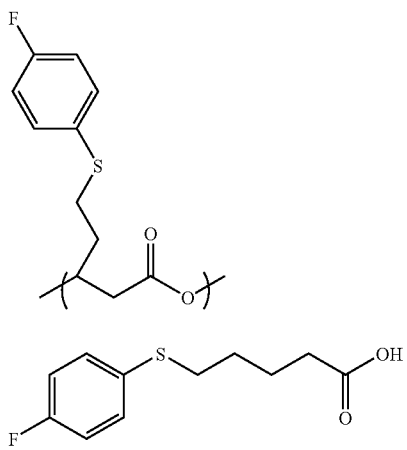

[35]

[36]

Further, a polyhydroxyalkanoate containing a 3-hydroxy-5-[(4-fluorophenylmethyl)sulfanyl]valeric acid monomer unit can be produced by culturing a microorganism that can produce a polyhydroxyalkanoate containing a 5-[(4-fluorophenylmethyl)sulfanyl]valeric acid monomer unit represented by the formula [37] given below from 5-[(4-fluorophenylmethyl)sulfanyl]valeric acid represented by the formula [38] given below.

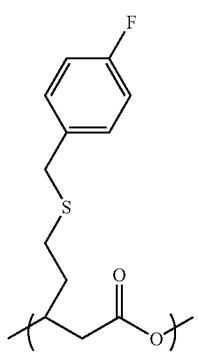

[37]

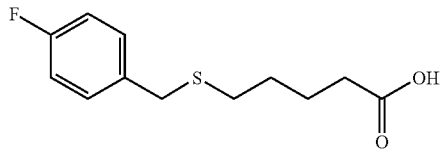

[38]

Further, a polyhydroxyalkanoate containing a 3-hydroxy-5-thiothienoxyvaleric acid (3HTTxV) monomer unit can be produced by culturing a microorganism that can produce a polyhydroxyalkanoate containing a 3HTTxV monomer unit represented by the formula [39] given below from 5-thiothienoxyvaleric acid (TTxVA) represented by the formula [40] given below.

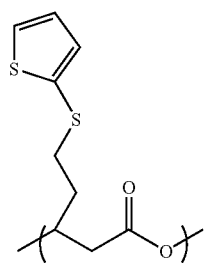

[39]

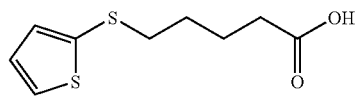

[40]

Further, a polyhydroxyalkanoate containing a 3-hydroxyoctanoic acid (3HO) monomer unit can be produced by culturing a microorganism that can produce a polyhydroxyalkanoate containing a 3HO monomer unit represented by the formula [41] given below from octanoic acid (OA) represented by the formula [42] given below.

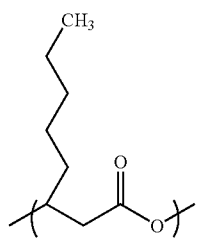

[41]

[42]

Further, a polyhydroxyalkanoate containing a 3-hydroxy-7,8-epoxyoctanoic acid monomer unit can be produced by culturing a microorganism that can produce a polyhydroxyalkanoate containing a 3-hydroxy-7,8-epoxyoctanoic acid monomer unit represented by the formula [43] given below from octene represented by the formula [44] given below.

[43]

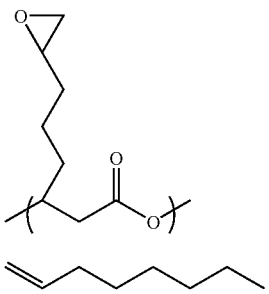

[44]

<Microorganism>

The microorganism that is used in the present invention may be any microorganism so far as it can produce PHA containing at least one of the units represented by the formulae (1) to (10) by culture in a medium containing the corresponding alkanoic acid.

Available microorganisms that synthesize PHA include PHB and PHB/V producing microorganisms and such microorganisms include: *Aeromonas* sp., *Alcaligenes* sp., *Chromatium* sp., *Comamonas* sp., *Methylobacterium* sp., *Paracoccus* sp., *Pseudomonas* sp., and so forth; and in addition, *Burkholderia cepacia* KK01, *Ralsotonia eutropha* TB64, *Alcaligenes* sp. TL2, and so forth isolated by the inventors of the present invention. The KK01 strain was deposited under accession number FERM BP-4235, the TB64 strain was deposited under accession number FERM BP-6933, and the TL2 strain was deposited under accession number FERM BP-6913. The depositions under FERM numbers BP-4235, BP-6933 and BP-6913 were made on Mar. 9, 1993, Nov. 9, 1999 and Oct. 12, 1999, respectively, at International Patent Organism Depositary (IPOD), National Institute of Advanced Industrial Science and Technology (AIST), incorporated administrative agency at Tsukuba Central 6, 1-1, Higashi 1-chome, Tsukuba-shi, Ibaraki-ken 305-8566 Japan (former name: National Institute of Bioscience and Human-Technology, Agency of Industrial Science and Technology, Ministry of Economy, Trade and Industry). BP indicates deposition under Budapest Treaty on the International Recognition of the Deposit of Microorganisms for the Purpose of Patent Procedure.

For example, microorganisms producing mcl-PHA and unusual-PHA can be used. Examples of such microorganisms that can be used include the above-mentioned *Pseudomonas oleovorans, Pseudomonas resinovorans, Pseudomonas* sp. 61-3, *Pseudomonas putida* KT2442, *Pseudomonas aeruginosa* and so forth; in addition, those microorganisms belonging to the genus *Pseudomonas*, such as *Pseudomonas putida* P91, *Pseudomonas chichorii* H45, *Pseudomonas cichorii* YN2, and *Pseudomonas jessenii* P161, isolated by the inventors of the present invention; and microorganisms belonging to the genus *Burkholderia* such as *Burkholderia* sp. OK3 (FERM P-17370) described in Japanese Patent Application Laid-open No. 2001-78753 and *Burkholderia* sp. OK4 (FERM P-17371) described in Japanese Patent Application Laid-open No. 2001-69968. In addition to those microorganisms, microorganisms belonging to the genus *Aeromonas* sp. and the genus *Comamonas* sp. that produce mcl-PHA or unusual-PHA can also be used.

Note that the P91 strain was deposited under accession number FERM BP-7373, the H45 strain was deposited under accession number FERM BP-7374, the YN2 strain was deposited under accession number FERM BP-7375, and the P161 strain was deposited under accession number FERM BP-7376. The depositions under FERM numbers BP-7373, BP-7374 and BP-7375 were made on Nov. 20, 2000 and FERM number BP-7376 was made on Nov. 27, 2000 at International Patent Organism Depositary (IPOD), National Institute of Advanced Industrial Science and Technology (AIST).

Note that the mycological characteristics of the above-mentioned P91 strain, H45 strain, YN2 strain, and P161 strain are listed as follows.

(Mycological Characteristics of *Pseudomonas putida* P91 Strain)

(1) Morphological Characteristics
Shape and size of cell: Rod of 0.6 μm×1.5 μm
Polymorphism of cell: No
Motility: Yes
Spore formation: No
Gram stain: Negative
Shape of colony: Circular, smooth on the entire periphery, low protrusions, smooth on the surface, glossy, and cream-colored (2) Physiological Properties
Catalase: Positive
Oxidase: Positive
O/F test: Oxidative
Reduction of nitrate: Negative
Production of indole: Negative
Acidification of glucose: Negative
Arginine dihydrolase: Positive
Urease: Negative
Hydrolysis of aesculin: Negative
Hydrolysis of gelatin: Negative
β-Galactosidase: Negative
Production of fluorescent pigment on King's B agar: Positive (3) Assimilability of Substrates
Glucose: Positive
L-Arabinose: Negative
D-mannose: Negative
D-mannitol: Negative
N-Acetyl-D-glucosamine: Negative
Maltose: Negative
Potassium gluconate: Positive
n-Capric acid: Positive
Adipic acid: Negative
dl-Malic acid: Positive
Sodium citrate: Positive
Phenyl acetate: Positive (Mycological Characteristics of *Pseudomonas cichorii* H45 Strain)

(1) Morphological Characteristics
Shape and size of cell: Rod of 0.8 μm×1.0 to 1.2 μm
Polymorphism of cell: No
Motility: Yes
Spore formation: No
Gram stain: Negative
Shape of colony: Circular, smooth on the entire periphery, low protrusions, smooth on the surface, glossy, and cream-colored (2) Physiological Properties
Catalase: Positive
Oxidase: Positive
O/F test: Oxidative
Reduction of nitrate: Negative
Production of indole: Negative
Acidification of glucose: Negative Arginine dihydrolase: Negative
Urease: Negative
Hydrolysis of aesculin: Negative
Hydrolysis of gelatin: Negative
β-Galactosidase: Negative
Production of fluorescent pigment on King's B agar: Positive
Growth in the presence of 4% NaCl: Negative
Accumulation of poly-β-hydroxybutyric acid: Negative (3) Assimilability of Substrates
Glucose: Positive
L-Arabinose: Negative
D-mannose: Positive
D-mannitol: Positive
N-Acetyl-D-glucosamine: Positive
Maltose: Negative
Potassium gluconate: Positive
n-Capric acid: Positive
Adipic acid: Negative
dl-Malic acid: Positive
Sodium citrate: Positive
Phenyl acetate: Positive (Mycological Characteristics of *Pseudomonas cichorii* YN2 Strain)

(1) Morphological Characteristics
Shape and size of cell: Rod of 0.8 μm×1.5 to 2.0 μm
Polymorphism of cell: No
Motility: Yes
Spore formation: No
Gram stain: Negative
Shape of colony: Circular, smooth on the entire periphery, low protrusions, smooth on the surface, glossy, and translucent (2) Physiological Properties
Catalase: Positive
Oxidase: Positive
O/F test: Oxidative
Reduction of nitrate: Negative
Production of indole: Positive
Acidification of glucose: Negative
Arginine dihydrolase: Negative
Hydrolysis of gelatin: Negative
β-Galactosidase: Negative
Production of fluorescent pigment on King's B agar: Positive
Growth in the presence of 4% NaCl: Positive (weak growth)
Accumulation of poly-β-hydroxybutyric acid: Negative
Hydrolysis of Tween 80: Positive (3) Assimilability of Substrates
Glucose: Positive
L-Arabinose: Positive
D-mannose: Negative
D-mannitol: Negative
N-Acetyl-D-glucosamine: Negative
Maltose: Negative
Potassium gluconate: Positive
n-Capric acid: Positive
Adipic acid: Negative
dl-Malic acid: Positive
Sodium citrate: Positive
Phenyl acetate: Positive (Mycological Characteristics of *Pseudomonas jessenii* P161 Strain)

(1) Morphological Characteristics
Shape and size of cell: Sphere Φ of 0.6 μm, Rod of 0.6 μm×1.5 to 2.0 μm
Polymorphism of cell: Yes (elongation type)
Motility: Yes
Spore formation: No
Gram stain: Negative
Shape of colony: Circular, smooth on the entire periphery, low protrusions, smooth on the surface, and cream-colored (2) Physiological Properties
Catalase: Positive
Oxidase: Positive
O/F test: Oxidative
Reduction of nitrate: Positive
Production of indole: Negative
Arginine dihydrolase: Positive
Urease: Negative
Hydrolysis of aesculin: Negative
Hydrolysis of gelatin: Negative
β-Galactosidase: Negative
Production of fluorescent pigment on King's B agar: Positive (3) Assimilability of Substrates
Glucose: Positive
L-Arabinose: Positive
D-mannose: Positive
D-mannitol: Positive
N-Acetyl-D-glucosamine: Positive
Maltose: Negative
Potassium gluconate: Positive
n-Capric acid: Positive
Adipic acid: Negative
dl-Malic acid: Positive
Sodium citrate: Positive
Phenyl acetate: Positive <Culture Step>

In the production method for PHA of the present invention, the microorganisms having the ability to produce PHA described above are utilized to produce, from alkanoic acids as raw materials, corresponding PHAs containing 3-hydroxyalkanoic acid units having various functional groups at the termini of side chains, represented by the general formulae (1) to (10) given above and accumulated in the cells.

For usual culture of microorganisms, for example, for the preparation of stock strains, the growth for maintaining the number of cells and viability necessary for the production of PHA, and so forth, media that contain components necessary for the growth of the microorganism are appropriately selected and used. For example, any kinds of media such as generally used natural media (bouillon medium, yeast extracts, etc.), synthetic media to which nutrient sources are added, etc. can also be used unless they give adverse influences on the growth or survival of the microorganism. The culture conditions such as temperature and agitation are selected appropriately depending on the kind of microorganism used.

On the other hand, when the PHA containing the target 3-hydroxyalkanoic acid unit is produced by using the above-mentioned PHA producing microorganism, an inorganic medium that contains at least a carbon source for growth in addition to the alkanoic acid corresponding to the monomer unit can be used as a raw material for the production of PHA. It is preferable that the alkanoic acid, raw material, is set to an initial content within the range of 0.01% to 1% (mass/volume), more preferably 0.02% to 0.2% (mass/volume) based on the medium. Depending on the kind of alkanoic acids, raw materials, the alkanoic acid has insufficient solubility in water; however, when the above-mentioned microorganisms are used in the present invention, the use of alkanoic acid in a state suspended in the medium will cause no problem.

To increase the solubility of the alkanoic acid, raw material, in the medium, it is possible in some cases to dissolve it in a solvent such as 1-hexadecene or n-hexadecane, or it may be added to the medium in the form of a fine suspension. In this case, the concentration of the solvent to be added, such as 1-hexadecene or n-hexadecane, needs to be 3% (volume/volume) or less based on the medium.

It is preferable that substrates for growth that the microorganism utilizes for the growth are added separately. For the growth substrates, nutrients such as yeast extract, polypeptone, and meat extract can be used. Further, the growth substrates may be selected appropriately from saccharides, organic acids that are generated as intermediates in the TCA cycle, organic acids that are generated through one step or two steps of biochemical reaction from the TCA cycle or salts thereof, and amino acids or salts thereof in consideration of utility as growth substrate depending on the microbial strains used. When only a small ratio of the target monomer is sufficient, a straight chain alkanoic acid having 4 to 12 carbon atoms or salts thereof may be used as a substrate. In this case, however, care must be taken that the ratio of a simple monomer that is a straight chain and has no substituents (hereinafter, abbreviated as "mcl") becomes high.

Of those, one or more compounds selected from: aldoses such as glyceroaldehyde, erythrose, arabinose, xylose, glucose, galactose, mannose, and fructose; alditols such as glycerol, erythritol, and xylitol; aldonic acids such as gluconic acid; uronic acids such as glucuronic acid and galacturonic acid; and disaccharides such as maltose, sucrose, and lactose can be suitably used as saccharides.

In addition, one or more compounds selected from: organic acids such as pyruvic acid, oxalacetic acid, citric acid, isocitric acid, ketoglutaric acid, succinic acid, fumaric acid, malic acid, and lactic acid; and salts thereof can be suitably used as organic acids or salts thereof.

In addition, one or more compounds selected from glutamic acid, aspartic acid, and salts thereof can be suitably used as amino acids or salts thereof.

Generally, it is more preferable that polypeptone and saccharides from among these various growth substrates are used. It is desirable that the contents of the growth substrates that are allowed to coexist with the raw material compound are selected within the range of 0.1% to 5% (mass/volume), more preferably 0.2% to 2% (mass/volume) based on the medium.

When the culture method for making the microorganism to produce and accumulate PHA is a method in which after the microorganism is temporarily allowed to grow sufficiently, the cells are transferred to a medium containing a limited content of nitrogen source, such as ammonium chloride and further cultured therein in a state where a compound that serves as a substrate of the target unit is added, so that an increase in productivity is obtained in some cases. For example, multi-step process consisting of a plurality of steps with different culture conditions connected in series may be adopted.

On this occasion, the culture temperature may be any temperature so far as the microbial strain can grow at that temperature; for example, the culture temperature may be appropriately selected within the range of 15 to 40° C., preferably 20 to 35° C., more preferably 20 to 30° C.

Any culture method can be used so far as it allows the microorganism in use to grow and produce PHA containing the units represented by the general formulae (1) to (10) given above from the alkanoic acid, raw material, contained in the medium, such as a liquid culture method and a solid culture method. Further, assuming that supply of the raw material, growth substrates, and further oxygen is made properly, the kind of culture such as batch culture, fed batch culture, semi-continuous culture, or continuous culture is not questioned. For example, modes of liquid batch culture may include a method in which shaking flasks are shaken to supply oxygen and a method of supplying oxygen in the form of agitation aeration with a jar fermenter.

The inorganic medium used in the above-mentioned culture methods may be any medium so far as it contains components with which the microorganism can grow, such as phosphorus source (for example, phosphates, etc.), nitrogen source (for example, ammonium salts, nitrates, etc.), and so forth. For example, the inorganic salt media include MSB medium, E medium (J. Biol. Chem., 218, 97-106 (1956)), and M9 medium. Note that the composition of M9 medium used in the examples of the present invention is as follows.

[M9 Medium]
$Na_2HPO_4$: 6.2 g
$KH_2PO_4$: 3.0 g
NaCl: 0.5 g
$NH_4Cl$: 1.0 g
(In 1 liter of medium, pH 7.0)

Further, for good growth and production of PHA synthetic enzyme, it is preferable that about 0.3% (volume/volume) of a solution of trace components given below is added to the above-mentioned inorganic medium.

(Trace Component Solution)
Nitrilotriacetic acid: 1.5 g, $MgSO_4$: 3.0 g, $MnSO_4$: 0.5 g, NaCl: 1.0 g, $FeSO_4$: 0.1 g, $CaCl_2$: 0.1 g, $CoCl_2$: 0.1 g, $ZnSO_4$: 0.1 g, $CuSO_4$: 0.1 g, $AlK(SO_4)_2$: 0.1 g, $H_3BO_3$: 0.1 g, $Na_2MoO_4$: 0.1 g, and $NiCl_2$: 0.1 g (in 1 liter)

<Recovery of PHA>

To obtain PHA from the culture broth of the present invention, a usually used method can be applied. When PHA is secreted in the culture broth, an extraction and purification method from the culture broth is used. On the other hand, when PHA is accumulated in the microbial cells, an extraction and purification method from cells is used. For example, to recover PHA from cultured cells of the microorganism, extraction with an organic solvent such as chloroform, which is usually performed is simplest; however, besides chloroform, dioxane, tetrahydrofuran, acetonitrile, or acetone is used in some cases. Further, in an environment where it is difficult to use organic solvents, a method of recovering only PHA can be adopted, which is performed by removing the cell components except PHA by a treatment with a surfactant such as SDS, a treatment with an enzyme such as lysozyme, or a treatment with a chemical such as EDTA, sodium hypochlorite, hydrogen peroxide, or ammonia.

Note that culture of the microorganism, production and accumulation of PHA in the cell of the microorganism, and recovery of PHA from the cell are not particularly limited to those described above. For example, the microorganisms utilized in the production method of PHA according to the present invention may be microorganisms that have productivities of PHA production according to the present invention similar to those of the four strains described above.

<Biosynthesis Using Transformants>

Further, it is also possible to produce a desired PHA by using transformants obtained by introducing the gene for a PHA synthetic enzyme of the above-mentioned PHA producing microorganism into other microorganisms. Cloning of the gene for PHA synthetic enzyme, preparation of expression vectors, and preparation of transformants can be conducted by conventional methods. Media used for culturing transformants that are obtained by using bacteria such as *Escherichia coli* as a host include, for example, LB medium, M9 medium, and so forth. Aerobic culture is performed at a culture temperature within the range of 25 to 37° C. for 8 to 27 hours in order to grow the microorganism. After that, the cells can be collected to recover PHA accumulated in the cells. Antibiotics such as kanamycin, ampicillin, tetracycline, chloramphenicol, and streptomycin may be added to the medium as necessary. Further, when an inducible promoter is used in the expression vector, an inducing substance corresponding to the promoter may be added to the medium to promote expression upon culture of transformants. Examples of the inducing substance include isopropyl-β-D-thiogalactopyranoside (IPTG), tetracycline, indoleacrylic acid (IAA), and so forth.

<3-hydroxyacyl CoA>

In the capsulation method utilizing bioengineering technique according to the present invention, specific examples of the 3-hydroxyacyl CoA used as a substrate for PHA synthetic enzyme include those 3-hydroxyacyl CoA represented by the formulae [11] to [20] given below.

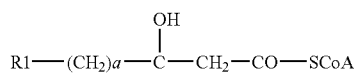

[11]

(In the above formula, —SCoA represents coenzyme A bound to an alkanoic acid, and R1 and a are defined in the same manner as in the formula [1] given above.)

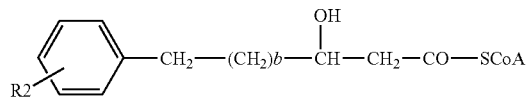

[12]

(In the above formula, —SCoA represents coenzyme A bound to an alkanoic acid, and b and R2 are defined in the same manner as in the formula [2] given above.)

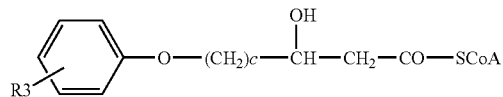

[13]

(In the above formula, —SCoA represents coenzyme A bound to an alkanoic acid, and c and R3 are defined in the same manner as in the formula [3] given above.)

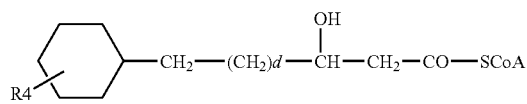

[14]

(In the above formula, —SCoA represents coenzyme A bound to an alkanoic acid, and d and R4 are defined in the same manner as in the formula [4] given above.)

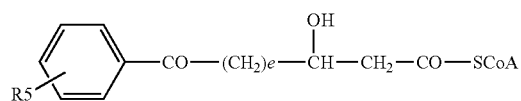

[15]

(In the above formula, —SCoA represents coenzyme A bound to an alkanoic acid, and e and R5 are defined in the same manner as in the formula [5] given above.)

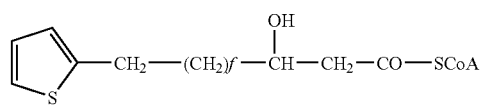

[16]

(In the above formula, —SCoA represents coenzyme A bound to an alkanoic acid, and f is defined in the same manner as in the formula [6] given above.)

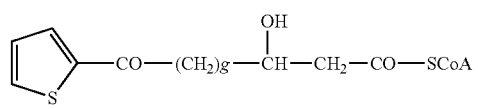

[17]

(In the above formula, —SCoA represents coenzyme A bound to an alkanoic acid, and g is defined in the same manner as in the formula [7] given above.)

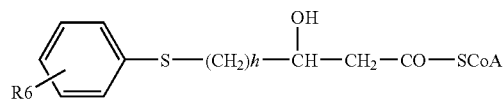

[18]

(In the above formula, —SCoA represents coenzyme A bound to an alkanoic acid, and h and R6 are defined in the same manner as in the formula [8] given above.)

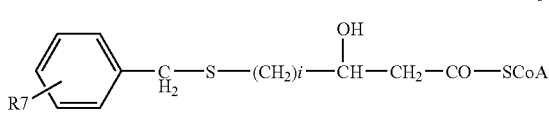

[19]

(In the above formula, —SCoA represents coenzyme A bound to an alkanoic acid, and I and R7 are defined in the same manner as in the formula [9] given above.)

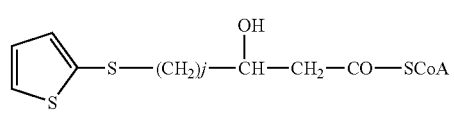

[20]

(In the above formula, —SCoA represents coenzyme A bound to an alkanoic acid, and j is defined in the same manner as in the formula [10] given above.)

These 3-hydroxyacyl CoAs can be synthesized by a method appropriately selected from an in vitro synthesis method using an enzyme, an in vivo synthesis method using a living body such as a microorganism or a plant, a chemical synthesis method, and so forth and used. In particular, the enzyme synthesis method is generally used in the synthesis of the substrate, examples of which method include a method using the following reaction using commercially available acyl CoA synthetase (acyl CoA ligase E.C.6.2.1.3):

Acyl CoA Synthetase 3-Hyroxyalkanoic acid+CoA→3-hydroxyacyl CoA (Eur. J. Biochem., 250, 432-439 (1997), Appl. Microbiol. Biotechnol., 54, 37-43 (2000), etc.). In the synthesis step using enzyme or organism, a batch-type synthesis method may be used. Alternatively, a continuous production may be performed by using immobilized enzymes or immobilized cells.

<PHA Synthetic Enzyme and its Producing Microorganism>

In the present invention, the PHA synthetic enzyme used may be produced by microorganisms appropriately selected from microorganisms that produce the enzyme or transformants in which the gene for PHA synthetic enzyme of the microorganism is transduced. The above-mentioned PHA producing microorganisms may be used preferably.

<Obtaining PHA Synthetic Enzyme>

For ordinary culture of microorganisms used in the production of PHA synthetic enzyme according to the present invention, for example, preparation of stock strain, growth for securing the number of cells or viability required for the production of PHA synthetic enzyme, and so forth, media containing components necessary for the growth of the microorganism used can be appropriately selected and used.

Any culture method can be used so far as the method allows growth of the microorganisms, such as a liquid culture method and a solid culture method. Further, the kind of batch culture, fed batch culture, semi-continuous culture, or continuous culture is not questioned. The modes of liquid batch culture include a method of supplying oxygen by using a shaking flask and a method of supplying oxygen of agitation aeration by using a jar fermenter. Further, a multi-step process using a plurality of such steps connected in series may be adopted.

When PHA synthetic enzymes are produced by using PHA producing microorganisms as mentioned above, for example, a method of growing the microorganism in an inorganic medium containing an alkanoic acid such as octanoic acid or nonanoic acid, centrifuging the microorganism in a logarithmic growth stage to an early stationary stage to recover the cells, and extracting a desired enzyme may be used. Note that culture under the conditions as mentioned above results in synthesis of mcl-PHA derived from the added alkanoic acid occurs in the cells. In this case, it is generally believed that PHA synthetic enzymes exist as being bound to microspheres of PHA formed in the cells. However, the study by the inventors of the present invention revealed that a considerable degree of enzyme activity exists also in a supernatant separated by centrifugation from a solution of disrupted cells cultured by the above-mentioned method. This is presumed to be attributable to existence of a considerable amount of PHA synthetic enzyme in a free state because vigorous production of the enzyme in the cells is continued in the relatively early stage of culture from the above-mentioned logarithmic growth stage to the early stationary stage.

The inorganic medium used in the above-mentioned culture method may include any medium so far as it contains components that allow the microorganism to grow, such as a phosphorus source (for example, phosphates, etc.) and a nitrogen source (for example, ammonium salts, nitrates, etc.). Examples of the inorganic medium include MSB medium, E medium (J. Biol. Chem., 218, 97-106 (1956)), M9 medium, and so forth. Note that the composition of the M9 medium is as described above. Further, for better growth and production of PHA synthetic enzyme, it is preferable that about 0.3% (volume/volume) of the above-mentioned solution of trace components is added to the above-mentioned inorganic medium. The culture temperature may be any temperature so far as the above-mentioned strain can well grow; for example, about 15 to about 40° C., preferably about 20 to about 35° C. is suitable.

Further, it is also possible to produce a desired PHA synthetic enzyme by using transformants in which the gene for PHA synthetic enzyme of the above-mentioned PHA producing microorganism is transduced. Cloning of the gene for PHA synthetic enzyme, preparation of expression vectors, and preparation of transformants can be conducted by conventional methods. Media used for culturing transformants that are obtained by using bacteria such as *Escherichia coli* as a host include, for example, LB medium, M9 medium, and so forth. Aerobic culture is performed at a culture temperature within the range of 25 to 37° C. for 8 to 27 hours in order to grow the microorganism. After that, the cells can be collected to recover PHA synthetic enzyme accumulated in the cells. Antibiotics such as kanamycin, ampicillin, tetracycline, chloramphenicol, and streptomycin may be added to the medium as necessary. Further, when an inducible promoter is used in the expression vector, an inducing substance corresponding to the promoter may be added to the medium to promote expression upon culture of transformants. Examples of the inducing substance include isopropyl-β-D-thiogalactopyranoside (IPTG), tetracycline, indoleacrylic acid (IAA), and so forth.

The PHA synthetic enzymes that can be used may also include cell homogenates of the microorganism, crude enzymes such as ammonium sulfate salting out product obtained by precipitating and recovering protein components with ammonium sulfate. Further, purified enzymes that are purified by various methods. Stabilizers and activators such as metal salts, glycerol, dithiothreitol, EDTA, and bovine serum albumin (BSA) may be added to the enzyme before use as necessary.

Any separation/purification method for PHA synthetic enzyme may be used so far as the enzyme activity of PHA synthetic enzyme is retained. For example, a crude enzyme solution obtained by disrupting the obtained microbial cells by using a French press, an ultrasonic disintegrator, lysozyme, or various surfactants, followed by centrifugation, or ammonium sulfate salting out product prepared therefrom may be subjected to affinity chromatography, cation or anion exchange resin chromatography, gel filtration, and the like means alone or in appropriate combinations to obtain a purified enzyme. In particular, genetic recombinant protein can be purified more simply by expressing it in the form of a fused protein to which a "tag" such as a histidine residue at the N-terminal or C-terminal is bound and allowing the protein to bind to a resin having affinity therefor through the tag. To separate the target protein from the fused protein, cleaving with a protease such as thrombin, blood coagulating factor Xa, or the like, reducing pH, adding imidazole as a binding competitor in a high concentration, and so forth may be used advantageously. Alternatively, when the tag contains an intein in such a case where pTYB1 (manufactured by New England Biolab) is used as an expression vector, the fused protein is cleaved with dithiothreitol or the like under reducing conditions. Known fused proteins that enable purification by affinity chromatography include besides histidine tag, glutathione S-transferase (GST), chitin-binding domain (CBD), maltose binding protein (MBP), and thioredoxin (TRX). GST fused protein can be purified with a resin having affinity for GST.

Measurement of activity of PHA synthetic enzyme may be performed by using various known methods. For example, the measurement may be performed by the following method that is based on a measuring principle in that CoA released during polymerization of 3-hydroxyacyl CoA by the catalytic action of PHA synthetic enzyme to obtain PHA forms a color with 5,5'-dithiobis-(2-nitrobenzoic acid). Reagent 1: bovine serum albumin (manufactured by Sigma) dissolved in 0.1 M Tris hydrochloride buffer (pH 8.0) 3.0 mg/ml; Reagent 2: 3-hydroxyoctanoyl CoA dissolved in 0.1 M Tris hydrochloride buffer (pH 8.0) in 3.0 mM; Reagent 3: Trichloroacetic acid dissolved in 0.1 M Tris hydrochloride buffer (pH 8.0) in 10 mg/ml; Reagent 4: 5,5'-dithiobis-(2-nitrobenzoic acid) dissolved in 0.1 M Tris hydrochloride buffer (pH 8.0) in 2.0 mM. First reaction (PHA synthesis reaction): 100 μl of Reagent 1 is added to 100 μl of a sample (enzyme) solution and mixed. The mixture is preincubated at 30° C. for 1 minute. Then, 100 μl of Reagent 2 is added to the resultant and mixed. The mixture is preincubated at 30° C. for 1 to 30 minutes, followed by addition of Reagent 3 to stop the reaction. Second reaction (coloring reaction of free CoA): The first reaction mixture of which the reaction is stopped is centrifuged (15,000×g, 10 minutes). 500 μl of Reagent 4 is added to 500 μl of the resultant supernatant and the resultant is incubated at 30° C. for 10 minutes and then measured for optical density (absorbance) at 412 nm. Calculation of enzyme activity: an amount of enzyme that releases 1 μmol CoA in 1 minute is defined to be 1 unit (U).

Note that PHA synthesized by the enzyme generally is an isotactic polymer consisting of R form only.

<Magnetic Substance>

The magnetic substance to be contained in the structure of the present invention can be used by selecting the kind and configuration thereof depending upon the intended use and characteristics of the structure.

Examples of the magnetic substance include metal or metal compounds having magnetism. More specific examples thereof include, but are not limited to: various kinds of ferrites such as triiron tetroxide ($Fe_3O_4$), γ-diiron trioxide (γ-$Fe_2O_3$), MnZn ferrite, NiZn ferrite, YFe garnet, GaFe garnet, Ba ferrite, and Sr ferrite; metal such as iron, manganese, cobalt, nickel, and chromium; and alloys of iron, manganese, cobalt, nickel, and the like. Herein, for example, in the case of fixing a biomaterial, administering a magnetic substance to a living body, or the like, not only magnetite ($Fe_3O_4$) satisfactorily compatible with a living body but also various kinds of ferrite compositions obtained by substituting at least one kind of another metal element for a part of a metal element of magnetite if required are preferably applicable. The shape of those magnetic substances varies depending upon the generation conditions, and examples of the shape include a polyhedron, an octahedron, a hexahedron, a sphere, a bar-shape, and a scale-shape. A configuration with less anisotropy is more preferable for stable expression of a function. The particle size of primary particles of a magnetic substance constituting the structure of the present invention can be appropriately selected depending upon the use. The particles having a particle size, for example, in the range of 0.001 to 10 μm may be used.

Furthermore, magnetic substances having super paramagnetism also can be used preferably. For example, in the case where the particle size of ferrite is small (i.e., about 20 nm or less), the ferrite is influenced by thermal disturbance to exhibit super paramagnetism, and cannot hold residual magnetization and a coercive force. Even when the magnetic substance has super paramagnetism, it can be magnetically operated by applying a magnetic field. Furthermore, the magnetic substance having super paramagnetism does not have residual magnetization and a coercive force. Therefore, the substance may not magnetically gather in the absence of a magnetic field.

Furthermore, the magnetic substance may be a composite such as a matrix containing metal or a metal compound, and a matrix is formed of various kinds of organic or inorganic materials.

In addition, magnetic substances that have been made hydrophobic by a method of covering the surfaces of particles with fatty acid, a method of performing treatments with various kinds of coupling agents typified by a treatment with a silane coupling agent, and the like also can be used preferably as the magnetic substance of the present invention.

The content of the magnetic substance in the structure according to the present invention is 1 to 80 mass %, preferably 5 to 70 mass %, and more preferably 10 to 60 mass %. When the amount of the magnetic substance is less than 1 mass %, magnetic performance is insufficient, and the performance as the structure may be insufficient. Furthermore, when the content of the magnetic substance exceeds 80 mass %, the amount of the magnetic substance is too large, so that the original function of the structure is impaired, and practical performance may not be satisfied.

<Structure and Method of Producing the Same—Inclusion of Hydrophilic Drug—>

According to one aspect of the present invention, there is provided a structure containing at least a drug, a magnetic substance, and PHA, which may have various forms such as a microsphere and a microcapsule. Specific examples thereof include a microcapsule containing a drug in a core portion in a shell containing PHA and a structure (microsphere) in which a portion containing a drug is dispersed as an internal phase in an external phase containing PHA. The magnetic substance is contained in at least one of an external phase and an internal phase depending upon the configuration of the structure.

The sustained-release formulation of the present invention can be prepared using as an effective component the structure containing the above-mentioned drug. The sustained-release formulation can be prepared, for example, with a W/O type emulsion including a drug-containing solution as an internal water phase and a solution containing PHA and a magnetic substance as an oil phase, a structure obtained by further emulsifying the W/O type emulsion in an external water phase to obtain a W/O/W type emulsion, and pulverizing the W/O/W type emulsion, or a structure and various kinds of adders added if required.

The pulverization can be performed, for example, by a submerged drying method, a phase separation method, a spray-drying method, or methods similar thereto.

Furthermore, the following in-vitro synthesis also can be used preferably. A W/O type emulsion including, as an internal water phase, a solution containing a drug, PHA synthetic enzyme, and 3-hydroxyacyl CoA is obtained, or a W/O type emulsion composed of an internal water phase and an oil phase is further emulsified in an external water phase to obtain a W/O/W type emulsion (PHA synthetic enzyme and 3-hydroxyacyl CoA is contained in at least one of an internal water phase and an external water phase), and a PHA synthesis reaction is effected, whereby a structure is prepared.

Furthermore, a method of preparing a structure, which include: obtaining a W/O/W type emulsion in which a W/O type emulsion including a drug-containing solution as an internal water phase is emulsified in an external water phase containing PHA synthetic enzyme and 3-hydroxyacyl CoA; and effecting a PHA synthesis reaction to prepare a structure, also can be used preferably.

<Preparation of W/O Type Emulsion—Inclusion of Hydrophilic Drug—>

The W/O type emulsion including a drug-containing solution as an internal water phase and a solution containing PHA and a magnetic substance as an oil phase can be produced as follows.

First, a water-soluble drug is dissolved or dispersed in water. A drug-holding material such as gelatin, agar, polyvinyl alcohol, or basic amino acid (e.g., arginine, histidine, and lysine) is dissolved or suspended in the resultant solution to obtain an internal water phase. The concentration of the drug in the internal water phase is about 0.001 to 90 mass %, and preferably about 0.01 to 80 mass %. The added amount of the drug-holding material is generally about 0.01 to about 100 times by weight, and more preferably about 0.05 to about 50 times by weight with respect to the physiologically active material. Those drug-holding materials can be previously dissolved in water together with the physiologically active material in an arbitrary concentration, filtered with a disinfecting/dust-removing filter, freeze-dried to be stored, and dissolved during preparation for use. In the sustained-release formulation of the present invention, even in the case where a drug-holding material is not used in an internal water phase, an uptake ratio of the physiologically active material is sufficiently satisfactory.

Carbonic acid, acetic acid, oxalic acid, citric acid, phosphoric acid, hydrochloric acid, sodium hydroxide, arginine, lysine, or a salt of them may be added as a pH regulator to the internal water phase for maintaining the stability and solubility of the drug. In addition, a surfactant such as: albumin, gelatin, trehalose, citric acid, sodium ethylenediaminetetraacetate, dextrin, cyclodextrin (α-, β-, γ-), or a derivative of them (for example, maltosil β-cyclodextrin or β-cyclodextrin sulfobutylether); sodium hydrogen sulfite; a polyol compound such as polyethylene glycol; a polyoxyethylene sorbitan fatty acid ester [for example, Tween 80 or Tween 60 (Kao Corporation, Japan)]; or a polyoxyethylene castor oil derivative [for example, HCO-60 or HCO-70 (Nikko Chemicals Co., Ltd., Japan)] may be added as a stabilizer for the drug. Alternatively, a parahydroxybenzoate (for example, methylparaben or propylparaben), benzyl alcohol, chlorobutanol, thimerosal, or the like, which are generally used, may be added as preservatives.

The internal water phase thus obtained and a solution (oil phase) containing PHA and a magnetic substance are mixed with each other, followed by an emulsification operation to prepare a W/O type emulsion. A known method is used as the emulsification operation. Examples of the method include: an intermittent shaking method; a stirring method using a mixer such as a propeller stirrer or a turbine stirrer; a colloid mill method; a homogenizer method; and an ultrasonic irradiation method. According to the present invention, these methods may be combined appropriately. The W/O type emulsion is preferable for the following reasons. The release of a drug is influenced by the degree of emulsification. When the degree of emulsification is insufficient, an initial burst tends to increase. As the internal water phase is finer to a certain degree or more, the interaction between the drug and the PHA is strong. Thus, the release control by PHA can be performed more exactly for a long period of time, depending upon the kind/composition ratio/molecular weight/crystallinity of PHA.

The above-mentioned solution (oil phase) containing PHA and a magnetic substance is obtained by including PHA and a magnetic substance in an organic solvent that is not substantially miscible with water. The solubility of the organic solvent with respect to water is preferably 3 mass % or less at room temperature (20° C.). Furthermore, the boiling point of the organic solvent is preferably 120° C. or lower. Examples of the organic solvent include halogenated hydrocarbons (e.g., dichloromethane, chloroform, chloroethane, dichloroethane, trichloroethane, carbon tetrachloride, etc.), ketones (e.g., acetone, methyl ethyl ketone, methyl isobutyl ketone, etc.), ethers (e.g., tetrahydrofuran, ethyl ether, isopropyl ether, etc.), esters (e.g., ethyl acetate, butyl acetate, etc.), and aromatic hydrocarbons (e.g., benzene, toluene, xylene, etc.). Those solvents may be used in combination of two or more kinds in an appropriate ratio. The organic solvent is more preferably a halogenated hydrocarbon (e.g., dichloromethane, chloroform, chloroethane, dichloroethane, trichloroethane, carbon tetrachloride, etc.). The concentration of PHA in the oil phase varies depending upon the kind and molecular weight of the PHA and the kind of a solvent, and preferably about 0.01 to 80 mass %, more preferably about 0.1 to 70 mass %, and particularly preferably about 1 to 60 mass %. Examples of the magnetic substance to be dispersed in the oil phase include metal or metal compounds having magnetism. More specific examples thereof include: various kinds of ferrites such as triiron tetroxide ($Fe_3O_4$), γ-diiron trioxide (γ-$Fe_2O_3$), MnZn ferrite, NiZn ferrite, YFe garnet, GaFe garnet, Ba ferrite, and Sr ferrite; metal such as iron, manganese, cobalt, nickel, and chromium; and alloys of iron, manganese, cobalt, nickel, and the like. The prescription amount of the magnetic substance in the oil phase varies depending upon the kind of the magnetic substance, the kind of the solvent, the prescription amount of PHA, and the like. The magnetic substance may be prescribed so that the amount of the magnetic substance in the structure is 1 to 80 mass %, preferably 5 to 70 mass %, and more preferably 10 to 60 mass %.

In order to change the compatibility with respect to the internal water phase, the distribution of the organic solvent in the external water phase (described later), vaporization, and the like, an organic solvent that is partially hydrophilic (e.g., ethanol, acetonitrile, acetone, tetrahydrofuran, or the like) may be added to the oil phase. Furthermore, in order to dissolve or stabilize a drug in an inner portion, a surfactant such as a sucrose aliphatic acid ester or the like may be added. Furthermore, depending upon the stability of PHA, the solution containing PHA may be stored in a sealed container at room temperature or in a cold place.

The mixing ratio between the drug-containing aqueous solution and the organic solvent solution containing PHA and a magnetic substance is about 0.1 to 1,000 parts by weight, preferably about 1 to 100 parts by weight of the latter with respect to one part by weight of the former. Although the mixed amount of the drug in the sustained-release formulation varies depending upon the kind of the drug, desired pharmacological effect, duration of an effect, and the like, about 0.01 to 50 mass %, preferably about 0.1 to 40 mass %, and particularly preferably about 1 to 30 mass % of the drug is used with respect to the PHA.

<Preparation and Submerged Drying Method of W/O/W Type Emulsion—Inclusion of Hydrophilic Drug>

Next, the W/O type emulsion thus obtained is subjected to pulverization. For example, in the case of performing pulverization by a submerged drying method or the like, the W/O type emulsion is further added to an water phase (hereinafter, abbreviated as an external water phase) to produce a W/O/W type emulsion, an organic solvent is removed from the oil phase, and a structure such as a microcapsule is prepared.

The volume of the external water phase is generally selected from the range of about 1 to about 10,000 times, more preferably about 2 to about 5,000 times, and particularly preferably about 5 to about 2,000 times the volume of the oil phase.

An emulsifier may be added to an external water phase. In general, any emulsifier that can form a stable W/O/W type emulsion may be used. Examples of the emulsifier include an anionic surfactant (e.g., sodium oleate, sodium stearate, sodium lauryl sulfate, etc.), a nonionic surfactant (polyoxyethylene sorbitan fatty acid ester (Tween 80, Tween 60, produced by Atlas Powder Company (U.S.)), a polyoxyethylene castor oil derivative (HCO-70, HCO-60, HCO-50, produced by Nikko Chemical Co., Ltd.), etc.), polyvinylpyrrolidone, polyvinyl alcohol, carboxymethylcellulose, lecitin, gelatin, hyaluronic acid, and derivatives thereof. Those emulsifiers may be used alone or in combination. The concentration of the emulsifier in the external water phase is appropriately determined from the range of about 0.01 to 20 mass %, and preferably about 0.05 to 10 mass %.

An osmoregulatory agent may be added to the external water phase. Any material exhibiting an osmotic pressure may be used as the osmoregulatory agent in the case of an aqueous solution used in the present invention. Specific examples of the osmoregulatory agent include: water-soluble polyhydric alcohols; water-soluble monovalent alcohols; water-soluble monosaccharide, disaccharide, and oligosaccharide or derivatives thereof; and water-soluble amino acid; a water-soluble peptide, and a protein, or derivatives thereof.

Examples of the above water-soluble polyhydric alcohols include: dihydric alcohols such as glycerin; pentahydric alcohols such as arabitol, xylitol, and adonitol; and hexahydric alcohols such as mannitol, sorbitol, and dulcitol. Of those, hexahydric alcohols are preferable. Of those, mannitol is particularly preferable. Examples of the above water-soluble monohydric alcohols include methanol, ethanol, and isopropyl alcohol. Of those, ethanol is preferable. Examples of the water-soluble monosaccharides include: pentoses such as arabinose, xylose, ribose, and 2-deoxyribose; and hexoses such as glucose, fructose, galactose, mannose, sorbose, rhamnose, and fucose. Of those, hexoses are preferable. Examples of the water-soluble disaccharides include maltose, cellobiose, α,α-trehalose, lactose, and sucrose. Of those, lactose and sucrose are preferable. Examples of the above water-soluble oligosaccharides include: trisaccharides such as maltotriose and raffinose; and tetrasaccharides such as stachyose. Of those, trisaccharides are preferable. Examples of derivatives of the above water-soluble monosaccharides, disaccharides, and oligosaccharides include glucosamine, galactosamine, glucuronic acid, and galacturonic acid.

Examples of the above water-soluble amino acids include: neutral amino acids such as glycine, alanine, valine, leucine, isoleucine, phenylalanine, tyrosine, tryptophan, serine, threonine, proline, hydroxyproline, cysteine, and methionine; acidic amino acids such as aspartic acid and glutamic acid; and basic amino acids such as lysine, arginine, and histidine. In addition, salts of those water-soluble amino acids with acids (for example, hydrochloric acid, sulfuric acid, and phosphoric acid) or with alkalis (for example, alkali metals such as sodium and potassium) may be used. Examples of water-soluble peptides, proteins, and derivatives thereof include casein, globulin, prolamin, albumin, and gelatin.

Of the above-mentioned osmoregulatory agents, water-soluble polyhydric alcohols, and water-soluble monosaccharide, disaccharide, and oligosaccharide or derivatives thereof are preferable. The water-soluble polyhydric alcohols and water-soluble monosaccharide are further preferable. The water-soluble polyhydric alcohols are particularly preferable. Those osmoregulatory agents may be used alone or in combination. Those osmoregulatory agents are used in such a concentration that the osmotic pressure of the external water phase is about 1/50 to about 5 times, preferably about 1/25 to about 3 times the osmotic pressure of physiological salt solution. Specifically, the concentration of those osmoregulatory agents in the external water phase is about 0.001 to 60 mass %, preferably about 0.01 to 40 mass %, particularly preferably about 0.05 to 30 mass %, and most preferably about 1 to 10 mass %, in the case where the osmoregulatory agents are nonionic substances. Furthermore, in the case where the osmoregulatory agents are ionic substances, the concentration obtained by dividing the above-mentioned concentration by the entire ionic valence is used. The added concentration of the osmoregulatory agents is not required to be a solubility or less, and the osmoregulatory agents may be partially dispersed.

According to the production method of the present invention, when a W/O/W type emulsified substance is formed, it is preferable that the viscosity of a W/O type emulsified substance be adjusted in the range of 50 cp to 10,000 cp. Examples of the method of adjusting the viscosity include (1) a method involving adjusting the concentration of PHA and a magnetic substance in an oil phase, (2) a method involving adjusting the amount ratio between an water phase and an oil phase, (3) a method involving adjusting the temperature of a W/O type emulsified substance, (4) a method involving adjusting the temperature of an external water phase, and (5) a method involving adjusting the temperature of a W/O type emulsified substance with, for example, a line heater or a cooler when the W/O type emulsified substance is injected to an external water phase. Those methods may be used alone or in combination. When the W/O type emulsified substance is formed into a W/O/W type emulsified substance using the above method, the viscosity of the W/o type emulsified substance only needs to be in the range of 50 cp to 10,000 cp. In the above (1), in the case of adjusting the concentration of PHA in an oil phase, the concentration of PHA is not determined uniquely since the concentration varies depending upon the kind of PHA, the kind of an organic solvent, and the like. The concentration of PHA is preferably about 10 to 80 mass %. In the above (2), the amount ratio between the water phase and the oil phase is not determined uniquely by the kind and amount of a drug and the property of the oil phase, but is preferably W/O=about 1 to 50 volume %. In the above (3), in the case of adjusting the temperature of a W/O type emulsified substance, the temperature is, for example, in the range of about −20° C. to the boiling point of an organic solvent, preferably about 0 to 30° C., and more preferably about 10 to 20° C. In the cases of the above (1) and (2), the viscosity of the W/O type emulsified substance can be adjusted in the course of producing the W/O type emulsified substance. Furthermore, in the above (4), for example, when the W/O type emulsified substance is added to an external water phase, the temperature of the external water phase is previously adjusted, whereby the same results as those in the above (3) may be obtained. The temperature of the external water phase is, for example, about 5 to 30° C., preferably about 10 to 25° C., and more preferably about 12 to 20° C.

An organic solvent can be removed by a known method. Examples of such a method include: a method of evaporating an organic solvent at atmospheric pressure or by gradually reducing the pressure while stirring the organic solvent with a propeller stirrer, a magnetic stirrer, or the like; and a method of evaporating an organic solvent while regulating the vacuum degree and temperature with a rotary evaporator or the like.

After that, the structure is aliquoted by centrifugation or filtering. The free drug, drug-holding material, emulsifier, and the like adhering to the surface of the structure are washed off with distilled water several times repeatedly. Furthermore, the structure is dried under reduced pressure, freeze-dried after being re-dispersed in distilled water, or the like, whereby the remaining solvent and water are removed.

<Phase Separation Method—Inclusion of Hydrophilic Drug—>

In the case of performing granulation by a phase separation method, a coacervation agent is added gradually to a W/O type emulsion with stirring, and PHA is precipitated and solidified, whereby a structure is prepared. A compound of a polymer type, a mineral oil type, or a plant oil type that is miscible with a solvent of PHA but does not dissolve PHA for granulation may be used as the coacervation agent. Examples of the coacervation agent include silicone oil, sesame oil, soybean oil, corn oil, cottonseed oil, coconut oil, linseed oil, mineral oil, n-hexane, n-heptane, methanol, and ethanol. Those compounds may be used in combination of two or more kinds. The use amount of the coacervation agent is, for example, about 0.01 to 1,000 volume times, and preferably about 0.1 to 200 volume times with respect to the W/O type emulsion. The structure thus obtained is aliquoted by centrifugation or filtering, and washed repeatedly with a surfactant such as hexane or heptane to remove the coacervation agent. After that, the resultant structure is heated or placed under reduced pressure to evaporate the surfactant. Furthermore, if desired, a free drug and an organic solvent is removed in the same way as the case of the above-mentioned submerged drying method.

<Spray Drying Method—Inclusion of Hydrophilic Drug—>

In the case of performing granulation by a spray drying method, a W/O type emulsion or a W/O/W type emulsion produced in the same way as in the case of the submerged drying method is sprayed to a dry chamber of a spray drier apparatus (spray drier) using a nozzle to volatilize an organic solvent and water in pulverized liquid droplets in a very short period of time, whereby a structure such as a microcapsule in the shape of fine particle is prepared. The nozzle may be of, for example, a two-liquid nozzle type, a pressure nozzle type, and a rotary disk type. The structure thus obtained is washed several times repeatedly with distilled water, if desired, to remove a free drug, a drug holding material, an emulsifier, and the like adhering to the surface of the structure such as a microcapsule. Then, the organic solvent may be further removed by drying the washed microcapsule under reduced pressure or re-dispersing them in distilled water, followed by freeze-drying.

<Structure such as Microcapsule and Method of Producing the same—Inclusion of Lipophilic Drug—>

Hereinafter, a structure including a lipophilic drug will be described. The structure may be in a form of a microcapsule or a microsphere, in the same way as in the previously described hydrophilic drug. In this case, a magnetic substance is contained in at least one of an external phase part and an internal phase part, depending upon the configuration of the structure.

The structure including a lipophilic drug can be produced by removing an organic solvent from an oil phase containing a drug, a magnetic substance, PHA, and the organic solvent. In the production method of the present invention, any method can be used as a method of producing an organic solvent solution containing (a) a drug and (b) PHA in which (a) and (b) are finally formed in a dissolved state or in a uniform dispersion with a solvent system. Examples of the method include: (1) mixing (a) formed in a solution or dispersion state using a solvent with (b) formed in a solution or dispersion state using a solvent; (2) mixing (a) formed in a solution or dispersion state using a solvent with (b); (3) mixing (b) formed in a solution or dispersion state using a solvent with (a); and (4) mixing (a), (b), and a solvent, thereby forming (a) and (b) in a solution state using a solvent system. The above-mentioned solvent is appropriately selected so that each solvent is mixed to be a solvent system that enables (a) and (b) to be a dissolved state. Specifically, the above-mentioned solvent is obtained, for example, by mixing one or more kinds of the above organic solvents in an appropriate ratio, and adding the above organic solvent to the resultant mixture to such a degree as not to inhibit the dissolution of (a) and (b), if desired.

By removing the organic solvent from an oil phase composed of the solution or dispersion of a drug, a magnetic substance, and PHA thus produced, the structure such as a microcapsule or the like of the present invention can be produced.

Specifically, known methods of preparing a structure such as a microcapsule are used. Examples thereof include: a method involving transpiring a solvent to solidify a structure (submerged dry method); a method involving adding a solvent (so-called a poor solvent), which is miscible with the above solution or suspension and does not dissolve PHA, to the above solution or suspension with stirring, and subjecting PHA to phase separation to prepare a solidified structure (phase separation method); obtaining a solidified structure by a spray dry method or the like; a gas milling method involving removing an organic solvent of the oil phase, and milling the remaining solid to a structure using a jet mill or the like; and method similar thereto.

Furthermore, the following in-vitro synthesis method also can be used preferably. A drug and a magnetic substance are dissolved and/or suspended in an organic solvent. The organic phase is placed in a great amount of water containing PHA synthetic enzyme and 3-hydroxyacyl CoA and emulsified to obtain an O/W type emulsion. A PHA synthesis reaction is effected, whereby a structure such as a microcapsule is prepared.

<Specific Examples of Organic Solvent—Inclusion of Lipophilic Drug—>

An organic solvent having the solubility in water of 3 mass % (mass/mass) or less at room temperature (20° C.) is preferable as the organic solvent. Furthermore, the boiling point of the organic solvent is preferably 120° C. or lower. Examples of the organic solvent include: halogenated hydrocarbons (dichloromethane, chloroform, chloroethane, dichloroethane, trichloroethane, carbon tetrachloride, etc.); ketones (acetone, methyl ethyl ketone, methyl isobutyl ketone, etc.); ethers (tetrahydrofuran, ethyl ether, isopropyl ether, etc.); esters (ethyl acetate, butyl acetate, etc.); and aromatic hydrocarbons (benzene, toluene, xylene, etc.). Those organic solvents may be used in combination of two or more kinds in an appropriate ratio. The organic solvent is more preferably a halogenated hydrocarbon (dichloromethane, chloroform, chloroethane, dichloroethane, trichloroethane, carbon tetrachloride, etc.).

<Concentration of Drug/PHA—Inclusion of Lipophilic Drug—>

The use amount of a drug varies depending upon the kind of a drug and a desired persistence providing period. The concentration of a drug in a solution is about 0.001% to about 200% (mass/mass), more preferably 0.001% to 100% (mass/mass), and particularly preferably 0.01% to 50% (W/W). Furthermore, the blending amount of a drug varies depending upon the kind of a drug, a desired pharmacological effect, the duration of an effect, and the like. The drug is used in an amount of about 0.01 to about 60% (mass/mass), preferably about 0.1 to about 55% (mass/mass), and particularly, preferably about 1 to about 50% (mass/mass) with respect to PHA. The concentration of PHA varies depending upon a molecular weight and the kind of a solvent. The concentration of PHA is preferably about 0.01 to about 80% (mass/mass), more preferably about 0.1 to about 70% (mass/mass), and particularly preferably about 1 to about 60% (mass/mass).

<Submerged Dry Method—Inclusion of Lipophilic Drug—>

In the case of producing a structure such as a microcapsule by a submerged dry method, generally, an oil phase containing a drug, a magnetic substance, PHA, and an organic solvent is dispersed in an water phase to form an O/W type emulsion, and thereafter, the solvent in the oil phase is removed. The volume of the water phase is generally selected from about 1 to about 10,000 times, preferably about 2 to about 5,000 times, more preferably, about 5 to about 2,000 times, and particularly preferably about 50 to about 1,000 times the volume of an oil phase. The temperature of the water phase may be previously adjusted to be, for example, about 5° C. to about 30° C., preferably about 10° C. to about 25° C., and more preferably about 10° C. to about 20° C. An emulsifier may be added to the water phase. The emulsifier may be generally any one of those which can form a stable O/W type emulsion.

A non-toxic and non-antigenic emulsifier is preferably used as the emulsifier, and specific examples of such an emulsifier include: anionic surfactants (such as sodium oleate, sodium stearate, and sodium lauryl sulfate); cationic surfactants (such as lauryl trimethyl ammonium chloride); amphoteric surfactants (such as N-lauryl glycine); nonionic surfactants (such as polyoxyethylene sorbitan fatty acid esters [Tween 80, Tween 60, Tween 40, and Tween 20 from Atlas Powder Company] and polyoxyethylene castor oil derivatives [HCO-70, HCO-60, and HCO-50 from Nikko Chemicals Co., Ltd.]); polyvinyl pyrrolidone; polyvinyl alcohol; methylcellulose; carboxymethylcellulose; hydroxyethylcellulose; lecithin; starch; casein; pectin; gelatin; alginic acid; alginates; locust bean gum; guar gum; gum arabic; xanthan gum; agar; carageenan; hyaluronic acid; bile salts; sodium cholate; and polyoxyethylene ether. Two or more kinds of those emulsifiers may be mixed in an appropriate ratio before use.

The concentration of the emulsifier for use can be appropriately selected from the range of about 0.001 to about 20% (mass/volume). More preferably, the emulsifier is used in the range of about 0.01 to about 10% (mass/volume). The emulsifier is used particularly preferably in the range of about 0.05 to about 5% (mass/volume). Various known mixing apparatuses can be used in an emulsifying process. For example, there are an intermittent shaking method, a method using a mixer such as a propeller stirrer or a turbine stirrer, a method in which the distance between a rotor and a stator is set to be small and the rotor is rotated at a high speed, an ultrasonic vibration method, a method of allowing the object to pass through a narrow interval at a speed equal to or higher than a sonic speed, a method of allowing the object to pass through an inorganic film having fine pores obtained by sintering a Shirasu-balloon, and the like.

The degree of emulsification of the O/W type emulsion influences the release of a drug. When the emulsification degree is insufficient, an initial burst tends to increase. An internal oil phase is preferably finer than a certain degree because the interaction between the drug and the PHA is strong, and the release control of PHA for a long period of time can be performed exactly depending upon the biodegradability of PHA.

Various methods of supplying components for producing the O/W type emulsion of the present invention can also be performed in accordance with known techniques. Examples thereof include: a method involving previously placing a solution of PHA and a magnetic substance in a container and adding an water phase component containing an emulsifier to the container; a method in which the above addition order is reversed; and a method in which both of them are continuously supplied in a constant ratio. In the case of mixing by rotation, the firstly shown order is preferable. In this case, in an initial stage, a so-called W/O type emulsion is obtained in which PHA and a magnetic substance assume a continuous phase, and an water phase forms a dispersion phase. As the added amount of an water phase component increases, a W/O type is converted to an O/W type, whereby pulverization of an oil phase is promoted.

An organic solvent can be removed by a known method. Examples of such a method include: a method of evaporating an organic solvent at atmospheric pressure or by gradually reducing the pressure while stirring the organic solvent with a propeller stirrer, a magnetic stirrer, or the like; and a method of evaporating an organic solvent while regulating the vacuum degree with a rotary evaporator or the like. When the O/W type emulsion is subjected to submerged dry, an organic solvent is volatized, and a structure such as a microcapsule is solidified, whereby the configuration thereof is determined. The structure thus obtained is aliquoted by centrifugation or filtering, a free drug, a drug holding material, an emulsifier, or the like adhering to the surface of the structure is washed with distilled water several times, and the remainder is re-dispersed in distilled water or the like, followed by freeze-drying.

<Phase Separation Method—Inclusion of Lipophilic Drug—>

In the case of producing a structure such as a microcapsule by a phase separation method, a coacervation agent is gradually added to an organic solvent solution containing a drug, a magnetic substance, and PHA at a constant speed with stirring to precipitate and solidify PHA. The coacervation agent is added in a volume amount of about 0.01 times to about 1,000 times, preferably about 0.05 times to about 500 times, and particularly preferably about 0.1 times to about 200 times the volume of the organic solvent solution of a drug and PHA. The coacervation agent may be a compound of a polymer type, a mineral oil type, or a plant oil type that is miscible with a solvent of PHA and does not dissolve PHA. Specific examples of the coacervation agent include silicone oil, sesame oil, soybean oil, corn oil, cottonseed oil, coconut oil, linseed oil, mineral oil, n-hexane, n-heptane, methanol, and ethanol.

The above-mentioned coacervation agents may be used in combination of two or more kinds. The structure such as a microcapsule thus obtained is aliquoted by filtration, and repeatedly washed with heptane or the like. The coacervation agent is removed, and a free drug and a solvent are removed further.

<Microcapsule and Method of Producing the same—Inclusion of Liquid Phase—>

The microcapsule in the present invention can be formed as a structure in a fine particle shape in which PHA is contained in a shell portion, a core portion has at least a liquid phase, and a magnetic substance is contained in the shell portion and/or the core portion. The form has been described above in detail.

The microcapsule is produced by microcapsulation of, for example, a W/O type emulsion containing an internal water phase and an oil phase having PHA and a magnetic substance, a W/O/W type emulsion obtained by further emulsifying the W/O type emulsion to an external water phase; or an O/W type emulsion containing an internal oil phase of a solution containing an oil phase having PHA and a magnetic substance, and an external water phase. The microcapsulation is performed by, for example, a submerged dry method, a phase separation method, a spray dry method, or methods similar thereto.

The following in-vitro synthesis method of preparing a microcapsule also can be preferably used. A W/O type emulsion containing as an internal water phase a solution of PHA synthetic enzyme and 3-hydroxyacyl CoA, a W/O/W type emulsion obtained by emulsifying a W/O type emulsion composed of an internal water phase and an oil phase to an external water phase (PHA synthetic enzyme and 3-hydroxyacyl CoA are contained in at least one of the internal water phase and the external water phase), an O/W type emulsion containing as an external water phase a solution of PHA synthetic enzyme and 3-hydroxyacyl CoA, or an O/W/O type emulsion obtained by further emulsifying the O/W type emulsion to an external oil phase is produced, and a PHA synthesis reaction is effected, whereby a microcapsule is prepared.

<Preparation of W/O Type Emulsion—Inclusion of Liquid Phase—>

A W/O type emulsion composed of an internal water phase and an oil phase containing PHA and a magnetic substance can be prepared as described below.

First, water used in an internal water phase can be formed as an aqueous solution in which an inorganic salt or an organic salt is dissolved in order to match the specific gravity thereof with that of an organic solvent solution in an external oil phase. Examples of the inorganic salt include calcium chloride, sodium chloride, potassium chloride, calcium bromide, sodium bromide, sodium carbonate, sodium hydrogen carbonate, potassium carbonate and potassium hydrogen carbonate.

Furthermore, examples of the organic salt include sodium salts and potassium salts, of organic acids (e.g., acetic acid, oxalic acid, citric acid, tartaric acid, succinic acid, and phosphoric acid, ascorbic acid). Among those, according to the present invention, in terms of the economy, ease of adjustment of specific gravity, and ease of washing, an aqueous solution of calcium chloride is particularly desirably used. Those inorganic salts or organic salts are added to water in concentration of about 1 to 60 (weight/volume)%, and preferably about 20 to 50 (weight/volume)% in order to match the specific gravity thereof with that of an organic solvent solution of PHA and a magnetic substance. Thus, a W/O type emulsion in which water droplets are uniformly dispersed in an oil phase can be obtained.

The thus obtained internal water phase is mixed with a solution (oil phase) containing PHA and a magnetic substance, followed by an emulsification operation, to prepare a W/O type emulsion. A known method is used for the emulsification operation. Examples of the method include: an intermittent shaking method; a stirring method using a mixer such as a propeller stirrer or a turbine stirrer; a colloid mill method; a homogenizer method; and an ultrasonic irradiation method. According to the present invention, those methods may be combined appropriately. In particular, primary emulsification for preparing the W/O type emulsion is important for assuring the uniformity of a microcapsule configuration that is the final object. It is necessary that the internal water phase be dispersed as uniformly as possible in an organic solvent solution containing PHA in this stage. In view of this, it is preferable to minimize the diameter of water droplets of an internal water phase, so that a combination of an ultrasonic irradiation method and another dispersion method is adopted preferably.

The above-mentioned solution (oil phase) containing PHA and a magnetic substance is obtained by dissolving the PHA in an organic solvent that is substantially unmiscible with water. The solubility of the organic solvent in water is preferably 3 mass % or less at room temperature (20° C.). Furthermore, the boiling point of the organic solvent is preferably 120° C. or lower. Examples of the organic solvent include: halogenated hydrocarbons (dichloromethane, chloroform, chloroethane, dichloroethane, trichloroethane, carbon tetrachloride, etc.); ketones (acetone, methyl ethyl ketone, methyl isobutyl ketone, etc.); ethers (tetrahydrofuran, ethyl ether, isopropyl ether, etc.); esters (ethyl acetate, butyl acetate, etc.); and aromatic hydrocarbons (benzene, toluene, xylene, etc.). Those may be used in combination of two or more kinds in an appropriate ratio. The organic solvent is more preferably a halogenated hydrocarbon (dichloromethane, chloroform, chloroethane, dichloroethane, trichloroethane, carbon tetrachloride, etc.). The concentration of PHA in an oil phase varies depending upon the kind and molecular weight of the PHA, and the kind of a solvent. The concentration is preferably about 0.01 to 80 mass %, more preferably about 0.1 to 70 mass %, and particularly preferably about 1 to 60 mass %.

Examples of the magnetic substances to be dispersed in the oil phase include metal or metal compounds having magnetism. More specific examples thereof include: various kinds of ferrites such as triiron tetraoxide ($Fe_3O_4$), γ-diiron trioxide (γ-$Fe_2O_3$), MnZn ferrite, NiZn ferrite, YFe garnet, GaFe garnet, Ba ferrite, and Sr ferrite; metal such as iron, manganese, cobalt, nickel, and chromium; and alloys of iron, manganese, cobalt, nickel, and the like. The prescription amount of the magnetic substances in the oil phase varies depending on the kind of the magnetic substances, the kind of the solvent, the prescription amount of PHA, and the like. The magnetic substance may be prescribed so that the amount of the magnetic substance in the structure is 1 to 80 mass %, preferably 5 to 70 mass %, more preferably 10 to 60 mass %.

In order to change the compatibility with an internal water phase, the distribution, volatilization, and the like of an organic solvent to an external water phase as described below, an organic solvent that is partially hydrophilic (ethanol, acetonitrile, acetone, tetrahydrofuran, etc.) may be added to an oil phase. Furthermore, although depending upon the stability of PHA, the solution containing PHA may be stored in a sealed container at room temperature or a cool place.

The mixing ratio of the organic solvent solution containing PHA is about 0.1 to 1,000 parts by weight, and preferably about 1 to 100 parts by weight with respect to one part by weight of the aqueous solution.

<Preparation of W/O/W Type Emulsion and Submerged Dry Method—Inclusion of Liquid Phase—>

Then, the thus obtained W/O type emulsion is subjected to a microcapsulation step. For example, in the case of performing microcapsulation by a submerged dry method or the like, the W/O type emulsion is further added to an water phase (external water phase) to produce a W/O/W type emulsion. After that, an organic solvent in the oil phase is removed to prepare a microcapsule.

The volume of an external water phase is generally selected from about 1 to about 10,000 times, preferably about 2 to about 5,000 times, and particularly preferably about 5 to about 2,000 times the volume of an oil phase.

An emulsifier may be added to the external water phase. As an example, generally, any emulsifier that forms a stable W/O/W type emulsion may be used. Examples of the emulsifier include: an anionic surfactant (sodium oleate, sodium stearate, sodium lauryl sulfate, etc.); a nonionic surfactant (polyoxyethylene sorbitan fatty acid ester (Tween 80 or Tween 60, available from Atlas Powder Company (U.S.)); a polyoxyethylene castor oil derivative (HCO-70, HCO-60, HCO-50, produced by Nikko Chemicals Co., Ltd.), etc.); and polyvinyl pyrrolidone, polyvinyl alcohol, carboxymethylcellulose, lecitin, gelatin, hyaluronic acid, and derivatives thereof. Those emulsifiers may be used alone or in combination. The concentration of the emulsifier in the external water phase is appropriately determined from the range of about 0.01 to 20 mass %, and preferably about 0.05 to 10 mass %.

An osmoregulatory agent may be added to the external water phase. Any material exhibiting an osmotic pressure may be used as the osmoregulatory agent in the case of an aqueous solution used in the present invention. Specific examples of the osmoregulatory agent include: water-soluble polyhydric alcohols; water-soluble monohydric alcohols, water-soluble monosaccharides, disaccharides, and oligosaccharides and derivatives thereof; water-soluble amino acids; water-soluble peptides, protein, and derivatives thereof.

Examples of the above water-soluble polyhydric alcohols include: dihydric alcohols such as glycerin; pentahydric alcohols such as arabitol, xylitol, and adonitol; and hexahydric alcohols such as mannitol, sorbitol, and dulcitol. Of those, hexahydric alcohols are preferable. Of those, mannitol is particularly preferable. Examples of the above water-soluble monohydric alcohols include methanol, ethanol, and isopropyl alcohol. Of those, ethanol is preferable. Examples of the water-soluble monosaccharides include: pentoses such as arabinose, xylose, ribose, and 2-deoxyribose; and hexoses such as glucose, fructose, galactose, mannose, sorbose, rhamnose, and fucose. Of those, hexoses are preferable. Examples of the water-soluble disaccharides include maltose, cellobiose, α,α-trehalose, lactose, and sucrose. Of those, lactose and sucrose are preferable. Examples of the above water-soluble oligosaccharides include: trisaccharides such as maltotriose and raffinose; and tetrasaccharides such as stachyose. Of those, trisaccharides are preferable. Examples of derivatives of the above water-soluble monosaccharides, disaccharides, and oligosaccharides include glucosamine, galactosamine, glucuronic acid, and galacturonic acid.

Examples of the above water-soluble amino acids include: neutral amino acids such as glycine, alanine, valine, leucine, isoleucine, phenylalanine, tyrosine, tryptophan, serine, threonine, proline, hydroxyproline, cysteine, and methionine; acidic amino acids such as aspartic acid and glutamic acid; and basic amino acids such as lysine, arginine, and histidine. In addition, salts of those water-soluble amino acids with acids (for example, hydrochloric acid, sulfuric acid, and phosphoric acid) or with alkalis (for example, alkali metals such as sodium and potassium) may be used. Examples of the water-soluble peptides, proteins, and derivatives thereof include casein, globulin, prolamin, albumin, and gelatin.

Among the above-mentioned osmoregulatory agents, water-soluble polyhydric alcohols, and water-soluble monosaccharides, disaccharides, and oligosaccharides and derivatives thereof are preferable. Water-soluble polyhydric alcohols and water-soluble monosaccharides are more preferable. Water-soluble polyhydric alcohols are particularly preferable. Those osmoregulatory agents may be used alone or in combination. Those osmoregulatory agents are used in such a concentration that the osmotic pressure of an external water phase is about 1/50 to about 5 times, preferably about 1/25 to about 3 times the osmotic pressure of a physiological saline. Specifically, the concentration of the osmoregulatory agent in an external water phase is about 0.001 to 60 mass %, preferably about 0.01 to 4.0 mass %, more preferably about 0.05 to 30 mass %, and particularly preferably about 1 to 10 mass %, in the case where the osmoregulatory agent is a nonionic material. Furthermore, in the case where the osmoregulatory agent is an ionic material, the concentration obtained by dividing the above-mentioned concentration by an entire ionic valence is used. The addition concentration of the osmoregulatory agent is not required to be equal to or lower than a solubility, and the osmoregulatory agent may be partially dispersed.

When the W/O type emulsion is emulsified into water, the W/O type emulsion is dispersed in water, followed by stirring. Any of the above-mentioned emulsifying methods can be adopted as a stirring operation. It is particularly preferable to use a homogenizer in terms of obtaining microcapsules of an organic solvent solution having a configuration in which water is enveloped with a single layer of an organic solvent solution phase. In the case of using a homogenizer, the homogenizer is operated at 100 to 100,000 rpm, preferably 1,000 to 50,000 rpm for 0.1 to 30 minutes, preferably 0.5 to 20 minutes.

The above-mentioned operation can reduce the outer diameter of W/O type emulsion droplets in an external water phase. That is, stirring with a homogenizer is effective for reducing the outer diameter of W/O type emulsion droplets without changing the dispersed state: of an water phase in W/O type emulsion droplets. Herein, to decrease the outer diameter of W/O type emulsion droplets to 1 to 20 µm is important for final microcapsules to have a polymer single film structure. Next, in this state, the W/O type emulsion droplets are allowed to stand with stirring using a propeller stirrer or the like. At this time, an internal water phase in the W/O type emulsion droplets is unstable. Therefore, before PHA is solidified, the water phase is joined to be mixed to form one large water droplet. On the other hand, the W/O type emulsion itself is stabilized with an emulsifier in an external water phase. Consequently, formed is a capsule configuration in which an internal water phase is covered with a single layer of an organic solvent solution phase of PHA.

In order to promote the formation of W/O type emulsion droplets having such a capsule configuration, it is preferable to appropriately adjust the kind and amount of a salt in an internal water phase, the concentration of a polymer in an oil phase, each temperature of the oil phase (W/O type emulsion droplets) and an external water phase that emulsifies the oil phase, and the amount ratio between the oil phase and the water phase. In particular, by using an inorganic salt in an internal water phase, the surface tension of the internal water phase is increased, instability of an water phase is promoted, water phases in the W/O type emulsion droplets during formation of particles are joined to be mixed, and the ratio of an emulsion having a single film configuration is increased.

According to the production method of the present invention, when a W/O/W type emulsified substance is formed, it is preferable that the viscosity of a W/O type emulsified substance be adjusted in the range of 50 cp to 10,000 cp. Examples of the method of adjusting the viscosity include (1) a method involving adjusting the concentration of PHA and a magnetic substance in an oil phase, (2) a method involving adjusting the amount ratio between an water phase and an oil phase, (3) a method involving adjusting the temperature of a W/O type emulsified substance, (4) a method involving adjusting the temperature of an external water phase, and (5) a method involving adjusting the temperature of a W/O type emulsified substance with, for example, a line heater or a cooler when the W/O type emulsified substance is injected to an external water phase. Those methods may be used alone or in combination. The point is that when the W/O type emulsified substance is formed into a W/O/W type emulsified substance using the above method, the viscosity of the W/O type emulsified substance only needs to be in the range of 50 cp to 10,000 cp. In the above (1), in the case of adjusting the concentration of PHA in an oil phase, the concentration of PHA is not determined uniquely since the concentration varies depending upon the kind of PHA, the kind of an organic solvent, and the like. The concentration of PHA is preferably about 10 to 80 mass %. In the above (2), the amount ratio between the water phase and the oil phase is not determined uniquely by the property of the oil phase and the like, but is preferably W/O=about 1 to 50 (volume)%. In the above (3), in the case of adjusting the temperature of a W/O type emulsified substance, the temperature is, for example, in the range of about −20° C. to the boiling point of an organic solvent, preferably about 0 to 30° C., and more preferably about 10 to 20° C. In the cases of the above (1) and (2), the viscosity of the W/O type emulsified substance can be adjusted in the course of producing the W/O type emulsified substance. Furthermore, in the above (4), for example, when the W/O type emulsified substance is added to an external water phase, the temperature of the external water phase is previously adjusted, whereby the same results as those in the above (3) may be obtained. The temperature of the external water phase is, for example, about 5 to 30° C., preferably about 10 to 25° C., and more preferably about 12 to 20° C.

An organic solvent can be removed by a known method. Examples of such a method include: a method of evaporating an organic solvent at atmospheric pressure or by gradually reducing the pressure while stirring the organic solvent with a propeller stirrer, a magnetic stirrer, or the like; and a method of evaporating an organic solvent while regulating the vacuum degree and temperature with a rotary evaporator or the like.

After that, microcapsules are aliquoted by centrifugation or filtering, an emulsifier and the like adhering to the surface of the microcapsules are washed with distilled water repeatedly several times if required. Furthermore, the microcapsules are dried under reduced pressure or re-dispersed in distilled water, followed by freeze-drying or the like, whereby remaining solvent and water are removed. Further, microcapsule slurry prepared in the above-mentioned step may be dispersed as it is in an appropriate dispersion medium and used. A dispersant may be added when the microcapsules are re-dispersed in distilled water. The dispersant has a function of preventing the aggregation of the microcapsules. Examples of the dispersant include a Tween 80 surfactant, sucrose fatty acid ester, mannitol, sorbitol, glucose, galactose, and sucrose. This dispersant is used by being dissolved in water in concentration of about 0.001 to 30 mass %.

Furthermore, the microcapsules having a PHA single film configuration thus produced may be re-dispersed as they are. Since some of them have a porous structure, they may be washed and then, centrifuged at a low speed into a non-precipitate and a precipitate. The centrifugation is appropriately performed at about 50 to 3,000 rpm for 1 to 60 minutes. Furthermore, the centrifugation is preferably performed several times.

As a result of the centrifugation, microcapsules of a single film configuration composed of PHA is collected in a non-precipitate phase. Furthermore, in order to obtain dry microcapsules, drying under reduced pressure while heating, freeze-drying, and the like, if required, can be used. It is preferable to use freeze-drying.

Thus, microcapsules with a particle size of 1 to 10 µm are obtained. The microcapsules have a spherical shape without pores on the capsule surface of as described later in examples.

<Phase Separation Method—Inclusion of Liquid Phase—>

In the case of performing microcapsulation by a phase separation method, a coacervation agent is added gradually to a W/O type emulsion with stirring, and PHA is precipitated and solidified, whereby microcapsules are prepared. A compound of a polymer type, a mineral oil type, or a plant oil type that is miscible with a solvent of PHA but does not dissolve PHA for capsulation may be used as the coacervation agent. Examples of the coacervation agent include silicone oil, sesame oil, soybean oil, corn oil, cottonseed oil, coconut oil, linseed oil, mineral oil, n-hexane, n-heptane, methanol, and ethanol. Those compounds may be used in combination of two or more kinds. The use amount of the coacervation agent is, for example, about 0.01 to 1,000 volume times, and preferably about 0.1 to 200 volume times with respect to the W/O type emulsion. The microcapsules thus obtained are aliquoted by centrifugation or filtering, and washed repeatedly with a surfactant such as hexane or heptane to remove the coacervation agent. After that, the resultant microcapsules are heated or placed under reduced pressure to evaporate the surfactant. Furthermore, if desired, an organic solvent is removed in the same way as the case of the above-mentioned submerged drying method.

<Spray Drying Method—Inclusion of Liquid Phase—>

In the case of performing microcapsulation by a spray drying method, a W/O type emulsion or a W/O/W type emulsion produced in the same way as in the case of the submerged drying method is sprayed to a dry chamber of a spray drier apparatus (spray drier) using a nozzle to volatilize an organic solvent and water in pulverized liquid droplets in a very short period of time, whereby microcapsules in the shape of fine particle are prepared. The nozzle may be of, for example, a two-liquid nozzle type, a pressure nozzle type, and a rotary disk type. The microcapsules thus obtained are washed several times repeatedly with distilled water, if desired, to remove an emulsifier and the like adhering to the surface of the microcapsules. Then, the organic solvent may be further removed by drying the washed microcapsules under reduced pressure or re-dispersing them in distilled water, followed by freeze-drying.

<Preparation of O/W Type Emulsion—Inclusion of Liquid Phase—>

In the case of producing microcapsules by a submerged drying method, generally, an oil phase containing PHA, a magnetic substance, and an organic solvent is dispersed in an water phase to form an O/W type emulsion, and the organic solvent in the oil phase is removed, whereby microcapsules are produced. The volume of the water phase is generally selected from about 1 to about 10,000 times, preferably about 2 to about 5,000 times, more preferably about 5 to about 2,000 times, and particularly about 50 to about 1,000 times the volume of the oil phase. The temperature of the water phase may be previously adjusted to, for example, about 5° C. to about 30° C., preferably about 10° C. to about 25° C., and more preferably about 10° C. to about 20° C. An emulsifier may be added to the water phase. Any emulsifier may be used, which is generally capable of forming a stable O/W type emulsion, and the above-mentioned emulsifiers can be used preferably. The concentration of the emulsifier during use can be selected appropriately from the range of about 0.001 to about 20% (mass/volume). The emulsifier is used in the range of preferably about 0.01 to about 10% (mass/volume), and more preferably about 0.05 to about 5% (mass/volume). Furthermore, in an emulsifying process, various kinds of the above-mentioned known mixers can be used.

In particular, emulsification for preparing an O/W type emulsion is important for ensuring the uniformity of a microcapsule configuration that is the final object. It is important to disperse an internal oil phase containing PHA and a magnetic substance in an external water phase as uniformly as possible at this stage. For this purpose, it is preferable to minimize the liquid droplet diameter of the internal oil phase, so that a combination of an ultrasonic irradiation method with another dispersion method is adopted preferably.

In an embodiment of supplying components for producing an O/W type emulsion of the present invention, various methods can be performed in accordance with a known technique. Examples of the method include: a method involving previously placing a solution containing PHA in a container and adding an water phase component containing an emulsifier thereto; a method involving previously placing an water phase component containing an emulsifier in a container and adding a solution containing PHA thereto; and a method involving continuously supplying both of them at a constant ratio. In the case of mixing by rotation, the firstly shown order is preferable. Formed initially in this case is a so-called W/O type emulsion in which PHA and a magnetic substance form a continuous phase, and an water phase forms a dispersion phase. In accordance with an increase in an addition amount of an water phase component, a W/O phase is changed to an O/W phase, and pulverization from an oil phase is promoted.

An organic solvent can be removed in accordance with the above-mentioned method. It is possible that the microcapsule thus obtained be aliquoted by centrifugation or filtration if required, and thereafter, an emulsifier and the like adhering to the surface of the microcapsule be washed repeatedly several times with distilled water, and the remainder be re-dispersed in distilled water or the like, followed by freeze-drying. Alternatively, a microcapsule slurry prepared in the above-mentioned step may be dispersed directly in an appropriate dispersion medium.

<Hollow Structure and Method of Producing the same>

The hollow structure such as a hollow microcapsule in the present invention can have a form of fine particle containing air bubbles at least in an inner portion, and containing PHA in its capsule coating. The form has been described above in detail.

The hollow structure available to an ultrasonic contrast agent of the present invention is produced as follows. Based on, for example, a W/O type emulsion containing an internal water phase and an oil phase of a solution containing an organic solvent, a magnetic substance, and PHA, a W/O/W type emulsion obtained by further emulsifying the W/O type emulsion to an external water phase; or an O/W type emulsion containing an internal oil phase of a solution containing an organic solvent, a magnetic substance, and PHA, and an external water phase, PHA in the oil phase is solidified to be a hollow microcapsule. The hollow microcapsulation is performed by, for example, a submerged dry method, a phase separation method, a spray dry method, or methods similar thereto.

The following in-vitro synthesis method of preparing a hollow structure also can be preferably used. A W/O type emulsion containing as an internal water phase a solution of PHA synthetic enzyme and 3-hydroxyacyl CoA, a W/O/W type emulsion obtained by emulsifying a W/O type emulsion composed of an internal water phase and an oil phase to an external water phase (PHA synthetic enzyme and 3-hydroxyacyl CoA are contained in at least one of the internal water phase and the external water phase), an O/W type emulsion containing as an external water phase a solution of PHA synthetic enzyme and 3-hydroxyacyl CoA, or an O/W/O type emulsion obtained by emulsifying the O/W type emulsion to an external oil phase is produced, and a PHA synthesis reaction is effected in an water phase, followed by capsulation, whereby a hollow structure is prepared.

<Preparation of W/O Type Emulsion—Hollow Structure—>

A W/O type emulsion composed of an internal water phase and an oil phase containing PHA and a magnetic substance, which is used for producing the hollow structure of the present invention, can be prepared as described below.

First, water used in an internal water phase can be formed as an aqueous solution in which an inorganic salt or an organic salt is dissolved if required, in order to match the specific gravity thereof with that of an organic solvent solution in an external oil phase. Examples of the inorganic salt include calcium chloride, sodium chloride, potassium chloride, calcium bromide, sodium bromide, sodium carbonate, sodium hydrogen carbonate, potassium carbonate and potassium hydrogen carbonate. Furthermore, examples of the organic salt include sodium salts and potassium salts, of organic acids (e.g., acetic acid, oxalic acid, citric acid, tartaric acid, succinic acid, and phosphoric acid, ascorbic acid).

Among the above-mentioned water-soluble salts, according to the present invention, in terms of the economy, ease of adjustment of specific gravity, and ease of washing, calcium chloride is particularly desirably used. Those inorganic salts or organic salts are added to water in a concentration of about 1 to 60 (mass/volume)%, and preferably about 20 to 50 (mass/volume)% in order to match the specific gravity thereof with that of an organic solvent solution of PHA. In such a concentration, the difference in specific gravity between an aqueous solution and an oil phase containing PHA and a magnetic substance is eliminated, whereby a W/O type emulsion in which water droplets are uniformly dispersed in an oil phase can be obtained.

An aqueous solution subjected to the above-mentioned specific gravity adjustment to be an internal water phase is mixed with a solution (oil phase) containing PHA and a magnetic substance, followed by an emulsification operation, to prepare a W/O type emulsion. A known method is used for the emulsification operation. Examples of the method include: an intermittent shaking method; a stirring method using a mixer such as a propeller stirrer or a turbine stirrer; a colloid mill method; a homogenizer method; and an ultrasonic irradiation method. According to the present invention, those methods may be combined appropriately. In particular, primary emulsification for preparing the W/O type emulsion is important for assuring the uniformity of a hollow configuration of an intended hollow structure. This is because the diameter of water droplets of the internal water phase of the W/O type emulsion defines the size of a hollow portion of a hollow structure to be formed and the outer diameter of the hollow structure. That is, in order to allow any hollow structure to have one film hollow configuration of the same degree, it is necessary that the internal water phase be dispersed as uniformly possible in an organic solvent solution containing PHA and a magnetic substance in this stage. In addition, in order to use the produced hollow structure as an ultrasonic contrast agent, the outer diameter of the hollow structure is desirably set to be 10 μm or less, for example. In view of this, it is preferable to minimize the diameter of water droplets of an internal water phase, so that a combination of an ultrasonic irradiation method and another dispersion method is adopted preferably.

The above-mentioned solution (oil phase) containing PHA and a magnetic substance is obtained by dissolving the PHA in an organic solvent that is substantially unmiscible with water. The solubility of the organic solvent in water is preferably 3 mass % or less at room temperature (20° C.). Furthermore, the boiling point of the organic solvent is preferably 120° C. or lower. Examples of the organic solvent include: halogenated hydrocarbons (dichloromethane, chloroform, chloroethane, dichloroethane, trichloroethane, carbon tetrachloride, etc.); ketones (acetone, methyl ethyl ketone, methyl isobutyl ketone, etc.); ethers (tetrahydrofuran, ethyl ether, isopropyl ether, etc.); esters (ethyl acetate, butyl acetate, etc.); and aromatic hydrocarbons (benzene, toluene, xylene, etc.). Those organic solvents may be used in combination of two or more kinds in an appropriate ratio. The organic solvent is more preferably a halogenated hydrocarbon (dichloromethane, chloroform, chloroethane, dichloroethane, trichloroethane, carbon tetrachloride, etc.). The concentration of PHA in an oil phase varies depending upon the kind and molecular weight of the PHA, and the kind of a solvent. The concentration is preferably about 0.01 to 80 mass %, more preferably about 0.1 to 70 mass %, and particularly preferably about 1 to 60 mass %.

Examples of the magnetic substances to be dispersed in the oil phase include metal or metal compounds having magnetism. More specific examples thereof include: various kinds of ferrites such as triiron tetraoxide ($Fe_3O_4$), γ-diiron trioxide (γ-$Fe_2O_3$), MnZn ferrite, NiZn ferrite, YFe garnet, GaFe garnet, Ba ferrite, and Sr ferrite; metal such as iron, manganese, cobalt, nickel, and chromium; and alloys of iron, manganese, cobalt, nickel, and the like. The prescription amount of the magnetic substances in the oil phase varies depending on the kind of the magnetic substances, the kind of the solvent, the prescription amount of PHA, and the like. The magnetic substance may be prescribed so that the amount of the magnetic substance in the structure is 1 to 80 mass %, preferably 5 to 70 mass %, more preferably 10 to 60 mass %.

In order to change the compatibility with an internal water phase, the distribution, volatilization, and the like of an organic solvent to an external water phase, an organic solvent that is partially hydrophilic (ethanol, acetonitrile, acetone, tetrahydrofuran, etc.) may be added to an oil phase. Furthermore, although depending upon the stability of PHA, after a solution containing PHA is prepared, the solution may be stored in a sealed container at room temperature or a cool place.

The mixing ratio of the organic solvent solution containing PHA is about 0.1 to 1,000 parts by mass, and preferably about 1 to 100 parts by mass with respect to one part by mass of the aqueous solution.

<Preparation of W/O/W Type Emulsion and Submerged Dry Method—Hollow Structure—>

Then, the obtained W/O type emulsion is subjected to a hollow microcapsulation step. For example, in the case of performing hollow microcapsulation by a submerged dry method or the like, the W/O type emulsion is added to an water phase (hereinafter, the resultant phase is abbreviated as an external water phase) to produce a W/O/W type emulsion. After that, an organic solvent in the oil phase is removed to prepare a hollow structure.

The volume of an external water phase is generally selected from about 1 to about 10,000 times, preferably about 2 to about 5,000 times, and particularly preferably about 5 to about 2,000 times the volume of an oil phase.

An emulsifier may be added to the external water phase. As an example, generally, any emulsifier that forms a stable W/O/W type emulsion may be used. Examples of the emulsifier include: an anionic surfactant (sodium oleate, sodium stearate, sodium lauryl sulfate, etc.); a nonionic surfactant (polyoxyethylene sorbitan fatty acid ester (Tween 80 or Tween 60, produced by Atlas Powder Company (U.S.), etc.); a polyoxyethylene castor oil derivative (HCO-70, HCO-60, HCO-50, produced by Nikko Chemical Co., Ltd.), etc.); and polyvinylpyrrolidone, polyvinyl alcohol, carboxymethylcellulose, lecitin, gelatin, hyaluronic acid, and derivatives thereof. Those emulsifiers may be used alone or in combination. The concentration of the emulsifier in the external water phase is appropriately determined from the range of about 0.01 to 20 mass %, and preferably about 0.05 to 10 mass %.

An osmoregulatory agent may be added to the external water phase. Any material exhibiting an osmotic pressure may be used as the osmoregulatory agent in the case of an aqueous solution used in the present invention. Specific examples of the osmoregulatory agent include: water-soluble polyhydric alcohols; water-soluble monohydric alcohols; water-soluble monosaccharides, disaccharides, and oligosaccharides and derivatives thereof; water-soluble amino acids; water-soluble peptides, protein, and derivatives thereof.

Examples of the above water-soluble polyhydric alcohols include: dihydric alcohols such as glycerin; pentahydric alcohols such as arabitol, xylitol, and adonitol; and hexahydric alcohols such as mannitol, sorbitol, and dulcitol. Of those, hexahydric alcohols are preferable. Of those, mannitol is particularly preferable. Examples of the above water-soluble monohydric alcohols include methanol, ethanol, and isopropyl alcohol. Of those, ethanol is preferable. Examples of the water-soluble monosaccharides include: pentoses such as arabinose, xylose, ribose, and 2-deoxyribose; and hexoses such as glucose, fructose, galactose, mannose, sorbose, rhamnose, and fucose. Of those, hexoses are preferable. Examples of the water-soluble disaccharides include maltose, cellobiose, α,α-trehalose, lactose, and sucrose. Of those, lactose and sucrose are preferable. Examples of the above water-soluble oligosaccharides include: trisaccharides such as maltotriose and raffinose; and tetrasaccharides such as stachyose. Of those, trisaccharides are preferable. Examples of derivatives of the above water-soluble monosaccharides, disaccharides, and oligosaccharides include glucosamine, galactosamine, glucuronic acid, and galacturonic acid.

Examples of the above water-soluble amino acids include: neutral amino acids such as glycine, alanine, valine, leucine, isoleucine, phenylalanine, tyrosine, tryptophan, serine, threonine, proline, hydroxyproline, cysteine, and methionine; acidic amino acids such as asparaginic acid and glutamic acid; and basic amino acids such as lysine, arginine, and histidine. In addition, salts of those water-soluble amino acids with acids (for example, hydrochloric acid, sulfuric acid, and phosphoric acid) or with alkalis (for example, alkali metals such as sodium and potassium) may be used. Examples of the water-soluble peptides, proteins, and derivatives thereof include casein, globulin, prolamin, albumin, and gelatin.

Among the above-mentioned osmoregulatory agents, water-soluble polyhydric alcohols, and water-soluble monosaccharides, disaccharides, and oligosaccharides and derivatives thereof are preferable. Water-soluble polyhydric alcohols and water-soluble monosaccharides are more preferable. Water-soluble polyhydric alcohols are particularly preferable. Those osmoregulatory agents may be used alone or in combination. Those osmoregulatory agents are used in such a concentration that the osmotic pressure of an external water phase is about 1/50 to about 5 times, preferably about 1/25 to about 3 times the osmotic pressure of a physiological saline. Specifically, the concentration of the osmoregulatory agent in an external water phase is about 0.001 to 60 mass %, preferably about 0.01 to 40 mass %, more preferably about 0.05 to 30 mass %, and particularly preferably about 1 to 10 mass %, in the case where the osmoregulatory agent is a nonionic material. Furthermore, in the case where the osmoregulatory agent is an ionic material, the concentration obtained by dividing the above-mentioned concentration by an entire ionic valence is used. The addition concentration of the osmoregulatory agent is not required to be equal to or lower than a solubility, and the osmoregulatory agent may be partially dispersed.

When the W/O type emulsion is emulsified into water, the W/O type emulsion is dispersed in water, followed by stirring. Any of the above-mentioned emulsifying methods can be adopted as a stirring operation. It is particularly preferable to use a homogenizer in terms of obtaining emulsion particles (microcapsules) of an organic solvent solution having a configuration in which water is enveloped with a single layer of an organic solvent solution phase. In the case of using a homogenizer, the homogenizer is operated at 100 to 100,000 rpm, preferably 1,000 to 50,000 rpm for 0.1 to 30 minutes, preferably 0.5 to 20 minutes.

The above-mentioned operation can reduce the outer diameter of W/O type emulsion droplets in an external water phase. That is, stirring with a homogenizer is effective for reducing the outer diameter of W/O type emulsion droplets without changing the dispersed state of an water phase in a W/O type emulsion droplets. Herein, to decrease the outer diameter of W/O type emulsion droplets to 1 to 20 μm is important for final fine particles to have a polymer single film configuration. Next, in this state, the W/O type emulsion droplets are allowed to stand with stirring using a propeller stirrer or the like. At this time, an internal water phase in the W/O type emulsion droplets is unstable. Therefore, before PHA is solidified, fine water droplets are joined to be mixed to form one larger fine water droplet. On the other hand, the W/O type emulsion itself is stabilized with an emulsifier in an external water phase. Consequently, formed is a capsule configuration in which an internal water phase is covered with a single layer of an organic solvent solution phase of PHA and a magnetic substance.

In order to promote the formation of W/O type emulsion droplets having such a capsule configuration, it is preferable to appropriately adjust the kind and amount of a salt in an internal water phase, the concentration of a polymer in an oil phase, each temperature of the oil phase (W/O type emulsion droplets) and an external water phase that emulsifies the oil phase, and the amount ratio between the oil phase and the water phase. In particular, by using an inorganic salt in an internal water phase, the surface tension of the internal water phase is increased, instability of an water phase is promoted, water phases in the W/O type emulsion droplets during formation of particles are joined to be mixed, and the ratio of an emulsion having a single film configuration is increased.

According to the production method of the present invention, when a W/O/W type emulsified substance is formed, it is preferable that the viscosity of a W/O type emulsified substance be adjusted in the range of 50 cp to 10,000 cp. Examples of the method of adjusting the viscosity include (1) a method involving adjusting the concentration of PHA and a magnetic substance in an oil phase, (2) a method involving adjusting the amount ratio between an water phase and an oil phase, (3) a method involving adjusting the temperature of a W/O type emulsified substance, (4) a method involving adjusting the temperature of an external water phase, and (5) a method involving adjusting the temperature of a W/O type emulsified substance with, for example, a line heater or a cooler when the W/O type emulsified substance is injected to an external water phase. Those methods may be used alone or in combination. When the W/O type emulsified substance is formed into a W/O/W type emulsified substance using the above method, the viscosity of the W/O type emulsified substance only needs to be adjusted temporarily to be in the range of 50 cp to 10,000 cp. In the above (1), in the case of adjusting the concentration of PHA in an oil phase, the concentration of PHA is not determined uniquely since the concentration varies depending upon the kind of PHA, the kind of an organic solvent, and the like. The concentration of PHA is preferably about 10 to 80 mass %. In the above (2), the amount ratio between the water phase and the oil phase is not determined uniquely by the property of the oil phase and the like, but is preferably W/O=about 1 to 50 (volume/volume)%. In the above (3), in the case of adjusting the temperature of a W/O type emulsified substance, the temperature is, for example, in the range of about −20° C. to the boiling point of an organic solvent, preferably about 0 to 30° C., and more preferably about 10 to 20° C. In the cases of the above (1) and (2), the viscosity of the W/O type emulsified substance can be adjusted in the course of producing the W/O type emulsified substance. Furthermore, in the above (4), for example, when the W/O type emulsified substance is added to an external water phase, the temperature of the external water phase is previously adjusted, whereby the same results as those in the above (3) may be obtained. The temperature of the external water phase is, for example, about 5 to 30° C., preferably about 10 to 25° C., and more preferably about 12 to 20° C.

An organic solvent can be removed by a known method. Examples of such a method include: a method of evaporating an organic solvent at atmospheric pressure or by gradually reducing the pressure while stirring the organic solvent with a propeller stirrer, a magnetic stirrer, or the like; and a method of evaporating an organic solvent while regulating the vacuum degree and temperature with a rotary evaporator or the like.

After that, a hollow structure in the shape of fine particle is aliquoted by centrifugation or filtering, an emulsifier and the like adhering to the surface of the hollow structure are washed with distilled water repeatedly several times. Furthermore, the hollow structure is dried under reduced pressure or re-dispersed in distilled water, followed by freeze-drying or the like, whereby remaining solvent and water are removed.

A dispersant may be added when the hollow structure is re-dispersed in distilled water. The dispersant has a function of preventing the aggregation of the hollow structure. Examples of the dispersant include a Tween 80 surfactant, sucrose fatty acid ester, mannitol, sorbitol, glucose, galactose, and sucrose. This dispersant is used by being dissolved in water in concentration of about 0.001 to 30 mass %.

Furthermore, the microcapsules having a PHA single film configuration thus produced may be re-dispersed as they are. Since some of them have a porous structure, they may be washed and then, centrifuged at a low speed into a non-precipitate and a precipitate. The centrifugation is appropriately performed at about 50 to 3,000 rpm for 1 to 60 minutes. Furthermore, the centrifugation is preferably performed several times.

As a result of the centrifugation, a hollow structure containing a magnetic substance of a single film configuration composed of PHA is collected in a non-precipitate phase, and an ultrasonic contrast agent using this hollow structure of a single film configuration exhibits a high ultrasonic image-forming effect. Furthermore, in order to obtain dry fine particles, drying under reduced pressure, freeze-drying, and the like, which are performed during heating if required, can be used. It is preferable to use freeze-drying.

Thus, a hollow structure with a particle size of 1 to 10 µm is obtained. The hollow structure has a spherical shape containing a large amount of hollow bodies without pores on the surface of fine particles as described later in examples.

<Phase Separation Method—Hollow Structure—>

In the case of performing hollow microcapsulation by a phase separation method, a coacervation agent is added gradually to a W/O type emulsion with stirring, and PHA is precipitated and solidified, whereby a hollow structure is prepared. A compound of a polymer type, a mineral oil type, or a plant oil type that is miscible with a solvent of PHA but does not dissolve PHA for capsulation may be used as the coacervation agent. Examples of the coacervation agent include silicone oil, sesame oil, soybean oil, corn oil, cottonseed oil, coconut oil, linseed oil, mineral oil, n-hexane, n-heptane, methanol, and ethanol. Those compounds may be used in combination of two or more kinds. The use amount of the coacervation agent is, for example, about 0.01 to 1,000 volume times, and preferably about 0.1 to 200 volume times with respect to the W/O type emulsion. The hollow structure in the shape of fine particle thus obtained is aliquoted by centrifugation or filtering, and washed repeatedly with a surfactant such as hexane or heptane to remove the coacervation agent. After that, the resultant hollow structure is heated or placed under reduced pressure to evaporate the surfactant. Furthermore, if desired, an organic solvent is removed in the same way as the case of the above-mentioned submerged drying method.

<Spray Drying Method—Hollow Structure—>

In the case of performing hollow microcapsulation by a spray drying method, a W/O type emulsion or a W/O/W type emulsion produced in the same way as in the case of the submerged drying method is sprayed to a dry chamber of a spray drier apparatus (spray drier) using a nozzle to volatilize an organic solvent and water in pulverized liquid droplets in a very short period of time, whereby a hollow structure in the shape of fine particle is prepared. The nozzle may be of, for example, a two-liquid nozzle type, a pressure nozzle type, and a rotary disk type. The hollow structure thus obtained is washed several times repeatedly with distilled water, if desired, to remove an emulsifier and the like adhering to the surface of the hollow structure. Then, the organic solvent may be further removed by drying the washed fine particles under reduced pressure or re-dispersing them in distilled water, followed by freeze-drying.

<Preparation of O/W Type Emulsion—Hollow Structure—>

In the case of producing a hollow structure by a submerged drying method based on an O/W type emulsion, generally, an oil phase containing PHA, a magnetic substance, and an organic solvent is dispersed in an water phase to form an O/W type emulsion, and the organic solvent in the oil phase is removed, whereby a hollow structure is produced. The volume of the water phase is generally selected from about 1 to about 10,000 times, preferably about 2 to about 5,000 times, more preferably about 5 to about 2,000 times, and particularly about 50 to about 1,000 times the volume of the oil phase. The temperature of the water phase may be previously adjusted to, for example, about 5° C. to about 30° C., preferably about 10° C. to about 25° C., and more preferably about 10° C. to about 20° C. An emulsifier may be added to the water phase. Any emulsifier may be used, which is generally capable of forming a stable O/W type emulsion, and the above-mentioned emulsifiers can be used preferably. The concentration of the emulsifier during use can be selected appropriately from the range of about 0.001 to about 20% (mass/volume). The emulsifier is used in the range of preferably about 0.01 to about 10% (mass/volume), and more preferably about 0.05 to about 5% (mass/volume). Furthermore, in an emulsifying process, various kinds of the above-mentioned known mixers can be used.

In particular, emulsification of preparing an O/W type emulsion is important for ensuring the uniformity of a hollow configuration of a hollow structure that is the final object. This is because the liquid droplet diameter of an oil phase defines the outer diameter of a hollow structure, and defines the configuration of a hollow portion. In order to allow any of the hollow structures to have a hollow structure to the same degree, it is important to disperse an internal oil phase containing PHA and a magnetic substance in an external water phase as uniformly as possible at this stage. For this purpose, it is preferable to minimize the liquid droplet diameter of the internal oil phase, so that a combination of an ultrasonic irradiation method with another dispersion method is adopted preferably.

In an embodiment of supplying components for producing an O/W type emulsion used in the production method of the present invention, various methods can be performed in accordance with a known technique. Examples of the method include: a method involving previously placing a solution containing PHA and a magnetic substance in a container and adding an water phase component containing an emulsifier thereto; a method involving previously placing an water phase component containing an emulsifier in a container and adding a solution containing PHA and a magnetic substance thereto; and a method involving continuously supplying both of them in a constant ratio. In the case of mixing by rotation, the firstly shown order is preferable. Formed in this case is a so-called W/O type emulsion in which an oil phase containing PHA and a magnetic substance initially forms a continuous phase, and an water phase forms a dispersion phase. In accordance with an increase in an addition amount of an water phase component, a W/O phase is changed to an O/W phase, and formation (pulverization) of a hollow structure from an oil phase is promoted.

An organic solvent can be removed in accordance with the above-mentioned method applied to the W/O emulsion. The hollow structure thus obtained is aliquoted by centrifugation or filtration, and thereafter, an emulsifier and the like adhering to the surface of the hollow structure be washed repeatedly several times with distilled water, and the washed hollow structure is re-dispersed in distilled water or the like, followed by freeze-drying.

<In-Vitro Synthesis Method>

The process of producing a structure by in-vitro synthesis includes the step of preparing a W/O type emulsion, a W/O/W type emulsion prepared from the W/O type emulsion or a separately prepared W/O/W type emulsion, an O/W type emulsion, or an O/W/O type emulsion from the O/W type emulsion, and the step of reacting 3-hydroxyacyl CoA with PHA synthetic enzyme to synthesize PHA.

An enzyme protein such as PHA synthetic enzyme is a polypeptide in which a number of amino acids are bonded to each other. The enzyme protein exhibits hydrophilicity due to an amino acid having a free ionic group such as lysine, histidine, arginine, aspartic acid, or glutamic acid, and exhibits hydrophobicity due to an amino acid having a free hydrophobic group such as alanine, valine, leucine, isoleucine, methionine, tryptophan, phenylalanine, or proline, and because the enzyme protein is an organic polymer. Thus, although there is a difference in degree, the enzyme protein can be present at an interface between an water phase and an oil phase having both the properties: hydrophilicity and hydrophobicity.

Herein, the polarity, charge amount, and hydrophobicity of a surface charge of PHA synthetic enzyme vary depending upon the pH, salt concentration, and temperature of a reaction solution (water phase). Therefore, it is desirable to adjust the reaction solution in a range allowable in terms of enzyme activity. For example, lowering the salt concentration can increase the charge amount of PHA synthetic enzyme. Furthermore, changing the pH can increase the opposite charge. Furthermore, increasing the salt concentration can increase the hydrophobicity. Furthermore, by previously measuring electrophoresis, a wet angle, and the like, and checking PHA synthetic enzyme for charge state and hydrophobicity, solution conditions suitable for the reaction can be set. Furthermore, the present amount of PHA synthetic enzyme at an interface between an water phase and an oil phase in each emulsion is directly measured, whereby conditions can be obtained. The present amount at the interface can be obtained, for example, by preparing each emulsion by using a PHA synthetic enzyme solution with a known concentration, and measuring the concentration of free PHA synthetic enzyme in an water phase.

Assuming that the amount of PHA synthetic enzyme at which the amount of CoA released during the reaction in which PHA is synthesized by the polymerization of 3-hydroxyacyl CoA is 1 µmol per minute is 1 unit (U), the amount of enzyme to be reacted is, for example, in the range of 10 units (U) to 1,000 units (U), and desirably 50 units (U) to 500 units (U) based on one gram of oil phase.

PHA is synthesized by PHA synthetic enzyme at an interface between an water phase and an oil phase in a reaction solution containing the above-mentioned PHA synthetic enzyme and 3-hydroxyacyl CoA to be a desired material of PHA, whereby a structure covered with PHA with an water phase being an internal water phase is formed. The water phase in the W/O type emulsion or the O/W type emulsion should be configured as a reaction system adjusted to the condition capable of allowing the activity of PHA synthetic enzyme to be exhibited. For example, the water phase is prepared with a buffer so as to have generally pH of 5.5 to 9.0, and preferably 7.0 to 8.5. Depending upon the optimum pH and pH stability of PHA synthetic enzyme to be used, the conditions outside of the above range are not excluded. The kind of the buffer can be appropriately selected depending upon the pH region and the like to be set, as long as the activity of PHA synthetic enzyme to be used can be exhibited. For example, a buffer used in a general biochemical reaction, specifically, an acetate buffer, a phosphate buffer, a potassium phosphate buffer, a 3-(N-morpholino)propane sulfonic acid (MOPS) buffer, an N-tris(hydroxymethyl)methyl-3-amino-propane sulfonic acid (TAPS) buffer, a tris hydrochloride buffer, a glycine buffer, a 2-(cyclohexylamino)ethanesulfonic acid (CHES) buffer, and the like are desirably used. The concentration of the buffer is not particularly limited as long as the activity of PHA synthetic enzyme to be used can be exhibited. Generally, a buffer with a concentration of 5.0 mM to 1.0 M, and preferably 0.1 M to 0.2 M may be used. The reaction temperature is appropriately set in accordance with the characteristics of PHA synthetic enzyme to be used, and may be generally 4° C. to 50° C., and preferably 20° C. to 40° C. Depending upon the optimum temperature and heat resistance of PHA synthetic enzyme to be used, the conditions outside of the above range are not excluded. The reaction time is appropriately selected to be set, generally, at one minute to 24 hours, and preferably 30 minutes to 3 hours, depending upon the stability and the like of PHA synthetic enzyme to be used. The concentration of 3-hydroxyacyl CoA in the reaction solution is appropriately set in such a range that the activity of PHA synthetic enzyme to be used can be exhibited, and may be set generally in the range of 0.1 mM to 1.0 M, and preferably 0.2 mM to 0.2 M. In the case where the concentration of 3-hydroxyacyl CoA in the reaction solution is high, generally, pH of the reaction system tends to decrease. Therefore, in the case of setting the concentration of 3-hydroxyacyl CoA to be high, it is preferable that the concentration of the buffer be set to be high.

Furthermore, in the PHA synthesis step, by changing the kind and composition such as a concentration of 3-hydroxyacyl CoA in the aqueous reaction solution with the passage of time, the composition of a monomer unit of PHA constituting the structure can be changed in a direction from an inside to an outside. In the case of forming a microcapsule structure, the composition of a monomer unit of PHA can be changed in a direction from an inside to an outside of PHA constituting a shell.

As the form of the structure in which the composition of a monomer unit is changed, for example, there is a microcapsule in which a drug is covered with a single layer of PHA with the composition of a PHA coating changing continuously and the gradient of the composition being formed in a direction from an inside to an outside. For example, a method involving adding 3-hydroxyacyl CoA with another composition to a reaction solution during the synthesis of PHA may be used as the production method.

As another embodiment, there is a microcapsule in which the composition of a PHA coating varies in stages, and a drug is covered in multi-layers with PHA having different compositions. As the production method thereof, for example, the following may be performed. PHA is synthesized with a composition of 3-hydroxyacyl CoA, a microcapsule during preparation is collected once from a reaction solution by centrifugation or the like, the reaction solution composed of 3-hydroxyacyl CoA with different compositions is added again to the microcapsule.

Formation of a structure including microcapsulation from a W/O type emulsion and an O/W type emulsion have been described. With respect to a W/O/W type emulsion or an O/W/O type emulsion, a structure can be produced in the same way. With respect to a W/O/W type emulsion, it is possible to include PHA synthetic enzyme and 3-hydroxyacyl CoA in an internal water phase and an external water phase. In order to enhance the uptake ratio of a drug, it is preferable to synthesize PHA only in an external water phase. Furthermore, in order to include a magnetic substance in a capsule and minimize the exposure of the magnetic substance to the surface of a capsule, it is more preferable to synthesize PHA in an external water phase. Furthermore, with respect to an O/W/O type emulsion, in order to minimize the exposure of the magnetic substance to the surface of a capsule, it is more preferable that the magnetic substance be contained only in an internal oil phase. With respect to a W/O/W type emulsion, three kinds of combinations are considered in the presence form of PHA synthetic enzyme and 3-hydroxyacyl CoA in an internal water phase and an external water phase. The present form may be determined in view of the uptake ratio of a drug, release characteristics thereof, the ease of a production process, a cost, and the like.

The structure obtained in the above reaction is subjected to a washing process if required. There is no particular limit to a method of washing particles as long as the method does not change a structure such as a microcapsule in an unpreferable manner in the production of the structure. For example, the structure is aliquoted by filtering, and washed repeatedly with heptane or the like to remove a free drug and a solvent. Furthermore, the structure is precipitated by centrifugation to remove a supernatant, whereby unnecessary components contained in a reaction solution can be removed. The following can also be performed. A surfactant in which the PHA is insoluble, such as heptane, is added, followed by centrifugation, whereby the structure is washed. Furthermore, the structure can be subjected to a drying process if required. Furthermore, the structure can be subjected to various kinds of secondary treatments, chemical modification, and the like to be used.

For example, chemically modifying PHA on a surface layer of the structure such as a microcapsule can result in a structure with more useful function and characteristics. For example, by introducing a graft chain, a structure such as a microcapsule with various characteristics due to the graft chain (e.g., control of sustained-release, and retention function of a liquid phase or a gas phase) improved can be obtained. Furthermore, by cross-linking PHA on a surface layer of a structure such as a microcapsule, the control of sustained-release of a microcapsule, and the retention function of a liquid phase or a gas phase are can be improved.

There is no particular limit to the chemical modification method as long as the purpose of obtaining desired function and structure can be satisfied. For example, a method involving synthesizing PHA having a reactive functional group at a side chain, and performing chemical modification using a chemical reaction of the functional group can be used as a preferable method.

There is no particular limit to the kind of the above-mentioned reactive functional group as long as the purpose of obtaining desired function and structure is satisfied. For example, the above-mentioned epoxy group can be exemplified. PHA having an epoxy chain at a side chain can perform a chemical conversion similar to that of a general polymer having an epoxy group. For example, such PHA can perform conversion to a hydroxyl group and introduce a sulfonic group. Furthermore, a compound having thiol and amine can be added. For example, a compound having a reactive functional group at an end, specifically, a compound having at an end an amino group having high reactivity with an epoxy group or the like is added for reaction, whereby a graft chain of a polymer is formed.

Examples of the compound having an amino group at its end include amino-denatured polymers such as polyvinylamine, polyethyleneimine, amino-denatured and polysiloxane (amino-denature silicone oil). Of those, commercially available denatured silicone oil may be used as amino-denatured polysiloxane, and amino-denatured polysiloxane may be synthesized by a method described in J. Amer. Chem. Soc., 78, 2278 (1956) or the like. The effects of controlling sustained-release by the addition of the graft chain of the polymer, enhancing the retention function of a liquid phase or a gas phase, enhancing the self-dispersibility in an aqueous solution, and the like can be expected.

Furthermore, another example of the chemical conversion of a polymer having an epoxy group includes a cross-linking reaction with a diamine compound such as hexamethylenediamine, succinic anhydride, 2-ethyl-4-methylimidazole, or the like. An example of a physiochemical conversion includes a cross-linking reaction by electron beam irradiation or the like. Among them, the reaction between PHA having an epoxy group at a side chain and hexamethylenediamine proceeds in the form as shown in the following scheme to generate a cross-linked polymer.

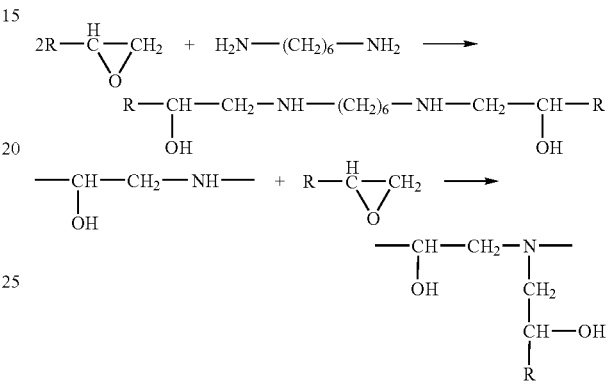

The volume ratio of a capsule portion accounting for the entire particle in the structure thus obtained is in the range of about 10% to 90%, and in view of the function, mechanical strength, and the like of the structure, the range of about 35% to about 85% is more preferable.

A method of a combination of the composition analysis by gas chromatography or the like and the observation of a form with an electron microscope or the like, a method of determining the configuration from the mass spectrum of each constituent layer using time-of-flight type secondary ion mass spectrometer (TOF-SIMS) and ion sputtering, and the like can be generally used as a method of confirming that a drug is covered with PHA in the structure such as a microcapsule thus obtained. However, a method of a combination of Nile blue-A dyeing and fluorescence microscope observation, newly developed by the inventors of the present invention, can also be used as a more direct and simple confirmation method. The inventors of the present invention have continued to earnestly study a method with which PHA synthesis in an acelluar system (in vitro) using PHA synthetic enzyme can be easily determined. As a result, the inventors have found that Nile blue-A that is a drug having a property of specifically binding PHA to emit fluorescence and is reported to be used for easily determining the production of PHA in cells of a microorganism (in vivo) can also be used for determining the PHA synthesis in an acelluar system by setting an appropriate use method and use condition, thereby achieving the above method. More specifically, according to this method, a Nile blue-A solution in a predetermined concentration is filtered and mixed in a reaction solution containing PHA. The resultant solution is observed under the irradiation with excited light with a predetermined wavelength with a fluorescence microscope, whereby fluorescence is allowed to be emitted only from synthesized PHA and observed. Thus, the PHA synthesis can be determined easily in an acellular system. Applying the above-mentioned method to the production of the structure of the present invention allows PHA covering the surface of a hydrophobic solution to be observed directly and evaluated.

<Excipient—Inclusion of Hydrophilic Drug—>

It is preferable that the sustained release preparation of the present invention contain an excipient. It is desirable that the excipient have low toxicity even when administered to a living body, can be easily dried by freeze-drying, spray drying, or the like, and can be dissolved rapidly when administered to a living body or dissolved before using. Examples of the excipient include sugar, a cellulose derivative, amino acid, protein, a polyacrylic acid derivative, an organic salt, and an inorganic salt. Two or more kinds of those excipients may be mixed in an appropriate ratio. Here, examples of the sugars include D-mannitol, sodium alginate, fructose, dextran, dextrin, saccharose, D-sorbitol, lactose, glucose, maltose, starches, and trehalose. Examples of the cellulose derivatives include carboxymethylcellulose, hydroxypropylmethylcellulose, ethylcellulose, hydroxymethylcellulose, hydroxypropylcellulose, celluloseacetatephthalate, hydroxypropylmethylcellulosephthalate, and hydroxymethylcelluloseacetatesuccinate. Examples of the amino acids include glycine, alanine, tyrosine, arginine, and lysine. Examples of the proteins include gelatin, fibrin, collagen, and albumin. Examples of the polyacrylic acid derivatives include sodium polyacrylate, and methacrylate/acrylate copolymers (such as Eudragit manufactured by ROHM GmbH, Germany). Examples of the organic salts include sodium citrate, disodium tartrate, sodium carbonate, and potassium carbonate. Examples of the inorganic salts include sodium chloride, potassium chloride, sodium phosphate, and potassium phosphate. Examples of excipients except those described above include water-soluble polymers that do not dissolve polymers used as sustained release preparation bases, such as polyvinyl pyrrolidone and polyvinyl alcohol. The excipient is preferably a saccharide and is more preferably D-mannitol as it is easily freeze-dried and has low toxicity.

The use amount of the excipient is determined by the solubility of the excipient and the tonicity, viscosity, dispersibility, stability, and the like of a solution obtained by dissolving the excipient. The excipient is used so that, in the case where the sustained release preparation is dried, the content of the excipient in a dry sustained release preparation is, for example, about 0.5 to 99 mass %, preferably about 1 to 90 mass %, and more preferably about 2 to 60 mass %. In the case of using D-mannitol as the excipient, it is particularly preferable that the content of the excipient in a dry sustained release preparation be about 2 to 40 mass %. Adding those excipients provides the following excellent effects: 1) the frequency of contact and collision of particles during drying and after drying of the sustained release preparation (particularly, microspheres) is reduced, and the uniformity of particles during freeze-drying or spray drying is maintained; 2) drying can be performed at a temperature equal to or higher than the glass transition temperature of the sustained release preparation, and more complete removal of water or an organic solvent can be performed; and 3) a sustained release preparation can be obtained, which has enhanced economic stability, satisfactory dispersibility, and a long-period use limit, for example, at room temperature, without being limited to the storage in a cold place.

According to the present invention, the sustained release preparation containing an excipient can be produced, for example, by mixing a structure obtained by the above-mentioned submerged drying method, phase separation method, or spray drying method with an excipient. The structure may be obtained by drying under reduced pressure after washing, or may be obtained by being re-dispersed in distilled water after washing, followed by freeze-drying. There is no particular limit to a mixing method. For example, a mixer or the like is used. A method enabling a uniform mixture to be obtained is preferable. Furthermore, the sustained release preparation containing an excipient can also be produced, for example, by spraying an aqueous solution of an excipient from another nozzle simultaneously with the spraying of a W/O type emulsion in the case of producing a structure by a spray drying method. Furthermore, the sustained release preparation containing an excipient can also be produced by using an aqueous solution of an excipient in an external water phase when producing a W/O/W type emulsion used in a submerged drying method and a spray drying method. The sustained release preparation containing an excipient can be produced preferably by washing a structure obtained by a submerged drying method, a phase separation method, or a spray drying method, and dispersing the washed structure in distilled water in which an excipient is dissolved or suspended, followed by freeze-drying or drying under reduced pressure. Furthermore, the following may be performed. The washed structure is dispersed in distilled water, an excipient is dissolved or suspended in the resultant dispersion, and thereafter, freeze-drying or drying under reduced pressure is performed. In particular, after the washed structure is dispersed in distilled water in which an excipient is dissolved, or an excipient is dissolved in a dispersion obtained by dispersing the washed structure in distilled water, freeze-drying is performed, whereby a uniform mixture is obtained.

<Heat Treatment—Inclusion of Hydrophilic Drug—>

Furthermore, the above-mentioned structure obtained by a submerged drying method, a phase separation method, or a spray drying method is heated, if desired, at a temperature equal to or higher than the glass transition temperature (Tg) of PHA to such a degree that respective particles of the structure do not adhere to each other, whereby water and an organic solvent in the structure can be removed more completely, and sustained-release can be improved. In this case, it is preferable that the organic solvent be removed to an amount of less than about 1,000 ppm, preferably less than about 500 ppm, and more preferably less than about 100 ppm. It is preferable that heating be performed after an excipient is added if desired, and a structure is freeze-dried, or dried under reduced pressure. However, there is no particular limit, and for example, heating may be performed after subdivision.

When the heating temperature is lower than the glass transition temperature of PHA, water or an organic solvent may not be removed sufficiently. When the heating temperature is too high, the possibility of fusion and deformation of the structure, decomposition and degradation of a drug, and the like increases. Therefore, the heating temperature is not defined uniquely. The heating time can be appropriately determined in view of the physical properties (molecular weight, stability, etc.) of PHA, the average particle size of a drug and a structure, a heating time, the dry degree of the structure, a heating method, and the like. Preferably, the structure is dried by heating at a temperature equal to or higher than the glass transition temperature of PHA to such a degree that the respective particles of the structure do not adhere to each other. More preferably, the heating temperature is in the range of the glass transition temperature of PHA to a temperature equal to or lower than a temperature that is higher by about 30° C. than the glass transition temperature, and still more preferably, in the range of the glass transition temperature of PHA to a temperature equal to or lower than a temperature that is higher by about 20° C. than the glass transition temperature. The heating time varies depending upon the heating temperature, the amount of a structure to be treated, and the like. The heating time is generally about 6 to 120 hours, and preferably about 12 to 96 hours after the temperature of the structure itself has reached a predetermined temperature. Furthermore, the upper limit of a heating time is not particularly limited as long as the remaining amounts of an organic solvent and water reach allowable values or less. Under the condition of the glass transition temperature or higher, the structure is softened, and deformed due to the physical contact of the structures or the load during stacking of the structures. Therefore, it is preferable that heating be finished rapidly when the remaining amounts of the organic solvent and water reach the allowable values or less. There is no particular limit to the heating method. Any method enabling a structure to be heated uniformly may be used. As a preferable specific example of the drying method by heating, a method of drying by heating, for example, in a thermostat, a fluidized tank, a mobile tank, or kiln, a method of drying by heating with a micro-wave, and the like can be used. Of those, a method of drying by heating in a thermostat is preferable. As described above, the structure is heated under reduced pressure after freeze-drying, whereby an organic solvent in the structure is removed efficiently, and a structure safe to a living body can be obtained. The remaining amount of the organic solvent in the structure thus obtained is about 100 ppm or less.

<Aggregation Inhibitor—Inclusion of Lipophilic Drug—>

In the production by a submerged drying method, coacervation, and in-vitro synthesis, in order to prevent the aggregation of structures in the shape of particle during washing, an aggregation inhibitor may be added to distilled water that is a surfactant. Examples of the aggregation inhibitor include: water-soluble polysaccharide such as mannitol, lactose, glucose, and starches (e.g., corn starch); proteins such as glycine, fibrin, and collagen; and inorganic salts such as sodium chloride and sodium hydrogen phosphate.

<Spray Drying Method—Inclusion of Lipophilic Drug—>

In the case of producing a structure such as a microcapsule by a spray drying method, an organic solvent solution or dispersion of a drug and PHA is sprayed to a dry chamber of a spray drier using a nozzle, and an organic solvent in pulverized liquid droplets is volatized in a very short period of time, whereby a structure is prepared. The nozzle may be of, for example, a two-fluid nozzle type, a pressure nozzle type, or a rotary disk type. In this case, it is effective to spray an aqueous solution of the above-mentioned aggregation inhibitor through another nozzle for the purpose of preventing the aggregation of structures, if desired, at the same time with the organic solvent solution or dispersion of a drug and PHA. If required, water and the organic solvent in the structure thus obtained are removed further by heating under reduced pressure.

<Organic Solvent Removal Method—Inclusion of Lipophilic Drug—>

An organic solvent can be removed by a known method. Examples of such a method include: a method of evaporating an organic solvent at atmospheric pressure or by gradually reducing the pressure while stirring the organic solvent with a propeller stirrer, a magnetic stirrer, or the like; and a method of evaporating an organic solvent while regulating the vacuum degree with a rotary evaporator or the like. When the O/W type emulsion is subjected to submerged drying, an organic solvent is volatized, and the emulsion is solidified, whereby the configuration thereof is determined. The structure thus obtained is aliquoted by centrifugation or filtering, a free drug, a drug holding material, an emulsifier, or the like adhering to the surface of the structure is washed with distilled water several times, and the remainder is re-dispersed in distilled water or the like, followed by freeze-drying.

<Aggregation Inhibitor—Inclusion of Lipophilic Drug—>

An aggregation inhibitor may be added during freeze-drying. Examples of the aggregation inhibitor include: water-soluble polysaccharide such as mannitol and starches (e.g., corn starch); inorganic salts; amino acids; and proteins. Of those, mannitol is preferable. The mixing ratio (mass ratio) of the structure to the aggregation inhibitor is about 50:1 to about 1:1, preferably about 20:1 to about 1:1, and most preferably about 10:1 to about 5:1. In order to prevent the aggregation of the particles during washing, an aggregation inhibitor may be added to distilled water that is a surfactant. Examples of the aggregation inhibitor include: water-soluble polysaccharide such as mannitol, lactose, glucose, and starches (e.g., corn starch); proteins such as glycine, fibrin, and collagen; and inorganic salts such as sodium chloride and sodium hydrogen phosphate. The aggregation inhibitor is preferably mannitol.

<Heat Treatment—Inclusion of Lipophilic Drug—>

Furthermore, by further removing water and an organic solvent in the structure by heating under pressure after freeze-drying, the sustained-release may be improved. When the heating temperature is lower than the glass transition temperature of PHA, there is no alleviating effect on the problem of an initial release of an excess amount of a drug. When the heating temperature is too high, the possibility of fusion and deformation of the structure, decomposition and degradation of a drug, and the like increases. Therefore, the heating temperature is not defined uniquely. The heating temperature can be appropriately determined in view of the physical properties (molecular weight, stability, etc.) of PHA, the average particle size of a drug and a structure such as a microcapsule, a heating time, the dry degree of the structure, a heating method, and the like. It is preferable that the organic solvent be removed to an amount of less than about 1,000 ppm, preferably less than about 500 ppm, and more preferably less than about 100 ppm.

Preferably, the structure is dried by heating at a temperature equal to or higher than the glass transition temperature of PHA to such a degree that the respective particles of the structure do not adhere to each other. Preferably, the structure is dried by heating in the temperature range of the glass transition temperature of PHA to a temperature equal to or lower than a temperature that is higher by about 30° C. than the glass transition temperature, more preferably in the temperature range of the glass transition temperature of PHA to a temperature equal to or lower than a temperature that is higher by about 10° C. than the glass transition temperature, and still more preferably in the temperature range of the glass transition temperature of PHA to a temperature equal to or lower than a temperature that is higher by about 5° C. than the glass transition temperature (particularly at a temperature higher by 3 to 4° C. than the glass transition temperature), whereby sustained-release is enhanced. The drying time by heating varies depending upon the heating temperature, the amount of a structure to be treated, and the like. In general, the drying time by heating is preferably about 24 to about 120 hours, more preferably about 48 to about 120 hours, and still more preferably about 48 to about 96 hours after the temperature of the structure itself such as a microcapsule has reached a predetermined temperature. Above all, there is no particular limit to the upper limit of the heating time as long as the remaining amounts of the organic solvent and water are equal to or lower than allowable values. Under the condition of the glass transition temperature or higher, the structure is softened, and deformed due to the physical contact of the structures or the load during stacking of the structures. Therefore, it is desirable that drying by heating be finished rapidly when the remaining amounts of the organic solvent and water reach the allowable values or less.

There is no particular limit to the heating method. Any method enabling a structure to be heated uniformly may be used. As a preferable specific example of the drying method by heating, a method of drying by heating, for example, in a thermostat, a fluidized tank, a mobile tank, or kiln, a method of drying by heating with a micro-wave, and the like can be used. Of those, a method of drying by heating in a thermostat is preferable.

<Substance Containing Oil Phase or Water Phase—Inclusion of Liquid Phase—>

The material to be carried on the above-mentioned microcapsule is appropriately selected depending upon the application purpose of the microcapsule of the present invention.

In the case where the microcapsules of the present invention are used as, for example, those for artificial red blood cells, examples of the material to be carried on the microcapsules include haemoglobin and haemocyanin.

In the case where the microcapsule of the present invention is used for ink, toner, or pigment microcapsules for example, materials carried by the microcapsule include aqueous dye solutions and pigment dispersions. Specific examples thereof include: acidic dyes such as C.I. Acid Red 52, C.I. Acid Blue 1, C.I. Acid Black 2, and C.I. Acid Black 123; basic dyes such as C.I. Basic Blue 7 and C.I. Basic Red 1; direct dyes such as C.I. Direct Black 19 and C.I. Direct Blue 86; oil-soluble dyes such as C.I. Solvent Black 7, C.I. Solvent Black 123, C.I. Solvent Red 8, C.I. Solvent Red 49, C.I. Solvent Red 100, C.I. Solvent Blue 2, C.I. Solvent Blue 25, C.I. Solvent Blue 55, C.I. Solvent Blue 70, C.I. Solvent Green 3, C.I. Solvent Yellow 21, C.I. Solvent Yellow 61, C.I. Solvent Orange 37, C.I. Solvent Violet 8, and C.I. Solvent Violet 21; reactive dyes such as C.I. Reactive Yellow 15, C.I. Reactive Yellow 42, C.I. Reactive Red 24, C.I. Reactive Red 218, C.I. Reactive Blue 38, and C.I. reactive Blue 220; black pigments such as carbon black, copper oxide, manganese dioxide, aniline black, activated carbon, non-magnetic ferrite, and magnetite; yellow pigments such as chrome yellow, zinc yellow, yellow oxide, cadmium yellow, mineral fast yellow, nickel titanium yellow, navels yellow, naphthol yellow-S, Hansa Yellow G, Hansa Yellow 10G, benzidine yellow G, benzidine yellow GR, quinoline yellow lake, permanent yellow NCG, and tartrazine lake; orange pigments such as chrome orange, molybdenum orange, permanent orange GTR, pyrazolone orange, vulcan orange, benzidine orange G, indanthrene brilliant orange RK, and indanthrene brilliant orange GK; red pigments such as blood red, cadmium red lead oxide, mercury sulfide, cadmium, permanent red 4R, lithol red, pyrazolone red, watching red, calcium salt, lake red C, lake red D, brilliant carmine 6B, brilliant carmine 3B, eosine lake, rhodamine lake B, and alizarin lake; blue pigments such as Prussian blue, cobalt blue, alkali blue lake, Victoria blue lake, phthalocyanine blue, metal-free phthalocyanine blue, part chlorine compounds of phthalocyanine blue, fast sky blue, and indanthrene blue BC; purple pigments such as manganese purple, fast violet B, and methyl violet lake; green pigments such as chromium oxide, chrome green, pigment green B, malachite green lake, and final yellow green G; white pigments such as zinc white, titanium oxide, antimony white, and zinc sulfide; and extender pigments such as baryta powder, barium carbonate, clay, silica, white carbon, talc, and alumina white. Of course, the aqueous dye solutions and pigment dispersions are not limited to those.

In the case where the microcapsule of the present invention is used for drug-sustaining capsules, for example, drugs carried by the microcapsule include both readily water-soluble and slightly water-soluble (fat-soluble) drugs. Examples of those kinds of drugs include: sterols (such as cholesterol and sitosterol); estrogens (such as estron, estradiol and esters thereof, and ethynyl estradiol); corticoid and esters thereof; peptide hormones such as calcitonin; antibiotics (such as gentamicin, vancomycin, amikacin, kanamycin, streptomycin, minocycline, and tetracycline); chloramphenicol; macrolide antibiotics (such as erythromycin and derivatives thereof and specifically palmitates and stearates, and spiramycin); antiprobiotic agents and skin pharmaceuticals (such as clotrimazol, miconazole, and dithranol); anti-inflammatory/analgesic agents (such as indomethacin, dichlofenac, flurbiprofen, ketoprofen, and 4-biphenyl acetic acid and ethyl esters thereof), vitamins such as cyanocobalamin; enzyme agents such as urokinase; and carcinostatics such as fluorouracil and aracytidine.

<Excipient—Inclusion of Gas Phase—>

The ultrasonic contrast agent prepared by using a hollow structure of the present invention may contain an excipient. It is desirable that the excipient have low toxicity even when administered to a living body, can be easily dried by freeze-drying, spray drying, or the like, and can be dissolved rapidly when administered to a living body or dissolved before using. Examples of the excipient include sugar, a cellulose derivative, amino acid, protein, a polyacrylic acid derivative, an organic salt, and an inorganic salt. Two or more kinds of those excipients may be mixed in an appropriate ratio.

Examples of the sugars which can be used as the excipient include D-mannitol, sodium alginate, fructose, dextran, dextrin, saccharose, D-sorbitol, lactose, glucose, maltose, starches, and trehalose. Examples of the cellulose derivatives include carboxymethylcellulose, hydroxypropylmethylcellulose, ethylcellulose, hydroxymethylcellulose, hydroxypropylcellulose, celluloseacetatephthalate, hydroxypropylmethylcellulosephthalate, and hydroxymethylcelluloseacetatesuccinate.

Further, examples of the amino acids include glycine, alanine, tyrosine, arginine, and lysine. Examples of the proteins include gelatin, fibrin, collagen, and albumin. Examples of the polyacrylic acid derivatives include sodium polyacrylate, and methacrylate/acrylate copolymers (such as Eudragit manufactured by ROHM GmbH, Germany). Examples of the organic salts include sodium citrate, disodium tartrate, sodium carbonate, and potassium carbonate. Examples of the inorganic salts include sodium chloride, potassium chloride, sodium phosphate, and potassium phosphate.

Examples of excipients except those described above include water-soluble polymers that do not dissolve PHA such as polyvinyl pyrrolidone and polyvinyl alcohol. The excipient is preferably a saccharide and is more preferably D-mannitol as it is easily freeze-dried and has low toxicity.

The use amount of the excipient is determined by the solubility of the excipient and the tonicity, viscosity, dispersibility, stability, and the like of a solution obtained by dissolving the excipient. The excipient is used so that, in the case where the ultrasonic contrast agent is dried, the content of the excipient in a dry ultrasonic contrast agent is, for example, about 0.5 to 99 mass %, preferably about 1 to 90 mass %, and more preferably about 2 to 60 mass %. In the case of using D-mannitol as the excipient, it is particularly preferable that the content of the excipient in a dry ultrasonic contrast agent be about 2 to 40 mass %. Adding those excipients provides the following excellent effects: 1) the frequency of contact and collision of particles during drying and after drying of the ultrasonic contrast agent (particularly, microspheres) is reduced, and the uniformity of particles during freeze-drying or spray drying is maintained; 2) drying can be performed at a temperature equal to or higher than the glass transition temperature of the ultrasonic contrast agent, and more complete removal of water or an organic solvent can be performed; and 3) an ultrasonic contrast agent can be obtained, which has enhanced economic stability, satisfactory dispersibility, and a long-period use limit, for example, at room temperature, without being limited to the storage in a cold place.

According to the present invention, the ultrasonic contrast agent containing also an excipient can be produced, for example, by mixing a hollow structure obtained by the above-mentioned submerged drying method, phase separation method, or spray drying method with an excipient. The hollow structure may be obtained by drying under reduced pressure after washing, or may be obtained by being re-dispersed in distilled water after washing, followed by freeze-drying. There is no particular limit to a mixing method. For example, a mixer or the like is used. A method enabling a uniform mixture to be obtained is preferable.

Furthermore, the ultrasonic contrast agent containing an excipient can also be produced, for example, by spraying an aqueous solution of an excipient from another nozzle simultaneously with the spraying of a W/O type emulsion in the case of producing a hollow structure by a spray drying method. Furthermore, the ultrasonic contrast agent containing an excipient can also be produced by using an aqueous solution of an excipient for an external water phase when producing a W/O/W type emulsion used in a submerged drying method and a spray drying method. The ultrasonic contrast agent containing an excipient can be produced preferably by washing a hollow structure obtained by a submerged drying method, a phase separation method, or a spray drying method, and dispersing the washed hollow structure in distilled water in which an excipient is dissolved or suspended, followed by freeze-drying or drying under reduced pressure. Furthermore, the following may be performed. The washed hollow structure is dispersed in distilled water, an excipient is dissolved or suspended in the resultant dispersion, and thereafter, freeze-drying or drying under reduced pressure is performed. In particular, after the washed hollow structure is dispersed in distilled water in which an excipient is dissolved, or an excipient is dissolved in a dispersion obtained by dispersing the washed hollow structure in distilled water, freeze-drying is performed, whereby a uniform mixture is obtained.

<Heat Treatment—Inclusion of Gas Phase—>

Furthermore, the above-mentioned hollow structure obtained by a submerged drying method, a phase separation method, or a spray drying method is heated, if desired, at a temperature equal to or higher than the glass transition temperature (Tg) of PHA to such a degree that respective particles of the hollow structure do not adhere to each other, whereby water and an organic solvent in the hollow structure can be removed more completely, and air bubble retention function can be improved. In this case, it is preferable that the organic solvent be removed to an amount of less than about 1,000 ppm, preferably less than about 500 ppm, and more preferably less than about 100 ppm. It is preferable that heating be performed after an excipient is added if desired, and a hollow structure is freeze-dried, or dried under reduced pressure. However, there is no particular limit, and for example, heating may be performed after subdivision.

When the heating temperature is lower than the glass transition temperature of PHA, water or an organic solvent may not be removed sufficiently. When the heating temperature is too high, the possibility of fusion and deformation of the structure, decomposition, degradation, or the like of hollow structure fine particles increases. Therefore, the heating temperature is not defined uniquely. The heating temperature can be appropriately determined in view of the physical properties (molecular weight, stability, etc.) of PHA, the average particle size of a hollow structure, a heating time, the dry degree of the hollow structure, a heating method, and the like. Preferably, the hollow structure is dried by heating at a temperature equal to or higher than the glass transition temperature of PHA to such a degree that the respective particles of the structure do not adhere to each other. More preferably, the heating temperature is in the range of the glass transition temperature of PHA to a temperature equal to or lower than a temperature that is higher by about 30° C. than the glass transition temperature, and still more preferably, in the range of the glass transition temperature of PHA to a temperature equal to or lower than a temperature that is higher by about 20° C. than the glass transition temperature.

The heating time varies depending upon the heating temperature, the amount of a hollow structure to be treated, and the like. The heating time is generally about 6 to 120 hours, and preferably about 12 to 96 hours after the temperature of the hollow structure itself has reached a predetermined temperature. Furthermore, the upper limit of a heating time is not particularly limited as long as the remaining amounts of an organic solvent and water reach allowable values or less. Under the condition of the glass transition temperature or higher, the hollow structure is softened, and deformed due to the physical contact of the hollow structures or the load during stacking of the hollow structures. Therefore, it is preferable that heating be finished rapidly when the remaining amounts of the organic solvent and water reach the allowable values or less.

There is no particular limit to the heating method. Any method enabling a hollow structure to be heated uniformly may be used. As a preferable specific example of the drying method by heating, a method of drying by heating, for example, in a thermostat, a fluidized tank, a mobile tank, or kiln, a method of drying by heating with a micro-wave, and the like can be used. Of those, a method of drying by heating in a thermostat is preferable. As described above, the hollow structure is heated under reduced pressure after freeze-drying, whereby an organic solvent in the hollow structure is removed efficiently, and a hollow structure safe to a living body can be obtained. The remaining amount of the organic solvent in the structure thus obtained is about 100 ppm or less.

<Application—Inclusion of Hydrophilic Drug>

The drugs used in the present invention are not particularly limited in their types. One or two or more kinds selected from biologically active peptides, antibiotics, antimycotics, antihyperlipemic agents, circulatory organ agents, antiplatelets (platelet aggregation inhibitors), antilipemic agents, anticoagulants, hemostats, antitumor agents, antipyretic agents, analgesic agents, anti-inflammatory agents, antitussive expectorant agents, sedatives, antiepileptic agents, antiulcer agents, antidepressant agents, antiallergic agents, cardiotonic agents, agents for treatment of arrhythmia, angiectatic agents, hypotensive diuretic agents, agents for treatment of diabetes, hormonal agents, antituberculous agents, antinarcotics, bone resorption controlling agents, osteogenesis promoters and angiogenesis inhibitors can be used. Water-soluble drugs are particularly preferable.

<Formulation—Inclusion of Hydrophilic Drug—>

The structure such as a microcapsule of the present invention may be used as it is as the sustained release preparation of the present invention. Alternatively, the structure of the present invention may be used as a raw material and formulated into various dosage forms such as an injection, an implant agent, an oral administration formulation (powder, granules, capsules, tablets, syrup, an emulsion, a suspension, etc.), a transnasal administration formulation, and a suppository (a rectal suppository, a vagina suppository, etc.). Those formulations can be produced by a known method generally used in the field of formulations. For example, an injection can be produced by dispersing the above-mentioned structure in an aqueous or oil-based dispersion medium. Examples of the aqueous dispersion medium include solutions in which an isotonizing agent (sodium chloride, glucose, D-mannitol, sorbitol, glycerin, etc.), a dispersant (Tween 80, HCO-50, HCO-60, carboxymethylcellulose, sodium alginate, etc.), a preservative (benzyl alcohol, benzalkonium chloride, phenol, etc.), a soothing agent (glucose, calcium gluconate, procaine hydrochloride, etc.), and the like are dissolved in distilled water. Furthermore, examples of the oil-based dispersion medium include olive oil, sesame oil, peanut oil, soybean oil, corn oil, and medium chain fatty acid glyceride. The injection may be filled in a chamber of a pre-filled syringe. Furthermore, the dispersion medium and the structure may be filled separately in different chambers in a so-called double-chamber pre-filled syringe (DPS). Furthermore, in the course of producing an injection, by further adding an excipient (mannitol, sorbitol, lactose, glucose, etc.) to the structure in addition to the above-mentioned compositions, re-dispersing the mixture, solidifying the structure by freeze-drying or spray drying, and adding distilled water for an injection or an appropriate dispersion medium before using, a more stable sustained-release injection can be obtained. The particle size in this case may be in a range satisfying the dispersion degree and needle-passage property in the case where the structure is used as, for example, a suspension injection. For example, an average particle size is in the range of about 0.1 to about 500 µm, preferably about 1 to about 300 µm, and more preferably about 2 to about 200 µm. Adding an osmoregulatory agent to an water phase as described above can form the shape of the structure into a sphere more suitable for the passage of a needle. Examples of the method of forming the structure into a sterile formulation include a method of rendering the entire production process sterile, a method for sterilization with a gamma-ray, and a method of adding an antiseptic. However, the method is not particularly limited to those examples.

The oral administration formulation may be formed by adding, to the above structure such as a microcapsule, for example, excipients (such as lactose, saccharose, and starch), disintegrators (such as starch and calcium carbonate), binders (such as starch, gum arabic, carboxymethylcellulose, polyvinyl pyrrolidone, and hydroxypropylcellulose), and lubricants (such as talc, magnesium stearate, and polyethylene glycol 6000), followed by compression molding, and then where necessary coating using a known method for the purpose of masking the taste, enteric coating, or persistence. Examples of the coating agent include hydroxypropylmethylcellulose, ethylcellulose, hydroxymethylcellulose, hydroxypropylcellulose, polyoxyethylene glycol, Tween 80, Prulonic F68, celluloseacetatephthalate, hydroxypropylmethylcellulosephthalate, hydroxymethylcelluloseacetatesuccinate, Eudragit (methacrylate-acrylate copolymer, manufactured by ROHM GmbH, Germany), and dyes (such as titanium oxide and blood red).

The transnasal administration formulation may be any of solid, semi-solid, and liquid. A solid transnasal administration formulation may be the above structure such as a microcapsule as it is, or may also be formed by adding and mixing, to the structure, for example, excipients (such as glucose, mannitol, starch, and microcrystalline cellulose), and thickening agents (such as natural rubbers, cellulose derivatives, and acrylic acid polymers). A liquid transnasal administration formulation may be formed in the same manner as the above mentioned injections. Further, those transnasal administration formulations may contain pH regulators (such as carbonic acid, phosphoric acid, citric acid, hydrochloric acid, and sodium hydroxide), preservatives (such as paraoxybenzoates, chlorobutanol, and benzalkonium chloride), and the like.

The suppository may be oily or aqueous, and may be any of solid, semi-solid, and liquid. A suppository is generally formed by using an oily base, an aqueous base, or an aqueous gel base. Examples of the oily base include: glycerides of higher fatty acid [such as cacao butter and Witepsol (Dynamit Nobel AG, Germany)]; medium fatty acids [such as miglyol (manufactured by Dynamit Nobel AG, Germany)]; and vegetable oils (such as sesame oil, soybean oil, and cottonseed oil). Examples of the aqueous base include polyethylene glycols and polypropylene glycols. Examples of the aqueous gel base include natural rubbers, cellulose derivatives, vinyl polymers, and acrylic acid polymers.

The sustained release preparation of the present invention has low toxicity and can be used safely with respect to mammals (a human being, a bovine, a swine, a dog, a cat, a mouse, a rat, a rabbit, etc.). The administration amount of the sustained release preparation varies depending upon the kind and content of a drug, the dosage form, the duration time of drug release, target disease (prostatic cancer, prostatic hypertrophy, endometriosis, uterine myoma, uterine fibroma, precocious puberty, breast cancer, bladder cancer, carcinoma of uterine cervix, chronic lymphatic leukemia, chronic myelocytic leukemia, colon cancer, stomach inflammation, Hodgkin's disease, malignant melanoma, metastasis, multiple myeloma, non Hodgkin's lymphoma, non small cell lung cancer, ovarian cancer, peptic ulcer, systemic mycosis, small cell lung cancer, valvulitis, mastopathy, a polycystic ovary, sterility, appropriate induction of ovulation in a chronic anovulation woman, acne, amenorrhea (e.g., sequential amenorrhea), cystic disease of an ovary and a breast (including a polycystic ovary), gynecological cancer, ovarian hyperandrogenism and polytrichosis, AIDS caused by T-cell production via thymic blast formation, treatment of hormone-dependent disease such as male contraception for treating a male sexual offender and contraception, alleviation of a condition of premenstrual syndrome (PMS), in vitro fertilization (IVF), etc.), the target animal, and the like. The administration of the sustained release preparation may be an effective amount of a drug. For example, in the case where the sustained-release agent is a one-month formulation, the administration amount of a drug for each time can be appropriately selected from the range of, preferably about 0.01 mg to about 100 mg/kg (body weight), more preferably about 0.05 mg to about 50 mg/kg (body weight), and particularly preferably about 0.1 mg to about 10 mg/kg (body weight) per adult. The administration amount of the sustained release preparation for each time can be appropriately selected from the range of about 0.1 mg to about 500 mg/kg (body weight), and more preferably about 0.2 mg to about 300 mg/kg (body weight) per adult. The administration number of times can be appropriately selected (once in several weeks, once for one month, once for several months, etc.), depending upon the kind and amount of a drug, the dosage form, the duration time of drug release, the target disease, the target animal, and the like.

<Application—Inclusion of Lipophilic Drug>

The drugs used in the present invention are not particularly limited in their types. One or two or more kinds selected from antibiotics, antimycotics, antihyperlipemic agents, circulatory organ agents, antiplatelets (platelet aggregation inhibitors), antitumor agents, antipyretic agents, analgesic agents, anti-inflammatory agents, antitussive expectorant agents, sedatives, antiepileptic agents, antiulcer agents, antidepressant agents, antiallergic agents, cardiotonic agents, agents for treatment of arrhythmia, angiectatic agents, hypotensive diuretic agents, agents for treatment of diabetes, hormonal agents, and bone resorption controlling agents can be used. Slightly water-soluble agents are particularly preferable. For example, carcinostatic agents such as steroid series drugs, protein drugs, peptide drugs, 5-fluorouracil, Me-CCUN, omeprazole, and platinum formulations (specifically cisplatin, carboplatin, isoplatin, and modifications thereof), and other general antibiotic agents may be suitably used.

<Preparation—Inclusion of Lipophilic Drug—>

The structure such as a microcapsule of the present invention may be used as it is as the sustained release preparation of the present invention. Alternatively, the structure of the present invention may be used as a raw material and formulated into various dosage forms such as an injection, an implant agent, an oral administration formulation (powder, granules, capsules, tablets, syrup, an emulsion, a suspension, etc.), a transnasal administration formulation, and a suppository (a rectal suppository, a vagina suppository, etc.).

Those formulations can be produced by a known method generally used in the field of formulations. For example, an injection can be produced by dispersing the above-mentioned structure in an aqueous or oil-based dispersion medium. Examples of the aqueous dispersion medium include solutions in which an isotonizing agent (sodium chloride, glucose, D-mannitol, sorbitol, glycerin, etc.), a dispersant (Tween 80, HCO-50, HCO-60, carboxymethylcellulose, sodium alginate, etc.), a preservative (benzyl alcohol, benzalkonium chloride, phenol, etc.), a soothing agent (glucose, calcium gluconate, procaine hydrochloride, etc.), and the like are dissolved in distilled water. Furthermore, examples of the oil-based dispersion medium include olive oil, sesame oil, peanut oil, soybean oil, corn oil, and medium chain fatty acid glyceride. The injection may be filled in a chamber of a pre-filled syringe. Furthermore, the dispersion medium and the structure may be filled separately in different chambers in a so-called double-chamber pre-filled syringe (DPS). Furthermore, in the course of producing an injection, by further adding an excipient (mannitol, sorbitol, lactose, glucose, etc.) to the structure in addition to the above-mentioned compositions, re-dispersing the mixture, solidifying the structure by freeze-drying or spray drying, and adding distilled water for an injection or an appropriate dispersion medium before using, a more stable sustained-release injection can be obtained. The particle size in this case may be in a range satisfying the dispersion degree and needle-passage property in the case where the structure is used as, for example, a suspension injection. For example, an average particle size is in the range of about 0.1 to about 500 µm, preferably about 1 to about 300 µm, and more preferably about 2 to about 200 µm. Adding an osmoregulatory agent to an water phase as described above can form the shape of the structure into a sphere more suitable for the passage of a needle. Examples of the method of forming the structure into a sterile formulation include a method of rendering the entire production process sterile, a method for sterilization with a gamma-ray, and a method of adding an antiseptic. However, the method is not particularly limited to those examples.

The oral administration formulation may be formed by adding, to the above structure such as a microcapsule, for example, excipients (such as lactose, saccharose, and starch), disintegrators (such as starch and calcium carbonate), binders (such as starch, gum arabic, carboxymethylcellulose, polyvinyl pyrrolidone, and hydroxypropylcellulose), and lubricants (such as talc, magnesium stearate, and polyethylene glycol 6000), followed by compression molding, and then where necessary coating using a known method for the purpose of masking the taste, enteric coating, or persistence. Examples of the coating agent include hydroxypropylmethylcellulose, ethylcellulose, hydroxymethylcellulose, hydroxypropylcellulose, polyoxyethylene glycol, Tween 80, Prulonic F68, celluloseacetatephthalate, hydroxypropylmethylcellulosephthalate, hydroxymethylcelluloseacetatesuccinate, Eudragit (methacrylate-acrylate copolymer, manufactured by ROHM GmbH, Germany), and dyes (such as titanium oxide and blood red).

The transnasal administration formulation may be any of solid, semi-solid, and liquid. A solid transnasal administration formulation may be the above structure such as a microcapsule as it is, or may also be formed by adding and mixing, to the structure, for example, excipients (such as glucose, mannitol, starch, and microcrystalline cellulose), and thickening agents (such as natural rubbers, cellulose derivatives, and acrylic acid polymers). A liquid transnasal administration formulation may be formed in the same manner as the above-mentioned injection. Further, those transnasal administration formulations may contain pH regulators (such as carbonic acid, phosphoric acid, citric acid, hydrochloric acid, and sodium hydroxide), preservatives (such as paraoxybenzoates, chlorobutanol, and benzalkonium chloride), and the like.

The suppository may be oily or aqueous, and may be any of solid, semi-solid, and liquid. A suppository is generally formed by using an oily base, an aqueous base, or an aqueous gel base. Examples of the oily base include: glycerides of higher fatty acid [such as cacao butter and Witepsol (available from Dynamit Nobel AG, Germany)]; medium fatty acids [such as Miglyol (available from Dynamit Nobel AG, Germany)]; and vegetable oils (such as sesame oil, soybean oil, and cottonseed oil). Examples of the aqueous base include polyethylene glycols and polypropylene glycols. Examples of the aqueous gel base include natural rubbers, cellulose derivatives, vinyl polymers, and acrylic acid polymers.

The sustained release preparation of the present invention has low toxicity and can be used safely with respect to mammals (a human being, a bovine, a swine, a dog, a cat, a mouse, a rat, a rabbit, etc.). The administration amount of the sustained release preparation varies depending upon the kind and content of a drug, the dosage form, the duration time of drug release, target disease (prostatic cancer, prostatic hypertrophy, endometriosis, uterine myoma, uterine fibroma, precocious puberty, breast cancer, bladder cancer, carcinoma of uterine cervix, chronic lymphatic leukemia, chronic myelocytic leukemia, colon cancer, stomach inflammation, Hodgkin's disease, malignant melanoma, metastasis, multiple myeloma, non Hodgkin's lymphoma, non small cell lung cancer, ovarian cancer, peptic ulcer, systemic mycosis, small cell lung cancer, valvulitis, mastopathy, a polycystic ovary, sterility, appropriate induction of ovulation in a chronic anovulation woman, acne, amenorrhea (e.g., sequential amenorrhea), cystic disease of an ovary and a breast (including a polycystic ovary), gynecological cancer, ovarian hyperandrogenism and polytrichosis, AIDS caused by T-cell production via thymic blast formation, treatment of hormone-dependent disease such as male contraception for treating a male sexual offender and contraception, alleviation of a condition of premenstrual syndrome (PMS), in vitro fertilization (IVF), etc.), the target animal, and the like. The administration of the sustained release preparation may be an effective amount of a drug. For example, in the case where the sustained-release agent is a one-month formulation, the administration amount of a drug for each time can be appropriately selected from the range of, preferably about 0.01 mg to about 100 mg/kg (body weight), more preferably about 0.05 mg to about 50 mg/kg (body weight), and particularly preferably about 0.1 mg to about 10 mg/kg (body weight) per adult. The administration amount of the sustained release preparation for each time can be appropriately selected from the range of about 0.1 mg to about 500 mg/kg (body weight), and more preferably about 0.2 mg to about 300 mg/kg (body weight) per adult. The administration number of times can be appropriately selected (once in several weeks, once a month, once in several months, etc.), depending upon the kind and amount of a drug, the dosage form, the duration time of drug release, the target disease, the target animal, and the like.

<Application—Inclusion of Liquid Phase—>

In the case of using the microcapsule of the present invention, for example, as an artificial red blood cell composition, slurry obtained during microcapsulation is suspended in physiologic saline, and the suspension is subjected to a known method such as gel filtration or centrifugation to remove large particles.

In the case of using the microcapsule of the present invention, for example, as an ink composition, the microcapsule is dispersed in an aqueous medium. For the purpose of assisting in dispersion in an aqueous medium, a surfactant, a protective colloid, a water-soluble organic solvent, and the like may be added in a range that does not remarkably reduce the water resistance of a coating film. Furthermore, a preservative, a viscosity modifier, a pH regulator, a chelating agent, and the like may be added. Specific examples of the protective colloid that may be added to aqueous pigment ink of the present invention include: natural protein such as glue, gelatin, casein, albumin, gum arabic, and fish glue; alginic acid; and synthetic polymers such as methyl cellulose, carboxymethyl cellulose, polyethylene oxide, hydroxyethyl cellulose, polyvinyl alcohol, polyacrylamide, aromatic amide, polyacrylic acid, polyvinyl ether, polyvinyl pyrrolidone, acrylic resin, and polyester. The protective colloid is used, if required, for the purpose of enhancing a fixing property, viscosity modification, and quick drying, and the content ratio of the protective colloid in ink is preferably 30 mass % or less, and more preferably 20 mass % or less.

The surfactant which may be added to the aqueous pigment ink of the present invention may be an anionic, cationic, amphoteric, or nonionic surfactant. Examples of the anionic surfactant include: salts of fatty acids such as sodium stearate, potassium oleate, and sodium partially hydrogenated tallow fatty acids; alkylsulfate salts such as sodium dodecylsulfate, tris(2-hydroxyethyl)ammonium dodecyl sulfate, and sodium octadecyl sulfate; benzenesulfonate salts such as sodium nonylbenzenesulfonate, sodium dodecylbenzenesulfonate, sodium octadecylbenzenesulfonate, and sodium dodecyl diphenyl ether disulfonate; naphthalenesulfonate salts such as sodium dodecyl naphthalenesulfonate and a naphthalenesulfonic acid-formalin condensate; sulfosuccinate salts such as sodium didodecyl sulfosuccinate and sodium dioctadecyl sulfosuccinate; polyoxyethylene sulfonate salts such as sodium polyoxyethylene dodecyl ether sulfonate, tris(2-hydroxyethyl)ammonium polyoxyethylene dodecyl ether sulfonate, sodium polyoxyethylene octadecyl ether sulfonate, and sodium polyoxyethylene dodecylphenyl ether sulfonate; and phosphate salts such as potassium dodecyl phosphate and sodium octadecyl phosphate. Examples of the cationic surfactant include: alkylamine salts such as octadecylammonium acetate and coconut oil amine acetate; and quaternary ammonium salts such as dodecyltrimethylammonium chloride, octadecyltrimethylammonium chloride, dioctadecyldimethylammonium chloride, and dodecylbenzyldimethylammonium chloride. Examples of the amphoteric surfactant include: alkylbetaines such as dodecyl betaine and octadecyl; and amine oxides such as dodecyldimethylamine oxide. Examples of the nonionic surfactant include: polyoxyethylene alkyl ethers such as polyoxyethylene dodecyl ether, polyoxyethylene hexadecyl ether, polyoxyethylene octadecyl ether, and polyoxyethylene (9-octadecenyl)ether; polyoxyethylene phenyl ethers such as polyoxyethylene octylphenyl ether and polyoxyethylene nonylphenyl ether; oxirane polymers such as polyethylene oxide and a polyoxyethylene-oxypropylene copolymer; sorbitan fatty acid esters such as sorbitan dodecanaote, sorbitan hexadecanoate, sorbitan octadecanoate, sorbitan (9-octadecenoate), sorbitan tri(9-octadecenoate), polyoxyethylene sorbitan dodecanoate, polyoxyethylene sorbitan hexadecanoate, polyoxyethylene sorbitan octadecanoate, polyoxyethylene sorbitan trioctadecanoate, polyoxyethylene sorbitan (9-octadecenoate), and polyoxyethylene sorbitan tri(9-octadecenoate); sorbitol fatty acid esters such as polyoxyethylene sorbitol tetra(9-octadecenoate); and glycerin fatty acid esters such as glycerin octadecanoate and glycerin (9-octadecenoate). Of the nonionic surfactants, a particularly preferable surfactant has a HLB of 14 or more. The blending amount of the surfactant used in the present invention varies depending on whether a single surfactant is used or two or more kinds thereof are mixed and used in combination. The surfactant is used in an amount of 0 to 10 mass %, preferably 0 to 5 mass % with respect to the total ink composition. The aqueous pigment ink composition according to the present invention preferably contains 20 to 95 mass % of water and 1 to 60 volume % of pigment with respect the total composition.

<Perfluorocarbon—Inclusion of Gas Phase—>

In order to fill a hollow portion of a hollow structure used for an ultrasonic contrast agent of the present invention with perfluorocarbon gas, the following only needs to be performed. The hollow structure is dispersed in water, and dried under reduced pressure. Then, perfluorocarbon gas is injected in a drier in a state under reduced pressure, and preferably returned to atmospheric pressure.

Herein, water in which the hollow structure is dispersed may contain the above-mentioned dispersant. A drying method under reduced pressure that is performed during heating if required, a freeze-drying method, and the like can be used as the drying method under reduced pressure. The freeze-drying method is preferably used. The boiling point of perfluorocarbon may be equal to or lower than the body temperature (preferably 10° C. or lower), so that a gas state is maintained even after a contrast agent is administered to the body. Specific examples of the perfluorocarbon include octafluorocyclobutane, octafluoropropane, and hexafluoroethane. Furthermore, it is preferable that the perfluorocarbon gas to be used have poor solubility in water, to thereby extend duration of a contrast effect without dissolving the perfluorocarbon gas in a body fluid such as blood.

<Aqueous Carrier—Inclusion of Gas Phase—>

The hollow structure obtained according to the method of the present invention is in a shape of dried fine particles. Thus, the hollow structure used as an ultrasonic contrast agent is administered orally or parenterally after dispersed in an appropriate aqueous carrier (e.g. physiological saline and aqueous solution of mannitol). Administration through injection is particularly desirable. A known dispersant may be added to the aqueous carrier as required. Further, the hollow structure used as an ultrasonic contrast agent is added such that concentration thereof is 0.01 to 80 mass %, preferably 0.01 to 50 mass % with respect to the total of the contrast agent containing the aqueous carrier.

EXAMPLES

Hereinafter, the present invention will be described in more detail with reference to Examples, Comparative Examples, and Experimental Examples, but the present invention is not limited to these examples. Note that, "%" represents mass % in the following Examples, Comparative Examples, and Experimental Examples, unless otherwise specified. Further, "microcapsules" below include two forms described above, that is, a one layer (monolithic) type and a two layer (core/shell) type, which are collectively described as "microcapsules".

Reference Example 1

Preparation of Transformant Having PHB Synthetic Enzyme Producing Ability

The inventors of the present invention have already filed an application regarding a preparation method for a transformant having an ability to produce a PHB synthetic enzyme originated from a TB64 strain, and a specific example thereof will be described here. The TB64 strain was cultured overnight in 100 ml of an LB medium (1% polypeptone, 0.5% yeast extract, 0.5% sodium chloride, pH 7.4) at 30° C. Then, chromosomal DNA was separated and recovered according to a method proposed by Marmur et al. The obtained chromosomal DNA was partially degraded by a restriction enzyme, Sau3AI. A vector pUC18 was cleaved by a restriction enzyme BamHI, and subjected to dephosphorylation treatment (Molecular Cloning, Vol. 1, p. 572, 1989, Cold Spring Harbor Laboratory Press). The cleaved vector was then ligated to a fragment of the chromosomal DNA partially degraded by Sau3AI using a DNA ligation kit Ver. II (available from Takara Shuzo Co., Ltd.). Next, the ligated DNA fragment was used to transform an HB101 strain of Escherichia coli, thereby preparing a chromosomal DNA library of the TB64 strain.

Next, phenotypic screening was conducted for obtaining a DNA fragment containing a PHB synthetic enzyme gene of the TB64 strain. An LB medium containing 2% glucose was used as a selective medium, and a Sudan black B solution was sprayed when colonies on an agar plate medium had grown to a suitable size, to thereby acquire colonies emitting fluorescence by UV irradiation. A DNA fragment containing the PHB synthetic enzyme gene was able to be obtained by recovering a plasmid from the acquired colonies through alkaline lysis.

The acquired gene fragment was recombined with a vector pBBR122 (available from MoBiTec GmbH) containing a broad host replication region not belonging to any of incompatible groups IncP, IncQ, and IncW. The recombinant plasmid was transformed to a TB64m1 strain (strain lacking PHB synthesizing ability) of Ralstonia eutropha through electroporation, to thereby restore the PHB synthesizing ability of the TB64m1 strain and become complementary.

Next, an oligonucleotide containing a base sequence in the vicinity of an initiation codon of the PHB synthetic enzyme gene was designed and synthesized (Amersham Pharmacia Biotech). The PCR was conducted using the oligonucleotide as a primer, to thereby amplify the fragment containing the PHB synthetic enzyme gene (LA-PCR kit, available from Takara Shuzo Co., Ltd.).

Next, the obtained PCR-amplified fragment was completely degraded using the restriction enzyme BamHI. The resulting product was ligated to an expression vector pTrc99A, which was cleaved by the restriction enzyme BamHI and subjected to the dephosphorylation treatment (Molecular Cloning, Vol. 1, p. 572, 1989, Cold Spring Harbor Laboratory Press), using a DNA ligation kit Ver. II (available from Takara Shuzo Co., Ltd.). The obtained recombinant plasmid was used to transform Escherichia coli HB101 through a calcium chloride method (Takara Shuzo Co., Ltd.), and a recombinant plasmid pTB64-PHB was recovered from the resulting recombinant. Escheichia coli HB101 was transformed by the pTB64-PHB through a calcium chloride method, to thereby obtain a pTB64-PHB recombinant strain.

Reference Example 2

Preparation of Transformant Having GST-Fused PHB Synthetic Enzyme Producing Ability The pTB64-PHB recombinant strain was inoculated to 200 ml of an LB medium, and was cultured at 37° C. by shaking at 125 strokes/minute for 12 hours. The resulting bacterial cells were recovered through centrifugation, to thereby recover plasmid DNA through a conventional procedure.

An oligonucleotide (SEQ ID NO: 1) as a primer upstream to the pTB64-PHB and an oligonucleotide (SEQ ID NO: 2) as a primer downstream thereto were respectively designed and synthesized (Amersham Pharmacia Biotech). The PCR was conducted using the oligonucleotides as the primers and the pTB64-PHB as a template, to thereby amplify the full length of the PHB synthetic enzyme gene containing a BamHI restriction site in the upstream and an XhoI restriction site in the downstream (LA-PCR kit, available from Takara Shuzo Co., Ltd.).

The purified PCR-amplified product was digested with BamHI and XhoI, and inserted to a corresponding site of a plasmid pGEX-6P-1 (available from Amersham Pharmacia Biotech). Escherichia coli (JM109) was transformed using those vectors, to thereby obtain an expression strain. The obtained strain was identified using a DNA fragment obtained by cleaving plasmid DNA, prepared in a large amount using Miniprep (Wizard Minipreps DNA Purification Systems, manufactured by Promega Corporation), with BamHI and XhoI.

Reference Example 3

Preparation of PHB Synthetic Enzyme

The obtained expression strain was precultured overnight at 30° C. in 100 ml of a 2×YT medium (polypeptone 16 g/l, yeast extract 10 g/l, NaCl 5 g/l, pH 7.0) containing ampicillin (100 µg/l).

This culture was added to 10 liters of a 2×YT medium (polypeptone 16 g/l, yeast extract 10 g/l, NaCl 5 g/l, pH 7.0)

containing ampicillin (100 µg/l), and the whole was cultured at 30° C. for 3 hours. Isopropyl-β-D-thiogalactopyranoside (IPTG) was added to the culture to final concentration of 1 mM, and the culture was continued at 30° C. for 3 hours.

The recovered culture solution was centrifuged at 4° C. and 78,000 m/s$^2$ (=8,000 G) for 10 minutes. After a supernatant had been removed, bacterial pellets were resuspended in 500 ml of a PBS solution at 4° C. This bacterial suspension was poured in 40 ml portions to a vessel cooled to 4° C. in advance. The bacterial cells were crushed using a French press at a pressure of 216 MPa (=2,200 kg/cm$^2$) by gradually releasing the bacterium suspension through a nozzle. The crushed bacterium suspension was centrifuged at 4° C. and 78,000 m/s$^2$ (=8,000 G) for 10 minutes, and the supernatant was recovered. The recovered supernatant was filtered through a 0.45 µm filter to remove a solid contaminant. The SDS-PAGE confirmed the presence of the target PHB synthetic enzyme having glutathione S-transferase (GST) fused thereto in the supernatant.

Next, the GST-fused PHB synthetic enzyme was purified using Glutathione Sepharose 4B (available from Amersham Pharmacia Biotech). 6.65 ml of 75% slurry of the Glutathione Sepharose 4B was centrifuged at 4° C. and 4,900 m/s$^2$ (=500 G) for 5 minutes to remove the supernatant. The recovered solid was resuspended in 200 ml of a PBS solution at 4° C. The suspension was further centrifuged at 4° C. and 4,900 m/s$^2$ (=500 G) for 5 minutes to remove the supernatant. The obtained solid was resuspended in 5 ml of a PBS solution at 4° C., to thereby prepare 50% slurry of the Glutathione Sepharose 4B.

To 10 ml of the 50% slurry of the Glutathione Sepharose 4B, the entire amount of the above prepared supernatant was added, and a target fused protein in the supernatant was allowed to adsorb onto the Glutathione Sepharose 4B through affinity adsorption through gentle shaking at room temperature for 30 minutes. The mixture was then centrifuged at 4° C. and 4,900 m/s$^2$ (=500 G) for 5 minutes. After the supernatant had been removed, the obtained solid was resuspended in 5 ml of a PBS solution at 4° C. The suspension was centrifuged similarly, and the supernatant was removed. The resulting Glutathione Sepharose 4B having the GST-fused PHB synthetic enzyme immobilized thereon was resuspended in a PBS solution and centrifuged twice, washed, and finally suspended in 5 ml of a Cleavage Buffer (Tris-HCl 50 mM, NaCl 150 mM, EDTA 1 mM, Dithiothreitol 1 mM, pH 7). 0.5 ml of a 4% solution of PreScission. Protease (available from Amersham Pharmacia Biotech) in a Cleavage buffer solution was added to the suspension, and the mixture was shaken gently at 5° C. for 4 hours. The mixture was then centrifuged at 4° C. and 4,900 m/s$^2$ (=500 G) for 5 minutes to recover the supernatant. Next, 1 ml of 50% slurry of the Glutathione Sepharose 4B prepared in the same manner as described above was centrifuged at 4° C. and 4,900 m/s$^2$ (=500 G) for 5 minutes to remove the supernatant. The supernatant previously recovered was added to the Glutathione Sepharose 4B from which the supernatant had been removed, and the mixture was stirred gently to allow the PreScission Protease remaining in the supernatant to adsorb onto the Glutathione Sepharose 4B. The supernatant was then recovered through centrifugation at 4° C. and 4,900 m/s$^2$ (=500 G) for 5 minutes. The SDS-PAGE analysis of the supernatant resulted in a single band, confirming that the supernatant was purified.

Enzyme activity of the contained PHB synthetic enzyme was measured according to the method described below. First, 100 µl of a 3.0 mg/ml solution of bovine serum albumin (available from Sigma Co.) in a 0.1 M Tris-HCl buffer (pH 8.0) was added to 100 µl of an enzyme solution, and the whole was mixed. The mixture was preincubated at 30° C. for 1 minute. 100 µl of a 3.0 mM solution of 3-hydroxybutyryl CoA in a 0.1 M Tris-HCl buffer (pH 8.0) was then added to the mixture, and the resultant mixture was incubated at 30° C. for 1 to 30 minutes. A reaction was terminated by adding 300 µl of a 10 mg/ml trichloroacetic acid solution in a 0.1 M Tris-HCl buffer (pH 8.0). The solution after the termination of the reaction was centrifuged (at 147,000 m/s$^2$ (=15,000 G) for 10 minutes). 500 µl of a 2.0 mM 5,5'-dithiobis(2-nitrobenzoic acid) solution in a 0.1 M Tris-HCl buffer (pH 8.0) was added to 500 µl of the supernatant. The mixture was incubated at 30° C. for 10 minutes. Then, absorbance of the mixture was measured at 412 nm. The enzyme activity was calculated by defining the amount of the enzyme for releasing 1 µmol of CoA per minute as one unit (U) of the enzyme. As a result, relative activity of the PHB synthetic enzyme was found to be 7.5 U/ml. This mixture was concentrated through ultrafiltration by adding a Reiho gel to concentration of 10 U/ml, and the resultant solution is referred to as "purified enzyme solution (1)".

Reference Example 4

Preparation of Crude Enzyme Solution Containing PHB Synthetic Enzyme

Each of KK01 and TL2 strains was cultured at 30° C. for 24 hours in 10 liters of an M9 medium (of following composition) containing 0.5% yeast extract and 0.3% mineral solution (see following). The recovered medium solution was centrifuged at 4° C. and 78,000 m/s$^2$ (=8,000 G) for 10 minutes. After the supernatant had been removed, the bacterial pellets were resuspended in 500 ml of a PBS solution at 4° C. The bacterial suspension was poured in 40 ml portions to a vessel cooled to 4° C. in advance. The bacterial cells were crushed using a French Press at a pressure of 2,200 kg/cm$^2$ by gradually releasing the bacterial suspension through a nozzle. The crushed bacterial suspension was centrifuged at 4° C. and 78,000 m/s$^2$ (=8,000 G) for 10 minutes, and the supernatant was recovered. The recovered supernatant was filtered through a 0.45 µm filter to remove the solid contaminant. The activity of the PHB synthetic enzyme in the supernatant was measured through the method described above. As a result, the relative activities of the KK01 strain and the TL2 strain were 1.6 U/ml and 1.2 U/ml, respectively. Each of the supernatants was concentrated through ultrafiltration by adding a biological sample concentrating agent (trade name: Mizubutorikun, available from Atto Corporation) to concentration of 10 U/ml, thereby obtaining "crude enzyme solution (1)" originated from the KK01 strain and "crude enzyme solution (2)" originated from the TL2 strain.

[M9 Medium]
$Na_2HPO_4$ 6.2 g
$KH_2PO_4$ 3.0 g
NaCl 0.5 g
$NH_4Cl$ 1.0 g (in 1 liter of medium, pH 7.0)
(Mineral Solution)
Nitrilotriacetic acid 1.5 g, $MgSO_4$ 3.0 g, $MnSO_4$ 0.5 g, NaCl 1.0 g, $FeSO_4$ 0.1 g, $CaCl_2$ 0.1 g, $CoCl_2$ 0.1 g, $ZnSO_4$ 0.1 g, $CuSO_4$ 0.1 g, $AlK(SO_4)_2$ 0.1 g, $H_3BO_3$ 0.1 g, $Na_2MoO_4$ 0.1 g, $NiCl_2$ 0.1 g (per liter, pH 7.0)

Reference Example 5

Preparation of Transformant Having PHA Synthetic Enzyme Producing Ability

A transformant having a PHA synthetic enzyme producing ability was prepared

A YN2 strain was cultured overnight in 100 ml of an LB medium (1% polypeptone (available from Nihon Pharmaceutical Co., Ltd.), 0.5% yeast extract (available from Difco Laboratories), and 0.5% sodium chloride, pH 7.4) at 30° C. Then, chromosomal DNA was separated and recovered according to a method proposed by Marmur et al. The obtained chromosomal DNA was completely degraded by a restriction enzyme, HindIII. A vector pUC18 was cleaved by the restriction enzyme HindIII, and a terminus of the vector was subjected to dephosphorylation treatment (Molecular Cloning, Vol. 1, p. 572, 1989, Cold Spring Harbor Laboratory Press). A cleaved site (cloning site) of the vector was then ligated to a fragment of the chromosomal DNA completely degraded by HindIII using a DNA ligation kit Ver. II (available from Takara Shuzo Co., Ltd.). Next, a plasmid vector incorporating the ligated chromosomal DNA fragment was used to transform an HB101 strain of *Escherichia coli*, thereby preparing a DNA library of the YN2 strain.

Next, a probe for colony hybridization was prepared for selecting a DNA fragment containing the PHA synthetic enzyme gene of the YN2 strain. Oligonucleotides composed of the base sequences of SEQ ID NO: 3 and SEQ ID NO: 4 were synthesized (Amersham Pharmacia Biotech). Then, the PCR was conducted using the oligonucleotides as the primers and the chromosomal DNA as the template. The DNA fragment obtained through PCR amplification was used as a probe. The probe was labeled using a commercially available labeling kit AlkPhosDirect (Amersham Pharmacia Biotech).

The obtained labeled probe was used for selecting the *Escherichia coli* strain having a recombinant plasmid containing the PHA synthetic enzyme gene from the chromosomal DNA library of the YN2 strain through the colony hybridization method. The plasmid was recovered from the selected strain through alkaline lysis, to thereby obtain a DNA fragment containing the PHA synthetic enzyme gene.

The acquired gene DNA fragment was recombined with a vector pBBR122 (available from MoBiTec GmbH) containing a broad host replication region not belonging to any of incompatible groups IncP, IncQ, and IncW. The recombinant plasmid was transformed to a YN2 ml strain (strain lacking PHA synthesizing ability) of *Pseudomonas cichorii* through electroporation, to thereby restore the PHA synthesizing ability of the YN2 ml strain and become complementary. Consequently, the selected DNA fragment contained a PHA synthetic enzyme gene region that can be translated to the PRA synthetic enzyme within *Pseudomonas cichorii* YN2 ml strain.

The base sequence of the DNA fragment was determined through Sanger's method. As a result, the determined base sequences included sequences represented by SEQ ID NO: 5 and SEQ ID NO: 6 which respectively encode peptide chains. The PCR was conducted on the PHA synthetic enzyme genes using the chromosomal DNA as the template, to thereby prepare the full lengths of the PHA synthetic enzyme genes again.

That is, a primer upstream (SEQ ID NO: 7) and a primer downstream (SEQ ID NO: 8) to the PHA synthetic enzyme gene composed of the base sequence represented by SEQ ID NO: 5, and a primer upstream (SEQ ID NO: 9) and a primer downstream (SEQ ID NO: 10 to the PHA synthetic enzyme gene composed of the base sequence represented by SEQ ID NO: 6 were respectively synthesized (Amersham Pharmacia. Biotech). The PCR was conducted respectively for the base sequences represented by SEQ ID NO: 5 and SEQ ID NO: 6 using those primers, to thereby amplify the full lengths of the PHA synthetic enzyme genes (LA-PCR kit: Takara Shuzo Co., Ltd.).

Next, the obtained PCR amplified fragment and the expression vector pTrc99A were cleaved by the restriction enzyme HindIII and dephosphorylated (Molecular Cloning, Vol. 1, p. 572, 1989, Cold Spring Harbor Laboratory Press). Then, the DNA fragment containing the full lengths of the PHA synthetic enzyme genes excluding unnecessary base sequences at both termini was ligated to a cleavage site of the expression vector pTrc99A using a DNA ligation kit Ver. II (available from Takara Shuzo Co., Ltd.).

*Escherichia coli* HB101 (available from Takara Shuzo Co., Ltd.) was transformed with the obtained recombinant plasmids through the calcium chloride method. The obtained recombinants were cultured, and the recombinant plasmids were amplified. Then, the recombinant plasmids were respectively recovered. The recombinant plasmid having the gene DNA of SEQ ID NO: 5 and the recombinant plasmid having the gene DNA of SEQ ID NO: 6 were respectively referred to as pYN2-C1 and pYN2-C2. *Escherichia coli* HB101fB, a strain lacking fadB, was transformed with pYN2-C1 and pYN2-C2 through the calcium chloride method, to thereby obtain recombinant *Escherichia coli* strains having respective recombinant plasmids, i.e., a pYN2-C1 recombinant strain and a pYN2-C2 recombinant strain.

Reference Example 6

PHA Synthetic Enzyme Production 1

An oligonucleotide (SEQ ID NO: 11) as a primer upstream to the pYN2-C1 and an oligonucleotide (SEQ ID NO: 12) as a primer downstream thereto were designed and synthesized respectively (Amersham Pharmacia Biotech). The PCR was conducted using the oligonucleotides as the primers and the pYN2-C1 as the template, to thereby amplify the full length of the PHA synthetic enzyme gene having a BamHI restriction site in the upstream and an XhoI restriction site in the downstream (LA-PCR kit, available from Takara Shuzo Co., Ltd.).

Similarly, an oligonucleotide (SEQ ID NO: 13) as a primer upstream to the pYN2-C2 and an oligonucleotide (SEQ ID NO: 14) as a primer downstream thereto were designed and synthesized respectively (Amersham Pharmacia Biotech). The PCR was conducted using the oligonucleotides as the primers and the pYN2-C2 as the template, to thereby amplify the full length of the PHA synthetic enzyme gene having a BamHI restriction site in the upstream and an XhoI restriction site in the downstream (LA-PCR kit, available from Takara-Shuzo Co., Ltd.).

The respective purified PCR-amplified products were digested with BamHI and XhoI, then inserted into corresponding sites of the plasmid pGEX-6P-1 (Amersham Pharmacia Biotech). *Escherichia coli* (JM109) was transformed using those vectors, to thereby obtain an expression strain. The strain was identified using a DNA fragment obtained by cleaving the plasmid DNA, prepared in a large amount using Miniprep (Wizard Minipreps DNA Purification Systems, manufactured by Promega Corporation), with BamHI and XhoI. The obtained strain was precultured overnight in 10 ml of an LB-Amp medium. 0.1 ml of the medium was added to 10 ml of the LB-Amp medium, and the mixture was cultured at 37° C. by shaking at 170 rpm for 3 hours. Then, IPTG was added to final concentration of 1 mM, and the culture was continued at 37° C. for 4 to 12 hours.

The *Escherichia coli* induced by IPTG was collected (78, 000 m/s$^2$ (=8,000 G), 2 minutes, 4° C.), and was resuspended in 1/10 volume of a phosphate buffer physiological saline (PBS; 8 g NaCl, 1.44 g Na$_2$HPO$_4$, 0.24 g KH$_2$PO$_4$, 0.2 g KCl, 1,000 ml purified water) at 4° C. The bacterial cells were crushed by freeze thawing and sonication, and subjected to centrifugation (78,000 m/s$^2$ (=8,000 G), 10 minutes, 4° C.) to remove the solid contaminant. After the SDS-PAGE had confirmed the presence of the target expression protein in the supernatant, the induced and expressed GST fused protein was purified with Glutathione Sepharose 4B (Amersham Pharmacia Biotech).

The Glutathione Sepharose used was treated in advance to suppress nonspecific adsorption. That is, the Glutathione Sepharose was washed three times with an equivalent amount of PBS (78,000 m/s$^2$ (=8,000 G), 1 minute, 4° C.), and then an equivalent amount of PBS containing 4% bovine serum albumin was added thereto for treatment at 4° C. for 1 hour. The Glutathione Sepharose was then washed with an equivalent amount of PBS twice, and resuspended in ½ volume of PBS.

40 μl of the pretreated Glutathione Sepharose was added to 1 ml of a cell-free extract and the whole was gently stirred at 4° C., to thereby adsorb fused proteins GST-YN2-C1 and GST-YN2-C2 onto the Glutathione Sepharose. After the adsorption, the Glutathione Sepharose was recovered through centrifuging (78,000 m/s$^2$ (=8,000 G), 1 minute, 4° C.), and was washed three times with 400 μl of PBS. Then, 40 μl of 10 mM glutathione was added and the mixture was stirred at 4° C. for 1 hour, to thereby elute the adsorbed fused proteins. After the recovery of the supernatant through centrifugation (78,000 m/s$^2$ (=8,000 G), 2 minutes, 4° C.), dialysis was conducted against PBS to purify the GST fused proteins. Single bands were confirmed using SDS-PAGE.

500 μg of each GST fused protein was digested with PreScission protease (5 U, available from Amersham Pharmacia Biotech), and the protease and the GST were removed by passing through the Glutathione Sepharose. A flow-through fraction was further passed through a Sephadex G200 column equilibrated with PBS, to thereby obtain expression proteins YN2-C1 and YN2-C2 as final purified products. Single bands were confirmed respectively at 60.8 kDa and 61.5 kDa, using SDS-PAGE.

The enzymes were concentrated using a biological sample concentrating agent (trade name: Mizubutorikun AB-1100; available from Atto Corporation), to thereby obtain a purified enzyme solution of 10 U/ml.

The activity of each purified enzyme was measured according to the method described above. Further, protein concentration in the sample was determined using a micro BCA protein assay reagent kit (available from Pierce Chemical Inc.). The measured activities of the respective purified enzymes are shown in Table 1.

TABLE 1

| Origin | Activity | Relative activity |
|---|---|---|
| Purified enzyme solution (2) pYN2-C1 | 2.1 U/ml | 4.1 U/mg protein |
| Purified enzyme solution (3) pYN2-C2 | 1.5 U/ml | 3.6 U/mg protein |

Reference Example 7

PHA Synthetic Enzyme Production 2

P91, H45, YN2, and P161 strains were inoculated in 200 ml of an M9 medium containing 0.5% yeast extract (available from Difco Laboratories) and 0.1% octanoic acid, and were cultured at 30° C. by shaking at 125 strokes/minute. After 24 hours, the bacterial cells were recovered through centrifugation (98,000 m/s$^2$ (=10,000 G), 4° C., 10 minutes), and washed by resuspending in 200 ml of a 0.1 M Tris-HCl buffer (pH 8.0) and centrifuging again. The bacterial cells were resuspended in 2.0 ml of a 0.1 M Tris-HCl buffer (pH 8.0) and crushed using an ultrasonic homogenizer, then centrifuged (118,000 m/s$^2$ (=12,000 G), 4° C., 10 minutes) to recover the supernatant, to thereby obtain a crude enzyme solution. The activity of each crude enzyme was measured according to the method described above, and the results are shown in Table 2.

TABLE 2

| | Origin | Activity |
|---|---|---|
| Crude enzyme solution (3) | P91 strain | 0.1 U/ml |
| Crude enzyme solution (4) | H45 Strain | 0.2 U/ml |
| Crude enzyme solution (5) | YN2 Strain | 0.4 U/ml |
| Crude enzyme solution (6) | P161 Strain | 0.2 U/ml |

The crude enzyme solution was concentrated with a biological sample concentrating agent (trade name: Mizubutorikun AB-1100, available from Atto Corporation), to thereby obtain a crude enzyme solution of 10 U/ml.

Reference Example 8

Synthesis of 3-hydroxyacyl CoA (R)-3-hydroxyoctanoyl-CoA was synthesized according to Rehm B. H. A., Kruger N., Steinbuchel A., Journal of Biological Chemistry, 273, p. 24044-24051, 1998 with slight changes as described below. Acyl-CoA synthetic enzyme (available from Sigma Co.) was dissolved in a Tris-HCl buffer (50 mM, pH 7.5) containing 2 mM ATP, 5 mM MgCl$_2$, 2 mM coenzyme A, and 2 mM (R)-3-hydroxyoctanoate to concentration of 0.1 mU/μl. The mixture was retained in a warm bath at 37° C. and was sampled suitably to analyze progress of a reaction by HPLC. After the enzyme reaction was terminated by adding sulfuric acid to the sampled reaction solution to concentration of 0.02 N, the unreacted substrate (R)-3-hydroxyoctanoate was removed by extraction with n-heptane. The HPLC analysis employed RP18 column (nucleosil C18, 7 μm, Knauser), and elusion was conducted under a linear concentration slope of acetonitrile, using a 25 mM phosphoric acid buffer (pH 5.3) as a moving phase. A thioester compound produced through the enzymatic reaction was detected by monitoring an absorption spectrum of 200 to 500 nm using a diode array detector. (R)-3-hydroxy-5-phenylvaleryl CoA and (R)-3-hydroxy-5-(4-fluorophenyl)valeryl CoA were synthesized in a similar manner.

Reference Example 9

A Pseudomonas cichorii YN2 strain (FERM BP-7375) was inoculated in 20 l of an M9 medium containing 0.5% D-glucose and 0.1% 5-(4-fluorophenyl)valeric acid (FPVA) and was cultured at 30° C. under stirring at 80 rpm with an aeration of 2.5 l/minute. After 48 hours, the bacterial cells were recovered through centrifugation, then resuspended in 20 l of an M9 medium containing 0.5% D-glucose and 0.1% FPVA but not containing a nitrogen source (NH$_4$Cl), and cultured at 30° C. under stirring at 80 rpm with an aeration of 2.5 l/minute. After 48 hours, the bacterial cells were recovered through centrifugation, and 1 g thereof was separated for evaluation from the recovered wet cells. The recovered cells were then washed once with cold methanol and freeze-dried, to thereby obtain freeze-dried pellets.

The remaining wet bacterial cells were suspended in 500 ml of about 1.7% aqueous solution of sodium hypochlorite, and PHA was extracted by shaking at about 4° C. for 2 hours. PHA was recovered through centrifugation and dried, to thereby provide 0.87 g of PHA per liter of culture solution. This PHA is referred to as Example Compound 1.

The freeze-dried pellets were suspended in 20 ml of chloroform, and the suspension was stirred at 60° C. for 20 hours to extract PHA. The extract was filtered through a membrane filter having a pore size of 0.45 μm and concentrated using a rotary evaporator. The concentrate was reprecipitated in cold methanol, and the precipitate alone was further recovered and dried under vacuum, to thereby obtain PHA.

A composition of the obtained PHA was analyzed in the following manner. That is, about 10 mg of PHA was placed in a 25 ml eggplant flask and was dissolved in 2 ml of chloroform. 2 ml of a methanol solution containing 3% sulfuric acid was added to the mixture for a reaction for 3.5 hours under reflux at 100° C. After the reaction, 10 ml of deionized water was added, and the mixture was vigorously shaken for 10 minutes to be separated into two layers. After that, a lower chloroform layer was retrieved, and the chloroform layer was dehydrated with magnesium sulfate. The chloroform layer was analyzed using a gas chromatograph-mass spectrometer (GC-MS: Shimadzu QP-5050, column: DB-WAX (J&W Scientific, 0.32 mm×30 m), EI method), to thereby identify the methylesterified product of a PHA monomer unit. As a result, the PHA monomer unit contained 96% 3HFPV and 4% 3-hydroxyvalerate unit. Thus, PHA having a high ratio of the desired 3HFPV monomer unit originated from FPVA was able to be obtained in high yield.

Further, the molecular weights of the PHA were determined through gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn=71,500 and Mw=158,000.

Reference Example 10

Reference Example 9 was repeated under the same conditions except that FPVA was replaced by 4-phenoxybutyric acid (PxBA), to thereby obtain PHA containing a 3-hydroxy-4-phenoxybutyric acid (3HPxB) monomer unit, in an amount of 0.15 g per liter of culture solution. This PHA is referred to as Example Compound 2.

The obtained PHA was evaluated in the same manner as in Reference Example 9 and was confirmed to be a PHA monomer unit containing 95% PxBA and 5% 3-hydroxybutyrate unit. Thus, PHA having a high ratio of the desired 3HPxB monomer unit originated from PxBA was provided in high yield. Further, the molecular weights were Mn=71,500 and Mw=158,000.

Reference Example 11

Reference Example 9 was repeated under the same conditions except that FPVA was replaced by 4-cyclohexylbutyric acid (CHBA), to thereby obtain PHA containing a 3-hydroxy-4-cyclohexylbutyric acid (3HCHB) monomer unit, in an amount of 0.79 g per liter of culture solution. This PHA is referred to as Example Compound 3.

The obtained PHA was evaluated in the same manner as in Reference Example 9 and was confirmed to be a PHA monomer unit containing 98% 3HCHB and 2% 3-hydroxybutyrate unit. Thus, PHA having a high ratio of the desired 3HCHB monomer unit originated from CHBA was provided in high yield. Further, the molecular weights were Mn=92,200 and Mw=218,000.

Reference Example 12

Reference Example 9 was repeated under the same conditions except that FPVA was replaced by 5-benzoylvaleric acid (BzVA), to thereby obtain PHA containing a 3-hydroxy-5-benzoylvaleric acid (3HBzV) monomer unit, in an amount of 0.55 g per liter of culture solution. This PHA is referred to as Example Compound 4.

The obtained PHA was evaluated in the same manner as in Reference Example 9 and was confirmed to be a PHA monomer unit containing 88% 3HBzV and 12% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3HBzV monomer unit originated from BzVA was provided in high yield. Further, the molecular weights were Mn=325,000 and Mw=1,240,000.

Reference Example 13

Reference Example 9 was repeated under the same conditions except that FPVA was replaced by 5-(4-fluorobenzoyl) valeric acid (FBzVA), to thereby obtain PHA containing a 3-hydroxy-5-(4-fluorobenzoyl)valeric acid (3HFBzV) monomer unit, in an amount of 0.35 g per liter of culture solution. This PHA is referred to as Example Compound 5.

The obtained PHA was evaluated in the same manner as in Reference Example 9 and was confirmed to be a PHA monomer unit containing 79% 3HFBzV and 21% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3HFBzV monomer unit originated from FBzVA was provided in high yield. Further, the molecular weights were Mn=285,000 and Mw=833,000.

Reference Example 14

Reference Example 9 was repeated under the same conditions except that FPVA was replaced by 5-thienyl valeric acid (TVA), to thereby obtain PHA containing a 3-hydroxy-5-thienyl valeric acid (3HTV) monomer unit, in an amount of 0.85 g per liter of culture solution. This PHA is referred to as Example Compound 6.

The obtained PHA was evaluated in the same manner as in Reference Example 9 and was confirmed to be a PHA monomer unit containing 97% 3HTV and 3% 3-hydroxybutyrate unit. Thus, PHA having a high ratio of the desired 3HTV monomer unit originated from TVA was provided in high yield. Further, the molecular weights were Mn=75,000 and Mw=185,000.

Reference Example 15

Reference Example 9 was repeated under the same conditions except that FPVA was replaced by 5-thienoyl valeric acid (3HToV), to thereby obtain PHA containing a 3-hydroxy-5-thienoyl valeric acid. (3HToV) monomer unit, in an amount of 0.15 g per liter of culture solution. This PHA is referred to as Example Compound 7.

The obtained PHA was evaluated in the same manner as in Reference Example 9 and was confirmed to be a PHA monomer unit containing 62% 3HToV and 38% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3HToV monomer unit originated from ToVA was provided in high yield. Further, the molecular weights were Mn=105,000 and Mw=252,000.

Reference Example 16

Reference Example 9 was repeated under the same conditions except that FPVA was replaced by 5-(4-fluorothiophenoxy)valeric acid (FTPxVA), to thereby obtain PHA containing a 3-hydroxy-5-(4-fluorothiophenoxy)valeric acid (3HFTPxV) monomer unit, in an amount of 0.92 g per liter of culture solution. This PHA is referred to as Example Compound 8.

The obtained PHA was evaluated in the same manner as in Reference Example 9 and was confirmed to be a PHA monomer unit containing 82% 3HFTPxV and 18% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3HFTPxV monomer unit originated from FTPxVA was provided in high yield. Further, the molecular weights were Mn=95,000 and Mw=282,000.

Reference Example 17

Reference Example 9 was repeated under the same conditions except that FPVA was replaced by 5-[(4-fluorophenylmethyl)sulfanil]valeric acid, to thereby obtain PHA containing a 3-hydroxy-5-[(4-fluorophenylmethyl)sulfanil]valeric acid monomer unit, in an amount of 0.35 g per liter of culture solution. This PHA is referred to as Example Compound 9.

The obtained PHA was evaluated in the same manner as in Reference Example 9 and was confirmed to be a PHA monomer unit containing 89% 3-hydroxy-5-[(4-fluorophenylmethyl)sulfanil]valeric acid monomer unit and 11% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3-hydroxy-5-[(4-fluorophenylmethyl)sulfanil]valeric acid monomer unit originated from 5-[(4-fluorophenylmethyl)sulfanil]valeric acid was provided in high yield. Further, the molecular weights were Mn=35,000 and Mw=92,000.

Reference Example 18

Reference Example 9 was repeated under the same conditions except that FPVA was replaced by 5-thiothienoxy valeric acid (TTxVA), to thereby obtain PHA containing a 3-hydroxy-5-thiothienoxy valeric acid (3HTTxV) monomer unit, in an amount of 1.1 g per liter of culture solution. This PHA is referred to as Example Compound 10.

The obtained PHA was evaluated in the same manner as in Reference Example 9 and was confirmed to be a PHA monomer unit containing 90% 3HTTxV and 10% of at least one unit selected from the group consisting of 3-hydroxybutyric acid, 3-hydroxyhexanoic acid, 3-hydroxyoctanoic acid, 3-hydroxydecanoic acid, 3-hydroxydodecanoic acid, and 3-hydroxydodecenoic acid. Thus, PHA having a high ratio of the desired 3HTTxV monomer unit originated from TTxVA was provided in high yield. Further, the molecular weights were Mn=205,000 and Mw=550,000.

Reference Example 19

Reference Example 9 was repeated under the same conditions except that FPVA was replaced by octanoic acid (OA), to thereby obtain PHA containing a 3-hydroxyoctanoic acid (3HO) monomer unit, in an amount of 0.75 g per liter of culture solution. This PHA is referred to as Example Compound 11.

The obtained PHA was evaluated in the same manner as in Reference Example 9 and was confirmed to be a PHA monomer unit containing 65% 3HO and 35% of at least one unit selected from the group consisting of 3-hydroxybutyric acid, 3-hydroxyhexanoic acid, 3-hydroxyheptanoic acid, 3-hydroxynonanoic acid, 3-hydroxydedanoic acid, 3-hydroxydodecanoic acid, and 3-hydroxydodecenoic acid. Thus, PHA having a high ratio of the desired 3HO monomer unit originated from OA was provided in high yield. Further, the molecular weights were Mn=132,000 and Mw=312,000.

Reference Example 20

A colony of a YN2 strain on an M9 agar medium containing 0.1% yeast extract was suspended in a sterilized physiological saline to OD (600 nm)=1.0. The obtained suspension of the bacterial cells in Reference Example 9 was spread on 100 plates of a 1/10 N M9 agar medium not containing any carbon source prepared in advance, and the plates were statically cultured at 30° C. in an atmosphere of 1-octene.

The bacterial cells were collected after 4 days, washed with methanol, recovered through centrifugation, and dried under reduced pressure.

50 ml of chloroform was added to the dried bacterial cells, and the mixture was stirred at 30° C. for 48 hours to extract PHA. A chloroform layer was filtered, concentrated using an evaporator, and poured into cold methanol. A precipitate was recovered and dried under reduced pressure, to thereby obtain 0.26 g of PHA. This PHA is referred to as Example Compound 12.

The obtained PHA was evaluated in the same manner as in Reference Example 9 and was subjected to $^1$H-NMR analysis (equipment used: FT-NMR (Bruker DPX400); measured nuclide: $^1$H; solvent used: $CDCl_3$ (containing TMS)). The protons involved in methyne at the end of a side chain, a double bond at the end of a side chain, and an epoxy group were assigned according to Macromolecules, 31, 1480-1486, 1998. As a result, a PHA monomer unit consisted of 17% epoxy units, 30% saturated units, and 53% unsaturated units. The saturated and unsaturated units were at least one of 3-hydroxyhexanoic acid, 3-hydroxyheptanoic acid, 3-hydroxyoctanoic acid, 3-hydroxydecanoic acid, 3-hydroxydodecanoic acid, 3-hydroxyhexenoic acid, 3-hydroxyheptenoic acid, 3-hydroxyoctenoic acid, and 3-hydroxydodecenoic acid. Thus, PHA having a high ratio of the desired epoxy monomer unit originated from 1-octene was obtained in high yield. The molecular weights were Mn=251,000 and Mw=550,000.

Reference Example 21

Magnetic Substance Preparation 1

1.0 to 1.1 equivalents of a caustic soda solution with respect to iron ions was mixed to an aqueous solution of ferrous sulfate, to thereby prepare an aqueous solution containing iron hydroxide. The aqueous solution was aerated, for an oxidation reaction at 80 to 90° C. while the pH was maintained at about 8, to thereby prepare slurry for forming seed crystals.

Next, an aqueous solution of ferrous sulfate was added to the slurry so that ferrous sulfate would become 0.9 to 1.2 equivalents with respect to the initial amount of alkali (sodium component in caustic soda). Then, the mixture was aerated for an oxidation reaction while the pH was maintained to about 8. Magnetic iron oxide particles produced after the oxidation reaction were washed, filtered, and dried. Agglomerated particles were crushed, to thereby obtain particulate magnetic substances 1 having an average particle size of 0.1 µm.

Example 1

500 mg of N-(S)-2-tetrahydrofuroyl-Gly-D2Nal-D4ClPhe-D3 Pal-Ser-NMeTyr-DLys(Nic)-Leu-Lys(Nisp)-Pro-DAlaNH$_2$ (hereinafter abbreviated as peptide A) acetate (available from TAP Pharmaceutical Products Inc.) was dissolved in 0.6 ml of distilled water. The obtained solution was added to a solution containing 4.5 g of Example Compound 1 and 1.5 g of the magnetic substances 1 in 5.8 ml of dichloromethane, and the whole was mixed using a small homogenizer (manufactured by Kinematica AG) for 60 seconds, to thereby obtain a W/O type emulsion. The W/O type emulsion was cooled to 16° C. and was added to 1,000 ml of a 0.1% aqueous solution of polyvinyl alcohol (EG-40, available from Nippon Synthetic Chemical Industry Co., Ltd.) cooled to 16° C. in advance. The mixture was stirred at 7,000 rpm using a turbine-type homomixer (manufactured by Tokushu Kika Kogyo Co., Ltd.), to thereby obtain a W/O/W type emulsion. The W/O/W type emulsion was stirred at room temperature for 3 hours to vaporize dichloromethane to solidify the W/O type emulsion. The solidified emulsion was then centrifuged at 2,000 rpm using a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The dispersion was freeze-dried, to thereby obtain magnetic microcapsules 1 in powder form. The content of the peptide A in the microcapsules 1 is shown in Table 3.

Examples 2 to 12

Magnetic microcapsules 2 to 12 were obtained in the same manner as in Example 1 except that Example Compound 1 was replaced by Example Compounds 2 to 12. The contents of the peptide A in the microcapsules are shown in Table 3.

Example 13

50 parts by mass of the above-mentioned magnetic microcapsules 12 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain magnetic microcapsules 13. The content of the peptide A in the microcapsules is shown in Table 3.

Infrared absorption was measured for the magnetic microcapsules 13 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 13. The disappearance indicates that the magnetic microcapsules 13 coated with a crosslinked polymer were obtained through a reaction between PHA having an epoxy unit in the side chain and hexamethylene diamine.

Example 14

10 parts by mass of terminal amino group-modified polysiloxane (modified silicone oil TSF4700, available from GE Toshiba Silicones) was added to 50 parts by mass of the above-mentioned magnetic microcapsules 12, and the whole was reacted at 70° C. for 2 hours. The reacted-mixture was then washed by repeated suspension in methanol and centrifugation (10,000×g, 4° C., 20 minutes) and dried, to thereby obtain magnetic microcapsules 14 having a graft chain of polysiloxane. The content of the peptide A in the microcapsules is shown in Table 3.

Infrared absorption was measured for the magnetic microcapsules 14 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 14. The disappearance indicates that the magnetic microcapsules 14 having a graft chain of polysiloxane were obtained through a reaction between PHA having an epoxy unit in the side chain and terminal amino group-modified polysiloxane.

Comparative Example 1

Magnetic microcapsules 15 were obtained in the same manner as in Example 1 except that Example Compound 1 was replaced by a lactic acid-glycolic acid copolymer (hereinafter, abbreviated as PLGA) (lot No. 940810 available from Wako Pure Chemical Industries, Ltd.; lactic acid/glycolic acid (mole ratio): 74/26; GPC weight average molecular weight: 10,000; GPC number average molecular weight: 3,900; number average molecular weight by terminal group quantitative analysis: 3,700). The drug content in the microcapsules is shown in Table 3.

TABLE 3

| Example | Magnetic capsule No. | Example Compound No. | Drug content (%) |
|---|---|---|---|
| 1 | 1 | 1 | 12.1 |
| 2 | 2 | 2 | 12.8 |
| 3 | 3 | 3 | 12.7 |
| 4 | 4 | 4 | 13.1 |
| 5 | 5 | 5 | 13.4 |
| 6 | 6 | 6 | 12.0 |
| 7 | 7 | 7 | 13.0 |
| 8 | 8 | 8 | 12.4 |
| 9 | 9 | 9 | 12.1 |
| 10 | 10 | 10 | 13.2 |
| 11 | 11 | 11 | 12.9 |
| 12 | 12 | 12 | 13.2 |
| 13 | 13 | 12 + crosslinking | 12.7 |
| 14 | 14 | 12 + grafting | 12.2 |
| Comparative Example 1 | 15 | PLGA | 7.9 |

Example 15

500 mg of peptide A acetate (available from TAP Pharmaceutical Products Inc.) was dissolved in 0.6 ml of a 0.1 M phosphate buffer (pH 7.0), and 60 μl of purified enzyme solution (1), 60 mg of (R)-3-hydroxybutyryl CoA (available from Sigma Aldrich Japan K.K.), and 5 mg of bovine serum albumin were added and dissolved therein. The obtained solution was added to 5.8 ml of dichloromethane containing 1.5 g of the magnetic substances 1 dispersed therein, and the whole was mixed using a small homogenizer (manufactured by Kinematica AG) for 60 seconds, to thereby obtain a W/O type emulsion. The W/O type emulsion was cooled to 16° C. and added to 1,000 ml of a 0.1% aqueous solution of polyvinyl alcohol (EG-40, available from Nippon Synthetic Chemicals Co.) cooled to 16° C. in advance, to thereby obtain a W/O/W type emulsion through stirring at 7,000 rpm using a turbine-type homomixer (manufactured by Tokushu Kika Kogyo Co., Ltd.). The W/O/W type emulsion was stirred at room temperature for 3 hours for PHA synthesis while dichloromethane was vaporized. The solidified W/O type emulsion was centrifuged at 2,000 rpm with a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The mixture was freeze-dried, to thereby obtain magnetic microcapsules 16 in powder form. The content of the peptide A in the microcapsules is shown in Table 4.

Further, the magnetic microcapsules 16 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of a PHB monomer unit. The peak of the main component in the obtained chromatogram had the same retention time as that of a sample methylated compound of hydroxybutyric acid. This result confirmed that the main component of the coat of the obtained magnetic microcapsules 16 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mw=73,000.

Example 16

Magnetic microcapsules 17 were obtained in the same manner as in Example 15 except that the purified enzyme solution (1) in Example 15 was replaced by the crude enzyme solution (1). The drug content in the microcapsules is shown in Table 4.

The evaluation in the same manner as in Example 15 confirmed that the main component of the coat of the obtained magnetic microcapsules 17 was PHB. Further, the gel permeation chromatography analysis confirmed that PHA in the obtained magnetic microcapsules 17 had a number average molecular weight of 71,000.

Example 17

Magnetic microcapsules 18 were obtained in the same manner as in Example 15 except that the purified enzyme solution (1) in Example 15 was replaced by the crude enzyme solution (2). The drug content in the microcapsules is shown in Table 4.

The evaluation in the same manner as in Example 15 confirmed that the main component of the coat of the obtained magnetic microcapsules 18 was PHB. Further, the gel permeation chromatography analysis confirmed that PHA in the obtained magnetic microcapsules 18 had a number average molecular weight of 73,000.

Example 18

PHA in magnetic microcapsules 19 was obtained in the same manner as in Example 15 except that the purified enzyme solution (1) in Example 15 was replaced by the purified enzyme solution (2) and (R)-3-hydroxybutyryl CoA was replaced by (R)-3-hydroxyoctanoyl CoA (prepared following a procedure described in Eur. J. Biochem., 250, 432-439, 1997). The drug content in the microcapsules is shown in Table 4.

The evaluation in the same manner as in Example 15 confirmed that the main component of the coat of the obtained magnetic microcapsules 19 was PHA including a 3-hydroxyoctanoate unit. Further, the gel permeation chromatography analysis confirmed that PHA in the obtained magnetic microcapsules 19 had a number average molecular weight of 24,000.

Example 19

Magnetic microcapsules 20 were obtained in the same manner as in Example 15 except that the purified enzyme solution (1) in Example 15 was replaced by the purified enzyme solution (3) and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). The drug content in the microcapsules is shown in Table 4.

The evaluation in the same manner as in Example 15 confirmed that the main component of the coat of the obtained magnetic microcapsules 20 was PHA including a 3-hydroxy-5-phenylvalerate unit. Further, the gel permeation chromatography analysis confirmed that PHA in the obtained magnetic microcapsules 20 had a number average molecular weight of 21,000.

Example 20

Magnetic microcapsules 21 were obtained in the same manner as in Example 15 except that the purified enzyme solution (1) in Example 15 was replaced by the crude enzyme solution (3) and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). The drug content in the microcapsules is shown in Table 4.

The evaluation in the same manner as in Example 15 confirmed that the main component of the coat of the obtained magnetic microcapsules 21 was PHA including a 3-hydroxy-5-phenoxy valerate unit. Further, the gel permeation chromatography analysis confirmed that PHA in the obtained magnetic microcapsules 21 had a number average molecular weight of 24,000.

Example 21

A PHA synthesis reaction was conducted in the same manner as in Example 15 except that the purified enzyme solution (1) in Example 15 was replaced by the crude enzyme solution (4) and (R)-3-hydroxybutyryl CoA was replaced by (R,S)-3-hydroxy-5-phenylvaleryl CoA. After the reaction at room temperature for an hour, 60 mg of (R,S)-3-hydroxy-5-phenoxyvaleryl CoA was further added to the mixture for a reaction at room temperature for additional 2 hours. The subsequent treatment was conducted in the same manner as in Example 15, to thereby obtain magnetic microcapsules 22. The drug content in the microcapsules is shown in Table 4.

Mass of a polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement using TOF-SIMS in the same manner while cutting off the capsular structure surface little by little through ion sputtering confirmed that the main component of the PHA monomer unit constituting the capsular structure was replaced by a 3-hydroxy-5-phenylvalerate unit at a certain point in time. The results confirmed that a capsular structure of Example 21 had a desired structure containing poly(3-hydroxy-5-phenoxy valeric acid) coated on poly(3-hydroxy-5-phenylvaleric acid), which was coated with Drug 1. Further, the gel permeation chromatography analysis confirmed that the PHA in the obtained magnetic microcapsules 22 had a number average molecular weight of 21,000.

Example 22

Magnetic microcapsules 23 were obtained in the same manner as in Example 15 except that the purified enzyme solution (1) in Example 15 was replaced by the crude enzyme solution (5) and 60 mg of (R)-3-hydroxybutyryl CoA was replaced by 48 mg of (R,S)-3-hydroxy-5-phenylvaleryl CoA and 12 mg of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). The drug content in the microcapsules is shown in Table 4.

The results of $^1$H-NMR (equipment used: FT-NMR (Bruker DPX400); measured nuclide: $^1$H; solvent used: $CDCl_3$ (containing TMS)) analysis confirmed that the coat of the obtained magnetic microcapsules 23 was PHA including 75% 3-hydroxy-5-phenylvalerate unit and 25% 3-hydroxy-7,8-epoxyoctanoate unit. Further, the gel permeation chromatography analysis confirmed that the PHA in the obtained magnetic microcapsules 23 had a number average molecular weight of 22,000.

Example 23

50 parts by mass of the above-mentioned magnetic microcapsules 23 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain magnetic microcapsules 24. The drug content in the microcapsules is shown in Table 4.

Infrared absorption was measured for the magnetic microcapsules 24 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the magnetic microcapsules 24. The disappearance indicates that the magnetic microcapsules 24 coated with a crosslinked polymer were obtained through a reaction between PHA having an epoxy unit in the side chain and hexamethylene diamine.

Example 24

10 parts by mass of terminal amino group-modified polysiloxane (modified silicone oil TSF4700, available from GE Toshiba Silicones) was added to 50 parts by mass of the above-mentioned magnetic microcapsules 23, and the whole was reacted at 70° C. for 2 hours. The reacted mixture was then washed by repeated suspension in methanol and centrifugation (10,000×g, 4° C., 20 minutes) and dried, to thereby obtain magnetic microcapsules 25 having a graft chain of polysiloxane. The drug content in the microcapsules is shown in Table 4.

Infrared absorption was measured for the magnetic microcapsules 25 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the magnetic microcapsules 25. The disappearance indicates that the magnetic microcapsules 25 having a graft chain of polysiloxane were obtained through a reaction between PHA having an epoxy unit in the side chain and terminal amino group-modified polysiloxane.

TABLE 4

| Example | Magnetic capsule No. | Drug content (%) |
|---|---|---|
| 15 | 16 | 12.0 |
| 16 | 17 | 12.2 |
| 17 | 18 | 12.9 |
| 18 | 19 | 13.3 |
| 19 | 20 | 13.6 |
| 20 | 21 | 12.8 |
| 21 | 22 | 13.0 |
| 22 | 23 | 12.7 |
| 23 | 24 | 12.1 |
| 24 | 25 | 12.5 |

Example 25

500 mg of peptide A acetate (available from TAP Pharmaceutical Products Inc.) was dissolved in 0.6 ml of distilled water. The obtained solution was added to 5.8 ml of dichloromethane having 1.5 g of the magnetic substances 1 dispersed therein, and the whole was mixed using a small homogenizer (manufactured by Kinematica AG) for 60 seconds, to thereby obtain a W/O type emulsion. The W/O type emulsion was cooled to 16° C. and added to 100 ml of a 0.1 M aqueous phosphate buffer (pH 7.0) solution of 0.1% polyvinyl alcohol (EG-40, available from Nippon Synthetic Chemicals Co.) cooled to 16° C. in advance, to thereby obtain a W/O/W type emulsion through stirring at 7,000 rpm using a turbine-type homomixer (manufactured by Tokushu Kika Kogyo Co., Ltd.). 5 ml of the purified enzyme solution (1), 1 g of (R)-3-hydroxybutyryl CoA (available from Sigma Aldrich Japan K. K.), and 100 mg of bovine serum albumin (available from Sigma Co.) were added to the W/O/W type emulsion and dissolved therein.

The W/O/W type emulsion was stirred at room temperature for 3 hours for PHA synthesis while dichloromethane was vaporized. The solidified W/O type emulsion was centrifuged at 2,000 rpm with a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The mixture was freeze-dried, to thereby obtain magnetic microcapsules 26 in powder form. The peptide A content in the microcapsules is shown in Table 5.

Further, the magnetic microcapsules 26 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylated compound of hydroxybutyric acid. This result confirmed that the main component of the coat of the obtained magnetic microcapsules 26 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mw=78,000.

Example 26

Magnetic microcapsules 27 were obtained in the same manner as in Example 25 except that the purified enzyme solution (1) in Example 25 was replaced by the crude enzyme solution (1). The drug content in the microcapsules is shown in Table 5.

The evaluation in the same manner as in Example 25 confirmed that the main component of the coat of the obtained magnetic microcapsules 27 was PHB. Further, the gel permeation chromatography analysis confirmed that PHA in the obtained magnetic microcapsules 27 had a number average molecular weight of 75,000.

Example 27

Magnetic microcapsules 28 were obtained in the same manner as in Example 25 except that the purified enzyme solution (1) in Example 25 was replaced by the crude enzyme solution (2). The drug content in the microcapsules is shown in Table 5.

The evaluation in the same manner as in Example 25 confirmed that the main component of the coat of the obtained magnetic microcapsules 28 was PHB. Further, the gel permeation chromatography analysis confirmed that PHA in the obtained magnetic microcapsules 28 had a number average molecular weight of 77,000.

Example 28

Magnetic microcapsules 29 were obtained in the same manner as in Example 25 except that the purified enzyme solution (1) in Example 25 was replaced by the purified enzyme solution (2) and (R)-3-hydroxybutyryl CoA was replaced by (R)-3-hydroxyoctanoyl CoA (prepared following a procedure described in Eur. J. Biochem., 250, 432-439, 1997). The drug content in the microcapsules is shown in Table 5.

The evaluation in the same manner as in Example 25 confirmed that the main component of the coat of the obtained magnetic microcapsules 29 was PHA including a 3-hydroxyoctanoate unit. Further, the gel permeation chromatography analysis confirmed that PHA in the obtained magnetic microcapsules 29 had a number average molecular weight of 27,000.

Example 29

Magnetic microcapsules 30 were obtained in the same manner as in Example 25 except that the purified enzyme solution (1) in Example 25 was replaced by the purified enzyme solution (3) and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). The drug content in the microcapsules is shown in Table 5.

The evaluation in the same manner as in Example 25 confirmed that the main component of the coat of the obtained magnetic microcapsules 30 was PHA including a 3-hydroxy-5-phenylvalerate unit. Further, the gel permeation chromatography analysis confirmed that PHA in the obtained magnetic microcapsules 30 had a number average molecular weight of 22,000.

Example 30

Magnetic microcapsules 31 were obtained in the same manner as in Example 25 except that the purified enzyme solution (1) in Example 25 was replaced by the crude enzyme solution (3) and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). The drug content in the microcapsules is shown in Table 5

The evaluation in the same manner as in Example 25 confirmed that the main component of the coat of the obtained magnetic microcapsules 31 was PHA including a 3-hydroxy-5-phenoxy valerate unit. Further, the gel permeation chromatography analysis confirmed that PHA in the obtained magnetic microcapsules 31 had a number average molecular weight of 23,000.

Example 31

A PHA synthesis reaction was conducted in the same manner as in Example 25 except that the purified enzyme solution (1) in Example 25 was replaced by the crude enzyme solution (4) and (R)-3-hydroxybutyryl CoA was replaced by (R,S)-3-hydroxy-5-phenylvaleryl CoA. After the reaction at room temperature for an hour, 1 g of (R,S)-3-hydroxy-5-phenoxyvaleryl CoA was further added to the mixture for a reaction at room temperature for additional 2 hours. The subsequent treatment was conducted in the same manner as in Example 25, to thereby obtain magnetic microcapsules 32. The drug content in the microcapsules is shown in Table 5.

Mass of a polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement using TOF-SIMS in the same manner while cutting off the capsular structure surface little by little through ion sputtering confirmed that the main component of the PHA monomer unit constituting the capsular structure was replaced by a 3-hydroxy-5-phenylvalerate unit at a certain point in time. The results confirmed that a capsular structure of Example 31 had a desired capsular structure containing poly(3-hydroxy-5-phenoxy valeric acid) coated on poly(3-hydroxy-5-phenylvaleric acid), which was coated with Drug 1. Further, the gel permeation chromatography analysis confirmed that the PHA in the obtained magnetic microcapsules 32 had a number average molecular weight of 24,000.

Example 32

Magnetic microcapsules 33 were obtained in the same manner as in Example 25 except that the purified enzyme solution (1) in Example 25 was replaced by the crude enzyme solution (5) and 1 g of (R)-3-hydroxybutyryl CoA was replaced by 800 mg of (R,S)-3-hydroxy-5-phenylvaleryl CoA and 200 mg of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). The drug content in the microcapsules is shown in Table 5.

The results of $^1$H-NMR (equipment used: FT-NMR (Bruker DPX400); measured nuclide: $^1$H; solvent used: CDCl$_3$ (containing TMS)) analysis confirmed that the coat of the obtained magnetic microcapsules 33 was PHA including 78% 3-hydroxy-5-phenylvalerate unit and 22% 3-hydroxy-7,8-epoxyoctanoate unit. Further, the gel permeation chromatography analysis confirmed that the PHA in the obtained magnetic microcapsules 33 had a number average molecular weight of 25,000.

Example 33

50 parts by mass of the above-mentioned magnetic microcapsules 33 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain magnetic microcapsules 34. The drug content in the microcapsules is shown in Table 5.

Infrared absorption was measured for the magnetic microcapsules 34 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 34. The disappearance indicates that the magnetic microcapsules 34 coated with a crosslinked polymer were obtained through a reaction between PHA having an epoxy unit in the side chain and hexamethylene diamine.

Example 34

10 parts by mass of terminal amino group-modified polysiloxane (modified silicone oil TSF4700, available from GE Toshiba Silicones) was added to 50 parts by mass of the above-mentioned magnetic microcapsules 33, and the whole was reacted at 70° C. for 2 hours. The reacted mixture was then washed by repeated suspension in methanol and centrifugation (10,000×g, 4° C., 20 minutes) and dried, to thereby obtain magnetic microcapsules 35 having a graft chain of polysiloxane. The drug content in the microcapsules is shown in Table 5.

Infrared absorption was measured for the magnetic microcapsules 35 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 35. The disappearance indicates that the magnetic microcapsules 35 having a graft chain of polysiloxane were obtained through a reaction between PHA having an epoxy unit in the side chain and hexamethylene diamine.

TABLE 5

| Example | Magnetic capsule No. | Drug content (%) |
|---|---|---|
| 25 | 26 | 12.2 |
| 26 | 27 | 12.2 |
| 27 | 28 | 12.8 |
| 28 | 29 | 13.5 |
| 29 | 30 | 13.1 |
| 30 | 31 | 12.4 |
| 31 | 32 | 13.1 |
| 32 | 33 | 12.7 |
| 33 | 34 | 12.2 |
| 34 | 35 | 12.1 |

Experimental Example 1

About 20 mg of the magnetic microcapsules 12 was dispersed in 0.5 mg of a dispersion solvent (distilled water having dissolved therein 2.5 mg of carboxymethylcellulose, 0.5 mg of a polysorbate 80, and 25.0 mg of mannitol), and the dispersion was administered under dorsal skin of 10-week-old male SD rats using an injection needle 22G. The rats were slaughtered at regular time intervals after administration, and the microcapsules remaining in administered sites were taken out. The amounts of the peptide A in the microcapsules thus taken out were determined, and the results thereof are shown in Table 6.

Experimental Examples 2 to 9 and Comparative Experimental Example 1

Preparations were prepared in the same manner as in Experimental Example 1 except that the magnetic microcapsules 12, 13, 14, 15, 23, 24, 25, 33, 34, and 35 were used as the microcapsules, and the amounts of the peptide A were sequentially determined. Residual rates of the peptide A are shown in Table 6.

TABLE 6

| Experimental Example | Magnetic microcapsule | Residual amount according to time (week) after administration (%) | | | |
|---|---|---|---|---|---|
| | | 1 | 2 | 3 | 4 |
| 1 | 12 | 80.0 | 62.1 | 42.3 | 28.7 |
| 2 | 13 | 87.2 | 69.2 | 47.3 | 35.2 |
| 3 | 14 | 83.4 | 64.3 | 42.1 | 31.2 |
| 4 | 23 | 82.3 | 64.2 | 42.3 | 30.2 |
| 5 | 24 | 90.4 | 72.4 | 52.1 | 38.9 |
| 6 | 25 | 84.5 | 67.3 | 45.8 | 34.5 |
| 7 | 33 | 84.3 | 62.3 | 40.0 | 29.9 |
| 8 | 34 | 91.2 | 74.3 | 54.1 | 37.3 |
| 9 | 35 | 86.7 | 63.1 | 45.6 | 33.3 |
| Comparative Experimental Example 1 | 15 | 81.3 | 52.3 | 35.0 | 21.3 |

Example 35

Microcapsules carrying vancomycin as an antibiotic were prepared as described below.

10 ml of a 5% glucose solution containing 0.2 g of vancomycin, 10 U/ml of *Pseudomonas cichorii* YN2-originated PHA synthetic enzyme YN2-C2 prepared in Reference Example 6, and 1 mM (final concentration) of (R)-3-hydroxy-5-phenylvaleryl CoA prepared in Reference Example 8 was added to 70 ml of chloroform having the magnetic substances 1 (1.5 g) dispersed therein. The mixture was emulsified using a probe-type ultrasonic oscillator (manufactured by Ohtake. Seisakusho), to thereby prepare a W/O type emulsion. Ultrasonic irradiation was repeated ten times at 50 W for 30 seconds. The thus-prepared emulsion was incubated at 37° C. for 3 hours for a PHA synthesis reaction.

The reaction mixture was size-fractionated through gel filtration (column; Sephadex G-50), to thereby obtain magnetic microcapsules. A dynamic light-scattering method confirmed that the microcapsules had an average particle size of 840 nm and were monodispersed.

A part of the prepared magnetic microcapsules were dried under vacuum, suspended in 20 ml of chloroform, and stirred at 60° C. for 20 hours, to thereby extract PHA constituting a coat. The extract was filtered through a membrane filter having a pore size of 0.45 µm, concentrated under reduced pressure using a rotary evaporator, and then subjected to methanolysis according to a conventional method. The product was analyzed using a gas chromatograph-mass spectrometer (GC-MS: QP-5050, manufactured by Shimadzu Corporation; EI method) to identify a methylesterified compound of the PHA monomer unit. As a result, the PHA was identified as PHA containing 3-hydroxy-5-phenylvaleric acid as a monomer unit. Further, the molecular weight of the PHA was determined through gel permeation chromatography (GPC: HLC-8020, manufactured by Tosoh Corporation; column: PLgel MIXED-C (5 µm), available from Polymer Laboratories; solvent: chloroform; column temperature: 40° C.; polystyrene equivalents), resulting in Mn=15,000 and Mw=37,000.

Example 36

A solution containing 200 mg of 8-[1-oxo-3-[1-(phenylmethyl)piperidin-4-yl]propyl]-2,3,4,5-tetrahydro-1H-1-benzazepine (hereinafter, referred to as Drug 2), 2.0 g of Example Compound 1, and the magnetic substances 1 (2.0 g) dissolved in 2 ml of dichloromethane was cooled to 16 to 18° C. The solution was then added to 500 ml of a 0.1% aqueous solution of polyvinyl alcohol (EG-40, available from Nippon Synthetic Chemical Industry Co., Ltd.) cooled down to 16 to 18° C. in advance and stirred at 7,000 rpm using a turbine-type homomixer (manufactured by Tokushu Kika Kogyo Co., Ltd.), to thereby obtain an O/W type emulsion. The obtained O/W type emulsion was stirred at room temperature for 3 hours to vaporize dichloromethane for solidifying an oil phase, and centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 36 in powder form. The drug content in the microcapsules is shown in Table 7. Note that, the drug content was determined by measuring a sample containing the microcapsules (25 mg) dissolved in 10 µl of a 60% acetonitrile-containing phosphate buffer (pH 7) through an HPLC method.

Examples 37 to 47

Magnetic microcapsules 37 to 47 were prepared in the same manner as in Example 36 except that Example Compounds 2 to 12 were used. The drug contents in the microcapsules are shown in Table 7.

Example 48

50 parts by mass of the above-mentioned magnetic microcapsules 47 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain magnetic microcapsules 48.

Infrared absorption was measured for the magnetic microcapsules 48 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 48. The disappearance indicates that the magnetic microcapsules 48 coated with a crosslinked polymer were obtained through a reaction between PHA having an epoxy unit in the side chain and hexamethylene diamine.

Example 49

10 parts by mass of terminal amino group-modified polysiloxane (modified silicone oil TSF4700, available from GE Toshiba Silicones) was added to 50 parts by mass of the above-mentioned magnetic microcapsules 47, and the whole was reacted at 70° C. for 2 hours. The reacted mixture was then washed by repeated suspension in methanol and centrifugation (10,000×g, 4° C., 20 minutes) and dried, to thereby obtain magnetic microcapsules 49 having a graft chain of polysiloxane.

Infrared absorption was measured for the magnetic microcapsules 49 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the magnetic microcapsules 49. The disappearance indicates that the magnetic microcapsules 49 having a graft chain of polysiloxane were obtained through a reaction between PHA having an epoxy unit in the side chain and terminal amino group-modified polysiloxane.

Comparative Example 2

Magnetic microcapsules 50 were obtained in the same manner as in Example 36 except that the example compound was replaced by a lactic acid-glycolic acid copolymer (hereinafter, abbreviated as PLGA) (lot No. K1030 available from Wako Pure Chemical Industries, Ltd.; lactic acid/glycolic acid composition ratio (mole %): 75/25; and GPC weight average molecular weight: 13,000). The drug content in the microcapsules is shown in Table 7.

TABLE 7

| Example | Magnetic capsule No. | Example Compound No. | Drug content (%) |
|---|---|---|---|
| 36 | 36 | 1 | 6.5 |
| 37 | 37 | 2 | 5.8 |
| 38 | 38 | 3 | 6.0 |
| 39 | 39 | 4 | 6.1 |
| 40 | 40 | 5 | 6.5 |
| 41 | 41 | 6 | 5.5 |
| 42 | 42 | 7 | 5.8 |
| 43 | 43 | 8 | 6.0 |
| 44 | 44 | 9 | 5.5 |
| 45 | 45 | 10 | 6.4 |
| 46 | 46 | 11 | 6.4 |
| 47 | 47 | 12 | 6.9 |
| 48 | 48 | 12 + crosslinking | 6.7 |
| 49 | 49 | 12 + grafting | 6.4 |
| Comparative Example 2 | 50 | PLGA | 4.9 |

Comparative Example 3

Magnetic microcapsules 65 were obtained in the same manner as in Example 50 except that the example compound was replaced by a lactic acid-glycolic acid copolymer (hereinafter, abbreviated as PLGA) (lot No. K1030 available from Wako Pure Chemical Industries, Ltd.; lactic acid/glycolic acid composition ratio (mole %): 75/25; and GPC weight average molecular weight: 13,000). The drug content in the microcapsules is shown in Table 8.

TABLE 8

| Example | Magnetic capsule No. | Example Compound No. | Drug content (%) |
|---|---|---|---|
| 50 | 51 | 1 | 16.5 |
| 51 | 52 | 2 | 16.5 |
| 52 | 53 | 3 | 17.5 |
| 53 | 54 | 4 | 17.1 |
| 54 | 55 | 5 | 18.0 |
| 55 | 56 | 6 | 16.4 |
| 56 | 57 | 7 | 17.3 |
| 57 | 58 | 8 | 17.2 |
| 58 | 59 | 9 | 15.9 |
| 59 | 60 | 10 | 17.8 |
| 60 | 61 | 11 | 17.0 |
| 61 | 62 | 12 | 17.7 |
| 62 | 63 | 12 + crosslinking | 17.4 |
| 63 | 64 | 12 + grafting | 17.2 |
| Comparative Example 3 | 65 | PLGA | 14.9 |

Example 50

A solution containing 1.5 g of Drug 2, 4.5 g of Example Compound 1, and 1.5 g of the magnetic substances 1 dissolved in 9 ml of dichloromethane was cooled to 16 to 18° C. The solution was then added to 500 ml of a 0.1% aqueous solution of polyvinyl alcohol cooled down to 16 to 18° C. in advance and stirred at 8,000 rpm using a turbine-type homomixer (manufactured by Tokushu Kika Kogyo Co., Ltd.), to thereby obtain an O/W type emulsion. The obtained O/W type emulsion was stirred at room temperature for 3 hours to vaporize dichloromethane for solidifying an oil phase, and centrifuged with a centrifuge at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 51 in powder form. The drug content in the microcapsules is shown in Table 8.

Examples 51 to 61

Magnetic microcapsules 52 to 62 were prepared in the same manner as in Example 50 except that Example Compounds 2 to 12 were used. The drug contents in the microcapsules are shown in Table 8.

Example 62

Magnetic microcapsules 63 were prepared in the same manner as in Example 48 except that the magnetic microcapsules 62 were used. The drug content in the microcapsules is shown in Table 8.

Example 63

Magnetic microcapsules 64 were prepared in the same manner as in Example 49 except that the magnetic microcapsules 62 were used. The drug content in the microcapsules is shown in Table 8.

Example 64

A solution containing 200 mg of Drug 1 and 0.5 g of the magnetic substances 1 dissolved in 2 ml of dichloromethane was cooled to 16 to 18° C. The solution was then added to 100 ml of a 0.1 M phosphate buffer (pH 7.0) containing 0.1% polyvinyl alcohol (EG-40, available from Nippon Synthetic Chemical Industry Co., Ltd.) dissolved, cooled down to 16 to 18° C. in advance. The mixture was stirred at 7,000 rpm using a turbine-type homomixer (manufactured by Tokushu Kika Kogyo Co., Ltd.), to thereby obtain an O/W type emulsion. 5 ml of the purified enzyme solution (1), 1 g of (R)-3-hydroxybutyryl CoA (available from Sigma Aldrich Japan K. K.), and 0.1 g of bovine serum albumin (available from Sigma Co.) were added to the obtained O/W type emulsion and dissolved therein. The obtained O/W type emulsion was gently stirred at room temperature for 3 hours to synthesize PHA and vaporize dichloromethane for solidifying an oil phase, and centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 66 in powder form. The drug content in the microcapsules is shown in Table 9. Note that, the drug content was determined by measuring a sample containing the microcapsules (25 mg) dissolved in 10 ml of a 60% acetonitrile-containing phosphate buffer (pH 7) through an HPLC method.

Further, the magnetic microcapsules 66 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylated compound of hydroxybutyric acid. This result confirmed that the main component of the coat of the obtained magnetic microcapsules 66 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mw=78,000.

Example 65

Magnetic microcapsules 67 were obtained in the same manner as in Example 64 except that the purified enzyme solution (1) in Example 64 was replaced by the crude enzyme solution (1). The drug content in the microcapsules is shown in Table 9.

The evaluation in the same manner as in Example 64 confirmed that the main component of the coat of the obtained magnetic microcapsules 67 was PHB. Further, the gel permeation chromatography analysis confirmed that PHA in the obtained magnetic microcapsules 67 had a number average molecular weight of 75,000.

Example 66

Magnetic microcapsules 68 were obtained in the same manner as in Example 64 except that the purified enzyme solution (1) in Example 64 was replaced by the crude enzyme solution (2). The drug content in the microcapsules is shown in Table 9.

The evaluation in the same manner as in Example 64 confirmed that the main component of the coat of the obtained magnetic microcapsules 68 was PHB. Further, the gel permeation chromatography analysis confirmed that PHA in the obtained magnetic microcapsules 68 had a number average molecular weight of 74,000.

Example 67

Magnetic microcapsules 69 were obtained in the same manner as in Example 64 except that the purified enzyme solution (1) in Example 64 was replaced by the purified enzyme solution (2) and (R)-3-hydroxybutyryl CoA was replaced by (R)-3-hydroxyoctanoyl CoA (prepared following a procedure described in Eur. J. Biochem., 250, 432-439, 1997). The drug content in the microcapsules is shown in Table 9.

The evaluation in the same manner as in Example 64 confirmed that the main component of the coat of the obtained magnetic microcapsules 69 was PHA including a 3-hydroxyoctanoate unit. Further, the gel permeation chromatography analysis confirmed that PHA in the obtained magnetic microcapsules 69 had a number average molecular weight of 25,000.

Example 68

Magnetic microcapsules 70 were obtained in the same manner as in Example 64 except that the purified enzyme solution (1) in Example 64 was replaced by the purified enzyme solution (3) and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). The drug content in the microcapsules is shown in Table 9. The evaluation in the same manner as in Example 64 confirmed that the main component of the coat of the obtained magnetic microcapsules 70 was PHA including a 3-hydroxy-5-phenylvalerate unit. Further, the gel permeation chromatography analysis confirmed that PHA in the obtained magnetic microcapsules 70 had a number average molecular weight of 22,000.

Example 69

Magnetic microcapsules 71 were obtained in the same manner as in Example 64 except that the purified enzyme solution (1) in Example 64 was replaced by the crude enzyme solution (3) and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). The drug content in the microcapsules is shown in Table 9.

The evaluation in the same manner as in Example 64 confirmed that the main component of the coat of the obtained magnetic microcapsules 71 was PHA including a 3-hydroxy-5-phenoxy valerate unit. Further, the gel permeation chromatography analysis confirmed that PHA in the obtained magnetic microcapsules 71 had a number average molecular weight of 24,000.

Example 70

A PHA synthesis reaction was conducted in the same manner as in Example 64 except that the purified enzyme solution (1) in Example 64 was replaced by the crude enzyme solution (4) and (R)-3-hydroxybutyryl CoA was replaced by (R,S)-3-hydroxy-5-phenylvaleryl CoA. After the reaction at room temperature for an hour, 1 g of (R,S)-3-hydroxy-5-phenoxyvaleryl CoA was further added to the mixture for a reaction at room temperature for additional 2 hours. The subsequent treatment was conducted in the same manner as in Example 64, to thereby obtain magnetic microcapsules 72. The drug content in the microcapsules is shown in Table 9. Mass of a polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement using TOF-SIMS in the same manner while cutting off the capsular structure surface little by little through ion sputtering confirmed that the main component of the PHA monomer unit constituting the capsular structure was replaced by a 3-hydroxy-5-phenylvalerate unit at a certain point in time. The results confirmed that a capsular structure of Example 70 had a desired capsular structure containing poly(3-hydroxy-5-phenoxy valeric acid) coated on poly(3-hydroxy-5-phenylvaleric acid), which was coated with Drug 2. Further, the gel permeation chromatography analysis confirmed that the PHA in the obtained magnetic microcapsules 72 had a number average molecular weight of 23,000.

Example 71

Magnetic microcapsules 73 were obtained in the same manner as in Example 64 except that the purified enzyme solution (1) in Example 64 was replaced by the crude enzyme solution (5) and 1 g of (R)-3-hydroxybutyryl CoA was replaced by 0.8 g of (R,S)-3-hydroxy-5-phenylvaleryl CoA and 0.2 g of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). The drug content in the microcapsules is shown in Table 9.

The results of $^1$H-NMR (equipment used: FT-NMR (Bruker DPX400); measured nuclide: $^1$H; solvent used: $CDCl_3$ (containing TMS)) analysis confirmed that the coat of the obtained magnetic microcapsules 73 was PHA including 76% 3-hydroxy-5-phenylvalerate unit and 24% 3-hydroxy-7,8-epoxyoctanoate unit. Further, the gel permeation chromatography analysis confirmed that the PHA in the obtained magnetic microcapsules 73 had a number average molecular weight of 20,000.

Example 72

50 parts by mass of the above-mentioned magnetic microcapsules 73 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain magnetic microcapsules 74. The drug content in the microcapsules is shown in Table 9.

Infrared absorption was measured for the magnetic microcapsules 74 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the magnetic microcapsules 74. The disappearance indicates that the magnetic microcapsules 74 coated with a crosslinked polymer were obtained through a reaction between PHA having an epoxy unit in the side chain and hexamethylene diamine.

Example 73

10 parts by mass of terminal amino group-modified polysiloxane (modified silicone oil TSF4700, available from GE Toshiba Silicones) was added to 50 parts by mass of the above-mentioned magnetic microcapsules 73, and the whole was reacted at 70° C. for 2 hours. The reacted mixture was then washed by repeated suspension in methanol and centrifugation (10,000×g, 4° C., 20 minutes) and dried, to thereby obtain magnetic microcapsules 75 having a graft chain of polysiloxane. The drug content in the microcapsules is shown in Table 9.

Infrared absorption was measured for the magnetic microcapsules 75 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the magnetic microcapsules 75. The disappearance indicates that the magnetic microcapsules 75 having a graft chain of polysiloxane were obtained through a reaction between PHA having an epoxy unit in the side chain and terminal amino group-modified polysiloxane.

TABLE 9

| Example | Magnetic capsule No. | Drug content (%) |
|---|---|---|
| 64 | 66 | 6.0 |
| 65 | 67 | 6.3 |
| 66 | 68 | 5.7 |
| 67 | 69 | 6.4 |
| 68 | 70 | 6.0 |
| 69 | 71 | 6.2 |
| 70 | 72 | 7.0 |
| 71 | 73 | 7.0 |
| 72 | 74 | 6.7 |
| 73 | 75 | 6.8 |

Experimental Example 10

62.8 mg (30 mg/kg in body weight equivalents as drug) of the magnetic microcapsules 62 obtained in Example 61 was dispersed in 0.5 ml of a dispersion solvent (distilled water having dissolved therein 2.5 mg of carboxymethylcellulose, 1.0 mg of polysorbate 80, and 25 mg of mannitol), and the dispersion was administered under dorsal skin of 10-week-old male SD rats using an injection needle 22G. The rats were slaughtered at regular time intervals after administration, and the microcapsules remaining in administered sites were taken out. The amounts of the drug in the microcapsules thus taken out were determined, and residual amounts with respect to the dosage are shown in Table 10.

Experimental Examples 11 to 15 and Comparative Experimental Example 2

Preparations were prepared in the same manner as in Experimental Example 10 except that the magnetic microcapsules 62, 63, 64, 65, 73, 74, and 75 (30 mg/kg in body weight equivalents as drug) were used. The amounts of the drug were sequentially determined, and residual amounts are shown in Table 10.

TABLE 10

| Experimental Example | Magnetic microcapsule | Residual amount according to time (week) after administration (%) | | | |
|---|---|---|---|---|---|
| | | 1 | 2 | 3 | 4 |
| 10 | 62 | 82.1 | 59.5 | 18.2 | 7.9 |
| 11 | 63 | 92.3 | 73.1 | 35.2 | 15.3 |
| 12 | 64 | 85.6 | 63.2 | 27.2 | 12.1 |
| 13 | 73 | 88.1 | 62.3 | 19.8 | 12.1 |
| 14 | 74 | 91.3 | 74.2 | 37.4 | 18.1 |
| 15 | 75 | 89.9 | 65.4 | 23.9 | 14.2 |
| Comparative Experimental Example 2 | 65 | 88.8 | 57.1 | 5.6 | 0.9 |

Example 74

12 ml of purified water was added to a solution containing 2.0 g of Example Compound 1 and the magnetic substances 1 (1 g) dissolved in 20 ml of methylene chloride, and the mixture was shaken and stirred, to thereby prepare a W/O type emulsion. Further, the ultrasonic irradiation to the mixture reduced a diameter of an internal water phase. 32 ml of the W/O type emulsion was added to a 1 w/v % aqueous solution of polyvinyl alcohol with stirring using a small homogenizer (POLYTRON, manufactured by Kinematica AG (Switzerland)), to thereby obtain a W/O/W type emulsion. The W/O/W type emulsion was stirred using a stirrer for 6 hours to evaporate methylene chloride, which is an organic solvent in an oil phase, to solidify Example Compound 1 in the oil phase. Fine particles were collected through centrifugation, and washed simultaneously with cooled purified water. The fine particles were redispersed in a 0.1% aqueous solution of Tween 80 and freeze-dried, to thereby obtain the hollow magnetic microcapsules 1, which are fine particles in powder form. Further, an ultrasonic contrast agent employing the hollow magnetic microcapsules 1 is referred to as an ultrasonic contrast agent 1. Observation results of the obtained hollow microcapsule fine particles using an optical microscope and an electron microscope are shown in Table 11.

Examples 75 to 85

Hollow magnetic microcapsules 2 to 12 as fine particles in powder form, were obtained in the same manner as in Example 74 except that Example Compounds 2 to 12 were used as polymers dissolved in an oil phase of the W/O type emulsion during preparation thereof. Further, ultrasonic contrast agents employing the hollow magnetic microcapsules are referred to as ultrasonic contrast agents 2 to 12.

The observation results of the obtained hollow microcapsule fine particles using an optical microscope and an electron microscope are shown in Table 11.

Example 86

50 parts by mass of the above-mentioned hollow magnetic microcapsules 12 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain hollow magnetic microcapsules 13. An ultrasonic contrast agent employing the hollow magnetic microcapsules 13 subjected to crosslinking treatment is referred to as an ultrasonic contrast agent 13. The observation results of the obtained microcapsule fine particles using an optical microscope and an electron microscope are shown in Table 11.

Infrared absorption was measured for the hollow magnetic microcapsules 13 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 13. The disappearance indicates that the hollow magnetic microcapsules 13 having the surface coated with a polymer crosslinked through ring-opening addition of diamine and an epoxy group were obtained through a reaction between PHA containing a unit having an epoxy group in the side chain and hexamethylene diamine.

Example 87

10 parts by mass of terminal amino group-modified polysiloxane (modified silicone oil TSF4700, available from GE Toshiba Silicones) was added to 50 parts by mass of the above-mentioned hollow magnetic microcapsules 13, and the whole was reacted at 70° C. for 2 hours. The reacted mixture was then washed by repeated suspension in methanol and centrifugation (10,000×g, 4° C., 20 minutes) and dried, to thereby obtain hollow magnetic microcapsules 14 having a graft chain of polysiloxane. An ultrasonic contrast agent employing the hollow magnetic microcapsules 14 having the surface modified by a graft chain of polysiloxane is referred to as an ultrasonic contrast agent 14. The observation results of the obtained microcapsule fine particles using an optical microscope and an electron microscope are shown in Table 11.

Infrared absorption was measured for the hollow magnetic microcapsules 14 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 14. The disappearance indicates that the hollow magnetic microcapsules 14 modified by a graft chain of polysiloxane through ring-opening addition of an epoxy group and a terminal amino group were obtained through a reaction between PHA containing a unit having an epoxy group in the side chain and terminal amino group-modified polysiloxane.

Comparative Example 4

Hollow magnetic microcapsules 15 as fine particles in powder form, were obtained in the same manner as in Example 74 except that poly DL lactic acid (average molecular weight of 7,000) was used as a polymer dissolved in an oil phase of the W/O type emulsion during preparation thereof. An ultrasonic contrast agent employing the hollow magnetic microcapsules 15 constituted of poly DL lactic acid is referred to as an ultrasonic contrast agent 15. The observation results of the obtained microcapsule fine particles using an optical microscope and an electron microscope are shown in Table 11.

TABLE 11

| Example | Hollow magnetic capsule No. | Example Compound No. | Average particle size (μm) | Pore |
|---|---|---|---|---|
| 74 | 1 | 1 | 7.2 | None |
| 75 | 2 | 2 | 7.1 | None |
| 76 | 3 | 3 | 6.9 | None |
| 77 | 4 | 4 | 7.3 | None |
| 78 | 5 | 5 | 7.2 | None |
| 79 | 6 | 6 | 7.4 | None |
| 80 | 7 | 7 | 6.9 | None |
| 81 | 8 | 8 | 7.2 | None |
| 82 | 9 | 9 | 7.3 | None |
| 83 | 10 | 10 | 7.4 | None |
| 84 | 11 | 11 | 7.5 | None |
| 85 | 12 | 12 | 7.2 | None |
| 86 | 13 | 12 + crosslinking | 6.9 | None |
| 87 | 14 | 12 + grafting | 7.0 | None |
| Comparative Example 4 | 15 | PLGA | 6.3 | Present |

Pore: represent whether or not pores are formed on the coat through transpiration of inner phase water or organic solvent during drying Example 88

An aqueous solution containing 0.6 ml of the purified enzyme solution (1), 300 mg of (R)-3-hydroxybutyryl CoA (available from Sigma-Aldrich Japan K.K.), and 12 mg of bovine serum albumin (available from Sigma Co.) dissolved in 12 ml of a 0.1 M phosphate buffer (pH 7.0) was added to 20 ml of a methylene chloride solution having the magnetic substances 1 (2 g) dispersed therein. The mixture was shaken and stirred, to thereby prepare a W/O type emulsion. Further, the ultrasonic irradiation to the mixture reduced a diameter of an internal water phase. 32 ml of the W/O type emulsion was added to 200 ml of a 1 w/v % aqueous solution of polyvinyl alcohol with stirring using a small homogenizer (POLYTRON, manufactured by Kinematica AG (Switzerland)), to thereby obtain a W/O/W type emulsion. The W/O/W type emulsion was stirred using a stirrer for 6 hours for PHA synthesis and evaporation of methylene chloride in an oil phase to solidify PHA, to thereby prepare microcapsulated fine particles. The obtained fine particles were collected through centrifugation, and washed simultaneously with cooled purified water. The fine particles were redispersed in a 0.1% aqueous solution of Tween 80 and freeze-dried, to thereby obtain hollow magnetic microcapsules 16 as microcapsulated fine particles in powder form. An ultrasonic contrast agent employing the hollow magnetic microcapsules 16 is referred to as an ultrasonic contrast agent 16. The observation results of the obtained microcapsule fine particles using an optical microscope and an electron microscope are shown in Table 12.

Further, the hollow magnetic microcapsules 16 were suspended in 20 ml of chloroform and the suspension was stirred at 60° C. for 20 hours to extract PHB constituting a microcapsule coat. The extract was filtered through a membrane filter having a pore size of 0.45 µm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of 3-hydroxybutyric acid. This result confirmed that the main component of the coat of the obtained hollow magnetic microcapsules 16 was PHB.

Further, the molecular weight of the PHB was measured by gel permeation chromatography (GPC: HLC-8020, manufactured by Tosoh Corporation; column: PLgel MIXED-C (5 µm), available from Polymer Laboratories; solvent: chloroform; column temperature: 40° C.; polystyrene equivalents). As a result, Mw=72,000.

Example 89

Hollow magnetic microcapsules 17 were obtained under the same conditions as in Example 88 except that the purified enzyme solution (1) used in Example 88 was replaced by the crude enzyme solution (1) originated from a KK01 strain. An ultrasonic contrast agent employing the hollow magnetic microcapsules 17 is referred to as an ultrasonic contrast agent 17.

The observation results of the obtained microcapsule fine particles using an optical microscope and an electron microscope are shown in Table 12. The evaluation of the composition of PHA constituting a microcapsule coat in the same manner as in Example 88 confirmed that the main component of the coat of the obtained hollow magnetic microcapsules 17 was PHB. Further, the gel permeation chromatography analysis confirmed that PHA constituting a coat of the obtained hollow magnetic microcapsules 17 had a number average molecular weight of 73,000.

Example 90

Hollow magnetic microcapsules 18 were obtained under the same conditions as in Example 88 except that the purified enzyme solution (1) used in Example 88 was replaced by the crude enzyme solution (2) originated from a TL2 strain. An ultrasonic contrast agent employing the hollow magnetic microcapsules 18 is referred to as an ultrasonic contrast agent 18.

The observation results of the obtained microcapsule fine particles using an optical microscope and an electron microscope are shown in Table 12.

The evaluation of the composition of PHA constituting a microcapsule coat in the same manner as in Example 88 confirmed that the main component of the coat of the obtained hollow magnetic microcapsules 18 was PHB. Further, the gel permeation chromatography analysis confirmed that PHA constituting a coat of the obtained hollow magnetic microcapsules 18 had a number average molecular weight of 72,000.

Example 91

Hollow magnetic microcapsules 19 were obtained under the same conditions as in Example 88 except that the purified enzyme solution (1) used in Example 88 was replaced by the purified enzyme solution (2) of recombinant PHA synthetic enzyme and (R)-3-hydroxybutyryl CoA was replaced by (R)-3-hydroxyoctanoyl CoA (prepared following a procedure described in Eur. J. Biochem., 250, 432-439, 1997). An ultrasonic contrast agent employing the hollow magnetic microcapsules 19 is referred to as an ultrasonic contrast agent 19.

The observation results of the obtained microcapsule fine particles using an optical microscope and an electron microscope are shown in Table 12.

The evaluation of the composition of PHA constituting a microcapsule coat in the same manner as in Example 88 confirmed that the main component of the coat of the obtained hollow magnetic microcapsules 19 was PHA including a 3-hydroxyoctanoate unit. Further, the gel permeation chromatography analysis confirmed that PRA constituting a coat of the obtained hollow magnetic microcapsules 19 had a number average molecular weight of 25,000.

Example 92

Hollow magnetic microcapsules 20 were obtained under the same conditions as in Example 88 except that the purified enzyme solution (1) used in Example 88 was replaced by the purified enzyme solution (3) of recombinant PHA synthetic enzyme and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). An ultrasonic contrast agent employing the hollow magnetic microcapsules 20 is referred to as an ultrasonic contrast agent 20.

The observation results of the obtained microcapsule fine particles using an optical microscope and an electron microscope are shown in Table 12.

The evaluation of the composition of PHA constituting a microcapsule coat in the same manner as in Example 88 confirmed that the main component of the coat of the obtained hollow magnetic microcapsules 20 was PHA including a 3-hydroxy-5-phenylvalerate unit. Further, the gel permeation chromatography analysis confirmed that PHA constituting a coat of the obtained hollow magnetic microcapsules 20 had a number average molecular weight of 21,000.

Example 93

Hollow magnetic microcapsules 21 were obtained under the same conditions as in Example 88 except that the purified enzyme solution (1) used in Example 88 was replaced by the purified enzyme solution (3) of recombinant PHA synthetic enzyme and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). An ultrasonic contrast agent employing the hollow magnetic microcapsules 21 is referred to as an ultrasonic contrast agent 21.

The observation results of the obtained microcapsule fine particles using an optical microscope and an electron microscope are shown in Table 12.

The evaluation of the composition of PHA constituting a microcapsule coat in the same manner as in Example 88 confirmed that the main component of the coat of the obtained hollow magnetic microcapsules 21 was PHA including a 3-hydroxy-5-phenoxy valerate unit. Further, the gel permeation chromatography analysis confirmed that PHA constituting a coat of the obtained hollow magnetic microcapsules 21 had a number average molecular weight of 22,000.

Example 94

A PHA synthesis reaction was conducted in the same manner as in Example 88 except that the purified enzyme solution (1) used in Example 88 was replaced by the crude enzyme solution (4) originated from a P91 strain and (R)-3-hydroxybutyryl CoA was replaced by (R,S)-3-hydroxy-5-phenylvaleryl CoA. In Example 94, after the reaction at room temperature for 3 hours, 300 mg of (R,S)-3-hydroxy-5-phenoxyvaleryl CoA was further added to the water phase for a reaction at room temperature for additional 2 hours. The subsequent treatment such as evaporation of methylene chloride in the oil phase was conducted in the same manner as in Example 88, to thereby obtain hollow magnetic microcapsules 22. An ultrasonic contrast agent employing the hollow magnetic microcapsules 22 is referred to as an ultrasonic contrast agent 22.

The observation results of the obtained microcapsule fine particles using an optical microscope and an electron microscope are shown in Table 12.

Mass of monomer unit fragments in a PHA polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement of the monomer unit fragments in the PHA polymer using TOF-SIMS while cutting off the capsular structure surface little by little through ion sputtering confirmed that the main component of the PHA monomer unit constituting the capsular structure was replaced by a 3-hydroxy-5-phenylvalerate unit at a point in time when ion sputtering progressed to a certain depth from the coat surface. The results confirmed that a capsular structure of Example 94 was a desired capsular structure having a double layer coat including poly(3-hydroxy-5-phenoxy valeric acid) produced in the latter half of an enzymatic reaction coated on a coat layer of poly(3-hydroxy-5-phenylvaleric acid) produced at the beginning thereof. Further, the gel permeation chromatography analysis confirmed that the PHA constituting the coat surface of the obtained hollow magnetic microcapsules 22 had a number average molecular weight of 23,000.

Example 95

Hollow magnetic microcapsules 23 were obtained under the same conditions as in Example 88 except that the purified enzyme solution (1) used in Example 88 was replaced by the crude enzyme solution (5) originated from a YN2 strain and 60 mg of (R)-3-hydroxybutyryl CoA was replaced by 240 mg of (R,S)-3-hydroxy-5-phenylvaleryl CoA and 60 mg of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). An ultrasonic contrast agent employing the hollow magnetic microcapsules 23 is referred to as an ultrasonic contrast agent 23.

The observation results of the obtained microcapsule fine particles using an optical microscope and an electron microscope are shown in Table 12.

The evaluation results of a PHA composition constituting a microcapsule coat through $^1$H-NMR (equipment used: FT-NMR (Bruker DPX400); measured nuclide: $^1$H; solvent used: $CDCl_3$ (containing TMS)) analysis confirmed that the coat of the obtained hollow magnetic microcapsules 23 was PHA including 77% 3-hydroxy-5-phenylvalerate unit and 23% 3-hydroxy-7,8-epoxyoctanoate unit. Further, the gel permeation chromatography analysis confirmed that the PHA constituting a coat of the obtained hollow magnetic microcapsules 23 had a number average molecular weight of 25,000.

Example 96

50 parts by mass of the above-mentioned hollow magnetic microcapsules 23 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain hollow magnetic microcapsules 24 having the surface subjected to crosslinking treatment. An ultrasonic contrast agent employing the hollow magnetic microcapsules 24 subjected to crosslinking treatment is referred to as an ultrasonic contrast agent 24.

The observation results of the obtained microcapsule fine particles using an optical microscope and an electron microscope are shown in Table 12.

Infrared absorption was measured for the hollow magnetic microcapsules 24 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 24. The disappearance indicates that the hollow magnetic microcapsules 24 coated by a polymer crosslinked and formed through ring-opening addition of diamine and an epoxy group on the surface were obtained through a reaction between PHA containing a unit having an epoxy group in the side chain and hexamethylene diamine.

Example 97

10 parts by mass of terminal amino group-modified polysiloxane (modified silicone oil TSF4700, available from GE Toshiba Silicones) was added to 50 parts by mass of the above-mentioned hollow magnetic microcapsules 23, and the whole was reacted at 70° C. for 2 hours. The reacted mixture was washed by repeated suspension in methanol and centrifugation (10,000×g, 4° C., 20 minutes) and then dried, to thereby obtain hollow magnetic microcapsules 25 added and modified with a graft chain of polysiloxane. An ultrasonic contrast agent employing the hollow magnetic microcapsules 25 having the surface added and modified with a graft chain of polysiloxane is referred to as an ultrasonic contrast agent 25.

The observation results of the obtained microcapsule fine particles using an optical microscope and an electron microscope are shown in Table 12.

Infrared absorption was measured for the hollow magnetic microcapsules 25 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 25. The disappearance indicates that the hollow magnetic microcapsules 25 having surface PHA chemically modified with a graft chain of polysiloxane through ring-opening addition of an epoxy group and a terminal amino group were obtained through a reaction between PHA containing a unit having an epoxy group in the side chain and terminal amino group-modified polysiloxane.

TABLE 12

| Example | Hollow magnetic capsule No. | Average particle size (µm) | Pore |
| --- | --- | --- | --- |
| 88 | 16 | 6.9 | None |
| 89 | 17 | 7.0 | None |
| 90 | 18 | 7.2 | None |
| 91 | 19 | 7.5 | None |
| 92 | 20 | 7.4 | None |
| 93 | 21 | 7.2 | None |
| 94 | 22 | 7.1 | None |
| 95 | 23 | 7.4 | None |
| 96 | 24 | 7.3 | None |
| 97 | 25 | 7.2 | None |

Example 98

12 ml of purified water was added to 20 ml of a methylene chloride solution containing 2 g of the magnetic substances 1 dispersed therein, and the mixture was shaken and stirred, to thereby prepare a W/O type emulsion. Further, the ultrasonic irradiation to the mixture reduced a diameter of an internal water phase. 32 ml of the W/O type emulsion was added to 100 ml of an aqueous solution of a 0.1 M phosphate buffer (pH 7.0) having dissolved therein 1 w/v % of polyvinyl alcohol, 5 ml of the purified enzyme solution (1), 1 g of (R)-3-hydroxybutyryl CoA (available from Sigma-Aldrich Japan K.K.), and 100 mg of bovine serum albumin (available from Sigma Co.) while stirring the solution using (POLYTRON, manufactured by Kinematica AG (Switzerland)), to thereby obtain a W/O/W type emulsion. The W/O/W type emulsion was stirred using a stirrer for 6 hours for PHA synthesis and evaporation of methylene chloride to solidify the PHA produced, to thereby prepare microcapsulated fine particles. The obtained fine particles were collected through centrifugation, and washed simultaneously with cooled purified water. The fine particles were redispersed in a 0.1% aqueous solution of Tween 80 and freeze-dried, to thereby obtain hollow magnetic microcapsules 26 as microcapsulated fine particles in powder form. An ultrasonic contrast agent employing the hollow magnetic microcapsules 26 is referred to as an ultrasonic contrast agent 26.

The observation results of the obtained microcapsule fine particles using an optical microscope and an electron microscope are shown in Table 13. Further, the hollow magnetic microcapsules 26 were suspended in 20 ml of chloroform, and the suspension was stirred at 60° C. for 20 hours to extract PHB constituting a coat. The extract was filtered through a membrane filter having a pore size of 0.45 µm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of hydroxybutyric acid. This result confirmed that the main component of the coat of the obtained hollow magnetic microcapsules 26 was PHB.

Further, the molecular weight of the PHB was measured by gel permeation chromatography (GPC: HLC-8020, manufactured by Tosoh Corporation; column: PLgel MIXED-C (5 µm), available from Polymer Laboratories; solvent: chloroform; column temperature: 40° C.; polystyrene equivalents). As a result, number average molecular weight Mn=71,000.

Example 99

Hollow magnetic microcapsules 27 were obtained under the same conditions as in Example 98 except that the purified enzyme solution (1) used in Example 98 was replaced by the crude enzyme solution (1) originated from a KK01 strain. An ultrasonic contrast agent employing the hollow magnetic microcapsules 27 is referred to as an ultrasonic contrast agent 27.

The observation results of the obtained microcapsule fine particles using an optical microscope and an electron microscope are shown in Table 13.

The evaluation of the composition of PHA constituting a microcapsule coat in the same manner as in Example 98 confirmed that the main component of the coat of the obtained hollow magnetic microcapsules 27 was PHB. Further, the gel permeation chromatography analysis confirmed that PHA constituting a coat of the obtained hollow magnetic microcapsules 27 had a number average molecular weight of 76,000.

Example 100

Hollow magnetic microcapsules 28 were obtained under the same conditions as in Example 98 except that the purified enzyme solution (1) used in Example 98 was replaced by the crude enzyme solution (2) originated from a TL2 strain. An ultrasonic contrast agent employing the hollow magnetic microcapsules 28 is referred to as an ultrasonic contrast agent 28.

The observation results of the obtained microcapsule fine particles using an optical microscope and an electron microscope are shown in Table 13.

The evaluation of the composition of PHA constituting a microcapsule coat in the same manner as in Example 98 confirmed that the main component of the coat of the obtained hollow magnetic microcapsules 28 was PHB. Further, the gel permeation chromatography analysis confirmed that PHA constituting a coat of the obtained hollow magnetic microcapsules 28 had a number average molecular weight of 75,000.

Example 101

Hollow magnetic microcapsules 29 were obtained under the same conditions as in Example 98 except that the purified enzyme solution (1) used in Example 98 was replaced by the crude enzyme solution (2) originated from a TL2 strain and (R)-3-hydroxybutyryl CoA was replaced by (R)-3-hydroxyoctanoyl CoA (prepared following a procedure described in Eur. J. Biochem., 250, 432-439, 1997). An ultrasonic contrast agent employing the hollow magnetic microcapsules 29 is referred to as an ultrasonic contrast agent 29.

The observation results of the obtained microcapsule fine particles using an optical microscope and an electron microscope are shown in Table 13.

The evaluation of the composition of PHA constituting a microcapsule coat in the same manner as in Example 98 confirmed that the main component of the coat of the obtained hollow magnetic microcapsules 29 was PHA including a 3-hydroxyoctanoate unit. Further, the gel permeation chromatography analysis confirmed that PHA constituting a coat of the obtained hollow magnetic microcapsules 29 had a number average molecular weight of 25,000.

Example 102

Hollow magnetic microcapsules 30 were obtained under the same conditions as in Example 98 except that the purified enzyme solution (1) used in Example 98 was replaced by the crude enzyme solution (3) originated from a P91 strain and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). An ultrasonic contrast agent employing the hollow magnetic microcapsules 30 is referred to as an ultrasonic contrast agent 30.

The observation results of the obtained microcapsule fine particles using an optical microscope and an electron microscope are shown in Table 13.

The evaluation of the composition of PHA constituting a microcapsule coat in the same manner as in Example 98 confirmed that the main component of the coat of the obtained hollow magnetic microcapsules 30 was PHA including a 3-hydroxy-5-phenylvalerate unit. Further, the gel permeation chromatography analysis confirmed that PHA constituting a coat of the obtained hollow magnetic microcapsules 30 had a number average molecular weight of 21,000.

Example 103

Hollow magnetic microcapsules 31 were obtained under the same conditions as in Example 98 except that the purified enzyme solution (1) used in Example 98 was replaced by the crude enzyme solution (3) originated from a P91 strain and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). An ultrasonic contrast agent employing the hollow magnetic microcapsules 31 is referred to as an ultrasonic contrast agent 31.

The observation results of the obtained microcapsule fine particles using an optical microscope and an electron microscope are shown in Table 13.

The evaluation of the composition of PHA constituting a microcapsule coat in the same manner as in Example 98 confirmed that the main component of the coat of the obtained hollow magnetic microcapsules 31 was PHA including a 3-hydroxy-5-phenoxy valerate unit. Further, the gel permeation chromatography analysis confirmed that PHA constituting a coat of the obtained hollow magnetic microcapsules 31 had a number average molecular weight of 23,000.

Example 104

A PHA synthesis reaction was conducted in the same manner as in Example 98 except that the purified enzyme solution (1) in Example 98 was replaced by the crude enzyme solution (4) and (R)-3-hydroxybutyryl CoA was replaced by (R,S)-3-hydroxy-5-phenylvaleryl CoA. In Example 104, after the reaction at room temperature for 3 hours, 1 g of (R,S)-3-hydroxy-5-phenoxyvaleryl CoA was further added to the water phase for a reaction at room temperature for additional 2 hours. The subsequent treatment was conducted in the same manner as in Example 98, to thereby obtain hollow magnetic microcapsules 32. An ultrasonic contrast agent employing the hollow magnetic microcapsules 32 is referred to as an ultrasonic contrast agent 32.

The observation results of the obtained microcapsule fine particles using an optical microscope and an electron microscope are shown in Table 13.

Mass of a polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement using TOF-SIMS in the same manner while cutting off the capsular structure surface little by little through ion sputtering confirmed that the main component of the PHA monomer unit constituting the capsular structure was replaced by a 3-hydroxy-5-phenylvalerate unit at a certain point in time. The results confirmed that a capsular structure of Example 104 had a desired capsular structure of a double layer structure having poly(3-hydroxy-5-phenoxy valeric acid), produced in the latter half of an enzyme reaction, coated on a coat layer of poly(3-hydroxy-5-phenylvaleric acid), produced at the beginning thereof. Further, the gel permeation chromatography analysis confirmed that the PHA constituting a coat of the obtained hollow magnetic microcapsules 32 had a number average molecular weight of 22,000.

Example 105

Hollow magnetic microcapsules 33 were obtained in the same manner as in Example 98 except that the purified enzyme solution (1) in Example 98 was replaced by the crude enzyme solution (5) and 1 g of (R)-3-hydroxybutyryl CoA was replaced by 800 mg of (R,S)-3-hydroxy-5-phenylvaleryl CoA and 200 mg of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). An ultrasonic contrast agent employing the hollow magnetic microcapsules 33 is referred to as an ultrasonic contrast agent 33.

The observation results of the obtained microcapsule fine particles using an optical microscope and an electron microscope are shown in Table 13.

The results of $^1$H-NMR (equipment used: FT-NMR (Bruker DPX400); measured nuclide: $^1$H; solvent used: $CDCl_3$ (containing TMS)) analysis confirmed that the coat of the obtained hollow magnetic microcapsules 33 was PHA including 74% 3-hydroxy-5-phenylvalerate unit and 26% 3-hydroxy-7,8-epoxyoctanoate unit. Further, the gel permeation chromatography analysis confirmed that the PHA constituting a coat of the obtained hollow magnetic microcapsules 33 had a number average molecular weight of 23,000.

Example 106

50 parts by mass of the above-mentioned hollow magnetic microcapsules 33 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain hollow magnetic microcapsules 34. An ultrasonic contrast agent employing the hollow magnetic microcapsules 34 is referred to as an ultrasonic contrast agent 34. The observation results of the obtained microcapsule fine particles using an optical microscope and an electron microscope are shown in Table 13.

Infrared absorption was measured for the hollow magnetic microcapsules 34 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the hollow magnetic microcapsules 34. The disappearance indicates that the hollow magnetic microcapsules 34 coated with a crosslinked polymer were obtained through a reaction between PHA having an epoxy unit in the side chain and hexamethylene diamine.

Example 107

10 parts by mass of terminal amino group-modified polysiloxane (modified silicone oil TSF4700, available from GE Toshiba Silicones) was added to 50 parts by mass of the above-mentioned hollow magnetic microcapsules 33, and the whole was reacted at 70° C. for 2 hours. The reacted mixture was then washed by repeated suspension in methanol and centrifugation (10,000×g, 4° C., 20 minutes) and dried, to thereby obtain hollow magnetic microcapsules 35 having a graft chain of polysiloxane. An ultrasonic contrast agent employing the hollow magnetic microcapsules 35 is referred to as an ultrasonic contrast agent 35.

The observation results of the obtained microcapsule fine particles using an optical microscope and an electron microscope are shown in Table 13.

Infrared absorption was measured for the hollow magnetic microcapsules 35 (FT-IR: 1720X, manufactured by Perkin Elmer, Inc.). As a result, peaks assigned to an amine group (at about 3,340 cm$^{-1}$) and an epoxy group (at about 822 cm$^{-1}$), observed before the heating, disappeared with the hollow magnetic microcapsules 35. The disappearance indicates that the hollow magnetic microcapsules 35 having a graft chain of polysiloxane were obtained through a reaction between PHA having an epoxy unit in the side chain and terminal amino group-modified polysiloxane.

TABLE 13

| Example | Hollow magnetic capsule No. | Average particle size (μm) | Pore |
|---|---|---|---|
| 98 | 26 | 7.1 | None |
| 99 | 27 | 7.2 | None |
| 100 | 28 | 7.4 | None |
| 101 | 29 | 6.9 | None |
| 102 | 30 | 7.5 | None |
| 103 | 31 | 7.3 | None |
| 104 | 32 | 7.3 | None |
| 105 | 33 | 7.4 | None |
| 106 | 34 | 7.4 | None |
| 107 | 35 | 7.3 | None |

Example 108

2 ml of dichloromethane containing 0.2 g of the magnetic substances 1 dispersed was cooled to 16 to 18° C. and added to 100 ml of a 0.1 M phosphate buffer (pH 7.0) containing 0.1% polyvinyl alcohol dissolved (EG-40, available from Nippon Synthetic Chemical Industry Co., Ltd.) and cooled down to 16 to 18° C. in advance. The mixture was stirred at 7,000 rpm using a turbine-type homomixer (manufactured by Tokushu Kika Kogyo Co., Ltd.), to thereby obtain an O/W type emulsion. 5 ml of a purified enzyme solution (1), 1 g of (R)-3-hydroxybutyryl CoA (available from Sigma Aldrich Japan K.K.), and 0.1 g of bovine serum albumin (available from Sigma Co.) were added to and dissolved in the obtained O/W type emulsion. The mixture was gently stirred at room temperature for 3 hours for PHA synthesis and vaporization of dichloromethane to solidify PHA dissolved in an oil phase, and was centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain hollow magnetic microcapsules 36 in powder form. An ultrasonic contrast agent employing the hollow magnetic microcapsules 36 is referred to as an ultrasonic contrast agent 36.

The observation results of the obtained microcapsule fine particles using an optical microscope and an electron microscope are shown in Table 14.

Further, the hollow magnetic microcapsules 36 were suspended in 20 ml of chloroform, and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of hydroxybutyric acid. This result confirmed that the main component of the coat of the obtained hollow magnetic microcapsules 36 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloro-

Example 109

Hollow magnetic microcapsules 37 were obtained under the same conditions as in Example 108 except that the purified enzyme solution (1) used in Example 108 was replaced by the crude enzyme solution (1). An ultrasonic contrast agent employing the hollow magnetic microcapsules 37 is referred to as an ultrasonic contrast agent 37. The observation results of the obtained microcapsule fine particles using an optical microscope and an electron microscope are shown in Table 14.

The evaluation of the composition of PHA constituting a microcapsule coat in the same manner as in Example 108 confirmed that the main component of the coat of the obtained hollow magnetic microcapsules 37 was PHB. Further, the gel permeation chromatography analysis confirmed that PHB constituting a coat of the obtained hollow magnetic microcapsules 37 had a number average molecular weight of 73,000.

Example 110

Hollow magnetic microcapsules 38 were obtained under the same conditions as in Example 108 except that the purified enzyme solution (1) used in Example 108 was replaced by the crude enzyme solution (2). An ultrasonic contrast agent employing the hollow magnetic microcapsules 38 is referred to as an ultrasonic contrast agent 38. The observation results of the obtained microcapsule fine particles using an optical microscope and an electron microscope are shown in Table 14.

The evaluation of the composition of PHA constituting a microcapsule coat in the same manner as in Example 108 confirmed that the main component of the coat of the obtained hollow magnetic microcapsules 38 was PHB. Further, the gel permeation chromatography analysis confirmed that PHB constituting a coat of the obtained hollow magnetic microcapsules 38 had a number average molecular weight of 71,000.

Example 111

Hollow magnetic microcapsules 39 were obtained under the same conditions as in Example 108 except that the purified enzyme solution (1) used in Example 108 was replaced by the purified enzyme solution (2) and (R)-3-hydroxybutyryl CoA was replaced by (R)-3-hydroxyoctanoyl CoA (prepared following a procedure described in Eur. J. Biochem., 250, 432-439, 1997). An ultrasonic contrast agent employing the hollow magnetic microcapsules 39 is referred to as an ultrasonic contrast agent 39.

The observation results of the obtained microcapsule fine particles using an optical microscope and an electron microscope are shown in Table 14.

The evaluation of the composition of PHA constituting a microcapsule coat in the same manner as in Example 108 confirmed that the main component of the coat of the obtained hollow magnetic microcapsules 39 was PHA including a 3-hydroxyoctanoate unit. Further, the gel permeation chromatography analysis confirmed that PHA constituting a coat of the obtained hollow magnetic microcapsules 39 had a number average molecular weight of 23,000.

Example 112

Hollow magnetic microcapsules 40 were obtained under the same conditions as in Example 108 except that the purified enzyme solution (1) used in Example 108 was replaced by the purified enzyme solution (3) and (R)-3-hydroxybutyryl CoA was replaced by (R,S)-3-hydroxy-5-phenylvaleryl CoA (prepared by hydrolyzing 3-hydroxy-5-phenyl valerate obtained by a Reformatsky reaction to produce 3-hydroxy-5-phenylvaleric acid and then following a procedure described in Eur. J. Biochem., 250, 432-439, 1997). An ultrasonic contrast agent employing the hollow magnetic microcapsules 40 is referred to as an ultrasonic contrast agent 40.

The observation results of the obtained microcapsule fine particles using an optical microscope and an electron microscope are shown in Table 14.

The evaluation of the composition of PHA constituting a microcapsule coat in the same manner as in Example 108 confirmed that the main component of the coat of the obtained hollow magnetic microcapsules 40 was PHA including a 3-hydroxy-5-phenylvalerate unit. Further, the gel permeation chromatography analysis confirmed that PHA constituting a coat of the obtained hollow magnetic microcapsules 40 had a number average molecular weight of 20,000.

Example 113

Hollow magnetic microcapsules 41 were obtained under the same conditions as in Example 108 except that the purified enzyme solution (1) used in Example 108 was replaced by the crude enzyme solution (3) and (R)-3-hydroxybutyryl CoA was replaced by (R,S)-3-hydroxy-5-phenoxyvaleryl CoA (prepared by hydrolyzing 3-hydroxy-5-phenoxy valerate obtained through a Reformatsky reaction with zinc using 3-phenoxypropanal and ethyl bromoacetate as raw materials, which were synthesized according to a procedure described in J. Org. Chem., 55, 1490-1492, 1990, to produce 3-hydroxy-5-phenoxy valeric acid and then following a procedure described in Eur. J. Biochem., 250, 432-439, 1997). An ultrasonic contrast agent employing the hollow magnetic microcapsules 41 is referred to as an ultrasonic contrast agent 41.

The observation results of the obtained microcapsule fine particles using an optical microscope and an electron microscope are shown in Table 14.

The evaluation of the composition of PHA constituting a microcapsule coat in the same manner as in Example 108 confirmed that the main component of the coat of the obtained hollow magnetic microcapsules 41 was PHA including a 3-hydroxy-5-phenoxy valerate unit. Further, the gel permeation chromatography analysis confirmed that PHA constituting a coat of the obtained hollow magnetic microcapsules 41 had a number average molecular weight of 24,000.

Example 114

A PHA synthesis reaction was conducted in the same manner as in Example 108 except that the purified enzyme solution (1) used in Example 108 was replaced by the crude enzyme solution (4) and (R)-3-hydroxybutyryl CoA was replaced by (R,S)-3-hydroxy-5-phenylvaleryl CoA.

In Example 114, after 1-hour reaction at room temperature, 1 g of (R,S)-3-hydroxy-5-phenoxyvaleryl CoA was further added to a water phase for a reaction at room temperature for additional 2 hours. Hollow magnetic microcapsules 42 were obtained following a procedure in Example 108 thereafter. An ultrasonic contrast agent employing the hollow magnetic microcapsules 42 is referred to as an ultrasonic contrast agent 42.

The observation results of the obtained microcapsule fine particles using an optical microscope and an electron microscope are shown in Table 14. Mass of a polymer formed on a capsular structure surface was measured using a time-of-flight type secondary ion mass spectrometer (TOF-SIMS IV, manufactured by Cameca). The obtained mass spectrum confirmed that the PHA on the capsular structure surface was mainly constituted of a 3-hydroxy-5-phenoxy valerate unit. Further, mass spectrum measurement using TOF-SIMS while cutting off the capsular structure surface little by little through ion sputtering confirmed that the main component of the PHA monomer unit constituting the capsular structure was replaced by a 3-hydroxy-5-phenylvalerate unit at a point in time when ion sputtering progressed to a certain depth from the coat surface. The results confirmed that a capsular structure of Example 114 was a desired capsular structure having a double layer coat including poly(3-hydroxy-5-phenoxy valeric acid) produced in the latter half, coated on a coat layer of poly(3-hydroxy-5-phenylvaleric acid) produced at the beginning thereof. Further, the gel permeation chromatography analysis confirmed that the PHA constituting a coat of the obtained hollow magnetic microcapsules 42 had a number average molecular weight of 21,000.

Example 115

Hollow magnetic microcapsules 43 were obtained under the same conditions as in Example 108 except that the purified enzyme solution (1) used in Example 108 was replaced by the crude enzyme solution (5) and 1 g of (R)-3-hydroxybutyryl CoA was replaced by 0.8 g of (R,S)-3-hydroxy-5-phenylvaleryl CoA and 0.2 g of (R,S)-3-hydroxy-7,8-epoxyoctanoyl CoA (prepared by epoxidating an unsaturated part of 3-hydroxy-7-octenoic acid synthesized according to a procedure described in Int. J. Biol. Macromol., 12, 85-91, 1990 with 3-chlorobenzoic acid and then following a procedure described in Eur. J. Biochem., 250, 432-439, 1997). An ultrasonic contrast agent employing the hollow magnetic microcapsules 43 is referred to as an ultrasonic contrast agent 43.

The observation results of the obtained microcapsule fine particles using an optical microscope and an electron microscope are shown in Table 14. The results of $^1$H-NMR (equipment used: FT-NMR (Bruker DPX400); measured nuclide: $^1$H; solvent used: $CDCl_3$ (containing TMS)) analysis confirmed that the coat of the obtained hollow magnetic microcapsules 43 was PHA including 73% 3-hydroxy-5-phenylvalerate unit and 27% 3-hydroxy-7,8-epoxyoctanoate unit. Further, the gel permeation chromatography analysis confirmed that the PHA constituting a coat of the obtained hollow magnetic microcapsules 43 had a number average molecular weight of 21,000.

Example 116

50 parts by mass of the above-mentioned hollow magnetic microcapsules 43 were suspended in 50 parts by mass of purified water, and 0.5 parts by mass of hexamethylene diamine was then dissolved as a crosslinking agent in the suspension. After dissolution was confirmed, water was removed through freeze-drying, and the remainder was reacted at 70° C. for 12 hours, to thereby obtain hollow magnetic microcapsules 44 having the surface subjected to crosslinking treatment. An ultrasonic contrast agent employing the hollow magnetic microcapsules 44 is referred to as an ultrasonic contrast agent 44.

The observation results of the obtained microcapsule fine particles using an optical microscope and an electron microscope are shown in Table 14.

Infrared absorption was measured for the hollow magnetic microcapsules 44 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 44. The disappearance indicates that the hollow magnetic microcapsules 44 coated with a crosslinked polymer on a surface thereof were obtained through a reaction between PHA containing a unit having an epoxy group in the side chain and hexamethylene diamine.

Example 117

10 parts by mass of terminal amino group-modified polysiloxane (modified silicone oil TSF4700, available from GE Toshiba Silicones) was added to 50 parts by mass of the above-mentioned hollow magnetic microcapsules 43, and the whole was reacted at 70° C. for 2 hours. The reacted mixture was washed by repeated suspension in methanol and centrifugation (10,000×g, 4° C., 20 minutes) and then dried, to thereby obtain hollow magnetic microcapsules 45 having a graft chain of polysiloxane. An ultrasonic contrast agent employing the hollow magnetic microcapsules 45 is referred to as an ultrasonic contrast agent 45.

The observation results of the obtained microcapsule fine particles using an optical microscope and an electron microscope are shown in Table 14.

Infrared absorption was measured for the hollow magnetic microcapsules 45 (FT-IR: 1720X, manufactured by Perkin Elmer, Inc.). As a result, peaks assigned to an amine group (at about 3,340 $cm^{-1}$) and an epoxy group (at about 822 $cm^{-1}$), observed before the heating, disappeared with the hollow magnetic microcapsules 45. The disappearance indicates that the hollow magnetic microcapsules 45 having a graft chain of polysiloxane were obtained through a reaction between PHA having an epoxy unit in the side chain and terminal amino group-modified polysiloxane.

TABLE 14

| Example | Hollow magnetic capsule No. | Average particle size (μm) | Pore |
|---|---|---|---|
| 108 | 36 | 7.3 | None |
| 109 | 37 | 7.0 | None |
| 110 | 38 | 7.5 | None |
| 111 | 39 | 7.3 | None |
| 112 | 40 | 7.4 | None |
| 113 | 41 | 7.2 | None |
| 114 | 42 | 6.9 | None |
| 115 | 43 | 7.1 | None |
| 116 | 44 | 7.2 | None |
| 117 | 45 | 7.4 | None |

Experimental Example 16

(In Vitro Experiment on Ultrasonic Contrast Effect)

An ultrasonic contrast effect of the ultrasonic contrast agents employing the hollow magnetic microcapsules was examined using a testing equipment shown in FIG. 1. That is, a polypropylene vessel 1 containing 100 ml of a physiological saline was secured in place inside a water tank 2. A stirring bar 3 was placed inside the vessel 1, and the solution was stirred using a magnetic stirrer. Prescribed amounts of the hollow magnetic microcapsule fine particles obtained in Examples and Comparative Examples were suspended in 1 ml of a 1 w/v % aqueous solution of Tween 80, and the suspension was poured into the physiological saline in the vessel 1. Subsequently, the mixture was scanned using a diagnostic ultrasound system (Sonolayer αSSH-140, available from Toshiba Corporation) equipped with a sector-type probe having a center frequency of 5 MHz so that the vessel 1 is located at the center of a screen. Then, for a still image on a contrast screen, brightness of spots in a front portion of the vessel 1 or inside the whole vessel 1 was determined as an index of an ultrasound contrast effect.

1 w/v % aqueous solutions of Tween 80 (1 ml each) each containing different amounts of the ultrasonic contrast agents 12 to 14, 23 to 25, 33 to 35, 43 to 45, and 15 employing the respective fine particulate microcapsules obtained in Examples 85 to 87, 95 to 97, 105 to 107, and 115 to 117, and Comparative Example 4 were respectively added to 100 ml of the physiological saline. Changes with time in brightness of the spots in the front portion of the vessel 1 were examined.

As a result, an average value of initial spot brightness was constant at about 25 to 30 for any of the ultrasonic contrast agents 12 to 14, 23 to 25, 33 to 35, and 43 to 45 when 20 mg or less thereof was added. On the other hand, a sequential attenuation rate varied depending on the addition amount (suspension concentration), and the lower the suspension concentration of the hollow magnetic microcapsule fine particles, the larger the attenuation rate. For example, when the addition amount was 5 mg or 2.5 mg, the average value of the spot brightness declined to 20 or less in about 5 minutes after the addition. On the other hand, when the addition amount was 10 mg or 20 mg, the average value of the spot brightness remained 20 or more even about 30 minutes after the addition.

On the other hand, the amount of 40 mg or more of the hollow magnetic microcapsule fine particles resulted in acoustic shadow at an initial stage and an initial value of the spot brightness of about 23, which was lower than that obtained when adding in amount of 10 mg or 20 mg. The spot brightness, after addition and along with the progress of dispersion of the hollow magnetic microcapsule fine particles, sequentially increased to about 28 in about 10 minutes. Thereafter, high spot brightness was maintained for a while when the suspension concentration of the fine particles was high (addition amount of 80 mg), and gradually attenuated when the suspension concentration was low (addition amount of 40 mg). The average value of the brightness remained 25 or more at any concentration even about 30 minutes after the brightness reached a peak.

Therefore, a high contrast effect can be exerted over a long period of time by preparing the ultrasonic contrast agents employing the PHA hollow microcapsules of the present invention in an addition amount (suspension concentration) of 10 mg or more with respect to 1 ml of water.

On the other hand, the ultrasonic contrast agent 15 employing the hollow magnetic microcapsules 15 prepared using poly DL lactic acid (average molecular weight of 7,000) had an initial average spot brightness of 20 or more at any suspension concentration. However, the spot brightness rapidly attenuated thereafter to 10 or less after about 5 minutes and to about 5 after about 10 minutes. Persistence of the contrast effect after the addition was inferior to that of the ultrasonic contrast agent of the present invention.

Example 118

500 mg of peptide A acetate (available from TAP Pharmaceutical Products Inc.) was dissolved in 0.6 ml of distilled water. The obtained solution was added to a solution containing 4.5 g of Example Compound 1 and 1.5 g of nickel powder (referred to as magnetic substances 2) synthesized through a vapor phase method as magnetic metal ("Ni(200)UFMP", primary particle size of 0.02 μm, available from Vacuum Metallurgical Co., Ltd.) dissolved in 5.8 ml of dichloromethane, and the whole was mixed using a small homogenizer (manufactured by Kinematica AG) for 60 seconds, to thereby obtain a W/O type emulsion. The W/O type emulsion was cooled to 16° C. and added to 1,000 ml of a 0.1% aqueous solution of polyvinyl alcohol (EG-40, available from Nippon Synthetic Chemicals Co.) cooled to 16° C. in advance, to thereby obtain a W/O/W type emulsion through stirring at 7,000 rpm using a turbine-type homomixer (manufactured by Tokushu Kika Kogyo Co., Ltd.). The W/O/W type emulsion was stirred at room temperature for 3 hours to vaporize dichloromethane. The solidified. W/o type emulsion was centrifuged at 2,000 rpm with a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The mixture was freeze-dried, to thereby obtain magnetic microcapsules 76 in powder form. The content of the peptide A in the microcapsules is shown in Table 15.

Example 119

500 mg of peptide A acetate (available from TAP Pharmaceutical Products Inc.) was dissolved in 0.6 ml of a 0.1 M phosphate buffer (pH 7.0). 60 μl of the purified enzyme solution (1), 60 mg of (R)-3-hydroxybutyryl CoA (available from Sigma Aldrich Japan K.K.), and 5 mg of bovine serum albumin (available from Sigma Co.) were added and dissolved therein. The obtained solution was added to 5.8 ml of dichloromethane having 1.5 g of the magnetic substances 2 dispersed therein, and the whole was mixed using a small homogenizer (manufactured by Kinematica AG) for 60 seconds, to thereby obtain a W/O type emulsion. The W/O type emulsion was cooled to 16° C. and added to 1,000 ml of a 0.1% aqueous solution of polyvinyl alcohol (EG-40, available from Nippon Synthetic Chemicals Co.) cooled to 16° C. in advance, to thereby obtain a W/O/W type emulsion through stirring at 7,000 rpm using a turbine-type homomixer (manufactured by Tokushu Kika Kogyo Co., Ltd.). The W/O/W type emulsion was stirred at room temperature for 3 hours for PHA synthesis while dichloromethane was vaporized. The solidified W/O type emulsion was centrifuged at 2,000 rpm with a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The mixture was freeze-dried, to thereby obtain magnetic microcapsules 77 in powder form. The content of the peptide A in the microcapsules is shown in Table 15.

Further, the magnetic microcapsules 77 were suspended in 20 ml of chloroform, and the suspension was stirred at 60° C.

for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylated compound of hydroxybutyric acid. This result confirmed that the main component of the coat of the obtained magnetic microcapsules 77 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn=73,000.

Example 120

500 mg of peptide A acetate (available from TAP Pharmaceutical Products Inc.) was dissolved in 0.6 ml of distilled water. The obtained solution was added to 5.8 ml of dichloromethane having 1.5 g of the magnetic substances 2 dispersed therein, and the whole was mixed using a small homogenizer (manufactured by Kinematica AG) for 60 seconds, to thereby obtain a W/O type emulsion. The W/O type emulsion was cooled to 16° C. and added to 100 ml of a 0.1 M phosphate buffer (pH 7.0) containing 0.1% polyvinyl alcohol (EG-40, available from Nippon Synthetic Chemicals Co.) cooled to 16° C. in advance, to thereby obtain a W/O/W type emulsion through stirring at 7,000 rpm using a turbine-type homomixer (manufactured by Tokushu Kika Kogyo Co., Ltd.). 5 ml of the purified enzyme solution (1), 1 g of (R)-3-hydroxybutyryl CoA (available from Sigma Aldrich Japan K.K.), and 100 mg of bovine serum albumin (available from Sigma Co.) were then added to and dissolved in the W/O/W type emulsion.

The W/O/W type emulsion was stirred at room temperature for 3 hours for PHA synthesis and vaporization of dichloromethane. The solidified W/O type emulsion was centrifuged at 2,000 rpm with a centrifuge (05PR-22, manufactured by Hitachi, Ltd.). The obtained precipitate was redispersed in distilled water, and the dispersion was further centrifuged to wash and remove free drugs. The obtained microcapsules were redispersed in a small amount of distilled water, and 0.3 g of D-mannitol was added to the dispersion. The mixture was freeze-dried, to thereby obtain magnetic microcapsules 78 in powder form. The content of the peptide A in the microcapsules is shown in Table 15.

Further, the magnetic microcapsules 78 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylated compound of hydroxybutyric acid. This result confirmed that the main component of the coat of the obtained magnetic microcapsules 78 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn=78,000.

Example 121

A solution containing Drug 2 (200 mg), 2.0 g of Example Compound 1, and 2.0 g of γ-$Fe_2O_3$ fine powder (referred to as magnetic substances 3) synthesized through a vapor phase method ("NanoTek", primary particle size of 0.02 μm, available from C.I. Kasei Co., Ltd.) dissolved in 2 ml of dichloromethane was cooled to 16 to 18° C. The solution was then added to 500 ml of a 0.1% aqueous solution of polyvinyl alcohol (EG-40, available from Nippon Synthetic Chemical Industry Co., Ltd.) cooled down to 16 to 18° C. in advance and stirred at 7,000 rpm using a turbine-type homomixer (manufactured by Tokushu Kika Kogyo Co., Ltd.), to thereby obtain an O/W type emulsion. The obtained O/W type emulsion was stirred at room temperature for 3 hours to vaporize dichloromethane for solidifying an oil phase, and was centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 79 in powder form. The drug content in the microcapsules is shown in Table 15. Note that, the drug content was determined by measuring a sample containing the microcapsules (25 mg) dissolved in 10 ml of a 60% acetonitrile-containing phosphate buffer (pH 7) through an HPLC method.

Example 122

A solution containing 1.5 g of Drug 2, 4.5 g of Example Compound 1, and 1.5 g of the magnetic substances 3 dissolved in 9 ml of dichloromethane was cooled to 16 to 18° C. The solution was then added to 500 ml of a 0.1% aqueous solution of polyvinyl alcohol cooled down to 16 to 18° C. in advance and stirred at 8,000 rpm using a turbine-type homomixer (manufactured by Tokushu Kika Kogyo Co., Ltd.), to thereby obtain an O/W type emulsion. The obtained O/W type emulsion was stirred at room temperature for 3 hours to vaporize dichloromethane for solidifying an oil phase, and was centrifuged with a centrifuge at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 80 in powder form. The drug content in the microcapsules is shown in Table 15.

Example 123

A solution containing 200 mg of Drug 1 and 0.5 g of magnetic substances 3 in 2 ml of dichloromethane was cooled to 16 to 18° C. The solution was then added to 100 ml of a 0.1 M phosphate buffer (pH 7.0) containing 0.1% polyvinyl alcohol dissolved (EG-40, available from Nippon Synthetic Chemical Industry Co., Ltd.) and cooled down to 16 to 18° C. in advance and stirred at 7,000 rpm using a turbine-type homomixer (manufactured by Tokushu Kika Kogyo Co., Ltd.), to thereby obtain an O/W type emulsion. 5 ml of the purified enzyme solution (1), 1 g of (R)-3-hydroxybutyryl CoA (available from Sigma Aldrich Japan K.K.), and 0.1 g of bovine serum albumin (available from Sigma Co.) were then added to the obtained O/W type emulsion and the whole was gently stirred at room temperature for 3 hours for PHA synthesis and vaporization of dichloromethane to solidify an oil phase, and was centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain magnetic microcapsules 81 in powder form. The drug content in the microcapsules is shown in Table 15. Note that, the drug content was determined by measuring a sample containing the microcapsules (25 mg) dissolved in 10 ml of a 60% acetonitrile-containing phosphate buffer (pH 7) through an HPLC method.

Further, the magnetic microcapsules 81 were suspended in 20 ml of chloroform, and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylated compound of hydroxybutyric acid. This result confirmed that the main component of the coat of the obtained magnetic microcapsules 81 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn=78,000.

TABLE 15

| Example | Magnetic capsule No. | Example Compound No. | Drug content (%) |
|---|---|---|---|
| 118 | 76 | 1 | 12.5 |
| 119 | 77 | — | 12.3 |
| 120 | 78 | — | 12.8 |
| 121 | 79 | 1 | 6.2 |
| 122 | 80 | 1 | 15.9 |
| 123 | 81 | — | 6.3 |
| Comparative Example 1 | 15 | PLGA | 7.9 |
| Comparative Example 2 | 50 | PLGA | 4.9 |
| Comparative Example 3 | 65 | PLGA | 14.9 |

Example 124

12 ml of purified water was added to a solution containing 2.0 g of Example Compound 1 and 1 g of magnetite fine particles (referred to as magnetic substances 4) synthesized through a wet process ("magnetite EPT500", particle size of 0.3 μm, available from Toda Kogyo Corporation) dissolved in 20 ml of methylene chloride. The mixture was shaken and stirred, to thereby prepare a W/O type emulsion. Further, the ultrasonic irradiation to the mixture reduced a diameter of an internal water phase. 32 ml of the W/O type emulsion was added to 200 ml of a 1 w/v % aqueous solution of polyvinyl alcohol with stirring using a small homogenizer (POLYTRON, manufactured by Kinematica AG (Switzerland)), to thereby obtain a W/O/W type emulsion. The W/O/W type emulsion was stirred using a stirrer for 6 hours for evaporation of methylene chloride as an organic solvent in an oil phase to solidify Example Compound 1 in the oil phase, to thereby prepare microcapsulated fine particles. The obtained fine particles were collected through centrifugation, and washed simultaneously with cooled purified water. The fine particles were redispersed in a 0.1% aqueous solution of Tween 80 and freeze-dried, to thereby obtain hollow magnetic microcapsules 46 as microcapsulated fine particles in powder-form. An ultrasonic contrast agent employing the hollow magnetic microcapsules 46 is referred to as an ultrasonic contrast agent 46. The observation results of the obtained microcapsule fine particles using an optical microscope and an electron microscope are shown in Table 16.

Example 125

An aqueous solution containing 0.6 ml of the purified enzyme solution (1), 300 mg of (R)-3-hydroxybutyryl CoA (available from Sigma-Aldrich Japan K.K.), and 12 mg of bovine serum albumin (available from Sigma Co.) dissolved in 12 ml of a 0.1 M phosphate buffer (pH 7.0) was added to 20 ml of a methylene chloride solution having the magnetic substances 4 (2 g) dispersed therein. The mixture was shaken and stirred, to thereby prepare a W/O type emulsion. Further, the ultrasonic irradiation to the mixture reduced a diameter of an internal water phase. 32 ml of the W/O type emulsion was then added to 200 ml of a 1 w/v % aqueous solution of polyvinyl alcohol with stirring using a small homogenizer (POLYTRON, manufactured by Kinematica AG (Switzerland)), to thereby obtain a W/O/W type emulsion. The W/O/W type emulsion was stirred using a stirrer for 6 hours for PHA synthesis and evaporation of methylene chloride in an oil phase to solidify PHA, to thereby prepare microcapsulated fine particles. The obtained fine particles were collected through centrifugation, and washed simultaneously with cooled purified water. The fine particles were redispersed in a 0.1% aqueous solution of Tween 80 and freeze-dried, to thereby obtain hollow magnetic microcapsules 47 as microcapsulated fine particles in powder form. An ultrasonic contrast agent employing the hollow magnetic microcapsules 47 is referred to as an ultrasonic contrast agent 47. The observation results of the obtained microcapsule fine particles using an optical microscope and an electron microscope are shown in Table 16.

Further, the hollow magnetic microcapsules 47 were suspended in 20 ml of chloroform and the suspension was stirred at 60° C. for 20 hours to extract PHB constituting a microcapsule coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of hydroxybutyric acid. This result confirmed that the main component of the coat of the obtained hollow magnetic microcapsules 47 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn (number average molecular weight)=72,000.

Example 126

12 ml of purified water was added to 20 ml of a methylene chloride solution having 2 g of the magnetic substances 4 dispersed therein. The mixture was shaken and stirred, to thereby prepare a W/O type emulsion. Further, the ultrasonic irradiation to the mixture reduced a diameter of an internal water phase. Then, 32 ml of the W/O type emulsion was added to 100 ml of an aqueous solution containing 5 ml of the purified enzyme solution (1), 1 g of (R)-3-hydroxybutyryl CoA (available from Sigma-Aldrich Japan K.K.), and 100 mg of bovine serum albumin (available from Sigma Co.) dissolved in a 0.1 M phosphate buffer (pH 7.0) with stirring using a small homogenizer (POLYTRON, manufactured by Kinematica AG (Switzerland)), to thereby obtain a W/O/W type emulsion. The W/O/W type emulsion was stirred using a stirrer for 6 hours for PHA synthesis and evaporation of methylene chloride to solidify the produced PHA, to thereby prepare microcapsulated fine particles. The obtained fine particles were collected through centrifugation, and washed simultaneously with cooled purified water. The fine particles were redispersed in a 0.1% aqueous solution of Tween 80 and freeze-dried, to thereby obtain hollow magnetic microcapsules 48 as microcapsulated fine particles in powder form. An ultrasonic contrast agent employing the hollow magnetic microcapsules 48 is referred to as an ultrasonic contrast agent 48.

The observation results of the obtained microcapsule fine particles using an optical microscope and an electron microscope are shown in Table 16. Further, the hollow magnetic microcapsules 48 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of hydroxybutyric acid. This result confirmed that the main component of the coat of the obtained hollow magnetic microcapsules 48 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn (number average molecular weight)=71,000.

Example 127

A solution containing 0.2 g of the magnetic substances 4 dissolved in 2 ml of dichloromethane was cooled to 16 to 18° C. The solution was then added to 100 ml of a 0.1 M phosphate buffer (pH 7.0) containing 0.1% polyvinyl alcohol dissolved (EG-40, available from Nippon Synthetic Chemical Industry Co., Ltd.) and cooled down to 16 to 18° C. in advance and stirred at 7,000 rpm using a turbine-type homomixer (manufactured by Tokushu Kika Kogyo Co., Ltd.), to thereby obtain an O/W type emulsion. 5 ml of the purified enzyme solution (1), 1 g of (R)-3-hydroxybutyryl CoA (available from Sigma-Aldrich Japan K.K.), and 0.1 g of bovine serum albumin (available from Sigma Co.) were added to and dissolved in the obtained O/W type emulsion. The obtained O/W type emulsion was gently stirred at room temperature for 3 hours for PHA synthesis and vaporization of dichloromethane to solidify PHA dissolved in an oil phase, and was centrifuged at 1,500 rpm. The obtained precipitate was redispersed in distilled water, and the dispersion was further centrifuged to wash and remove free drugs. The obtained microcapsules were redispersed in a small amount of distilled water and freeze-dried, to thereby obtain hollow magnetic microcapsules 49 in powder form. An ultrasonic contrast agent employing the hollow magnetic microcapsules 49 is referred to as an ultrasonic contrast agent 49.

The observation results of the obtained microcapsule fine particles using an optical microscope and an electron microscope are shown in Table 16.

Further, the hollow magnetic microcapsules 49 were suspended in 20 ml of chloroform and the suspension was stirred at 60° C. for 20 hours to extract PHB constituting a coat. The extract was filtered through a membrane filter having a pore size of 0.45 μm, concentrated under reduced pressure using a rotary evaporator, and then subjected to methanolysis through a conventional method. The product was analyzed with a gas chromatograph-mass spectrometer (GC-MS: Shimadzu QP-5050; EI method) to identify a methylesterified compound of the PHB monomer unit. The peak of the main component in the obtained chromatogram had the same retention time as that of a sample methylesterified compound of hydroxybutyric acid. This result confirmed that the main component of the coat of the obtained hollow magnetic microcapsules 49 was PHB.

Further, the molecular weight of the PHB was measured by gel permeation chromatography (GPC: HLC-8020, manufactured by Tosoh Corporation; column: PLgel MIXED-C (5 μm), available from Polymer Laboratories; solvent: chloroform; column temperature: 40° C.; polystyrene equivalents). As a result, Mn (number average molecular weight)=75,000.

TABLE 16

| Example | Hollow magnetic capsule No. | Example Compound No. | Average particle size (μm) | Pore |
|---|---|---|---|---|
| 124 | 46 | 1 | 7.3 | None |
| 125 | 47 | — | 6.8 | None |
| 126 | 48 | — | 7.0 | None |
| 127 | 49 | — | 7.4 | None |
| Comparative Example 4 | 15 | PLGA | 6.3 | Present |

Experimental Example 17

1 mass % aqueous dispersions of the respective hollow magnetic capsule particles 1, 16, 26, 36, and 46 to 49 obtained in Examples 74, 88, 98, 108, and 124 to 127 were withdrawn into syringes, and 1 cc each thereof was injected to a model device assuming a bladder and observed for 10 minutes from the injection using a diagnostic ultrasound system (EUB-565, 3.5 MHz, attached with a linear scanning probe, manufactured by Hitachi, Ltd.). Flow of fluid was clearly observed as strong echoes by resonance scattering in each case.

Experimental Example 18

1 mass % aqueous solutions of the respective hollow magnetic capsule particles 1, 16, 26, 36, and 46 to 49 obtained in Examples 74, 88, 98, 108, and 124 to 127 were withdrawn into syringes, and 1 cc each thereof was injected to a human vascular wall model device (flow rate: 2 to 3 cm/second;

magnetic flux density at 1 cm from central portion of magnetic field: about 140 gausses; and magnetic gradient: 20 oersted/mm) and observed using a diagnostic ultrasound system (EUB-565, 3.5 MHz, attached with a linear scanning probe, manufactured by Hitachi, Ltd.). The observation at an initial stage of flow of the hollow magnetic capsule particles confirmed that all of the particles flowed by an inner wall of a tube. Further, the observation on the state 1 minute after the start of the flow confirmed that all of the particles aggregated at an inner wall surface of the tube.

Experimental Example 19

The hollow magnetic capsule particles 1 in Example 74 were filtered through a 0.22 μm filter, aseptically washed with a physiological saline sterilized under high pressure steam and substituted, to thereby prepare a 10 mass % dispersion in the physiological saline. 2 ml of a Ketalar (ketamine HCl) injection (50 mg/ml) was intramuscularly injected in the vicinity of a groin of a beagle (6 years old, 13 kg, male) for local anesthesia. No additional anesthetic was administered during observation, without restraint.

A catheter was inserted from the urethra and indwelled. 60 ml of the physiological saline was injected from the catheter using a syringe to fill and swell the bladder. 0.5 ml of a dispersion of the ferrite-coated glass balloon particles was then injected. Further, 10 ml of the physiological saline was injected, and the dispersion inside the catheter was completely injected. The observation from prior to the injection using a diagnostic ultrasound system (U-sonic RT5000, attached with 5 MHz probe, available from GE Yokokawa Medical Systems) confirmed that the hollow magnetic capsule particles were aggregated by a magnet. Detaching the magnet resulted in dispersion of the hollow magnetic capsule particles inside the bladder again. After the observation, the catheter was removed, and the beagle urinated freely. The beagle urinated urine which was turned black by the hollow magnetic capsule particles. After arousal, the beagle moved freely and recovered to normal. No particularly abnormal symptoms were apparent 30 days after the experiment.

The invention claimed is:

1. An encapsulated structure containing a mixture of a polyhydroxyalkanoate and a magnetic substance, comprising:
   an external phase part containing the polyhydroxyalkanoate and the magnetic substance; and
   an internal phase part contained in the external phase part.

2. A structure according to claim 1, wherein the structure is in the form of a microcapsule where the external phase part forms a shell and the internal phase part forms a core.

3. A structure according to claim 1, wherein the polyhydroxyalkanoate comprises polyhydroxyalkanoate including at least one selected from the group consisting of monomer units represented by the following formulae [1] to [10]:

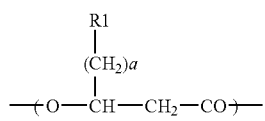

[1]

wherein the monomer unit is at least one selected from the group consisting of monomer units having respective combinations of R1 and a as follows:
a monomer unit where R1 represents a hydrogen atom and a represents an integer from 0 to 10;
a monomer unit where R1 represents a halogen atom and a represents an integer from 1 to 10;
a monomer unit where R1 represents a chromophore and a represents an integer from 1 to 10;
a monomer unit where R1 represents a carboxyl group or a salt thereof and a represents an integer from 1 to 10; and
a monomer unit where R1 represents

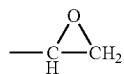

and a represents an integer from 1 to 7;

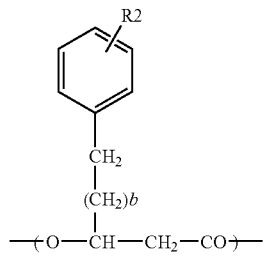

[2]

wherein b represents an integer from 0 to 7, and R2 represents one selected from the group consisting of a hydrogen atom, a halogen atom, —CN, NO$_2$, —CF$_3$, —C$_2$F$_5$, and —C$_3$F$_7$;

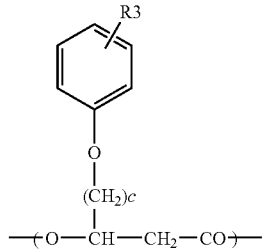

[3]

wherein c represents an integer from 1 to 8, and R3 represents one selected from the group consisting of a hydrogen atom, a halogen atom, —CN, —NO$_2$, —CF$_3$, —C$_2$F$_5$, and —C$_3$F$_7$;

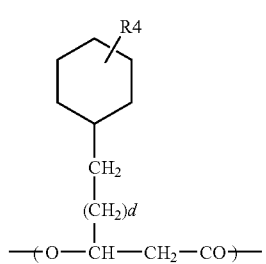

[4]

wherein d represents an integer from 1 to 7, and R4 represents one selected from the group consisting of a hydrogen atom, a halogen atom, —CN, —NO$_2$, —CF$_3$, —C$_2$F$_5$, and —C$_3$F$_7$;

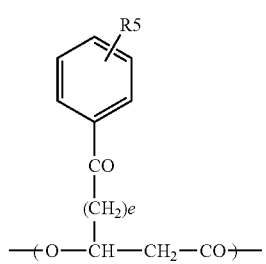

[5]

wherein e represents an integer from 1 to 8, and R5 represents one selected from the group consisting of a hydrogen atom, a halogen atom, —CN, —NO$_2$, —CF$_3$, —C$_2$F$_5$—, —C$_3$F$_7$, —CH$_3$, —C$_2$H$_5$, and —C$_3$H$_7$;

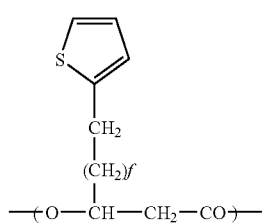

[6]

wherein f represents an integer from 0 to 7;

[7]

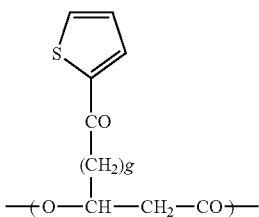

wherein g represents an integer from 1 to 8;

[8]

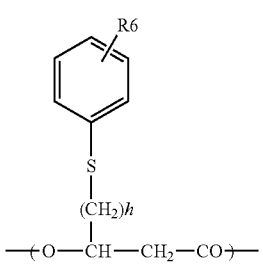

wherein h represents an integer from 1 to 7, and R6 represents one selected from the group consisting of a hydrogen atom, a halogen atom, —CN, —NO$_2$, —COOR', —SO$_2$R", —CH$_3$, —C$_2$H$_5$, —C$_3$H$_7$, —CH(CH$_3$)$_2$, and —C(CH$_3$)$_3$, where R' represents one of a hydrogen atom, Na, K, —CH$_3$, and —C$_2$H$_5$ and R" represents one of —OH, —ONa, —OK, a halogen atom, —OCH$_3$, and —OC$_2$H$_5$;

[9]

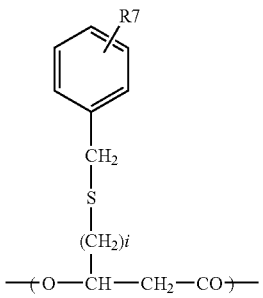

wherein i represents an integer from 1 to 7, and R7 represents one selected from the group consisting of a hydrogen atom, a halogen atom, —CN, —NO$_2$, —COOR', and —SO$_2$R", where R' represents one of a hydrogen atom, Na, K, —CH$_3$, and —C$_2$H$_5$ and R" represents one of —OH, —ONa, —OK, a halogen atom, —OCH$_3$, and —OC$_2$H$_5$; and

[10]

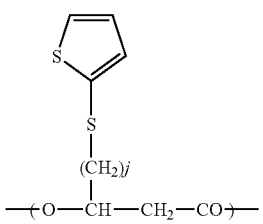

wherein j represents an integer from 1 to 9.

4. A structure according to claim 1, wherein the polyhydroxyalkanoate has a number average molecular weight of 5,000 to 1,000,000.

5. A structure according to claim 1, wherein a monomer unit composition of the polyhydroxyalkanoate varies in a direction from the inside toward the outside of the structure.

6. A structure according to claim 1, wherein at least a portion of the polyhydroxyalkanoate comprises a chemically modified polyhydroxyalkanoate.

7. A method for manufacturing an encapsulated structure containing a mixture of a polyhydroxyalkanoate and a magnetic substance, the structure having an external phase part containing the polyhydroxyalkanoate and the magnetic substance and an internal phase part, which is contained in the external phase part, the method comprising the steps of:
preparing a liquid raw material including an oil phase containing the polyhydroxyalkanoate and an organic solvent, a water phase, and the magnetic substance; and
removing at least one of the organic solvent and water from the liquid raw material,
wherein the inner phase part is contained in the external phase part including the polyhydroxyalkanoate derived from the oil phase or the water phase, and
wherein at least the external phase part contains the magnetic substance.

8. A method according to claim 7, further comprising a step of preparing an emulsion using the water phase and the oil phase.

9. A method according to claim 8, further comprising the steps of:
preparing a W/O emulsion by dispersing the water phase in the oil phase; and
removing at least one of the organic solvent and the water from the W/O emulsion.

10. A method according to claim 8, further comprising the steps of:
preparing a W/O emulsion by dispersing the water phase in the oil phase:
preparing a W/O/W emulsion by dispersing the W/O emulsion in a second water phase; and
removing at least one of the organic solvent and the water from the W/O/W emulsion.

11. A method according to claim 8, further comprising the steps of:
preparing an O/W emulsion by dispersing the oil phase in the water phase; and
removing at least one of the organic solvent and the water from the O/W emulsion.

12. A method according to claim 7, wherein the removal of at least one of the organic solvent and the water is performed by at least one method selected from the group consisting of a submerged drying method, a phase separation method, and a spray drying method.

13. A method for manufacturing an encapsulated structure containing a mixture of a polyhydroxyalkanoate and a magnetic substance, the structure having an external phase part containing the polyhydroxyalkanoate and the magnetic material and an internal phase part, which is contained in the external phase part the method comprising the steps of:
preparing a water phase containing a polyhydroxyalkanoate synthetic enzyme and a 3-hydroxyacyl coenzyme A;
preparing an oil phase containing an organic solvent;
preparing an emulsion containing the water phase, the oil phase, and the magnetic substance;

synthesizing the polyhydroxyalkanoate by polymerizing the 3-hydroxyacyl coenzyme A with the polyhydroxyalkanoate synthetic enzyme in the emulsion; and removing at least one of the organic solvent and water from the emulsion, wherein the inner phase part is contained in the external phase part including the polyhydroxyalkanoate derived from the oil phase or the water phase, and wherein at least the external phase part contains the magnetic substance.

14. A method according to claim 13, further comprising the steps of:

preparing a W/O emulsion by dispersing the water phase in the oil phase; and removing at least one of the organic solvent and the water from the W/O emulsion.

15. A method according to claim 13, comprising the steps of:

preparing a W/O emulsion by dispersing a first water phase in the oil phase;

preparing a W/O/W emulsion by further dispersing the W/O emulsion in a second water phase; and removing at least one of the organic solvent and the water from the W/O/W emulsion.

16. A method according to claim 15, wherein at least one of the first water phase and the second water phase contains a polyhydroxyalkanoate synthetic enzyme and a 3-hydroxyacyl coenzyme A.

17. A method according to claim 13, further comprising the steps of:

preparing an O/W emulsion by dispersing the oil phase in the water phase; and removing at least one of the organic solvent and the water from the O/W emulsion.

18. A method according to claim 13, comprising the steps of:

preparing an O/W emulsion by dispersing a first oil phase in the water phase;

preparing an O/W/O emulsion by further dispersing the O/W emulsion in a second oil phase; and removing at least one of the organic solvent and the water from the O/W/O emulsion.

19. A method according to claim 14, wherein a composition of a 3-hydroxyalkanoate unit in the polyhydroxyalkanoate varies in a direction from an inside to an outside of the structure by changing a composition of the 3-hydroxyacyl coenzyme A with time.

20. A structure according to claim 1, wherein the internal phase contains a pharmaceutical component.

21. A structure according to claim 1, wherein the internal phase also contains the magnetic substance.

* * * * *

```
                         SEQUENCE LISTING

<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 1
cgggatccag taacaagagt aacgatgagt                                          30

<210> SEQ ID NO 2
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 2
cgatctcgag ttaccgttcg tgcacgtacg                                          30

<210> SEQ ID NO 3
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 3
tgctggaact gatccagtac                                                     20

<210> SEQ ID NO 4
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 4
gggttgagga tgctctggat gtg                                                 23
```

<210> SEQ ID NO 5
<211> LENGTH: 1680
<212> TYPE: DNA
<213> ORGANISM: Pseudomonas cichorii YN2; FERM BP-7375

<400> SEQUENCE: 5

```
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccggctg caaccgacca gcgatgaccg tcgcttcgcc      240
gatccggcct ggagccagaa cccgctctat aaacgttatt gcaaaccta cctggcgtgg      300
cgcaaggaac tccacgactg gatcgatgaa agtaacctcg ccccaagga tgtggcgcgt      360
gggcacttcg tgatcaacct catgaccgaa gccatggcgc cgaccaacac cgcggccaac     420
ccggcggcag tcaaacgctt tttcgaaacc ggtggcaaaa gcctgctcga cggcctctcg     480
cacctggcca aggatctggt acacaacggc ggcatgccga gccaggtcaa catgggtgca     540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt ttcgacctga gcccggacaa gagcctggcg     720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgatgtc     840
gttaccgcga tcaccggcag caaagacgtg aacatgctcg gcgcctgctc cggcggcatc     900
acttgcaccg cgctgctggg ccattacgcg gcgattggcg aaaacaaggt caacgccctg     960
accttgctgt tgagcgtgct tgataccacc ctcgacagca tgttgccct gttcgtcaat    1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
accacacggt tgcccgcggc gttccacggc gacctgatcg aactgttcaa aaataaccca    1260
ctgattcgcc cgaatgcact ggaagtgtgc ggcaccccca tcgacctcaa gcaggtgacg    1320
gccgacatct tttccctggc cggcaccaac gaccacatca ccccgtggaa gtcctgctac    1380
aagtcggcgc aactgtttgg cggcaacgtt gaattcgtgc tgtcgagcag cgggcatatc    1440
cagagcatcc tgaacccgcc gggcaatccg aaatcgcgct acatgaccag caccgaagtg    1500
gcggaaaatg ccgatgaatg gcaagcgaat gccaccaagc ataccgattc ctggtggctg    1560
cactggcagg cctggcaggc ccaacgctcg ggcgagctga aaaagtcccc gacaaaactg    1620
ggcagcaagg cgtatccggc aggtgaagcg gcgccaggca cgtacgtgca cgaacggtaa    1680
```

<210> SEQ ID NO 6
<211> LENGTH: 1683
<212> TYPE: DNA
<213> ORGANISM: Pseudomonas cichorii YN2; FERM BP-7375

<400> SEQUENCE: 6

```
atgcgcgata aacctgcgag ggagtcacta cccacccccg ccaagttcat caacgcacaa      60
agtgcgatta ccggcctgcg tggccgggat ctggtttcga ctttgcgcag tgtcgccgcc     120
catggcctgc gccaccccgt gcacaccgcg cgacacgcct tgaaactggg tggtcaactg     180
ggacgcgtgt tgctgggcga caccctgcat cccaccaacc cgcaagaccg tcgcttcgac     240
```

```
gatccggcgt ggagtctcaa tcccttttat cgtcgcagcc tgcaggcgta cctgagctgg      300
cagaagcagg tcaagagctg gatcgacgaa agcaacatga gcccggatga ccgcgcccgt      360
gcgcacttcg cgttcgccct gctcaacgat gccgtgtcgc cgtccaacag cctgctcaat      420
ccgctggcga tcaaggaaat cttcaactcc ggcggcaaca gcctggtgcg cgggatcggc      480
catctggtcg atgacctctt gcacaacgat ggcttgcccc ggcaagtcac caggcatgca      540
ttcgaggttg gcaagaccgt cgccaccacc accggcgccg tggtgtttcg caacgagctg      600
ctggagctga tccaatacaa gccgatgagc gaaaagcagt attccaaacc gctgctggtg      660
gtgccgccac agatcaacaa gtactacatt tttgacctca gccccataa cagcttcgtc       720 cagttcgcgc tcaagaacgg cctgcaaacc ttcgtcatca gctggcgcaa tccggatgta      780
cgtcaccgcg aatggggcct gtcgacctac gtcaagcgg tggaagaagc catgaatgtc       840
tgccgggcaa tcaccggcgc gcgcgaggtc aacctgatgg gcgcctgcgc tggcgggctg      900
accattgctg ccctgcaggg ccacttgcaa gccaagcgac agctgcgccg cgtctccagc      960
gcgacgtacc tggtgagcct gctcgacagc caactggaca gcccggccac actcttcgcc     1020
gacgaacaga ccctggaggc ggccaagcgc cgctcctacc agaaaggtgt gctggaaggc     1080
cgcgacatgg ccaaggtttt cgcctggatg cgccccaacg atttgatctg gagctacttc     1140
gtcaacaatt acctgatggg caaggagccg ccggcgttcg acattctcta ctggaacaat     1200
gacaacacac gcctgccggc cgccctgcat ggtgacttgc tggacttctt caagcacaac     1260
ccgctgagcc atccgggtgg cctggaagtg tgcggcaccc cgatcgactt gcaaaaggtc     1320
accgtcgaca gtttcagcgt ggccggcatc aacgatcaca tcacgccgtg gacgcggtg      1380 tatcgctcaa ccctgttgct cggtggcgag cgtcgctttg tcctggccaa cagcggtcat     1440
gtgcagagca ttctcaaccc gccgaacaat ccgaaagcca actacctcga aggtgcaaaa     1500
ctaagcagcg accccaggc ctggtactac gacgccaagc ccgtcgacgg tagctggtgg      1560
acgcaatggc tgggctggat tcaggagcgc tcgggcgcgc aaaaagaaac ccacatggcc     1620
ctcggcaatc agaattatcc accgatggag gcggcgcccg gacttacgt gcgcgtgcgc      1680 tga                                                                   1683
```

<210> SEQ ID NO 7
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 7
ggaccaagct tctcgtctca gggcaatgg                                          29

<210> SEQ ID NO 8
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 8
cgagcaagct tgctcctaca ggtgaaggc                                          29

-continued

```
<210> SEQ ID NO 9
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 9
gtattaagct tgaagacgaa ggagtgttg                                29

<210> SEQ ID NO 10
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 10
catccaagct tcttatgatc gggtcatgcc                               30

<210> SEQ ID NO 11
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 11
cgggatccag taacaagagt aacgatgagt                               30

<210> SEQ ID NO 12
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 12
cgatctcgag ttaccgttcg tgcacgtacg                               30

<210> SEQ ID NO 13
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 13
cgggatcccg cgataaacct gcgagggagt                               30

<210> SEQ ID NO 14
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 14
cgatctcgag gcgcacgcgc acgtaagtcc                               30
```